US011369590B2

(12) United States Patent
Low et al.

(10) Patent No.: US 11,369,590 B2
(45) Date of Patent: *Jun. 28, 2022

(54) PSMA BINDING LIGAND-LINKER CONJUGATES AND METHODS FOR USING

(71) Applicant: Purdue Research Foundation, West Lafayette, IN (US)

(72) Inventors: Philip Stewart Low, West Lafayette, IN (US); Sumith A. Kularatne, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/359,277

(22) Filed: Jun. 25, 2021

(65) Prior Publication Data

US 2021/0338641 A1 Nov. 4, 2021

Related U.S. Application Data

(63) Continuation of application No. 15/990,152, filed on May 25, 2018, now Pat. No. 10,828,282, which is a continuation of application No. 15/606,913, filed on May 26, 2017, now Pat. No. 10,406,240, which is a continuation of application No. 14/794,482, filed on Jul. 8, 2015, now Pat. No. 10,046,054, which is a continuation of application No. 12/673,931, filed as application No. PCT/US2008/073375 on Aug. 15, 2008, now Pat. No. 9,193,763.

(60) Provisional application No. 61/074,358, filed on Jun. 20, 2008, provisional application No. 60/956,489, filed on Aug. 17, 2007.

(51) Int. Cl.
| | |
|---|---|
| *A61K 31/426* | (2006.01) |
| *C07C 323/52* | (2006.01) |
| *C07D 207/416* | (2006.01) |
| *A61K 47/54* | (2017.01) |
| *A61K 49/00* | (2006.01) |
| *A61K 51/04* | (2006.01) |
| *C07K 5/08* | (2006.01) |
| *A61K 31/4745* | (2006.01) |
| *A61K 31/475* | (2006.01) |
| *A61K 51/08* | (2006.01) |
| *A61K 47/64* | (2017.01) |

(52) U.S. Cl.
CPC .......... *A61K 31/426* (2013.01); *A61K 31/475* (2013.01); *A61K 31/4745* (2013.01); *A61K 47/54* (2017.08); *A61K 47/542* (2017.08); *A61K 47/547* (2017.08); *A61K 47/548* (2017.08); *A61K 47/64* (2017.08); *A61K 49/0041* (2013.01); *A61K 49/0043* (2013.01); *A61K 49/0052* (2013.01); *A61K 49/0056* (2013.01); *A61K 51/04* (2013.01); *A61K 51/0402* (2013.01); *A61K 51/0489* (2013.01); *A61K 51/088* (2013.01); *C07C 323/52* (2013.01); *C07D 207/416* (2013.01); *C07K 5/08* (2013.01)

(58) Field of Classification Search
None
See application file for complete search history.

(56) References Cited

U.S. PATENT DOCUMENTS

| | | | |
|---|---|---|---|
| 4,691,024 | A | 9/1987 | Shirahata et al. |
| 4,713,249 | A | 12/1987 | Schroder |
| 5,103,018 | A | 4/1992 | Motomichi et al. |
| 5,266,333 | A | 11/1993 | Cady et al. |
| 5,418,982 | A | 5/1995 | Kishi |
| 5,627,165 | A | 5/1997 | Glazier |
| 5,795,877 | A | 8/1998 | Jackson et al. |
| 5,863,536 | A | 1/1999 | Jackson et al. |
| 5,866,679 | A | 2/1999 | Defeo-jones et al. |
| 5,902,817 | A | 5/1999 | Jackson et al. |
| 5,948,750 | A | 9/1999 | Garsky et al. |
| 5,962,237 | A | 10/1999 | Ts'o et al. |
| 5,962,521 | A | 10/1999 | Jackson et al. |
| 5,968,915 | A | 10/1999 | Jackson et al. |
| 5,998,362 | A | 12/1999 | Feng et al. |
| 6,054,444 | A | 4/2000 | Jackson et al. |
| 6,127,333 | A | 10/2000 | Brady et al. |
| 6,174,858 | B1 | 1/2001 | Brady et al. |

(Continued)

FOREIGN PATENT DOCUMENTS

| | | |
|---|---|---|
| AU | 2008289108 A1 | 2/2009 |
| AU | 2008289108 B2 | 9/2014 |

(Continued)

OTHER PUBLICATIONS

"99mTc-MIP-1404 for Imaging Prostate Cancer: Phase I Clinical Study to Assess the Image Quality of a Simplified Kit Formulation Compared to a Multi-step Preparation of 99mTc-MIP-1404", ClinicalTrials.gov Identifier: NCT01654874, [online]. Retrieved from the Internet: <URL: https://clinicaltrials.gov/ct2/show/NCT01654874>, (Aug. 1, 2012), 7 pgs.

"A Phase 1 Pilot Study of 99mTc-MIP-1404 SPECT/CT Imaging to Histology in Men With Prostate Cancer", ClinicalTrials.gov Identifier: NCT01615406, [online]. Retrieved from the internet: <URL: https://clinicaltrials.gov/ct2/show/NCT01615406, (Jun. 8, 2012), 7 pgs.

(Continued)

*Primary Examiner* — Savitha M Rao
*Assistant Examiner* — Gregg Polansky
(74) *Attorney, Agent, or Firm* — Schwegman Lundberg & Woessner, P.A.

(57) ABSTRACT

Described herein are prostate specific membrane antigen (PSMA) binding conjugates that are useful for delivering therapeutic, diagnostic and imaging agents. Also described herein are pharmaceutical composition containing them and methods of using the conjugates and compositions. Also described are processes for manufacture of the conjugates and the compositions containing them.

30 Claims, 18 Drawing Sheets

(56) References Cited

U.S. PATENT DOCUMENTS

| | | |
|---|---|---|
| 6,177,404 B1 | 1/2001 | Defeo-jones et al. |
| 6,232,287 B1 | 5/2001 | Ruoslahti et al. |
| 6,368,598 B1 | 4/2002 | D'Amico et al. |
| 6,391,305 B1 | 5/2002 | Feng et al. |
| 6,428,785 B1 | 8/2002 | Gokcen |
| 6,479,470 B1 | 11/2002 | Kozikowski et al. |
| 6,528,499 B1 | 3/2003 | Kozikowski et al. |
| 6,692,724 B1 | 2/2004 | Yang et al. |
| 6,875,886 B2 | 4/2005 | Frangioni |
| 6,946,133 B1 | 9/2005 | Schlom et al. |
| 7,008,765 B1 | 3/2006 | Bussemakers et al. |
| 7,128,893 B2 | 10/2006 | Leamon et al. |
| 7,129,254 B2 | 10/2006 | Berger et al. |
| 7,147,837 B2 | 12/2006 | Lauffer et al. |
| 7,192,586 B2 | 3/2007 | Bander |
| 7,232,805 B2 | 6/2007 | Weinshenker et al. |
| 7,361,338 B2 | 4/2008 | Jakobovits et al. |
| 7,381,745 B2 | 6/2008 | Kozikowski et al. |
| 7,399,460 B2 | 7/2008 | Wedeking et al. |
| 7,408,079 B2 | 8/2008 | Pomper et al. |
| 7,485,299 B2 | 2/2009 | Afar et al. |
| 7,514,078 B2 | 4/2009 | Bander et al. |
| 7,534,580 B2 | 5/2009 | Reeves et al. |
| 7,601,332 B2 | 10/2009 | Vlahov et al. |
| 7,635,682 B2 | 12/2009 | Denmeade et al. |
| 7,638,122 B2 | 12/2009 | Yu et al. |
| 7,659,395 B2 | 2/2010 | Pajouhesh et al. |
| 7,662,795 B2 | 2/2010 | Rodriguez et al. |
| 7,696,185 B2 | 4/2010 | Berkman |
| 7,713,944 B2 | 5/2010 | Kinberger et al. |
| 7,740,847 B2 | 6/2010 | Allan et al. |
| 7,767,202 B2 | 8/2010 | Pardoll et al. |
| 7,767,803 B2 | 8/2010 | Diener et al. |
| 7,794,929 B2 | 9/2010 | Baylin et al. |
| 7,862,798 B2 | 1/2011 | Leamon et al. |
| 7,872,235 B2 | 1/2011 | Rousso et al. |
| 7,875,586 B2 | 1/2011 | Kovbasnjuk et al. |
| 7,879,981 B2 | 2/2011 | Obata |
| 7,910,594 B2 | 3/2011 | Vlahov et al. |
| RE42,275 E | 4/2011 | Berkman |
| 7,990,533 B2 | 8/2011 | Maier et al. |
| 8,000,773 B2 | 8/2011 | Rousso et al. |
| 8,101,369 B2 | 1/2012 | Nam et al. |
| 8,101,713 B2 | 1/2012 | Cuello et al. |
| 8,105,568 B2 | 1/2012 | Vlahov et al. |
| 8,153,595 B2 | 4/2012 | Chen |
| 8,211,401 B2 | 7/2012 | Babich et al. |
| 8,211,402 B2 | 7/2012 | Babich et al. |
| 8,211,473 B2 | 7/2012 | Troiano et al. |
| 8,211,635 B2 | 7/2012 | Barton |
| 8,227,634 B2 | 7/2012 | Pomper et al. |
| 8,236,330 B2 | 8/2012 | Zale et al. |
| 8,246,968 B2 | 8/2012 | Zale et al. |
| 8,258,111 B2 | 9/2012 | Shen et al. |
| 8,273,363 B2 | 9/2012 | Zale et al. |
| 8,313,128 B2 | 11/2012 | Belyea et al. |
| 8,313,728 B2 | 11/2012 | Leamon et al. |
| 8,388,977 B2 | 3/2013 | Low et al. |
| 8,404,817 B2 | 3/2013 | Sherman et al. |
| 8,414,898 B2 | 4/2013 | Afar et al. |
| 8,445,851 B2 | 5/2013 | Rousso et al. |
| 8,450,290 B2 | 5/2013 | Worm et al. |
| 8,465,725 B2 | 6/2013 | Babich et al. |
| 8,487,128 B2 | 7/2013 | Weissbach et al. |
| 8,487,129 B2 | 7/2013 | Babich et al. |
| 8,507,434 B2 | 8/2013 | Popel et al. |
| 8,557,772 B2 | 10/2013 | Karagiannis et al. |
| 8,562,945 B2 | 10/2013 | Babich et al. |
| 8,603,499 B2 | 12/2013 | Zale et al. |
| 8,603,500 B2 | 12/2013 | Zale et al. |
| 8,603,501 B2 | 12/2013 | Zale et al. |
| 8,606,349 B2 | 12/2013 | Rousso et al. |
| 8,644,910 B2 | 2/2014 | Rousso et al. |
| 8,685,891 B2 | 4/2014 | Muraca |
| 8,703,918 B2 | 4/2014 | Colombatti et al. |
| 8,709,483 B2 | 4/2014 | Farokhzad et al. |
| 8,772,226 B2 | 7/2014 | Denmeade et al. |
| 8,772,459 B2 | 7/2014 | Ho et al. |
| 8,778,305 B2 | 7/2014 | Pomper et al. |
| 8,802,153 B2 | 8/2014 | Cheng et al. |
| 8,816,095 B2 | 8/2014 | Brown et al. |
| 8,834,842 B2 | 9/2014 | Leamon et al. |
| 8,840,865 B2 | 9/2014 | Babich et al. |
| 8,852,630 B2 | 10/2014 | Spiegel et al. |
| 8,859,509 B2 | 10/2014 | Spiegel et al. |
| 8,865,126 B2 | 10/2014 | Leamon et al. |
| 8,877,970 B2 | 11/2014 | Zimmerman et al. |
| 8,907,058 B2 | 12/2014 | Low et al. |
| 8,916,161 B2 | 12/2014 | Buckley |
| 8,916,167 B2 | 12/2014 | Low et al. |
| 8,926,944 B2 | 1/2015 | Babich et al. |
| 8,926,945 B2 | 1/2015 | Port et al. |
| 8,940,871 B2 | 1/2015 | Wu et al. |
| 8,946,388 B2 | 2/2015 | Sahin et al. |
| 8,962,799 B2 | 2/2015 | Babich et al. |
| 8,987,319 B2 | 3/2015 | Miller |
| 9,044,468 B2 | 6/2015 | Pomper et al. |
| 9,056,841 B2 | 6/2015 | Pomper et al. |
| 9,193,763 B2 | 11/2015 | Low et al. |
| 9,226,981 B2 | 1/2016 | Pomper et al. |
| 9,242,012 B2 | 1/2016 | Ma et al. |
| 9,278,067 B2 | 3/2016 | Boulikas |
| 9,295,727 B2 | 3/2016 | Zale et al. |
| 9,309,193 B2 | 4/2016 | Babich et al. |
| 9,636,413 B2 | 5/2017 | Vlahov et al. |
| 9,687,572 B2 | 6/2017 | Babich et al. |
| 9,951,324 B2 | 4/2018 | Low et al. |
| 10,046,054 B2 | 8/2018 | Low et al. |
| 10,406,240 B2 | 9/2019 | Low et al. |
| 10,485,878 B2 | 11/2019 | Low et al. |
| 10,517,956 B2 | 12/2019 | Low et al. |
| 10,517,957 B2 | 12/2019 | Low et al. |
| 10,624,969 B2 | 4/2020 | Low et al. |
| 10,624,970 B2 | 4/2020 | Low et al. |
| 10,624,971 B2 | 4/2020 | Low et al. |
| 10,646,581 B2 | 5/2020 | Low et al. |
| 10,828,282 B2 | 11/2020 | Low et al. |
| 2001/0031252 A1 | 10/2001 | Low et al. |
| 2002/0001782 A1 | 1/2002 | Watanabe et al. |
| 2002/0055121 A1 | 5/2002 | Vielkind |
| 2002/0103136 A1 | 8/2002 | Feng |
| 2002/0115596 A1 | 8/2002 | Garsky et al. |
| 2002/0132983 A1 | 9/2002 | Junghans |
| 2003/0035804 A1 | 2/2003 | D'Amico et al. |
| 2003/0086900 A1 | 5/2003 | Low et al. |
| 2003/0133927 A1 | 7/2003 | Defeo-jones et al. |
| 2003/0138432 A1 | 7/2003 | Glazier |
| 2003/0207808 A1 | 11/2003 | Savitzky et al. |
| 2003/0215456 A1 | 11/2003 | Yao et al. |
| 2003/0220241 A1 | 11/2003 | Defeo-jones et al. |
| 2003/0232760 A1 | 12/2003 | Garsky et al. |
| 2004/0001846 A1 | 1/2004 | Israeli et al. |
| 2004/0002478 A1 | 1/2004 | Kozikowski et al. |
| 2004/0018203 A1 | 1/2004 | Pastan et al. |
| 2004/0029778 A1 | 2/2004 | Isaacs |
| 2004/0033195 A1 | 2/2004 | Leamon et al. |
| 2004/0052727 A1 | 3/2004 | Dalton et al. |
| 2004/0054190 A1 | 3/2004 | Pomper et al. |
| 2004/0058857 A1 | 3/2004 | Yao |
| 2004/0110723 A1 | 6/2004 | Frangioni |
| 2004/0146516 A1 | 7/2004 | Roben et al. |
| 2004/0213791 A1 | 10/2004 | Bander et al. |
| 2004/0229845 A1 | 11/2004 | Frangioni |
| 2004/0242582 A1 | 12/2004 | Green et al. |
| 2005/0002942 A1 | 1/2005 | Vlahov et al. |
| 2005/0107325 A1 | 5/2005 | Manoharan et al. |
| 2005/0119166 A1 | 6/2005 | Brady et al. |
| 2005/0158780 A1 | 7/2005 | Lupold et al. |
| 2005/0234247 A1 | 10/2005 | Klar et al. |
| 2005/0239138 A1 | 10/2005 | Hess et al. |
| 2005/0239739 A1 | 10/2005 | Matulic-adamic et al. |
| 2005/0245486 A1 | 11/2005 | Frangioni |
| 2005/0255042 A1 | 11/2005 | Lam et al. |
| 2006/0024317 A1 | 2/2006 | Boyd et al. |

(56) References Cited

U.S. PATENT DOCUMENTS

| | | |
|---|---|---|
| 2006/0052312 A1 | 3/2006 | Erhardt et al. |
| 2006/0062793 A1 | 3/2006 | Webb et al. |
| 2006/0105975 A1 | 5/2006 | Pendergrast et al. |
| 2006/0106047 A1 | 5/2006 | Jiang et al. |
| 2006/0140871 A1 | 6/2006 | Sillerud |
| 2006/0148718 A1 | 7/2006 | Brady et al. |
| 2006/0155021 A1 | 7/2006 | Lenges et al. |
| 2006/0155146 A1 | 7/2006 | Lenges et al. |
| 2007/0010014 A1 | 1/2007 | Wood et al. |
| 2007/0020327 A1 | 1/2007 | Fikes et al. |
| 2007/0031326 A1 | 2/2007 | Shirvan et al. |
| 2007/0031438 A1 | 2/2007 | Junghans |
| 2007/0041901 A1 | 2/2007 | Diener et al. |
| 2007/0117153 A1 | 5/2007 | Bieniarz et al. |
| 2007/0128670 A1 | 6/2007 | Klatzmann et al. |
| 2007/0134332 A1 | 6/2007 | Turnell et al. |
| 2007/0142296 A1 | 6/2007 | Mcbride et al. |
| 2007/0148662 A1 | 6/2007 | Israeli et al. |
| 2007/0160617 A1 | 7/2007 | Ma et al. |
| 2007/0172422 A1 | 7/2007 | Glazier |
| 2007/0179100 A1 | 8/2007 | Manoharan |
| 2007/0219165 A1 | 9/2007 | Berkman |
| 2007/0225213 A1 | 9/2007 | Kosak |
| 2007/0244055 A1 | 10/2007 | Brady et al. |
| 2007/0254316 A1 | 11/2007 | Rodriguez et al. |
| 2007/0254317 A1 | 11/2007 | Busseret-michel et al. |
| 2008/0008649 A1 | 1/2008 | Cappelletti et al. |
| 2008/0008719 A1 | 1/2008 | Bowdish et al. |
| 2008/0089869 A1 | 4/2008 | Denmeade et al. |
| 2008/0114153 A1 | 5/2008 | Steeves et al. |
| 2008/0175789 A1 | 7/2008 | Frangioni |
| 2008/0176821 A1 | 7/2008 | Kozikowski et al. |
| 2008/0193381 A1 | 8/2008 | Babich et al. |
| 2008/0214436 A1 | 9/2008 | Yu et al. |
| 2008/0248052 A1 | 10/2008 | Vlahov et al. |
| 2008/0269105 A1 | 10/2008 | Taft et al. |
| 2008/0311037 A1 | 12/2008 | Heston et al. |
| 2009/0117042 A1 | 5/2009 | Pomper et al. |
| 2009/0123467 A1 | 5/2009 | Bedi et al. |
| 2009/0180951 A1 | 7/2009 | Zimmerman et al. |
| 2009/0214636 A1 | 8/2009 | Low et al. |
| 2009/0247614 A1 | 10/2009 | Manoharan et al. |
| 2009/0258002 A1 | 10/2009 | Barrett et al. |
| 2009/0274625 A1 | 11/2009 | Denmeade et al. |
| 2010/0048490 A1 | 2/2010 | Vlahov et al. |
| 2010/0055735 A1 | 3/2010 | Low et al. |
| 2010/0092496 A1 | 4/2010 | Boyd et al. |
| 2010/0178246 A1 | 7/2010 | Babich et al. |
| 2010/0183509 A1 | 7/2010 | Babich et al. |
| 2010/0183517 A1 | 7/2010 | Berkman |
| 2010/0209343 A1 | 8/2010 | Bander et al. |
| 2010/0240701 A1 | 9/2010 | Vlahov et al. |
| 2010/0324008 A1 | 12/2010 | Low et al. |
| 2011/0008253 A1 | 1/2011 | Babich et al. |
| 2011/0027180 A1 | 2/2011 | Magnani |
| 2011/0027274 A1 | 2/2011 | Cheng et al. |
| 2011/0064657 A1 | 3/2011 | Pomper et al. |
| 2011/0142760 A1 | 6/2011 | Pomper et al. |
| 2011/0172254 A1 | 7/2011 | Leamon et al. |
| 2011/0176998 A1 | 7/2011 | Pomper et al. |
| 2011/0200677 A1 | 8/2011 | Chandran et al. |
| 2011/0288152 A1 | 11/2011 | Low et al. |
| 2012/0009121 A1 | 1/2012 | Pomper et al. |
| 2012/0276162 A1 | 11/2012 | Zale et al. |
| 2012/0322741 A1 | 12/2012 | Low et al. |
| 2013/0034494 A1 | 2/2013 | Babich et al. |
| 2013/0172406 A1 | 7/2013 | Zale et al. |
| 2013/0336888 A1 | 12/2013 | Babich et al. |
| 2014/0073763 A1 | 3/2014 | Low et al. |
| 2014/0107316 A1 | 4/2014 | Vlahov et al. |
| 2014/0140925 A1 | 5/2014 | Leamon et al. |
| 2014/0154702 A1 | 6/2014 | Parker et al. |
| 2014/0187501 A1 | 7/2014 | Bilodeau et al. |
| 2014/0314864 A1 | 10/2014 | Cheng et al. |
| 2015/0023875 A1 | 1/2015 | Farokhzad et al. |
| 2015/0079001 A1 | 3/2015 | Pomper et al. |
| 2015/0104387 A1 | 4/2015 | Pomper et al. |
| 2015/0110715 A1 | 4/2015 | Eder et al. |
| 2015/0246144 A1 | 9/2015 | Pomper et al. |
| 2015/0297735 A1 | 10/2015 | Vlahov et al. |
| 2015/0315196 A1 | 11/2015 | Howard |
| 2015/0366968 A1 | 12/2015 | Basilion |
| 2016/0067341 A1 | 3/2016 | Low et al. |
| 2016/0074526 A1 | 3/2016 | Bilodeau et al. |
| 2016/0114060 A1 | 4/2016 | Pomper et al. |
| 2016/0151508 A1 | 6/2016 | Low et al. |
| 2016/0220694 A1 | 8/2016 | Vlahov et al. |
| 2016/0287731 A1 | 10/2016 | Vlahov et al. |
| 2016/0361376 A1 | 12/2016 | Vlahov et al. |
| 2016/0361432 A1 | 12/2016 | Vlahov et al. |
| 2016/0361433 A1 | 12/2016 | Vlahov et al. |
| 2017/0258923 A1 | 9/2017 | Low et al. |
| 2018/0243431 A1 | 8/2018 | Low et al. |
| 2018/0271988 A1 | 9/2018 | Low et al. |
| 2018/0271989 A1 | 9/2018 | Low et al. |
| 2018/0271990 A1 | 9/2018 | Low et al. |
| 2018/0289827 A1 | 10/2018 | Low et al. |
| 2018/0289828 A1 | 10/2018 | Low et al. |
| 2018/0289829 A1 | 10/2018 | Low et al. |
| 2018/0303950 A1 | 10/2018 | Low et al. |
| 2020/0155695 A1 | 5/2020 | Low et al. |
| 2020/0155696 A1 | 5/2020 | Low et al. |
| 2020/0188523 A1 | 6/2020 | Low et al. |
| 2020/0261592 A1 | 8/2020 | Low et al. |
| 2020/0297701 A1 | 9/2020 | Low et al. |
| 2021/0077468 A1 | 3/2021 | Low et al. |

FOREIGN PATENT DOCUMENTS

| | | |
|---|---|---|
| CA | 2606138 A1 | 10/2005 |
| CA | 2696627 A1 | 2/2009 |
| CA | 2696627 C | 9/2016 |
| CN | 1662263 A | 8/2005 |
| CN | 101863924 A | 10/2010 |
| CN | 102014956 A | 4/2011 |
| CN | 102014956 B | 6/2015 |
| CN | 104873982 A | 9/2015 |
| EP | 0116208 A1 | 8/1984 |
| EP | 1177200 B1 | 6/2005 |
| EP | 1472541 B1 | 9/2009 |
| EP | 2170075 A2 | 4/2010 |
| EP | 2187965 A1 | 5/2010 |
| EP | 2318366 A2 | 5/2011 |
| EP | 2136788 B1 | 10/2011 |
| EP | 2373621 A2 | 10/2011 |
| EP | 2389361 A2 | 11/2011 |
| EP | 2408755 A2 | 1/2012 |
| EP | 1999136 B1 | 10/2012 |
| EP | 2644192 A1 | 10/2013 |
| EP | 2644594 A1 | 10/2013 |
| EP | 2648766 A1 | 10/2013 |
| EP | 2436376 B1 | 7/2014 |
| EP | 2759535 A1 | 7/2014 |
| EP | 2240171 B1 | 8/2014 |
| EP | 2170075 B1 | 12/2014 |
| EP | 2823826 A2 | 1/2015 |
| EP | 2097111 B1 | 7/2015 |
| EP | 2921482 A2 | 9/2015 |
| EP | 2938364 A1 | 11/2015 |
| EP | 2942065 A1 | 11/2015 |
| EP | 2958596 A1 | 12/2015 |
| EP | 2706057 B1 | 4/2016 |
| EP | 3038996 A1 | 7/2016 |
| EP | 3388086 A1 | 10/2018 |
| EP | 2187965 B1 | 10/2019 |
| EP | 3388086 B1 | 10/2020 |
| IL | 203998 A | 8/2015 |
| JP | 2002506204 A | 2/2002 |
| JP | 2004536034 A | 12/2004 |
| JP | 2005274569 A | 10/2005 |
| JP | 2006501149 A | 1/2006 |
| JP | 2006514961 A | 5/2006 |
| JP | 2006518712 A | 8/2006 |
| JP | 2007521803 A | 8/2007 |

(56) References Cited

FOREIGN PATENT DOCUMENTS

| | | |
|---|---|---|
| JP | 2009519209 A | 5/2009 |
| JP | 2010515732 A | 5/2010 |
| JP | 2010518112 A | 5/2010 |
| JP | 2010536790 A | 12/2010 |
| JP | 2014221779 A | 11/2014 |
| JP | 5902237 B2 | 4/2016 |
| JP | 2016153410 A | 8/2016 |
| JP | 2018150350 A | 9/2018 |
| JP | 2019503919 A | 2/2019 |
| JP | 6596479 B2 | 10/2019 |
| JP | 6625690 B2 | 12/2019 |
| JP | 2020073472 A | 5/2020 |
| JP | 2021075561 A | 5/2021 |
| WO | WO-8801622 A1 | 3/1988 |
| WO | WO-9107418 A1 | 5/1991 |
| WO | WO-9945374 A2 | 9/1999 |
| WO | WO-0064911 A1 | 11/2000 |
| WO | WO-0066091 A1 | 11/2000 |
| WO | WO-0243773 A2 | 6/2002 |
| WO | WO-02062398 A2 | 8/2002 |
| WO | WO-02098885 A1 | 12/2002 |
| WO | WO-03000201 A2 | 1/2003 |
| WO | WO-03060523 A1 | 7/2003 |
| WO | WO-03092742 A1 | 11/2003 |
| WO | WO-03097647 A1 | 11/2003 |
| WO | WO-2004010957 A2 | 2/2004 |
| WO | WO-2004069159 A2 | 8/2004 |
| WO | WO-2005082023 A2 | 9/2005 |
| WO | WO-2005112919 A2 | 12/2005 |
| WO | WO-2006012527 A1 | 2/2006 |
| WO | WO-2006093991 A1 | 9/2006 |
| WO | WO-2006096754 A2 | 9/2006 |
| WO | WO-2006136564 A1 | 12/2006 |
| WO | WO-2007006041 A2 | 1/2007 |
| WO | WO-2007022493 A2 | 2/2007 |
| WO | WO-2007022494 A2 | 2/2007 |
| WO | WO-2007042504 A2 | 4/2007 |
| WO | WO-2007106869 A1 | 9/2007 |
| WO | WO-2008057437 A2 | 5/2008 |
| WO | WO-2008058192 A2 | 5/2008 |
| WO | WO-2008088648 A2 | 7/2008 |
| WO | WO-2008098112 A2 | 8/2008 |
| WO | WO-2008101231 A2 | 8/2008 |
| WO | WO-2008121949 A1 | 10/2008 |
| WO | WO-2009002529 A2 | 12/2008 |
| WO | WO-2009002993 A1 | 12/2008 |
| WO | WO-2009026177 A1 | 2/2009 |
| WO | WO-2009070302 A1 | 6/2009 |
| WO | WO-2009082606 A2 | 7/2009 |
| WO | WO-2010014933 A2 | 2/2010 |
| WO | WO-2010065899 A2 | 6/2010 |
| WO | WO-2010065902 A2 | 6/2010 |
| WO | WO-2010065906 A2 | 6/2010 |
| WO | WO-2011014821 A1 | 2/2011 |
| WO | WO-2010108125 A3 | 3/2011 |
| WO | WO-2011106639 A1 | 9/2011 |
| WO | WO-2012078534 A1 | 6/2012 |
| WO | WO-2012166923 A2 | 12/2012 |
| WO | WO-2013022797 A1 | 2/2013 |
| WO | WO-2013028664 A1 | 2/2013 |
| WO | WO-2013130776 A1 | 9/2013 |
| WO | WO-2014062697 A2 | 4/2014 |
| WO | WO-2014078484 A1 | 5/2014 |
| WO | WO-2014106208 A1 | 7/2014 |
| WO | WO-2014127365 A1 | 8/2014 |
| WO | WO-2014134543 A1 | 9/2014 |
| WO | WO-2015055318 A1 | 4/2015 |
| WO | WO-2015057250 A1 | 4/2015 |
| WO | WO-2015171792 A1 | 11/2015 |
| WO | WO-2016030329 A1 | 3/2016 |
| WO | WO-2016040179 A1 | 3/2016 |

OTHER PUBLICATIONS

"A Phase 2 Study With MIP-1404 in Men With High-Risk PC Scheduled for RP and EPLND Compared to Histopathology", ClinicalTrials.gov Identifier: NCT01667536, [online]. Retrieved from the Internet: <URL: https://clinicaltrials.gov/ct2/show/NCT01667536&id-NCT01667536>, (Aug. 17, 2012), 10 pgs.

"U.S. Appl. No. 12/673,931,312 Amendment filed Jul. 2, 2015", 165 pgs.

"U.S. Appl. No. 12/673,931, Final Office Action dated Jan. 30, 2014", 14 pgs.

"U.S. Appl. No. 12/673,931, Non Final Office Action dated Apr. 11, 2013", 15 pgs.

"U.S. Appl. No. 12/673,931, Non Final Office Action dated Dec. 5, 2014", 11 pgs.

"U.S. Appl. No. 12/673,931, Notice of Allowance dated Apr. 9, 2015", 8 pgs.

"U.S. Appl. No. 12/673,931, Notice of Allowance dated Oct. 7, 2015", 8 pgs.

"U.S. Appl. No. 12/673,931, Preliminary Amendment filed Feb. 17, 2010", 6 pgs.

"U.S. Appl. No. 12/673,931, Preliminary Amendment filed Mar. 3, 2011", 7 pgs.

"U.S. Appl. No. 12/673,931, PTO Response to Rule 312 Communication dated Jul. 15, 2015", 2 pgs.

"U.S. Appl. No. 12/673,931, Response filed Mar. 5, 2015 to Non Final Office Action dated Dec. 5, 2014", 8 pgs.

"U.S. Appl. No. 12/673,931, Response filed May 30, 2014 to Final Office Action dated Jan. 30, 2014", 15 pgs.

"U.S. Appl. No. 12/673,931, Response filed Oct. 2, 2012 to Restriction Requirement dated Aug. 2, 2012", 12 pgs.

"U.S. Appl. No. 12/673,931, Response filed Oct. 11, 2013 to Non Final Office Action dated Apr. 11, 2013", 21 pgs.

"U.S. Appl. No. 12/673,931, Restriction Requirement dated Aug. 2, 2012", 9 pgs.

"U.S. Appl. No. 12/673,931, Supplemental Amendment filed Jan. 18, 2013", 9 pgs.

"U.S. Appl. No. 13/826,079, Notice of Allowance dated Jun. 2, 2014", 8 pgs.

"U.S. Appl. No. 13/826,079, Notice of Allowance dated Sep. 12, 2014", 8 pgs.

"U.S. Appl. No. 13/826,079, Preliminary Amendment filed Mar. 14, 2013", 4 pgs.

"U.S. Appl. No. 13/826,079, Preliminary Amendment filed May 16, 2014", 3 pgs.

"U.S. Appl. No. 14/794,482, Examiner Interview Summary dated Oct. 31, 2017", 3 pgs.

"U.S. Appl. No. 14/794,482, Non Final Office Action dated Aug. 10, 2017", 17 pgs.

"U.S. Appl. No. 14/794,482, Notice of Allowance dated Apr. 6, 2018", 8 pgs.

"U.S. Appl. No. 14/794,482, Notice of Non-Compliant Amendment dated May 22, 2017", 2 pgs.

"U.S. Appl. No. 14/794,482, Preliminary Amendment filed Jul. 8, 2015", 6 pgs.

"U.S. Appl. No. 14/794,482, Preliminary Amendment filed Nov. 23, 2015", 7 pgs.

"U.S. Appl. No. 14/794,482, Response filed Feb. 28, 2017 to Restriction Requirement dated Nov. 28, 2016", 2 pgs.

"U.S. Appl. No. 14/794,482, Response filed Jul. 19, 2017 to Notice of Non-Compliant Amendment dated May 22, 2017", 3 pgs.

"U.S. Appl. No. 14/794,482, Response filed Nov. 27, 2017 to Non Final Office Action dated Aug. 10, 2017", 5 pgs.

"U.S. Appl. No. 14/794,482, Restriction Requirement dated Nov. 28, 2016", 6 pgs.

"U.S. Appl. No. 15/606,913, 312 Amendment filed Jul. 1, 2019", 4 pgs.

"U.S. Appl. No. 15/606,913, Advisory Action dated Apr. 16, 2019", 3 pgs.

"U.S. Appl. No. 15/606,913, Corrected Notice of Allowability dated Jul. 29, 2019", 4 pgs.

"U.S. Appl. No. 15/606,913, Examiner Interview Summary dated May 8, 2019", 3 pgs.

(56) References Cited

OTHER PUBLICATIONS

"U.S. Appl. No. 15/606,913, Final Office Action dated Nov. 5, 2018", 8 pgs.
"U.S. Appl. No. 15/606,913, Non Final Office Action dated Apr. 3, 2018", 10 pgs.
"U.S. Appl. No. 15/606,913, Notice of Allowance dated Jun. 26, 2016", 10 pgs.
"U.S. Appl. No. 15/606,913, Preliminary Amendment filed May 26, 2017", 4 pgs.
"U.S. Appl. No. 15/606,913, Preliminary Amendment filed May 30, 2017", 5 pgs.
"U.S. Appl. No. 15/606,913, PTO Response to Rule 312 Communication dated Jul. 18, 2019", 2 pgs.
"U.S. Appl. No. 15/606,913, Response filed Apr. 4, 2019 to Non Final Office Action dated Nov. 5, 2018", 6 pgs.
"U.S. Appl. No. 15/606,913, Response filed Jul. 3, 2018 to Non Final Office Action dated Apr. 3, 2018", 7 pgs.
"U.S. Appl. No. 15/606,913, Response filed Dec. 29, 2017 to Restriction Requirement dated Nov. 3, 2017", 7 pgs.
"U.S. Appl. No. 15/606,913, Restriction Requirement dated Nov. 3, 2017", 6 pgs.
"U.S. Appl. No. 15/959,110, Advisory Action dated Apr. 17, 2019", 3 pgs.
"U.S. Appl. No. 15/959,110, Corrected Notice of Allowability dated Mar. 12, 2020", 2 pgs.
"U.S. Appl. No. 15/959,110, Final Office Action dated Jan. 11, 2019", 15 pgs.
"U.S. Appl. No. 15/959,110, Non Final Office Action dated Jun. 27, 2018", 9 pgs.
"U.S. Appl. No. 15/959,110, Non Final Office Action dated Jun. 27, 2019", 14 pgs.
"U.S. Appl. No. 15/959,110, Notice of Allowance dated Nov. 29, 2019", 9 pgs.
"U.S. Appl. No. 15/959,110, Preliminary Amendment filed Apr. 20, 2018", 4 pgs.
"U.S. Appl. No. 15/959,110, Preliminary Amendment filed Apr. 24, 2018", 6 pgs.
"U.S. Appl. No. 15/959,110, Response filed Aug. 27, 2019 to Non-Final Office Action dated Jun. 27, 2019", 7 pgs.
"U.S. Appl. No. 15/959,110, Response filed Sep. 25, 2018 to Non Final Office Action dated Jun. 27, 2018", 10 pgs.
"U.S. Appl. No. 15/959,116, Response filed Apr. 3, 2019 to Final Office Action dated Jan. 11, 2019", 8 pgs.
"U.S. Appl. No. 15/990,083, Corrected Notice of Allowability dated Oct. 17, 2019", 5 pgs.
"U.S. Appl. No. 15/990,083, Examiner Interview Summary dated Jun. 12, 2019", 4 pgs.
"U.S. Appl. No. 15/990,083, Non Final Office Action dated Jan. 25, 2019", 13 pgs.
"U.S. Appl. No. 15/990,083, Notice of Allowance dated Aug. 20, 2019", 9 pgs.
"U.S. Appl. No. 15/990,083, Preliminary Amendment filed May 25, 2018", 4 pgs.
"U.S. Appl. No. 15/990,083, Preliminary Amendment filed May 29, 2018", 5 pgs.
"U.S. Appl. No. 15/990,083, Response filed Sep. 27, 2018 to Restriction Requirement dated Jul. 27, 2018", 2 pgs.
"U.S. Appl. No. 15/990,083, Restriction Requirement dated Jul. 27, 2018", 6 pgs.
"U.S. Appl. No. 15/990,095, Corrected Notice of Allowability dated Mar. 24, 2020", 3 pgs.
"U.S. Appl. No. 15/990,095, Non Final Office Action dated Jan. 9, 2019", 8 pgs.
"U.S. Appl. No. 15/990,095, Non Final Office Action dated Jun. 13, 2019", 7 pgs.
"U.S. Appl. No. 15/990,095, Notice of Allowance dated Nov. 29, 2019", 8 pgs.
"U.S. Appl. No. 15/990,095, Preliminary Amendment filed May 25, 2018", 4 pgs.
"U.S. Appl. No. 15/990,095, Preliminary Amendment filed May 29, 2018", 4 pgs.
"U.S. Appl. No. 15/990,095, Response filed Feb. 20, 2019 to Non Final Office Action dated Jan. 9, 2019", 5 pgs.
"U.S. Appl. No. 15/990,095, Response filed Sep. 21, 2018 to Restriction Requirement dated Jul. 23, 2018", 2 pgs.
"U.S. Appl. No. 15/990,095, Restriction Requirement dated Jul. 23, 2018", 6 pgs.
"U.S. Appl. No. 15/990,111, Examiner Interview Summary dated May 8, 2019", 3 pgs.
"U.S. Appl. No. 15/990,111, Non Final Office Action dated Jan. 7, 2019", 16 pgs.
"U.S. Appl. No. 15/990,111, Notice of Allowance dated Jul. 25, 2019", 11 pgs.
"U.S. Appl. No. 15/990,111, Preliminary Amendment filed May 25, 2018", 4 pgs.
"U.S. Appl. No. 15/990,111, Preliminary Amendment filed May 29, 2018", 4 pgs.
"U.S. Appl. No. 15/990,111, Response filed Sep. 21, 2018 to Restriction Requirement dated Jul. 23, 2018", 2 pgs.
"U.S. Appl. No. 15/990,111, Restriction Requirement dated Jul. 23, 2018", 6 pgs.
"U.S. Appl. No. 15/990,136, Non Final Office Action dated Jan. 7, 2019", 11 pgs.
"U.S. Appl. No. 15/990,136, Notice of Allowance dated Jan. 6, 2020", 11 pgs.
"U.S. Appl. No. 15/990,136, Notice of Allowance dated Jul. 25, 2019", 10 pgs.
"U.S. Appl. No. 15/990,136, Preliminary Amendment filed May 25, 2018", 4 pgs.
"U.S. Appl. No. 15/990,136, Preliminary Amendment filed May 29, 2018", 4 pgs.
"U.S. Appl. No. 15/990,136, PTO Response to Rule 312 Communication dated Nov. 7, 2019", 2 pgs.
"U.S. Appl. No. 15/990,136, Response filed Sep. 27, 2018 to Restriction Requirement dated Jul. 27, 2018", 2 pgs.
"U.S. Appl. No. 15/990,136, Restriction Requirement dated Jul. 27, 2018", 6 pgs.
"U.S. Appl. No. 15/990,144, Examiner Interview Summary dated Jun. 13, 2019", 4 pgs.
"U.S. Appl. No. 15/990,144, Final Office Action dated Jul. 25, 2019", 9 pgs.
"U.S. Appl. No. 15/990,144, Non Final Office Action dated Jan. 15, 2019", 10 pgs.
"U.S. Appl. No. 15/990,144, Notice of Allowance dated Nov. 13, 2019", 8 pgs.
"U.S. Appl. No. 15/990,144, Preliminary Amendment filed May 25, 2018", 4 pgs.
"U.S. Appl. No. 15/990,144, Preliminary Amendment filed May 29, 2018", 3 pgs.
"U.S. Appl. No. 15/990,144, Response filed Sep. 21, 2018 to Restriction Requirement dated Jul. 23, 2018", 2 pgs.
"U.S. Appl. No. 15/990,144, Response filed Oct. 25, 2019 to Final Office Action dated Jul. 25, 2019", 7 pgs.
"U.S. Appl. No. 15/990,144, Restriction Requirement dated Jul. 23, 2018", 6 pgs.
"U.S. Appl. No. 15/990,152, Corrected Notice of Allowability dated Oct. 15, 2020", 3 pgs.
"U.S. Appl. No. 15/990,152, Examiner Interview Summary dated May 8, 2019", 4 pgs.
"U.S. Appl. No. 15/996,152, Examiner Interview Summary dated May 8, 2020", 3 pgs.
"U.S. Appl. No. 15/990,152, Final Office Action dated Jul. 29, 2019", 8 pgs.
"U.S. Appl. No. 15/990,152, Non Final Office Action dated Jan. 17, 2019", 10 pgs.
"U.S. Appl. No. 15/990,152, Non Final Office Action dated Feb. 21, 2020", 6 pgs.
"U.S. Appl. No. 15/990,152, Notice of Allowance dated Jun. 25, 2020", 8 pgs.
"U.S. Appl. No. 15/990,152, Preliminary Amendment filed May 25, 2018", 4 pgs.

(56) References Cited

OTHER PUBLICATIONS

"U.S. Appl. No. 15/990,152, Preliminary Amendment filed May 29, 2018", 4 pgs.
"U.S. Appl. No. 15/990,152, Response filed Jan. 22, 2020 to Final Office Action dated Jul. 29, 2019", 5 pgs.
"U.S. Appl. No. 15/990,152, Response filed Jun. 4, 2020 to Non Final Office Action dated Feb. 21, 2020", 5 pgs.
"U.S. Appl. No. 15/990,152, Response filed Sep. 27, 2018 to Restriction Requirement dated Jul. 27, 2018", 2 pgs.
"U.S. Appl. No. 15/990,152, Restriction Requirement dated Jul. 27, 2018", 6 pgs.
"U.S. Appl. No. 15/997,451, Examiner Interview Summary dated Jun. 12, 2019", 4 pgs.
"U.S. Appl. No. 15/997,451, Non Final Office Action dated Jan. 24, 2019", 12 pgs.
"U.S. Appl. No. 15/997,451, Notice of Allowance dated Aug. 7, 2019", 9 pgs.
"U.S. Appl. No. 15/997,451, Preliminary Amendment filed Jun. 4, 2018", 5 pgs.
"U.S. Appl. No. 15/997,451, Response filed Oct. 4, 2018 to Restriction Requirement dated Aug. 7, 2018", 3 pgs.
"U.S. Appl. No. 15/997,451, Restriction Requirement dated Aug. 7, 2018", 6 pgs.
"U.S. Appl. No. 16/507,713, Non Final Office Action dated Apr. 15, 2021", 12 pgs.
"U.S. Appl. No. 16/507,713, Response filed Dec. 28, 2020 to Restriction Requirement dated Jul. 24, 2020", 6 pgs.
"U.S. Appl. No. 16/507,713, Restriction Requirement dated Jul. 24, 2020", 6 pgs.
"U.S. Appl. No. 16/749,827, Non Final Office Action dated Dec. 9, 2020", 8 pgs.
"U.S. Appl. No. 16/749,827, Notice of Allowance dated Mar. 24, 2021", 7 pgs.
"U.S. Appl. No. 16/749,827, Notice of Non-Compliant Amendment dated Jul. 29, 2020", 2 pgs.
"U.S. Appl. No. 16/749,827, Response filed Feb. 26, 2021 to Non Final Office Action dated Dec. 9, 2020", 5 pgs.
"U.S. Appl. No. 16/749,827, Response filed May 4, 2020 to Restriction Requirement dated Mar. 5, 2020", 11 pgs.
"U.S. Appl. No. 16/749,827, Response filed Aug. 24, 2020 to Notice of Non-Compliant Amendment dated Jul. 29, 2020", 6 pgs.
"U.S. Appl. No. 16/749,827, Restriction Requirement dated Mar. 5, 2020", 6 pgs.
"Australian Application Serial No. 2008289108, First Examination Report dated Aug. 15, 2013", 2 pgs.
"Australian Application Serial No. 2008289108, Response filed Aug. 15, 2014 to First Examination Report dated Aug. 15, 2013", 14 pgs.
"Australian Application Serial No. 2018200419, First Examination Report dated Oct. 24, 2018", 4 pgs.
"Canadian Application Serial No. 2,696.627, Examiner's Rule 30(2) Requisition dated Jun. 22, 2015", 3 pgs.
"Canadian Application Serial No. 2,696,627, Examiner's Rule 30(2) Requisition dated Oct. 9, 2014", 3 pgs.
"Canadian Application Serial No. 2,696,627, Response filed Apr. 9, 2015 to Examiner's Rule 30(2) Requisition dated Oct. 9, 2014", 22 pgs.
"Canadian Application Serial No. 2,696,627, Response filed Dec. 18, 2015 to Examiner's Rule 30(2) Requisition dated Jun. 22, 2015", 12 pgs.
"Canadian Application Serial No. 2,696,627, Voluntary Amendment filed Apr. 24, 2015", 10 pgs.
"Canadian Application Serial No. 2,696,627, Voluntary Amendment filed May 18, 2010", 8 pgs.
"Canadian Application Serial No. 2,696,627, Voluntary Amendment filed Aug. 15, 2013", 15 pgs.
"Canadian Application Serial No. 2,924,360, Office Action dated Sep. 11, 2018", 3 pgs.
"Chinese Application Serial No. 2014800/1256.X, Office Action dated Apr. 20, 2017", 19 pgs.

"Chinese Application Serial No. 201510221167.5, Decision of Rejection dated Dec. 3, 2019", (w/ English Translation), 17pgs.
"Chinese Application Serial No. 201510221167.5, Notice of Reexamination dated May 12, 2021", (w/ English translation), 12 pgs.
"Chinese Application Serial No. 201510221167.5, Office Action dated Mar. 9, 2018", (w/ English Translation), 17 pgs.
"Chinese Application Serial No. 201510221167.5, Office Action dated Jun. 3, 2019", (w/ English Translation), 19 pgs.
"Chinese Application Serial No. 201510221167.5, Office Action dated Jun. 26, 2017", w/ English translation, 21 pgs.
"Chinese Application Serial No. 201510221167.5, Office Action dated Nov. 14, 2018", (w/ English Translation), 7 pgs.
"Chinese Application Serial No. 201510221167.5, Response filed Mar. 12, 2020 to Decision of Rejection dated Dec. 3, 2019", (w/ English Translation of Claims), 21 pgs.
"Chinese Application Serial No. 201510221167.5, Response filed Mar. 28, 2019 to Office Action dated Nov. 14, 2018", (w/ English Translation of Claims), 21 pgs.
"Chinese Application Serial No. 201510221167.5, Response filed Oct. 16, 2019 to Office Action dated Jun. 3, 2019", (w/ English Translation of Claims), 12.
"Chinese Application Serial No. 201510221167.5, Response filed Nov. 8, 2017 to Office Action dated Jun. 26, 2017", w/ English claims, 22 pgs.
"Chinese Application Serial No. 201610184873.1, Office Action dated Jul. 24, 2018", W/ English Translation, 15 pgs.
"Compound summary for: CID 58099954", Pubchem, (Aug. 19, 2012), 10 pgs.
"Definition of ligand, Random House Kernerman Webster's College Dictionary", downloaded on Jan. 25, 2014 from <http://www.thefreedictionary.com/liqand>, 1 pg.
"Eurasian Application Serial No. 16904952.8, Office Action dated Dec. 20, 2018", 4 pgs.
"Eurasian Application Serial No. 201690862/28, Office Action dated May 22, 2017", 2 pgs.
"European Application No. 20216457.0, Response filed Mar. 26, 2021", 5 pgs.
"European Application Serial No. 08798020.7, Communication of a Notice of Opposition dated Jul. 13, 2020", 114 pgs.
"European Application Serial No. 08798020.7, Communication Pursuant to Article 94(3) EPC dated May 13, 2016", 4 pgs.
"European Application Serial No. 08798020.7, Communication Pursuant to Article 94(3) EPC dated May 16, 2018", 3 pgs.
"European Application Serial No. 08798020.7, Communication Pursuant to Article 94(3) EPC dated Jun. 21, 2017", 3 pgs.
"European Application Serial No. 08798020.7, Decision revoking the European Patent (Art. 101(3)(b) EPC) mailed Nov. 30, 2020", 2 pgs.
"European Application Serial No. 08798020.7, Extended European Search Report dated Oct. 28, 2014", 4 pgs.
"European Application Serial No. 08798020.7, Intention to Grant dated Mar. 5, 2019", 102 pgs.
"European Application Serial No. 08798020.7, Response filed Apr. 27, 2010 to Communication pursuant to Rules 161(1) and 162 EPC dated Mar. 26, 2010", 14 pgs.
"European Application Serial No. 08798020.7, Response filed May 22, 2015 to Extended European Search Report dated Oct. 28, 2014", 10 pgs.
"European Application Serial No. 08798020.7, Response filed Sep. 20, 2018 to Communication Pursuant to Article 94(3) EPC dated May 16, 2018", 77 pgs.
"European Application Serial No. 08798020.7, Response filed Sep. 23, 2016 to Communication Pursuant to Article 94(3) EPC dated May 13, 2016", 12 pgs.
"European Application Serial No. 08798020.7, Response filed Nov. 20, 2020 to Communication of a Notice of Opposition dated Jul. 13, 2020", 1 pg.
, et al., "European Application Serial No. 08798020.7, Response filed Dec. 21, 2017 to Communication Pursuant to Article 94(3) EPC dated Jun. 21, 2017", 9 pgs.
"European Application Serial No. 14861854.9, extended European Search Report dated Sep. 7, 2017", 12 pgs.

(56) References Cited

OTHER PUBLICATIONS

"European Application Serial No. 14861854.9, Office Action dated Sep. 25, 2018", 4 pgs.
"European Application Serial No. 14861854.9, Partial Supplementary European Search Report dated May 19, 2017", 14 pgs.
"European Application Serial No. 14861854.9, Response filed Apr. 6, 2018 to Office Action dated Sep. 26, 2017", 15 pgs.
"European Application Serial No. 14861854.9, Result of Consultation mailed Jan. 25, 2019", 3 pgs.
"European Application Serial No. 18175078, Extended European Search Report dated Sep. 14, 2018", 5 pgs.
"European Application Serial No. 18175078.7, Extended European Search Report dated Sep. 14, 2018", 5 pgs.
"European Application Serial No. 18175078.7, Response filed Apr. 16, 2019 to Extended European Search Report dated Sep. 14, 2018", 81 pgs.
"European Application Serial No. 19188077.2, Extended European Search Report dated Mar. 19, 2020", 6 pgs.
"European Application Serial No. 19188077.2, Response filed Nov. 26, 2020 to Extended European Search Report dated Mar. 19, 2020", 142 pgs.
"European Application Serial No. 20196752.8, Response filed Dec. 2, 2020 to Invitation to Remedy Deficiencies (R. 58 EPC) mailed Oct. 2, 2020", 4 pgs.
"European Application Serial No. 20196755.1, Response filed Nov. 27, 2020 to Invitation to Remedy Deficiencies mailed Sep. 29, 2020", 4 pgs.
"Indian Application Serial No. 949/KOLNP/2010, Examination Report dated Mar. 31, 2015", 2 pgs.
"Indian Application Serial No. 949/KOLNP/2010, Response filed Mar. 22, 2016 to Examination Report dated Mar. 31, 2015", 8 pgs.
"International Application Serial No. PCT/US2008/073375, International Preliminary Report on Patentability dated Feb. 24, 2010", 6 pgs.
"International Application Serial No. PCT/US2008/073375, International Search Report dated Nov. 17, 2008", 1 pg.
"International Application Serial No. PCT/US2008/0/3375, Written Opinion dated Nov. 17, 2008", 5 pgs.
"International Application Serial No. PCT/US2009/061049, International Search Report dated Mar. 24, 2010", 5 pgs.
"International Application Serial No. PCT/US2009/061049, Written Opinion dated Mar. 24, 2010", 8 pgs.
"International Application Serial No. PCT/US2009/061067, International Search Report dated Jun. 17, 2010", 4 pgs.
"International Application Serial No. PCT/US2009/061067, Written Opinion dated Jun. 17, 2010", 6 pgs.
"International Application Serial No. PCT/US2011/026238, International Search Report dated Apr. 27, 2011", 3 pgs.
"International Application Serial No. PCT/US2011/026238, Written Opinion dated Apr. 27, 2011", 6 pgs.
"International Application Serial No. PCT/US2013/070007, International Search Report dated Mar. 5, 2014", 3 pgs.
"International Application Serial No. PCT/US2013/070007, Written Opinion dated Mar. 5, 2014", 11 pgs.
"International Application Serial No. PCT/US2014/065467, International Search Report dated Apr. 15, 2015", 5 pgs.
"International Application Serial No. PCT/US2014/065467, Written Opinion dated Apr. 15, 2015", 5 pgs.
"International Application Serial No. PCT/US2016/012653, International Search Report dated Mar. 11, 2016", 3 pgs.
"Istard Posters", Eur J Nucl Med Mol Imaging, 39 (Suppl2):, (2012), S304-S353.
"Japanese Application Serial No. 2016-046076, Notice dated Feb. 14, 2017", (w/ English Translation), 24 pgs.
"Japanese Application Serial No. 2016-046076, Notice dated Aug. 22, 2017", (w/ English Translation), 4 pgs.
"Japanese Application Serial No. 2016-046076, Written Argument and Amendment filed Jun. 28, 2017 to Notice dated Feb. 14, 2017", (w/ English Translation), 14 pgs.

"Japanese Application Serial No. 2017-210775, Office Action dated Nov. 6, 2018", w/English Translation, 4 pgs.
"Japanese Application Serial No. 2017-210775, Written Opinion and Amendment filed Apr. 22, 2019 to Office Action dated Nov. 6, 2018", (w/ English Translation), 12 pgs.
"Japanese Application Serial No. 2017-223872, Notification of Reasons for Rejection dated Jul. 2, 2019", (w/ English Translation), 4 pgs.
"Japanese Application Serial No. 2017-223872, Office Action dated Feb. 26, 2019", (w/ English Translation), 6 pgs.
"Japanese Application Serial No. 2017-223872, Office Action dated Oct. 9, 2018", (w/ English Translation), 6 pgs.
"Japanese Application Serial No. 2017-223872, Response filed May 22, 2019 to Office Action dated Feb. 26, 2019", w/ English Claims, 10 pgs.
"Japanese Application Serial No. 2017-223872, Response filed Jul. 12, 2019 to Notification of Reasons for Rejection dated Jul. 2, 2019", (w/ English Translation of Claims), 9 pgs.
"Japanese Application Serial No. 2017-223872, Written Amendment filed Feb. 7, 2018", (w/ English Translation), 13 pgs.
"Japanese Application Serial No. 2017-223872, Written Opinion and Amendment filed Jan. 7, 2019 in response to Office Action dated Oct. 9, 2018", (w/ English Translation), 14 pgs.
"Japanese Application Serial No. 2018-100343, Notification of Reasons for Rejection dated Mar. 5, 2019", (w/ English Translation), 5 pgs.
"Japanese Application Serial No. 2018-100343, Response filed Aug. 1, 2019 to Notification of Reasons for Rejection dated Mar. 5, 2019", (w/ English Translation of Claims), 25 pgs.
"Japanese Application Serial No. 2019-179190, Office Action dated Sep. 8, 2020", (w/ English Translation), 6 pgs.
"Japanese Application Serial No. 2019-179190, Response filed Nov. 26, 2020 to Office Action dated Sep. 8, 2020", (w/ English Translation to Claims), 5 pgs.
"Japanese Application Serial No. 2019-179190, Voluntary Amendment filed Aug. 3, 2020", (w/ English Translation of Claims), 3 pgs.
"Opposition re: EP 2187965 by Boult Wade Tennant LLP, Notice of Opposition filed Jul. 7, 2020", 78 pgs.
"Ouabain", [online]. Wikipedia. [retrieved Jun. 4, 2020]. Retrieved from the Internet: <URL: https://en.wikipedia.org/w/index.php?title=Ouabain&oldid=956105385>, (2020), 6 pgs.
"Pilot Study of 99mfc-MIP-1404 SPECT/CT Imaging in Men With Prostate Cancer Undergoing Prostatectomy and/or Pelvic Lymph Node Dissection", ClinicalTrials.gov Identifier: NCT01572701, (Apr. 6, 2012), 7 pgs.
"Radioisotopes in Medicine", [online]. [retrieved on May 12, 2017]. Retrieved from the Internet: <URL: http://www.word-nuclear.org/information-library/non-power-nuclearapplications/radioisotopes-research/radioisotopes-in-medicine.aspx>, From <http://www.word-nuclear.org/information-library/non-power-nuclearapplications/radioisotopes-research/radioisotopes-in-medicine.aspx>, (Dec. 28, 2016), 20 pages.
"South African Application Serial No. 2010/01875, Voluntary Amendment Filed Apr. 10, 2019", 8 pgs.
Afshar-Oromieh, A., et al., "[68Ga]Gallium-labelled PSMA ligand as superior PET tracer for the diagnosis of prostate cancer: comparison with 18F-FECH", Eur J Nucl Med Mol Imaging, 39, Haberkorn, (2012), 1085-1086.
Afshar-Oromieh, A., et al., "Comparison of PET imaging with a 68Ga-labelled PSMA ligand and 18F-choline-based PET/CT for the diagnosis of recurrent prostate cancer", Eur J Nucl Med Mol Imaging, 41, Zechmann, (2014), 11-20.
Afshar-Oromieh, A., et al., "Comparison of PET/CT and PET/MRI hybrid systems using a 68Ga-labelled PSMA ligand for the diagnosis of recurrent prostate cancer: initial experience", Eur J Nucl Med Mol Imaging, 41, Haber, (2014), 887-897.
Afshar-Oromieh, A., et al., "PET imaging with a [68Ga]gallium-labelled PSMA ligand for the diagnosis of prostate cancer: biodistribution in humans and first evaluation of tumour lesions", Eur J Nucl Med Mol Imaging, 40(4), (2013), 486-495.
Afshar-Oromieh, A., et al., "PET/MRI with a 68Ga-PSMA ligand for the detection of prostate cancer", Eur J Nucl Med Mol Imaging, 40, Haberkorn, (2013), 1629-1630.

(56) References Cited

OTHER PUBLICATIONS

Afshar-Oromieh, A., et al., "The diagnostic value of PET/CT imaging with the 68Ga-labelled PSMA ligand HBEDCC in the diagnosis of recurrent prostate cancer", Eur J Nucl Med Mol Imaging, 42(2), (2015), 197-209.
Aggarwal, S., et al., "A Dimeric Peptide That Binds Selectively to Prostate-Specific Membrane Antigen and Inhibits its Enzymatic Activity", Cancer Res, 66(18), (2006), 9171-9177.
Alt, K., et al., "High-Resolution Animal PET Imaging of Prostate Cancer Xenografts with Three Different 64Cu-Labeled Antibodies against Native Cell-Adherent PSMA", The Prostate 70(13), (2010), 1413-1421.
Ananias, H. J.K., et al., "Expression of the Gastrin-Releasing Peptide Receptor, the Prostate Stem Cell Antigen and the Prostate-Specific Membrane Antigen in Lymph Node and Bone Metastases of Prostate Cancer", The Prostate, 69, (2009), 1101-1108.
Anderson, M. O., et al., "Substrate specificity of prostate-specific membrane antigen", Bioorganic & Medicinal Chemistry 15, (2007), 6678-6686.
Antunes, A.. A., et al., "PGC and PSMA in prostate cancer diagnosis: tissue analysis from biopsy samples", Int Braz J Urol., 39(5), (2013), 649-56.
Armor, T., et al., "A comparison of 2D and 3D regions within the same patient to derive organ and tissue kinetics", (Abstract). J Nucl Med., vol. 53 No. Supplement 1 13, (May 2012), 1 pg.
Bacich, D. J., et al., "Cloning, expression, genomic localization, and enzymatic activities of the mouse homolog of prostate-specific membrane antigen/NAALADase/folate hydrolase", Mammalian Genome 12(2), (2001), 117-123.
Baiz, D., et al., "Synthesis and Characterization of a Novel Prostate Cancer-Targeted Phosphatidylinositol-3-kinase Inhibitor Prodrug", J. Med. Chem. 55, (2012), 8038-8046.
Banerjee, S. et al., "Sequential SPECT and Optical Imaging of Experimental Models of Prostate Cancer with a Dual Modality Inhibitor of the Prostate-Specific Membrane Antigen", Angewandte Chemie International Edition, 50(39), (2011), 9167-9170.
Banerjee, S R, et al., "Synthesis and Evaluation of Technetium-99m- and Rhenium-Labeled Inhibitors of the Prostate-Specific Membrane Antigen (PSMA)", J Med Chem., 51(15), (Aug. 14, 2008), 4504-4517.
Banerjee, S. R., et al., "64Cu-Labeled Inhibitors of Prostate-Specific Membrane Antigen for PET Imaging of Prostate Cancer", J. Med. Chem. 57, (2014), 2657-2669.
Banerjee, S. R., et al., "68Ga-Labeled Inhibitors of Prostate-Specific Membrane Antigen (PSMA) for Imaging Prostate Cancer", J. Med. Chem. 53, (2010), 5333-5341.
Banerjee, S. R., et al., "A Modular Strategy to Prepare Multivalent Inhibitors of Prostate-Specific Membrane Antigen CPSMA)", Oncotarget, vol. 2 No. 12, (2011), 1244-1253.
Banerjee, S. R., et al., "Effect of Chelators on the Pharmacokinetics of 99mTc-Labeled Imaging Agents for the Prostate-Specific Membrane Antigen (PSMA)", J. Med. Chem. 56, (2013), 6108-6121.
Barinka, C., et al., "A high-resolution structure of ligand-free human glutamate carboxypeptidase II", Acta Cryst, F63, (2007), 150-153.
Barinka, C., et al., "Interactions between Human Glutamate Carboxypeptidase II and Urea-Based Inhibitors: Structural Characterization", J. Med. Chem. 51, (2008), 7737-7743.
Barinka, C., et al., "Structural Insight into the Pharmacophore Pocket of Human Glutamate Carboxypeptidase II", J. Med. Chem., 50, (2007), 3267-3273.
Barrett, J. A., et al., "First-in-Man Evaluation of 2 High-Affinity PSMA-Avid Small Molecules for Imaging Prostate Cancer", J Nucl Med., 54(3), (2013), 380-387.
Beheshti, M., et al., "Prostate Cancer: Role of SPECT and PET in Imagine Bone Metastases", Semin Nucl Med 39(6), (2009), 396-407.
Belloli, S., et al., "Characterization of preclinical models of prostate cancer using PET—based molecular imaging", Eur J Nucl Med Mol Imaging 36:, (2009), 1245-1255.

Ben Jemaa, A., et al., "A Comparison of the Biological Features of Prostate Cancer with (PSA+, PSMA+) Profile according to RKIP", BioMed Research International vol. 2013, Article ID 409179, (2013), 7 pgs.
Ben Jemaa, A., et al., "A novel regulation of PSMA and PSA expression by Q640X AR in 22R v1 and LNCaP prostate cancer cells", Cell Biol Int, 37(5), (2013), 464-470.
Ben Jemaa, A., et al., "Cellular distribution and heterogeneity of PSA and PSMA expression in normal, hyperplasia and human prostate cancer", La Tunisie Medicale, 91(7), (2013), 458-463.
Benesova, M, et al., "Linker Modifications of DOT A-conjugated Inhibitors of the Prostate-Specific Membrane Antigen (PSMA)", Poster PW082, presented at the European Association of Nuclear Medicine Conference, (Oct. 21, 2013), 1 pg.
Benesova, M., et al., "Linker Modifications of DOT A-conjugated Inhibitors of the Prostate-Specific Membrane Antigen (PSMA)", Abstract, Eur. J. Nucl. Med. Mol. Imaging, 40, Suppl. 2, (Oct. 16, 2013), p. S93 (2 pages).
Benesova, Martina, et al., "Linker Modification Strategies to Control the Prostate-Specific Membrane Antigen (PSMA)-Targeting and Pharmacokinetic Properties of DOTA-Conjugated PSMA Inhibitors", Journal of Medicinal Chemistry, vol. 59(5), (2016), 1761-1775.
Bennett, V. J, et al., "Analysis of fluorescently labeled substance P analogs: binding, imaging and receptor activation", BMC Chemical Biology, 1:1. doi:10.1186/1472-6769-1-1, (2001), 12 pgs.
Bostwick, D. G., et al., "Prostate Specific Membrane Antigen Expression in Prostatic Intraepithelial Neoplasia and Adenocarcinoma", Cancer, 82, (1998), 2256-2261.
Bouchelouche, K., et al., "Image and treat: an individualized approach to urological tumors", Curr Opin Oncol, 22(3), (2010), 274-280.
Bouchelouche, K., et al., "Imaging Prostate Cancer: An Update on Positron Emission Tomography and Magnetic Resonance Imaging", Curr Urol Rep, 11, (2010), 180-190.
Bouchelouche, K., et al., "PET/CT Imaging and Radioimmunotherapy of Prostate Cancer", Semin Nucl Med, 41, (2011), 29-44.
Bouchelouche, K., et al., "Positron emission tomography/computed tomography and radioimmunotherapy of prostate cancer", Curr Opin Oncol, 21(5), 469-474.
Bouchelouche, K., et al., "Prostate Specific Membrane Antigen-A Target for Imaging and Therapy with Radionuclides", Discov Med. 9(44):, (Jan. 2010), 55-61.
Bzdega, T., et al., "The cloning and characterization of a second brain enzyme with NAAG peptidase activity", Journal of Neurochemistry, 89(3), (2004), 627-635.
Ceci, F., et al., "11C-Choline PET/CT in patients with hormone-resistant prostate cancer showing biochemical relapse after radical prostatectomy", Eur J Nucl Med Mol Imaging, 40, (2013), 149-155.
Chandran, S. S., et al., "Characterization of a targeted nanoparticle functionalized with a urea-based inhibitor of prostate-specific membrane antigen (PSMA)", Cancer Biology & Therapy, 7(6), (2008), 974-982.
Chang, S. S., et al., "Five Different Anti-Prostate-Specific Membrane Antigen (PSMA) Antibodies Confirm PSMA Expression in Tumor-Associated Neovasculature", Cancer Research, 59, (Jul. 1, 1999), 3192-3198.
Chang, S. S., et al., "The clinical role of prostate-specific membrane antigen (PSMA)", Urologic Oncology, 7(1), (2002), 7-12.
Chen, Y., et al., "2-(3-[1-Carboxy-5-[(6-[18F]Fluoro-Pyridine-3-Carbonyl)-Amino]-Pentyl]-Ureido)-Pentanedioic Acid, [18F]DCFPyL, a PSMA-Based PET Imaging Agent for Prostate Cancer", Clin Cancer Res, 17(24), (2011), 7645-7453.
Chen, Y., et al., "A low molecular weight PSMA-based fluorescent imaging agent for cancer", Biochemical and Biophysical Research Communications 390, (2009), 624-629.
Chen, Y., et al., "Synthesis and Biological Evaluation of Low Molecular Weight Fluorescent Imaging Agents for the Prostate-Specific Membrane Antigen", Bioconjugate Chem., 23(12), (2012), 2377-2385.

(56) References Cited

OTHER PUBLICATIONS

Chen, Ying, et al., "Radiohalogenated Prostate-Specific Membrane Antigen (PSMA)-Based Ureas as Imaging Agents for Prostate Cancer", J. Med. Chem. 51 (24), (2008), 7933-7943.

Chen, Z., et al., "PSMA-Targeted Theranostic Nanoplex for Prostate Cancer therapy", ACS Nano, 6(9), (2012), 7752-7762.

Chopra, A., et al., "68Ga-Labeled 2-[3-(1-carboxy-5-[7-[5-carboxy-5-(3-phenyl-2-[3-phenyl-2-[2-(4,7,10-tris-carboxymethyl-1,4,7,10-tetraazacyclododec-1-l)acetyiamino]propionylamino]propionylamino)pentylcarbamoyl]heptanoylamino]pentyl)ureid o]pentanedioic acid [68Ga]6", [Updated Dec. 28, 2010]. In: Molecular Imaging and Contrast Agent Database (MICAD) [Internet]. Bethesda (MD): National Center for Biotechnology Information (US);, (Sep. 2, 20107), 1-6.

Chopra, A., et al., "68Ga-labeled 2-{3-[5-(7-{1-benzyloxycarbonyl-5-[2-(4,7,10-triscarboxymethyl-1,4,7,10-tetraazacyclododec-1-1)acetylamino]pentylcarbamoyl]-heptanoylamino)-1-carboxypentyl]ureido}pentanedioic acid [68Ga]3", [Updated Dec. 28, 2010]. In: Molecular Imaging and Contrast Agent Database (MICAD) [Internet]. Bethesda (MD): National Center for Biotechnology Information (US), (Sep. 28, 2010), 1-6.

Chuu, C.-P., et al., "Androgen suppresses proliferation of castrationresistant LNCaP 104-R2 prostate cancer cells through androgen receptor, Skp2, and c-Myc", Cancer Sci, 102(11), (2011), 2022-2028.

Cimitan, M., et al., "[18F]fluorocholine PET/CT imaging for the detection of recurrent prostate cancer at PSA relapse: experience in 100 consecutive patients", Eur J Nucl Med Mol Imaging, 33, (2006), 1387-1398.

Colabufo, N. A., et al., "PB183, a sigma receptor ligand, as a potential PET probe for the imaging of prostate adenocarcinoma", Bioorganic & Medicinal Chemistry Letters, 18, (2008), 1990-1993.

Cole, et al., "Cancer theranostics: the rise of targeted magnetic nanoparticles", Trends in Biotechnology, 29(7), (2011), 323-332.

Cunha, A. C., et al., "Tissue-specificity of prostate specific antigens: Comparative analysis of transcript levels in prostate and non-prostatic tissues", Cancer Letters 236, (2006), 229-238.

Dahl, M., et al., "Sarcosine induces increase in HER2/neu expression in androgen-dependent prostate cancer cells", Mol Biol Rep, 38(7), (2011), 4237-4243.

Davis, Mindy I, et al., "Crystal Structure of Prostate-Specific Membrane Antigen, A Tumor Marker and Peptidase", PNAS, vol. 102, No. 17, (Apr. 26, 2005), 5981-5986.

De Santis, M., et al., "Rolle der Chemotherapie beim kastrationsresistenten Prostatakarzinom. Gibt es neue Ansätze? [Role of chemotherapy in castration-resistant prostate cancer. Are there new approaches?]", (w/ English Abstract), Urologe, 51(1), (2012), 39-43 (5 pgs.).

Degrado, T. R., et al., "Synthesis and Evaluation of 18F-Labeled Choline Analogs as Oncologic PET Tracers", J Nucl Med, 42(12), (2001), 1805-1814.

Degrado, T. R., et al., "Synthesis and Evaluation of 18F-labeled Choline as an Oncologic Tracer for Positron Emission Tomography: Initial Findings in Prostate Cancer", Cancer Research 61(1), (2001), 110-117.

Dimitrakopoulou-Strauss, A., et al., "PET Imaging of Prostate Cancer with 11C-Acetate", J. Nucl Med. 44(4), (2003), 556-558.

Dos Santos, Jose C, et al., "Development and dosimetry of 203Pb/212Pb-labelled PSMA ligands:bringing "the lead" into PSMA-targeted alpha therapy?", European Journal of Nuclear Medicine and Molecular Imaging, vol. 46(5), (2019), 1081-1091.

Dumas, F., et al., "Molecular Expression of PSMA mRNA and Protein in Primary Renal Tumors", Int. J. Cancer, 80(6), (1999), 799-803.

Dusich, Crystal, et al., "General Approach for the Preparation of Fluorescent PSMA/GCPII Inhibitors", Abstract ID: 470, board space 29, The Fifth Annual Meeting of the Society for Molecular Imaging, Molecular Imaging , vol. 5(3), (2006), 322-323.

Eder, et al., "68Ga-complex lipophilicity and the targeting property of a urea-based PSMA inhibitor for PET imaging", Bioconjugate Chemistry, 23(4), (2012), 688-697.

Eder, M., et al., "Novel Preclinical and Radiopharmaceutical Aspects of [68Ga]Ga-PSMA-HBED-CC: A New PET Tracer for Imaging of Prostate Cancer", Pharmaceuticals, 7(7), (2014), 779-796.

Eder, M., et al., "Pharmacokinetic Properties of Peptidic Radiopharmaceuticals: Reduced Uptake of (EH)3-Conjugates in Important Organs", J. Nucl Med, 54(6), (2013), 1327-1330.

Eder, M., et al., "Preclinical Evaluation of a Bispecific Low-Molecular HeterodimerTargeting Both PSMA and GRPR for Improved PET Imaging and Therapy of Prostate Cancer", The Prostate, 74, (2014), 659-668.

Eder, M., et al., "PSMA as a target for radiolabelled small molecules", Eur J Nucl Med Mol Imaging 40, (2013), 819-823.

Eiber, M., et al., "68Ga-PSMA PET/MR with multimodality image analysis for primary prostate cancer", Abdom Imaging, 40(6), (2015), 1769-1771.

Elsasser-Beile, U., et al., "A New Generation of Monoclonal and Recombinant Antibodies Against Cell-Adherent Prostate Specific Membrane Antigen for Diagnostic and Therapeutic Targeting of Prostate Cancer", The Prostate, 66, (2006), 1359-1370.

Elsasser-Beile, U., et al., "PET Imaging of Prostate Cancer Xenografts with a Highly Specific Antibody against the Prostate-Specific Membrane Antigen", J Nucl Med 50(4), (2009), 606-611.

Elsasser-Beile, U., et al., "Targeted Therapies for Prostate Cancer Against the Prostate Specific Membrane Antigen", Current Drug Targets, 10(2), (2009), 118-125.

El-Zaria, M. E., et al., "Preparation and evaluation of carborane-derived inhibitors of prostate specific membrane antigen (PSMA)", Dalton Trans., 43(13), (2014), 4950-4961.

Emonds, K. M., et al., "Do androgens control the uptake of 18F-FDG, 11C-choline and 11C-acetate in human prostate cancer cell lines?", Eur J Nucl Med Mol Imaging, 38, (2011), 1842-1853.

Evans, M. J., et al., "Noninvasive measurement of androgen receptor signaling with a positron-emitting radiopharmaceutical that targets prostate-specific membrane antigen", Proc. Natl. Acad. Sci. USA, 108(23), (Jun. 7, 2011), 9578-9582.

Fair, W. R., et al., "Prostate-Specific Membrane Antigen", The Prostate, 32, (1997), 140-148.

Fall, K., et al., "Prostate-Specific Antigen Levels as a Predictor of Lethal Prostate Cancer", J Natl Cancer Inst, 99(7), (2007), 526-532.

Farokhzad, et al., "Nanoparticle-Aptamer Bioconjugates: A New Approach for Targeting Prostate Cancer Celis", Cancer Research 64, (2004), 7668-7672.

Fortmuller, K., et al., "Effective Targeting of Prostate Cancer by Lymphocytes Redirected by a PSMA x CDS Bispecific Single-Chain Diabody", The Prostate, 71, (2011), 588-596.

Fortuin, A. S., et al., "Value of PET/CT and MR Lymphography in Treatment of Prostate Cancer Patients With Lymph Node Metastases", Int J Radiation Oncol Biol Phys, 84(3), (2012), 712-718.

Foss, C. A., et al., "GCPII Imaging and Cancer", Current Medicinal Chemistry, 19(9), (2012), 1346-1359.

Foss, Catherine A, et al., "Radiolabeled Small-Molecule Ligands for Prostate-Specific Membrane Antigen: in Vivo Imaging in Experimental Models of Prostate Cancer", Clinical cancer research 11.11, (2005), 4022-4028.

Franc, B. L., et al., "Detection and localization of carcinoma within the prostate using high resolution transrectal gamma imaging (TRGI) of monoclonal antibody directed at prostate specific membrane antigen (PSMA)-Proof of concept and initial imaging results", European Journal of Radiology, 82(11), (2013), 1877-1884.

Frigerio, B., et al., "A single-chain fragment against prostate specific membrane antigen as a tool to build theranostic reagents for prostate cancer", European Journal of Cancer, 49(9), (2013), 2223-2232.

Ghosh, A., et al., "Tumor Target Prostate Specific Membrane Antigen (PSMA) and its Regulation in Prostate Cancer", Journal of Cellular Biochemistry, 91(3), (2004), 528-539.

Giovacchini, et al., "Predictive factors of [11C]choline PET/CT in patients with biochemical failure after radical prostatectomy", Eur J Nucl Med Mol Imaging, 37, (2010), 301-309.

(56) References Cited

OTHER PUBLICATIONS

Gomez-Hens, et al., "Long Wavelength Fluorophores: New Trends in Their Analytical Use", Trends in Analytical Chemistry, 23, (127-136), 2004.
Goodman Jr., O. B., et al., "Interaction of prostate specific membrane antigen with clathrin and the adaptor protein complex-2", International Journal of Oncology, 31(5), (2007), 1199-1203.
Graham, et al., "Radiofluorinated derivatives of 2-(phosphonomethyl)pentanedioic acid as inhibitors of prostate specific membrane antigen (PSMA) for the imaging of prostate cancer", J. Med. Chem., 55, (2012), 9510-9520.
Grant, et al., "Prostate Specific Membrane Antigen (PSMA) Regulates Angiogenesis Independently of VEGF during Ocular Neovascularization", PLoS ONE 7(7): e41285., (2012), 1-10.
Greene, Theodora E, et al., "Protective Groups ion Organic Synthesis", 2d edition, John Wiley & Sons, Inc. New York, (1991).
Gregor, et al., "Induction of autoantibodies to syngeneic prostate-specific membrane antigen by xenogeneic vaccination", Int. J. Cancer, 116(3), (2005), 415-421.
Haberkorn, et al., "Mechanistic and high-throughput approaches for the design of molecular imaging probes and targeted therapeutics", Clin Transl Imaging, 2(1), (2014), 33-41.
Haffner, M. C., et al., "Prostate-specific membrane antigen expression in the neovasculature of gastric and colorectal cancers", Human Pathology, 40(12), (2009), 1754-1761.
Hain, S. F., et al., "Positron emission tomography for urological tumours", BJU International, 92(2), (2003), 159-164.
Hara, T., "11C-Choline and 2-Deoxy-2-[18F]Fluoro-D-Glucose in Tumor Imaging with Positron Emission Tomography", Molecular Imaging and Biology, 4(4), (2002), 267-273.
Hara, T., et al., "Development of 18F-Fluoroethylcholine for Cancer Imaging with PET: Synthesis, Biochemistry, and Prostate Cancer Imaging", J Nucl Med, 43(2), (2002), 187-199.
Hara, T., et al., "PET Imaging of Prostate Cancer Using Carbon-11-Choline", J Nucl Med, 39(6), (1998), 990-995.
Harada, N., et al., "Preparation of Asymmetric Urea Derivatives that Target Prostate-Specific Membrane Antigen for SPECT Imaging", J. Med. Chem. 56, (2013), 7890-7901.
Haseman, M K, et al., "Capromab Pendetide Imaging of Prostate Cancer", Cancer Biother Radiopharm, 15, (2000), 131-140.
Heidenreich, A., "Immuntherapie beim metastasierten Prostatakarzinom-brauchen wir diese wirklich? [Immunotherapy for metastatic prostate cancer: do we really need this?]", (w/ English Abstract), Urologe, 51(1), (2012), 32-38 (8 pgs.).
Henne, et al., "Synthesis and activity of a folate peptide camptothecin prodrug", ScienceDirect, Bioorganic & Medical Chemistry Letters 16, (2006), 5350-5355.
Henry, M, D., et al., "A Prostate-Specific Membrane Antigen-Targeted Monoclonal Antibody-Chemotherapeutic Conjugate Designed for the Treatment of Prostate Cancer", Cancer Research, 64(21), (2004), 7995-8001.
Hillier, S., et al., "[131I] MIP-1466, a small molecule prostate-specific membrane antigen (PSMA) inhibitor for targeted radiotherapy of prostate cancer (PCa)", J Nucl Med, vol. 53 No. supplement 1 170, (May 2012), 1 pg.
Hillier, S. M., et al., "123I-MIP-1072, a Small-Molecule Inhibitor of Prostate-Specific Membrane Antigen, Is Effective at Monitoring Tumor Response to Taxane Therapy", J Nucl Med, 52(7), (2011), 1087-1093.
Hillier, S. M., et al., "99mTc-Labeled Small-Molecule Inhibitors of Prostate-Specific Membrane Antigen for Molecular Imaging of Prostate Cancer", J Nucl Med, 54, (2013), 1369-1376.
Hillier, Shawn M, et al., "Preclinical Evaluation of Novel Glutamate-Urea-Lysine Analogues That Target Prostate-Specific Membrane Antigen as Molecular Imaging Pharmaceuticals for Prostate Cancer", Cancer Res. 69(17), (Sep. 1, 2009), 6932-40.
Hlouchova, K., et al., "Biochemical characterization of human glutamate carboxypeptidase III", Journal of Neurochemistry, 101(3), (2007), 682-696.
Hlouchova, K., et al., "GCPII Variants, Paralogs and Orthologs", Current Medicinal Chemistry, 19, (2012), 1316-1322.
Hlouchova, K., et al., "Structural insight into the evolutionary and pharmacologic homology of glutamate carboxypeptidases II and III", FEBS Journal, 276(16), (2009), 4448-4462.
Ho, C.-L., et al., "Molecular Imaging, Pharmacokinetics, and Dosimetry of 111In-AMBA in Human Prostate Tumor-Bearing Mice", Journal of Biomedicine and Biotechnology vol. 2011, Article ID 101497, (2011), 8 pgs.
Holland, J. P., et al., "89Zr-DFO-J591 for ImmunoPET of Prostate-Specific Membrane Antigen Expression In Vivo", J Nucl Med, 51(8), (2010), 1293-1300.
Hong, et al., "Positron emission tomography Imaging of prostate cancer", Amino Acids, 39(1), (2010), 11-27.
Hospers, G. A. P., et al., "PET Imaging of Steroid Receptor Expression in Breast and Prostate Cancer", Current Pharmaceutical Design, 14(28), (2008), 3020-3032.
Huang, B., et al., "PSMA-Targeted Stably Linked 'Dendrimer-Glutamate Urea-Methotrexate' as a Prostate Cancer Therapeutic", Biomacromolecules, 15(3), (2014), 915-923.
Huang, S. S., et al., "Improving the Biodistribution of PSMA-Targeting Tracers With Highly Negatively Charged Linker", The Prostate, 74, (2014), 702-713.
Humblet, et al., "High-affinity Near-infrared Fluorescent Small-molecule Contrast Agents for In Vivo Imaging of Prostate-specific Membrane Antigen", Molecular Imaging. 4(4), (Oct. 2005), 448-462.
Humblet, et al., "Multivalent Scaffolds for Affinity Maturation of Small Molecule Cell Surface Binders and Their Application to Prostate Tumor Targeting", J. Med. Chem, 52, (2009), 544-550.
Humblet, V, et al., "An HPLC/Mass Spectrometry Platform for the Development of Multimodality Contrast Agents and Targeted Therapeutics: Prostate-Specific Membrane Antigen Small Molecule Derivatives", Contrast Med. Mol. Imaging, 1, (2006), 196-211.
Husarik, et al., "Evaluation of [18F]-choline PET/CT for staging and restaging of prostate cancer", Eur J Nucl Med Mol Imaging, 35, (2008), 253-263.
Hwang, et al., "N-3-[18F]Fluoropropylputrescine as Potential PET Imaging Agent for Prostate and Prostate Derived Tumors", J Nucl Med, 30(7), (1989), 1205-1210.
Hwang, D.-R., et al., "Imaging Prostate Derived Tumors with PET and N-(3-[18F]Fluoropropyl)putrescine", Nucl. Med. Biol., 17(6), (1990), 525-532.
Igerc, I., et al., "The value of 18F-Choline PET/CT in patients with elevated PSA-level and negative prostate needle biopsy for localisation of prostate cancer", Eur J Nucl Med Mol Imaging, 35, (2008), 976-983.
Jackson, P. F., et al., "Design, Synthesis, and Biological Activity of a Potent Inhibitor of the Neuropeptidase N-Acetylated a-Linked Acidic Dipeptidase", Journal of Medicinal Chemistry, 39, (1996), 619-622.
Jackson, Paul F, et al., "Design of NAALADase Inhibitors: A Novel Neuroprotective Strategy", Current Medicinal Chemistry, vol. 8, No. 8, (2001), 949-957.
Jadvar, et al., "Glucose Metabolism of Human Prostate Cancer Mouse Xenografts", Molecular Imaging, 4(2), (Apr. 2005), 91-97.
Jadvar, et al., "Imaging evaluation of prostate cancer with 18F-fluorodeoxyglucose PET/CT: utility and limitations", Eur J Nucl Med Mol Imaging> 40 (Suppl 1), (2013), S5-S10.
Jadvar, et al., "Molecular imaging of prostate cancer with 18F-fluorodeoxyglucose PET", Nat. Rev. Urol., 6, (2009), 317-323.
Jadvar, et al., "Molecular Imaging of Prostate Cancer: PET Radiotracers", AJR Am J Roentgenol, 199(2), (2012), 278-291.
Jambor, et al., "Functional Imaging of Localized Prostate Cancer Aggressiveness Using 11C-Acetate PET/CT and 1H-MR Spectroscopy", J Nucl Med; 51:, (2010), 1676-1683.
James, S., "Urea based rhenium tricarbonyl dipeptide compounds as potential radiopharmaceuticals for PSMA imaging", INOR258, The 229th ACS National Meeting, San Diego, CA, (2005), 1 pg.
Jayaprakash, Sarva, et al., "Design and Synthesis of a PSMA Inhibitor-Doxorubicin Conjugate for Targeted Prostate Cancer Therapy", ChemMedChem 1.3, (2006), 299-302.

(56) References Cited

OTHER PUBLICATIONS

Kahn, D., et al., "111Indium-Capromab Pendetide in the Evaluation of Patients with Residual or Recurrent Prostate Cancer After Radical Prostatectomy", The Journal of Urology, 159(6), (Jun. 1998), 2041-2047.

Kasperzyk, J. L., et al., "Prostate-Specific Membrane Antigen Protein Expression in Tumor Tissue and Risk of Lethal Prostate Cancer", Cancer Epidemiol Biomarkers Prev; 22(12), (2013), 2354-2363.

Kasten, et al., "Targeting prostate cancer cells with PSMA inhibitor-guided gold nanoparticles", Bioorganic & Medicinal Chemistry Letters 23, (2013), 565-568.

Kaur, G, et al., "Biological evaluation of tubulysin A: a potential anticancer and antiangiogenic natural product", Biochem. J., 396, (2006), 235-242.

Kim, D., et al., "Tribady: Robust Self-Assembled Trimeric Targeting Ligands with High Stability and Significantly Improved Target-Binding Strength", Biochemistry, 52, (2013), 7283-7294.

Kinoshita, Y., et al., "Expression of Prostate-Specific Membrane Antigen in Normal and Malignant Human Tissues", World J Surg, 30, (2006), 628-636.

Klotz, Laurence, "Cancer overdiagnosis and overtreatment", Curr Opin Urol., 22, (2012), 203-209.

Klusak, et al., "Reaction Mechanism of Glutamate Carboxypeptidase II Revealed by Mutagenesis, X-ray Crystallography, and Computational Methods", Biochemistry, 48, (2009), 4126-4138.

Kosuri, et al., "Review of Salvage Therapy for Biochemically Recurrent Prostate Cancer: The Role of Imaging and Rationale for Systemic Salvage Targeted Anti-Prostate-SpecificMembrane Antigen Radioimmunotherapy", Advances in Urology vol. 2012, Article ID 921674, (2012), 8 pgs.

Kothari, P., et al., "18F-labeled small molecule inhibitors of prostate specific membrane antigen (PSMA) for PET imaging of prostate cancer", J Nucl Med, vol. 53 No. supplement 11721, (May 2012), 2 pgs.

Kotzerke, et al., "PET for Prostate Cancer Imaging: Still a Quandary or the Ultimate Solution?", The Journal of Nuclear Medicine, 43(2), (Feb. 2002), 200-202.

Kovar, et al., "Pharmacokinet and Biodistribution Assessment of a Near Infrared-Labeled PSMA-Specific Small Molecule in Tumor-Bearing Mice", Prostate Cancer vol. 2014, Article ID 104248, (2014), 10 pgs.

Kozikowski, Alan P, et al., "Design of Remarkably Simple, Yet Potent Urea-Based Inhibitors of Glutamate Carbozypeptidase II (NAALADase)", Journal of Medicinal Chemistry, vol. 44, No. 3, (2001), 298-301.

Kozikowski, Alan P, et al., "Synthesis of Urea-Based Inhibitors as Active Site Probes of Glutamate Carboxypeptodase II: Efficacy as Analgesic Agents", Journal of Medicinal Chemistry, vol. 47, No. 7, (Mar. 2, 2004), 1729-1738.

Krohn, et al., "[68Ga]PSMA-HBED uptake mimicking lymph node metastasis in coeliac ganglia: an important pitfall in clinical practice", Eur J Nucl Med Mol Imaging, 42, (2015), 210-214.

Kularatne, et al., "Prostate-Specific Membrane Antigen Targeted Imaging and Therapy of Prostate Cancer Using a PSMA Inhibitor as a Homing Ligand", Molecular Pharmaceutics, 6(3), (2009), 780-789.

Kularatne, S. A., et al., "Comparative Analysis of Folate Derived PET Imaging Agents with [18F]-2-Fluoro-2-deoxy-D-glucose Using Rodent Inflammatory Paw Model", Molecular Pharmaceutics, vol. 10, (2013), 3103-3111.

Kularatne, S. A., et al., "Design, Synthesis, and Preclinical Evaluation of Prostate-Specific Membrane Antigen Targeted 99mTc-Radioimaging Agents", Molecular Pharmaceuticals, 6(3), (2009), 790-800.

Kularatne, S., "Synthesis and Biological Analysis of Prostate-Specific Membrane Antigen-Targeted Anticancer Prodrugs", J. Med. Chem, 53(21), (2010), 7767-7777.

Kuru, T. H., et al., "MRT-navigierte stereotaktische Prostatabiopsie [MRI-navigated stereotactic prostate biopsy ]", (w/English Abstract), Urologe 51(1), (2012), 50-56 (8 pgs.).

Kwee, et al., "18F-choline PET/CT imaging of RECIST measurable lesions in hormone refractory prostate cancer", Ann Nucl Med 23(6), (2009), 541-548.

Lambert, et al., "Molecular Evolution of the transferrin Receptor/Glutamate Carboxypeptidase II Family", J Mol Evol. 64(1), (2007), 113-128.

Lange, P. H, "Prostascint Scan for Staging Prostate Cancer", Urology, 57, (2001), 402-406.

Lapi, S. E., et al., "Assessment of an 18F-Labeled Phosphoramidate Peptidomimetic as a New Prostate-Specific Membrane Antigen-Targeted Imaging Agent for Prostate Cancer", J Nucl Med; 50, (2009), 2042-2048.

Larson, S. M, et al., "Tumor Localization of 16?-18 F-Fiuoro-5?-Dihydrotestosterone Versus 18F -FDG in Patients with Progressive, Metastatic Prostate Cancer", J Nucl Med, 45, (2004), 366-373.

Leek, et al., "Prostate-specific membrane antigen: evidence for the existence of a second related human gene", British Journal of Cancer, 72(3), (1995), 583-588.

Lees, et al., "Active surveillance in prostate cancer: patient selection and triggers for intervention", Curr Opin Urol, 22(3), (2012), 210-215.

Lesche, et al., "Preclinical evaluation of BAY 1075553, a novel 18F-labelled inhibitor of prostate-specific membrane antigen for PET imaging of prostate cancer", Enr J Nucl Med Mol Imaging, 41, (2014), 89-101.

Leung, Kam, "In-Capromab Pendetide", National Center for Biotechnology Information, (2008), 1-6.

Li, X., et al., "C-11 Choline PET/CT Imaging for Differentiating Malignant From Benign Prostate Lesions", Clin Nucl Med, 33(10), (2008), 671-676.

Liu, HE, et al., "Constitutive and Antibody-Induced Internalization of Prostate-Specific Membrane Antigen", Cancer Research, 58, (Sep. 15, 1998), 4055-4060.

Liu, M., et al., "Synthesis and Biological Evaluation of Diethylenetriamine Pentaacetic acid-Polyethylene Glycol Folate: A new Folate-Derived, 99mTc-Based Radiopharmaceutical", Bioconjugate Chem, 16(5), (2005), 1126-1132.

Liu, T., et al., "A targeted low molecular weight near-infrared fluorescent probe for prostate cancer", Bioorganic & Medicinal Chemistry Letters, 20(23), (2010), 7124-7126.

Liu, T., et al., "Functional prostate-specific membrane antigen is enriched in exosomes from prostate cancer cells", International Journal of Oncology, 44, (2014), 918-922.

Liu, T., et al., "Prolonged androgen deprivation leads to downregulation of androgen receptor and prostate-specific membrane antigen in prostate cancer cells", International Journal of Oncology, 41, (2012), 2087-2092.

Liu, T., et al., "Pseudoirreversible Inhibition of Prostate-Specific Membrane Antigen by Phosphoramidate Peptidomimetics", Biochemistry, 47(48), (2008), 12658-12660.

Liu, T., et al., "Targeting prostate cancer cells with a multivalent PSMA inhibitor-guided streptavidin conjugate", Bioorganic & Medicinal Chemistry Letters 22, (2012), 3931-3934.

Lord, M., et al., "18F-Fluorocholine integrated PET/MRI for the initial staging or prostate cancer", Eur J Nucl Med Mol Imaging, 38(12), (2011), p. 2288.

Lu, G, et al., "Synthesis and SAR of 99mTc/Re-labeled small molecule prostate specific membrane antigen inhibitors with novel polar chelates", Bioorganic and Medicinal Chemistry Letters, 23, (2013), 1557-1563.

Luboldt, W., et al., "Prostate Carcinoma: Diffusion-weighted Imaging as Potential Alternative to Conventional MR and 11C-Choline PET/CT for Detection of Bone Metastases", Radiology, 249(3), (2008), 1017_1025.

Lupold, et al., "Identification and Characterization of Nuclease-Stabilized RNA Molecules That Bind Human Prostate Cancer Cells via the Prostate-Specific Membrane Antigen", Cancer Res.; 62, (2002), 4029-4033.

(56) References Cited

OTHER PUBLICATIONS

Lutje, S., et al., "Dual-Modality Image-Guided Surgery of Prostate Cancer with a Radiolabeled Fluorescent Anti-PSMA Monoclonal Antibody", J Nucl Med, 55(6), (2014), 995-1001.

Lutje, S., et al., "Prospects in Radionuclide Imaging of Prostate Cancer", The Prostate, 72, (2012), 1262-1272.

Majer, Pavel, et al., "Synthesis and Biological Evaluation of Thiol-Based Inhibitors of Glutamate Carboxypeptodase II: Discovery of an Orally Active GCP II Inhibitor", Journal of Medicinal Chemistry, vol. 46, No. 10, (2003), 1989-1996.

Malik, N., et al., "One pot radiofluorination of a new potential PSMA ligand [A118F]NOTA-DUPA-Pep", J. Label Compd. Radiopharm, 55(2), (2012), 320-325.

Malik, N., et al., "Radiosynthesis of a new PSMA targeting ligand ([18F]FPy-DU PA-Pep)", Applied Radiation and Isotopes, 69(7), (2011), 1014-1018.

Mannweiler, S., et al., "Heterogeneity of Prostate-Specific Membrane Antigen (PSMA) Expression in Prostate Carcinoma with Distant Metastasis", Pathol. Oncol. Res., 15(2), (2009), 167-172.

Maresca, K, et al., "Molecular Targeting of Prostate Cancer With Small Molecule Inhibitors of Prostate Specific Membrane Antigen (PSMA)", J. Nucl. Med. 48 (Supplement 2):25P, (2007).

Maresca, K. P, "A Series of Halogenated Heterodimeric Inhibitors of Prostate Specific Membrane Antigen (PSMA) as Radiolabeled Probes for Targeting Prostate Cancer", J. Med. Chem. 52(2), (2009), 347-357.

Maresca, K., et al., "Influence of functionalized chelators on affinity and pharmacokinetics of 99mTc(CO)3-labeled small molecules targeting prostate specific membrane antigen (PSMA)", (Abstract), J Nucl Med, vol. 51, No. Supplement 2, (May 2010), p. 250 (1 page).

Martin, P., "Ein Neuer Zugang Zu 2'-O-Alkylribonucleosiden and Elgenschaften deren Oligonucleotide", Helv. Chim. Acta, 78, no English translation, (1995), 486-504.

Matthies, A., et al., "Imaging of prostate cancer metastases with 18F-fluoroacetate using PET/CT", Eur J Nucl Med Mol Imaging, 31(5), (May 2004), p. 797.

McNamara, et al., "Cell type specific delivery of siRNAs with aptamer-siRNA chimeras", Nature Biotechnolgy; 24, (2006), 1005-1015.

Mease, R. C., et al., "PET Imaging in Prostate Cancer: Focus on Prostate-Specific Membrane Antigen", Current Topics In Medicinal Chemistry, 13, (2013), 951-962.

Mease, RC, et al., "N-[N-[(S)-1,3-Dicarboxypropyi]Carbamoyi]-4-[18F]Fluorobenzyi-LCysteine, [18F]DCFBC: A New Imaging Probe for Prostate Cancer", Clin Cancer Res., 14, (2008), 3036-3043.

Mease, Ron, "General Approach for the Preparation of Fluorescent PSMA/GCPII Inhibitors", Abstract ID: 470 Poster board space: 29, Molecular Imaging, vol. 5, No. 3, (Jul. 2006), 322-323.

Meighan, M. A., et al., "Recombinant Glutamate Carboxypeptidase II (Prostate Specific Membrane Antigen-PSMA)-Cellular Localization and Bioactivity Analyses", Journal of Protein Chemistry, 22(4), (May 2003), 317-326.

Meinhardt, W., et al., "Laparoscopic Sentinel Lymph Node Biopsy for Prostate Cancer: The Relevance of Locations Outside the Extended Dissection Area", Prostate Cancer, vol. 2012, Article ID 751753, (2012), 4 pgs.

Melby, E. L., et al., "Entry of Protein Toxins in Polarized Epithelial Cells", Cancer Research 53(8), (1993), 1755-1760.

Mertens, K., et al., "PET with 18F-labelled choline-based tracers for tumour imaging: a review of the literature", Eur J Nucl Med Mol Imaging, 37, (2010), 2188-2193.

Mesters, et al., "Structure of Glutamate Carboxypeptidase II, a Drug Target in Neuronal Damage and Prostate Cancer", The EMBO Journal, vol. 25, No. 6, (2006), 1375-1384.

Mhawech-Fauceglia, P., et al., "Prostate-specific membrane antigen (PSMA) protein expression in normal and neoplastic tissues and its sensitivity and specificity in prostate adenocarcinoma: an immunohistochemical study using mutiple tumour tissue microarray technique", Histopathology, 50(4), (2007), 472-483.

Mier, W., et al., "Conjugation of DOTA Using Isolated Phenolic Active Esters: The Labeling and Biodistribution of Albumin as Blood Pool Marker", Bioconjugate Chem., 16, (2005), 237-240.

Milowsky, M. I., et al., "Phase I Trial of Yttrium-90-Labeled Anti-Prostate-Specific Membrane Antigen Monoclonal Antibody J591 for Androgen-Independent Prostate Cancer", J Clin Oncol, 22(13), (2004), 2522-2531.

Min, Jung-Joon, "Specific Targeting Breast Cancer and Its Metastatic Lesions Using Light-Emitting Bacteria", Abstract ID: 464, Poster board space: 23, The Fifth Annual Meeting of the Society for Molecular Imaging, Molecular Imaging, vol. 5, No. 3, (2006), p. 321.

Minner, S., et al., "High Level PSMA Expression Is Associated With Early PSA Recurrence in Surgically Treated Prostate Cancer", The Prostate, 71, (2011), 281-288.

Mlcochova, P., et al., "Mapping of the active site of glutamate carboxypeptidase II by site-directed mutagenesis", FEBS Journal, 274(18), (2007), 4731-4741.

Moltzahn, F., et al., "Die ossare Metastasierung des Prostatakarzinoms [Bony metastasis of prostate cancer ]", (w/ English Abstract), Urologe, 51, (2012), 20-26 (8 pgs.).

Morris, M. J., et al., "11C-acetate PET Imaging in prostate cancer", Eur J Nucl Med Mol Imaging, 34, (2007), 181-184.

Muller, C., et al., "Synthesis and in Vitro/in Vivo Evaluation of Novel 99mTc(CO)3-Folates", Bioconjugate Chem, 17(3), (2006), 797-806.

Murphy, G. P., et al., "Current Evaluation of the Tissue Localization and Diagnostic Utility of Prostate Specific Membrane Antigen", Cancer, 83(11), (1998), 2259-2269.

Nan, F, et al., "Dual Function Glutamate-Related Ligands: Discovery of a Novel, Potent Inhibitor of Glutamate Carboxypeptidase II Possessing mGiuR3 Agonist Activity", J Med Chem, 43, (2000), 772-774.

Nedrow-Byers, J. R., et al., "A Phosphoramidate-Based Prostate-Specific Membrane Antigen-Targeted SPECT Agent", The Prostate, 72, (2012), 904-912.

Oehr, P., et al., "Imaging of prostate cancer", Curr Opin Oncol, 19, (2007), 259-264.

O'Keefe, D. S., et al., "Comparative Analysis of Prostate-Specific Membrane Antigen (PSMA) Versus a Prostate—Specific Membrane Antigen-Like Gene", The Prostate, 58:, (2004), 200-210.

Olsnes, S, et al., "", Immunology Today, 10, (1989), 291-295.

Omlin, A., et al., "Androgen-und Ostrogen-biosynthesehemmer beim kastrationsresistenten Prostatakarzinom [Inhibitors of androgen and estrogen biosynthesis in castration-resistant prostate cancer]", (w/ English Abstract), Urologe, 51, (2012), 8-14 (8 pgs.).

Osborne, J. R., et al., "A Prospective Pilot Study of 89Zr-J591/Prostate Specific Membrane Antigen Positron Emission Tomography in Men with Localized Prostate Cancer Undergoing Radical Prostatectomy", The Journal of Urology, 191(5), (May 2014), 1439-1445.

Oyama, et al., "PET Imaging in Prostate Cancer", Hinyokika Kiyo, 52, (2006), 503-505.

Oyama, N., et al., "11C-Acetate PET Imaging of Prostate Cancer", J Nucl Med, 43(2), (2002), 181-186.

Oyama, N., et al., "11C-Acetate PET Imaging of Prostate Cancer: Detection of Recurrent Disease at PSA Relapse", J Nucl Med, 44(4), (2003), 549-555.

Panchuk-Voloshina, Nataliya, et al., "Alexa dyes, a series of new fluorescent dyes that yield exceptionally bright, photostable conjuaates.", J Histochem Cytochem., 47(9), (1999), 1179-88.

Paranjpe, et al., "Tumor-targeted bioconjugate based delivery of camptothecin: design, synthesis and in vitro evaluation", ScienceDirect Journal of Controlled Release 100, (2004), 275-292.

Parker, et al., "Design, production, and characterization of a single-chain variable fragment (ScFv) derived from the prostate specific membrane antigen (PSMA) monoclonal antibody J591", Protein Expression and Purification, 89(2), (2013), 136-145.

Pathalk, et al., "Enzymic protecting group techniques in organic synthesis", Stereosel, Biocatal, (2000), 775-797.

Pavlicek, et al., "Glutamate Carboxypeptidase II: An Overview of Structural Studies and Their Importance for Structure-Based Drug

(56) References Cited

OTHER PUBLICATIONS

Design and Deciphering the Reaction Mechanism of the Enzyme", Current Medicinal Chemistry, 19(9), (2012), 1300-1309.
Pavlicek, et al., "Structural characterization of P1'-diversified urea-based inhibitors of glutamate carboxypeptidase II", Bioorganic & Medicinal Chemistry Letters 24, (2014), 2340-2345.
Peltier, et al., "The Total Synthesis of Tubulysin D", J. Am. Chem. Soc. 128, (2006), 16018-19.
Perner, et al., "Prostate-specific membrane antigen expression as a predictor of prostate cancer progression", Human Pathology 38, (2007), 696-701.
Pillarsetty, et al., "2-18F-Fluoropropionic Acid as a PET Imaging Agent tor Prostate Cancer", J Nucl Med, 50(10), (2009), 1709-1714.
Pinto, F., et al., "Imaging in Prostate Cancer Staging: Present Role and Future Perspectives", Urol Int; 88(2), (2012), 125-136.
Pomper, M. G, et al., "11C-MCG: synthesis, uptake selectivity, and primate PET of a probe for glutamate carboxypeptidase II (NAALADase)", Mol Imagine, 1, (2002), 96-101.
Ponde, D. E., et al., "18F-Fluoroacetate: A Potential Acetate Analog for Prostate Tumor Imaging—In Vivo Evaluation of 18F-Fluoroacetate Versus 11C-Acetate", J Nucl Med, 48(3), (2007), 420-428.
Poulsen, et al., "[18F] fluoromethylcholine (FCH) positron emission tomography/computed tomography (PET/CT) for lymph node staging of prostate cancer: a prospective study of 210 patients", BJU International, 110, (2012), 1666-1671.
Poulsen, M. H., et al., "[18F]-fluorocholine positron-emission/computed tomography for lymph node staging of patients with prostate cancer: preliminary results of a prospective study", BJU International, 106, (2010), 639-644.
Preusser, S., et al., "Kastrationsresistentes Prostatakarzinom [Castratopm-resistant prostate cancer]", (w/ English Abstract), Urologe 51(1), (2012), 27-31 (6 pgs.).
Rais, R., et al., "Bioanalytical method for evaluating the pharmacokinetics of the GCP-II inhibitor 2-phosphonomethylpentanedioicacid (2-PMPA)", Journal of Pharmaceutical and Biomedical Analysis 88, (2014), 162-169.
Rajasekaran, et al., "A Novel Cytoplasmic tail MXXXL Motif Mediates the Internalization of Prostatespecific Membrane Antigen", Molecular Biology of the Cell, vol. 14, (Dec. 2003), 4835-4845.
Ranasinghe, M. G, et al., "Facile Synthesis of Unsymmetrical Thiolsulfonates via Sulfonylation of Mercaptans", Synthetic Communications, vol. 18, No. 3, (1988), 227-232.
Reddy, et al., "PSMA-specific anti-tumor activity of the targeted-tubulysin conjugate, EC1169", Poster, American Association for Cancer Research Annual Meeting (Apr. 8, 2013), (Apr. 8, 2013), 1 pg.
Reddy, et al., "PSMA-specific anti-tumor activity of the targeted-tubulysin conjugate, EC1169", Presentation Abstract, American Association for Cancer Research Annual Meeting (Apr. 8, 2013), (Apr. 8, 2013), 1 pg.
Reddy, Joseph A, et al., "Preclinical Evaluation of Tc-EC20 for Imaging Folate Receptor-Positive Tumors", Journal of Nuclear Medicine, (2004), 857-866.
Reske, et al., "[11C]choline PET/CT imaging in occult local relapse of prostate cancer after radical prostatectomy", Eur J Nucl Med Mol Imaging 35:, (2008), 9-17.
Reske, et al., "[11C]Choline uptake with PET/CT for the initial diagnosis of prostate cancer: relation to PSA levels, tumour stage and anti-androgenic therapy", Eur J Nucl Med Mol Imaging 35(6), (2008), 1740-1741.
Reske, S. N, et al., "Imaging Prostate Cancer with 11C-Choline PET/CT", J Nucl Med, 47, (2006), 1249-1254.
Reske, S. N., et al., "Nuklearmedizinische Diagnostik beim Prostatakarzinom [Nuclear imaging of prostate cancer]", (w/ English Abstract), Urologe 46(11), (2007), 1485-1499 (16 pgs.).

Reske, S. N., et al., "PET und PET/CT in der Rezidivdiagnostik des Prostatakarzinoms [PET and PET / CT in the recurrence diagnosis of prostate cancer]", (w/ English Summary), Urologe 45(10), (2006), 1240-1250 (12 pgs.).
Reske, S. N., et al., "Weiterentwicklung der PET und des PET/CT beim Prostatakarzinom [Advancement of PET and PET/CT in prostate carcinoma]", (w/ English Abstract), Urologe 45, (2006), 707-714 (9 pgs.).
Rinnab, et al., "[11C]Choline PET/CT for Targeted Salvage Lymph Node Dissection in Patients with Biochemical Recurrence after Primary Curative Therapy for Prostate Cancer", Urol Int; 81, (2008), 191-197.
Rinnab, et al., "[11C]choline PET/CT in prostate cancer patients with biochemical recurrence after radical prostatectomy", World J Urol 27, (2009), 619-625.
Rinnab, L, et al., "Evaluation of [11C]-choline positron-emission/computed tomography in patients with increasing prostate-specific antigen levels after primary treatment for prostate cancer", BJU Int, 100, (2007), 786,793.
Rioja, et al., "Role of positron emission tomography in urological oncology", BJU International, 106, 1578-1594.
Ristau, et al., "The prostate-specific membrane antigen: Lessons and current clinical implications from 20 years of research", Urologic Oncology: Seminars and Original Investigations 32, (2014), 272-279.
Roethke, et al., "Hyrbid Positron Emission Tomography-Magnetic Resonance Imaging with Gallium 68 Prostate-specific Membrane Antigen Tracer: A Next Step for Imaging of Recurrent Prostate Cancer-Preliminary Results", (2013), 862-864.
Rosenthal, S. A, et al., "Utility of Capromab Pendetide (ProstaScint) Imaging in the Management of Prostate Cancer", Tech Urol, 7. (2001), 27-37.
Roy, et al., "DUPA Conjugation of a Cytotoxic Indenoisoquinoline Topoisomerase I Inhibitor for Selective Prostate Cancer Cell Targeting", J. Med. Chem. 58, (2015), 3094-3103.
Rybalov, et al., "Impact of total PSA, PSA doubling time and PSA velocity on detection rates of 11C-Choline positron emission tomography in recurrent prostate cancer", World J Urol 31, (2013), 319-323.
Sacha, et al., "Expression of Glutamate Carboxypeptidase II in Human Brain", Neuroscience 144, (2007), 1361-1372.
Scattoni, V., et al., "Detection of Lymph-Node Metastases with Integrated [11C]Choline PET/CT in Patients with PSA Failure after Radical Retropubic Prostatectomy: Results Confirmed by Open Pelvic-Retroperitoneal lymphadenectomy", European Uroloay, 52, (2007), 423-429.
Schafer, M., et al., "A dimerized urea-based inhibitor of the prostate-specific membrane antigen for 68Ga-PET imaging of prostate cancer", EJNMMI Research, 2:23, (2012), 11 pgs.
Scheffel, et al., "PET Imaging of GRP Receptor Expression in Prostate Cancer", J. Nucl Med, 45(8), (Aug. 2004), 1277-1278.
Scher, et al., "PET/CT imaging of recurrent prostate cancer", Enr J Nucl Med Mol Imaging 35:, (2008), 5-8.
Scher, B., et al., "Value of 11 C-choline PET and PET/CT in patients with suspected prostate cancer", Eur. J. Nucl. Med. Mol. Imaging., 34, (2007), 45-53.
Schulke, N, et al., "The homodimer of prostate-specific membrane antigen is a functional target for cancer therapy", Proc Natl Acad Sci U S A, 100, (2003), 12590-12595.
Schuster, D. M, et al., "Initial Experience with the Radiotracer Anti-1-Amino-3-18F-Fiuorocyclobutane-1-Carboxylic Acid with PET/CT in Prostate Carcinoma", J Nucl Med, 48, (2007), 56-63.
Shvarts, O., et al., "Positron Emission Tomography in Urologic Oncology", Cancer Control, vol. 9, No. 4, (2002), 335-342.
Silver, D. A, et al., "Prostate-specific Membrane Antigen Expression in Normal and Malignant Human Tissues", Clinical Cancer Research, 3, (Jan. 1997), 81-85.
Silverman, "The Organic Chemistry of Drug Design and Drug Action", Elsevier Academic Press (2nd Ed. 2003), (2003), 1-592 (304 pages).
Silvola, et al., "Al18F-NOTA-Folate Accumulates in Atherosclerotic Plaques and Can be Detected by PET/CT", Poster presented Nov, 7, 2015 in Orlando, FL at the 2015 American Heart Associa-

(56) References Cited

OTHER PUBLICATIONS tion, ReSuscitation Science Symposium, [Online] Retrieved from the Internet: <https://aha.scientificposters.com/epsView.cfm&Vud4dtl239pJgyhGx5DzRxHdvD8LemQoMXh31P5rozni1u5bJrEupTaGO9TFyJlzABwMcSXfczc%3D>, (Nov, 7, 2015), 1 pg.

Silvola, et al., "Al18F-NOTA-Folate Accumulates in Atherosclerotic Plaques and Can be Detected by PET/CT", Abstract 18873, Circulation [Online] Retrieved from the internet: <http://circ.ahajournals.org/contenU132/Suppi_3/A 18873?cited-by=&legid=circulationaha;132/Suppl 3/A18873;Circulation, 2015, 132:A18873>, (Nov. 10, 2015), 2 pgs.

Simone, et al., "What's in a Label? Radioimmunotherapy for Metastatic Prostate Cancer", Clin Cancer Res; 19(18), (2013), 4908-4910.

Slusher, et al., "Immunocytochemical Localization of the N-Acetyl-Aspartyl-Glutamate (NAAG) Hydrolyzing Enzyme N-Acetylated a-Linked Acidic Dipeptidase (NAALADase)", The Journal of Comparative Neuorology 315, (1992), 217-229.

Slusher, B. S., et al., "Selective inhibition of NAALADase, which converts NAAG to glutamate, reduces ischemic brain injury", Nature Medicine, 5(12), (Dec. 1999), 1396-1400.

Soloviev, D., et al., "PET imaging with 11C-acetate in prostate cancer: a biochemical, radiochemical and clinical perspective", Eur J Nucl Med Mol Imaging 35(5), (2008), 942-949.

Spahn, M., et al., "Wie soll die Hormontherapie beim kastrationsresistenten Prostatakarzinom fortgefuhrt werden? [How should hormone therapy for castration-resistant prostate cancer be continued?]", (w/ English Abstract), Urologe 51, (2012), 15-19 (6 pgs.).

Sweat, S. D., et al., "Prostate-Specific Membrane Antigen Expression Is Greatest in Prostate Adenocarcinoma and Lymph Node Metastases", Urology 52, (1998), 637-640.

Tang, H., et al., "Prostate targeting ligands based on N-acetylated a-iinked acidic dipeptidase", Biochemical and Biophysical Research Communications 307, (2003), 8-14.

Tang, Q.-I., et al., "Updated Application of Prostate-Specific Membrane Antigen to the Diagnosis and Treatment of Prostate Cancer", (w/ English Abstract), National Journal of Andrology, vol. 14, No. 1, (Jan. 2008), 79-82.

Tasch, J, et al., "A Unique Folate Hydrolase, Prostage-Specific Membrane Antingen (PSMA): A Target for Immunotherapy?", Crit. Rev. Immunol., 21, (2001), 249-261.

Taylor, R. M., et al., "Prostate Cancer Targeting Motifs: Expression of anb3, Neurotensin Receptor 1, Prostate Specific Membrane Antigen, and Prostate Stem Cell Antigen in Human Prostate Cancer Cell Lines and Xenografts", The Prostate 72, (2012), 523-532.

Tehrani, O. S, "Tumor Imaging Using 1-(2'-deoxy-2'—18F-Fluoro-?-D-Arabinofuranosyi)Thymine and PET", J Nuc/ Med, 48, (2007), 1436-1441.

Testa, C., et al., "Prostate Cancer: Sextant Localization with MR Imaging, MR Spectroscopy, and 11C-Choline PET/CT", Radiology, 244(3), (Sep. 2007), 797-806.

Thalmann,, G., "Fortgeschrittenes Prostatakarzinom [Advanced prostate cancer]", Urologe 51(1), (2012), p. 7 (2 pgs.).

Truffert, et al., "", Tetrahedron, 52, (1996).

Tykvart, J., et al., "Rational design of urea-based glutamate carboxypeptidase II (GCPII) inhibitors as versatile tools for specific drug targeting and delivery", Bioorganic & Medicinal Chemistry, 22, (2014), 4099-4108.

Uprimny, C., et al., "68Ga-PSMA ligand PET versus 18F-NaF PET: evaluation of response to 223Ra therapy in a prostate cancer patient", Eur J Nucl Med Mol Imaging 42(2), (2015), 362-363.

Vallabhajosula, S., et al., "Radioimmunotherapy of Prostate Cancer in Human Xenografts Using Monoclonal Antibodies Specific to Prostate Specific Membrane Antigen (PSMA): Studies in Nude Mice", The Prostate, 58, (2004), 145-155.

Vavere, A. L., et al., "1-11C-Acetate as a PET Radiopharmaceutical for Imaging Fatty Acid Synthase Expression in Prostate Cancer", J Nucl Med; 49(2), (2008), 327-334.

Vees, H, et al., "18F-choline and/or 11C-acetate positron emission tomography: detection of residual or progressive subclinicai disease at very low prostate-specific antigen values ( <1 ng/mL) after radical prostatectomy", BJU Int, 99, (2007), 1415-1420.

Viola-Villegas, N., et al., "Targeting Gallium to Cancer Cells through the Folate Receptor", Drug Target Insights, vol. 3, (2008), 13-25.

Viola-Villegas, N., et al., "Targeting the Folate Receptor (FR): Imaging and Cytotoxicity of Re1 Conjugates in FR-Overexpressing Cancer Cells", ChemMedChem, vol. 3, (2008), 1387-1394.

Vlahov, et al., "Design and regioselective synthesis of a new generation of targeted chemotherapeutics. Part 1: EC145, a folic acid conjugate of desacetylvinblastine monohydrazide", ScienceDirect, Bioorganic & Medical Chemistry Letters 16, (2006), 5093-5096.

Wang, H., et al., "Bioisosterism of urea-based GCPII inhibitors: Synthesis and structure-activity relationship studies", Bioorganic & Medicinal Chemistry Letters 20, (2010), 392-397.

Wang, K., et al., "Prostate-Specific Membrane Antigen Targeted Tubulysin Conjugates for Cancer Therapy", Poster, 246th American Chemical Society Meeting and Exposition (Sep. 8, 2013), (Sep. 8, 2013).

Wang, X., et al., "Development of Taraeted Near-Infrared Imaging Agents for Prostate Cancer", Mol Cancer Ther, 13(11), (2014), 2595-2606.

Weineisen, M., et al., "Synthesis and preclinical evaluation of DOTAGA-conjugated PSMA ligands for functional imaging and endoradiotherapy of prostate cancer", EJNMMI Research, 4:63, (2014), 15 pgs.

Weissbach, L., "Welche Inhalte sollte eine „living guideline" besetzen? [Which components should living guidelines contain?], (w/ English Abstract), Urologe, 51, (2012), 57-59 (5 pgs.).

Whitaker, H. C., et al., "N-acetyl-L-aspartyl-L-glutamate peptidase-like 2 is overexpressed in cancer and promotes a pro-migratory and pro-metastatic phenotype", Oncogene 33, (2014), 5274-5287.

Wiberg, et al., "A comparison of some properties of C=O and C=S bonds", ARKIVOC, (2011), 45-56.

Wiehr, S., et al., "Pharmacokinetics and PET Imaging Properties of Two Recombinant Anti-PSMA Antibody Fragments in Comparison to their Parental Antibody", The Prostate, 74, (2014), 743-755.

Wright, G. L., et al., "Expression of Prostate-Specific Membrane Antigen in Normal, Benign, and Malignant Prostate Tissues", Urol Oncol, 1(1), (1995), 18-28.

Wu, L. Y., et al., "the molecular pruning of a phosphoramidate peptidomimetic inhibitor of prostate-specific membrane antigen", Bioorganic & Medicinal Chemistry 15(23), (2007), 7434-7443.

Yamaguchi, T., et al., "Prostate cancer: a comparative study of 11C-choline PET and MR imaging combined with proton MR spectroscopy", Eur J Nucl Med Mol Imaging, 32, (2005), 742-748.

Yang, et al., "Characterization of the pH of Folate Receptor-Containing Endosomes and the Rate of Hydrolysis of Internalized Acid-Labile Folate-Drug Conjugates", JPET 321, (2007), 462-468.

Zacharias, Niki, et al., "Cation- Interactions in Ligand Recognition and Catalysis", TRENDS in Pharmacological Sciences, vol. 23, (Jun. 2002), 291-297.

Zaheer, A., et al., "New Agents and Techniques for Imaging Prostate Cancer", J Nucl Med, 50(9), (2009), 1387-1390.

Zechmann, C. M., et al., "Radiation dosimetry and first therapy results with a 124I/131 I-labeled small molecule (MIP-1095) targeting PSMA for prostate cancer therapy", Eur J Nucl Med Mol Imaging 41(7), (2014), 1280-1292.

Zhang, A. X., et al., "A Remote Arene-Binding Site on Prostate Specific Membrane Antigen Revealed by Antibody-Recruiting Small Molecules", J. Am. Chem. Soc., 132(36), (2010), 12711-12716.

Zhang, Y., et al., "Prostate Specific Membrane Antigen (PSMA): A Novel Modulator of p38 for Proliferation, Migration, and Survival in Prostate Cancer Ceils", The Prostate, 73(8), (2013), 835-841.

Zhou, J., "In vivo evaluation of medical device-associated inflammation using macrophage-specific position emission tomography (PET) imaging", Bioorganic and Medicinal Chemistry Letters, vol. 23, (2013), 2044-2047.

Zhou, J., et al., "Naag Peptidase Inhibitors and Their Potential for Diagnosis and Therapy", Nat Rev Drug Discovery, 4, (2005), 1015-1026.

(56) References Cited

OTHER PUBLICATIONS

Zophel, K, et al., "Is 11C-choline the most appropriate tracer for prostate cancer?", Eur J Nucl Med Mol Imaging, 31, (2004), 756-759.
"U.S. Appl. No. 16/717,753, Non Final Office Action dated Dec. 20, 2021", 12 pgs.

PSMA BINDING LIGAND-LINKER CONJUGATES AND METHODS FOR USING

CROSS-REFERENCE TO RELATED APPLICATIONS

This application is a continuation of U.S. application Ser. No. 17/086,063, filed Oct. 30, 2020 which is a continuation of U.S. application Ser. No. 15/990,152, filed May 25, 2018, now U.S. Pat. No. 10,828,282, which is a continuation of U.S. application Ser. No. 15/606,913, filed May 26, 2017, now U.S. Pat. No. 10,406,240 which is a continuation of U.S. patent application Ser. No. 14/794,482, filed Jul. 8, 2015, now U.S. Pat. No. 10,046,054, which is a continuation of U.S. patent application Ser. No. 12/673,931, filed Feb. 17, 2010, now U.S. Pat. No. 9,193,763, which is a U.S. national application under 37 C.F.R. § 371(b) of International Application Serial No. PCT/US2008/073375, filed Aug. 15, 2008, which claims priority to under 35 U.S.C. 119(e) to U.S. Provisional Application Ser. No. 60/956,489, filed Aug. 17, 2007, and U.S. Provisional Application Ser. No. 61/074,358, filed Jun. 20, 2008, the entire disclosure of which are hereby incorporated by reference in their entireties.

TECHNICAL FIELD

The invention described herein pertains to compounds and methods for treating diseases of the prostate, such as prostate cancer and related diseases. More specifically, embodiments of the invention described herein pertain to conjugates of biologically active agents conjugated to PSMA binding ligands.

BACKGROUND

The prostate is one of the male reproductive organs found in the pelvis below the urinary bladder. It functions to produce and store seminal fluid which provides nutrients and fluids that are vital for the survival of sperm introduced into the vagina during reproduction. Like many other tissues, the prostate glands are also prone to develop either malignant (cancerous) or benign (non-cancerous) tumors. The American Cancer Society predicted that over 230,000 men would be diagnosed with prostate cancer and over 30,000 men would die from the disease in year 2005. In fact, prostate cancer is one of the most common male cancers in western societies, and is the second leading form of malignancy among American men. Current treatment methods for prostrate cancer include hormonal therapy, radiation therapy, surgery, chemotherapy, photodynamic therapy, and combination therapy. The selection of a treatment generally varies depending on the stage of the cancer. However, many of these treatments affect the quality of life of the patient, especially those men who are diagnosed with prostrate cancer over age 50. For example, the use of hormonal drugs is often accompanied by side effects such as osteoporosis and liver damage. Such side effects might be mitigated by the use of treatments that are more selective or specific to the tissue being responsible for the disease state, and avoid non-target tissues like the bones or the liver. As described herein, prostate specific membrane antigen (PSMA) represents a target for such selective or specific treatments.

PSMA is named largely due to its higher level of expression on prostate cancer cells; however, its particular function on prostate cancer cells remains unresolved. PSMA is over-expressed in the malignant prostate tissues when compared to other organs in the human body such as kidney, proximal small intestine, and salivary glands. Though PSMA is expressed in brain, that expression is minimal, and most ligands of PSMA are polar and are not capable of penetrating the blood brain barrier. PSMA is a type II cell surface membrane-bound glycoprotein with ~110 kD molecular weight, including an intracellular segment (amino acids 1-18), a transmembrane domain (amino acids 19-43), and an extensive extracellular domain (amino acids 44-750). While the functions of the intracellular segment and the transmembrane domains are currently believed to be insignificant, the extracellular domain is involved in several distinct activities. PSMA plays a role in central nervous system, where it metabolizes N-acetyl-aspartyl glutamate (NAAG) into glutamic and N-acetyl aspartic acid. Accordingly, it is also sometimes referred to as an N-acetyl alpha linked acidic dipeptidase (NAALADase). PSMA is also sometimes referred to as a folate hydrolase I (FOLH I) or glutamate carboxypeptidase (CCP II) due to its role in the proximal small intestine where it removes γ-linked glutamate from poly-γ-glutamated folate and α-linked glutamate from peptides and small molecules.

PSMA also shares similarities with human transferrin receptor (TfR), because both PSMA and TfR are type II glycoproteins. More specifically, PSMA shows 54% and 60% homology to TfR1 and TfR2, respectively. However, though TfR exists only in dimeric form due to the formation of inter-strand sulthydryl linkages, PSMA can exist in either dimeric or monomeric form.

Unlike many other membrane-bound proteins, PSMA undergoes rapid internalization into the cell in a similar fashion to cell surface bound receptors like vitamin receptors. PSMA is internalized through clathrin-coated pits and subsequently can either recycle to the cell surface or go to lysosomes. It has been suggested that the dimer and monomer form of PSMA are inter-convertible, though direct evidence of the interconversion is being debated. Even so, only the dimer of PSMA possesses enzymatic activity, and the monomer does not.

Though the activity of the PSMA on the cell surface of the prostate cells remains under investigation, it has been recognized by the inventors herein that PSMA represents a viable target for the selective and/or specific delivery of biologically active agents, including diagnostic agents, imaging agents, and therapeutic agents to such prostate cells.

SUMMARY OF THE INVENTION

It has been discovered that biologically active compounds that are conjugated to ligands capable of binding to prostate specific membrane antigen (PSMA) via a linker may be useful in the imaging, diagnosis, and/or treatment of prostate cancer, and related diseases that involve pathogenic cell populations expressing or over-expressing PSMA. PSMA is a cell surface protein that is internalized in a process analogous to endocytosis observed with cell surface receptors, such as vitamin receptors. Accordingly, it has been discovered that certain conjugates that include a linker having a predetermined length, and/or a predetermined diameter, and/or preselected functional groups along its length may be used to treat, image, and/or diagnose such diseases.

In one illustrative embodiment of the invention, conjugates having the formula

B-L-D are described wherein B is a prostate specific membrane antigen (PSMA) binding or targeting ligand, L is a linker, and D is a drug. As used herein, the term drug D collectively includes therapeutic agents, cytotoxic agents, imaging agents, diagnostic agents, and the like, unless otherwise indicated or by the context. For example, in one illustrative configuration, the conjugate described herein is used to eliminate a pathogenic population of cells and therefore the drug D is a therapeutic agent, a cytotoxic agent, and the like. In another illustrative configuration, the conjugate described herein is used to image and/or diagnose a disease or disease state, and therefore the drug D is an imaging agent, a diagnostic agent, and the like. Other configurations are also contemplated and described herein. It is to be understood that analogs and derivatives of each of the foregoing B, L, and D are also contemplated and described herein, and that when used herein, the terms B, L, and D collectively refer to such analogs and derivatives.

In one illustrative embodiment, the linker L may be a releasable or non-releasable linker. In one aspect, the linker L is at least about 7 atoms in length. In one variation, the linker L is at least about 10 atoms in length. In one variation, the linker L is at least about 14 atoms in length. In another variation, the linker L is between about 7 and about 31, between about 7 and about 24, or between about 7 and about 20 atoms in length. In another variation, the linker L is between about 14 and about 31, between about 14 and about 24, or between about 14 and about 20 atoms in length.

In an alternative aspect, the linker L is at least about 10 angstroms (Å) in length. In one variation, the linker L is at least about 15 Å in length. In another variation, the linker L is at least about 20 Å in length. In another variation, the linker L is in the range from about 10 Å to about 30 Å in length.

In an alternative aspect, at least a portion of the length of the linker L is about 5 Å in diameter or less at the end connected to the binding ligand B. In one variation, at least a portion of the length of the linker L is about 4 Å or less, or about 3 Å or less in diameter at the end connected to the binding ligand B. It is appreciated that the illustrative embodiments that include a diameter requirement of about 5 Å or less, about 4 Å or less, or about 3 Å or less may include that requirement for a predetermined length of the linker, thereby defining a cylindrical-like portion of the linker. Illustratively, in another variation, the linker includes a cylindrical portion at the end connected to the binding ligand that is at least about 7 Å in length and about 5 Å or less, about 4 Å or less, or about 3 Å or less in diameter.

In another embodiment, the linker L includes one or more hydrophilic linkers capable of interacting with one or more residues of PSMA, including amino acids that have hydrophobic side chains, such as Ser, Thr, Cys, Arg, Orn, Lys, Asp, Glu, Gln, and like residues. In another embodiment, the linker L includes one or more hydrophobic linkers capable of interacting with one or more residues of PSMA, including amino acids that have hydrophilic side chains, such as Val, Leu, Ile, Phe, Tyr, Met, and like residues. It is to be understood that the foregoing embodiments and aspects may be included in the linker L either alone or in combination with each other. For example, linkers L that are at least about 7 atoms in length and about 5 Å, about 4 Å or less, or about 3 Å or less in diameter or less are contemplated and described herein, and also include one or more hydrophilic linkers capable of interacting with one or more residues of PSMA, including Val, Leu, Ile, Phe, Tyr, Met, and like residues are contemplated and described herein.

In another embodiment, one end of the linker is not branched and comprises a chain of carbon, oxygen, nitrogen, and sulfur atoms. In one embodiment, the linear chain of carbon, oxygen, nitrogen, and sulfur atoms is at least 5 atoms in length. In one variation, the linear chain is at least 7 atoms, or at least 10 atoms in length. In another embodiment, the chain of carbon, oxygen, nitrogen, and sulfur atoms are not substituted. In one variation, a portion of the chain of carbon, oxygen, nitrogen, and sulfur atoms is cyclized with a divalent fragment. For example, a linker (L) comprising the dipeptide Phe-Phe may include a piperazin-1,4-diyl structure by cyclizing two nitrogens with an ethylene fragment, or substituted variation thereof.

In another embodiment, pharmaceutical compositions are described herein, where the pharmaceutical composition includes the conjugates described herein in amounts effective to treat diseases and disease states, diagnose diseases or disease states, and/or image tissues and/or cells that are associated with pathogenic populations of cells expressing or over expressing PSMA. Illustratively, the pharmaceutical compositions also include one or more carriers, diluents, and/or excipients.

In another embodiment, methods for treating diseases and disease states, diagnosing diseases or disease states, and/or imaging tissues and/or cells that are associated with pathogenic populations of cells expressing or over expressing PSMA are described herein. Such methods include the step of administering the conjugates described herein, and/or pharmaceutical compositions containing the conjugates described herein, in amounts effective to treat diseases and disease states, diagnose diseases or disease states, and/or image tissues and/or cells that are associated with pathogenic populations of cells expressing or over expressing PSMA.

DETAILED DESCRIPTION

Figure 1A:
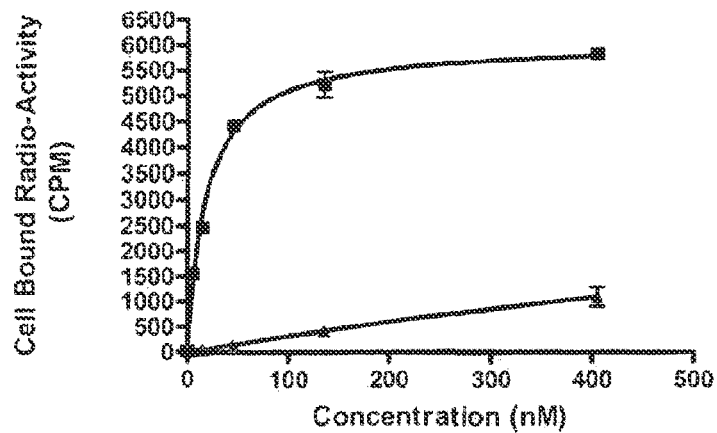
FIG. 1A. Cell bound radioactivity versus concentration of SK28-$^{99m}$Tc ($K_d$=18.12 nM) in the presence (▲) or absence (■) of excess PMPA.

Drug delivery conjugates are described herein where a PSMA binding ligand is attached to a releasable or non-releasable linker which is attached to a drug, therapeutic agent, diagnostic agent, or imaging agent.

Illustratively, the bivalent linkers described herein may be included in linkers used to prepare PSMA-binding drug conjugates, PSMA-binding imaging agent conjugates, and PSMA-binding diagnostic agent conjugates of the following formulae:

B-L-TA

B-L-IA

B-L-DA where B is a PSMA-binding moiety, including analogs or derivatives thereof, L is a linker, TA is a therapeutic agent, including analogs or derivatives thereof, IA is an imaging agent, including analogs or derivatives thereof, and DA is a diagnostic agent, including analogs or derivatives thereof. The linker L can comprise multiple bivalent linkers, including the bivalent linkers described herein. It is also to be understood that as used herein, TA collectively refers to therapeutic agents, and analogs and derivatives thereof, IA collectively refers to imaging agents, and analogs and derivatives thereof, and DA collectively refers to diagnostic agents, and analogs and derivatives thereof.

The linker may also include one or more spacer linkers and optionally additional releasable linkers. The spacer and releasable linkers may be attached to each other in any order or combination. Similarly, the PSMA binding ligand may be attached to a spacer linker or to a releasable linker. Similarly, the drug, therapeutic agent, diagnostic agent, or imaging agent may be attached to a spacer linker or to a releasable linker. Each of these components of the conjugates may be connected through existing or additional heteroatoms on the targeting ligand, drug, therapeutic agent, diagnostic agent, imaging agent, releasable or spacer linker. Illustrative heteroatoms include nitrogen, oxygen, sulfur, and the formulae —(NHR$^1$NHR$^2$)—, —SO—, —(SO$_2$)—, and —N(R$^3$)O—, wherein R$^1$, R$^2$, and R$^3$ are each independently selected from hydrogen, alkyl, heteroalkyl, heterocyclyl, aryl, heteroaryl, arylalkyl, heteroarylalkyl, and the like, each of which may be optionally substituted.

In one illustrative embodiment, compounds are described herein that include linkers having predetermined length and diameter dimensions. In one aspect, linkers are described herein that satisfy one or more minimum length requirements, or a length requirement falling within a predetermined range. In another aspect, satisfaction of a minimum length requirement may be understood to be determined by computer modeling of the extended conformations of linkers. In another aspect, satisfaction of a minimum length requirement may be understood to be determined by having a certain number of atoms, whether or not substituted, forming a backbone chain of atoms connecting the binding ligand (B) with the drug (D). In another embodiment, the backbone chain of atoms is cyclized with another divalent fragment. In another aspect, linkers are described herein that satisfy one or more maximum or minimum diameter requirements. In another aspect, satisfaction of a maximum or minimum diameter requirement may be understood to be determined by computer modeling of various conformations of linkers modeled as the space-filling, CPK, or like configurations. In another aspect, satisfaction of a maximum or minimum diameter requirement may be understood to be apply to one or more selected portions of the linker, for example the portion of the linker proximal to the binding ligand (B), or the portion of the linker proximal to the drug (D), and the like. In another aspect, linkers are described herein that satisfy one or more chemical composition requirements, such as linkers that include one or more polar groups that may positively interact with the one or more Arg or Lys side-chain nitrogens and/or Asp or Glu side chain oxygens found in the funnel portion of PSMA. In one variation, linkers are described herein that satisfy one or more chemical composition requirements, such as linkers that include one or more non-polar groups that may positively interact with the one or more Tyr or Phe side-chain carbons found in the funnel portion of PSMA.

In one embodiment, the atom-length of the linker is defined by the number of atoms separating the binding or targeting ligand B, or analog or derivative thereof, and the drug D, or analog or derivative thereof. Accordingly, in configurations where the binding ligand B, or analog or derivative thereof, is attached directly to the drug D, or analog or derivative thereof, the attachment is also termed herein as a "0-atom" linker. It is understood that such 0-atom linkers include the configuration wherein B and D are directly attached by removing a hydrogen atom from each attachment point on B and D, respectively. It is also understood that such 0-atom linkers include the configuration wherein B and D are attached through an overlapping heteroatom by removing a hydrogen atom from one of B or D, and a heteroatom functional group, such as OH, SH, NH$_2$, and the like from the other of B or D. It is also understood that such 0-atom linkers include the configuration wherein B and D are attached through a double bond, which may be formed by removing two hydrogen atoms from each attachment point on B and D, respectively, or whereby B and D are attached through one or more overlapping heteroatoms by removing two hydrogen atoms, one hydrogen and one heteroatom functional group, or two heteroatom functional groups, such as OH, SH, NH$_2$, and the like, from each of B or D. In addition, B and D may be attached through a double bond formed by removing a double bonded heteroatom functional group, such as O, S, NH, and the like, from one or both of B or D. It is also to be understood that such heteroatom functional groups include those attached to saturated carbon atoms, unsaturated carbon atoms (including carbonyl groups), and other heteroatoms. Similarly, the length of linkers that are greater than 0 atoms are defined in an analogous manner.

Accordingly, in another illustrative embodiment, linkers (L) are described having a chain length of at least 7 atoms. In one variation, linkers (L) are described having a chain length of at least 14 atoms. In another variation, linkers (L) are described having a chain length in the range from about 7 atoms to about 20 atoms. In another variation, linkers (L) are described having a chain length in the range from about 14 atoms to about 24 atoms.

In another embodiment, the length of the linker (L) is defined by measuring the length of an extended conformation of the linker. Such extended conformations may be measured in art-recognized computer modeling programs, such as PC Model 7 (MMX). Accordingly, in another illustrative embodiment, linkers are described having a chain length of at least 15 Å, at least 20 Å, or at least 25 Å.

In another embodiment, linkers are described having at least one hydrophobic side chain group, such as an alkyl, cycloalkyl, aryl, arylalkyl, or like group, each of which is optionally substituted. In one aspect, the hydrophobic group is included in the linker by incorporating one or more Phe or Tyr groups, including substituted variants thereof, and analogs and derivatives thereof, in the linker chain. It is appreciated that such Phe and/or Tyr side chain groups may form positive pi-pi ($\pi$-$\pi$) interactions with Tyr and Phe residues found in the funnel of PSMA. In addition, it is appreciated that the presence of large side chain branches, such as the arylalkyl groups found on Phe and Tyr may provide a level of conformational rigidity to the linker, thus limiting the degrees of freedom, and reducing coiling and promoting extended conformations of the linker. Without being bound by theory, it is appreciated that such entropy restrictions may increase the overall binding energy of the bound conjugates described herein. In addition, it is appreciated that the rigidity increases that may be provided by sterically hindered side chains, such as Phe and Tyr described herein, may reduce or prevent coiling and interactions between the ligand and the imaging agent. For example, computational energy minimization of a representative 9-atom and 14-atom linker (see, for example, FIGS. 15A and 15B) shows that there are no intra-molecular interactions between the ligand and the imaging agent. Moreover, the presence of side chain the two Phe side chains appears to promote a more extended conformation in syn-SK33 (FIG. 15B) than in the amino-hexanoic acid-containing conjugate (FIG. 15A)

It has been discovered herein that the funnel shaped tunnel leading to the catalytic site or active site of PSMA imposes length, shape, and/or chemical composition requirements on the linker portion of conjugates of PSMA binding ligands and therapeutic, diagnostic, and imaging agents that positively and negatively affect the interactions between PSMA and those conjugates. Described herein are illustrative embodiments of those conjugates that include such length, shape, and/or chemical composition requirements on the linker. Such length, shape, and/or chemical composition requirements were assessed using molecular modeling. For example, the space filling and surface model of the PSMA complex with (s)-2-(4-iodobenzensylphosphonomethyl)-pentanedioic [2-PMPA derivative] PDB ID code 2C6P were generated using PROTEIN EXPLORER. The PROTEIN EXPLORER model verified the 20 Å deep funnel, and also showed diameter features at various locations along the funnel that may be used to define linkers having favorable structural features. In addition, the model showed that close to the active site of PSMA, there are a higher number of hydrophobic residues that may provide additional binding interactions when the corresponding functional groups are included in the linker. Finally, the model showed the presence of three hydrophobic pockets that may provide additional binding interactions when the corresponding functional groups are included in the linker.

Figure 15A:
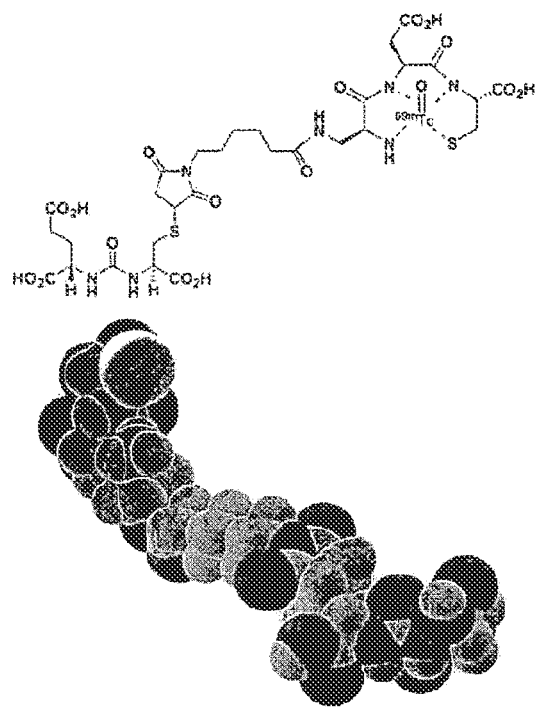
FIG. 15A. MUPA 99 mTc imaging agent conjugate (9-atom linker) with energy minimized computer model.
Figure 15B:
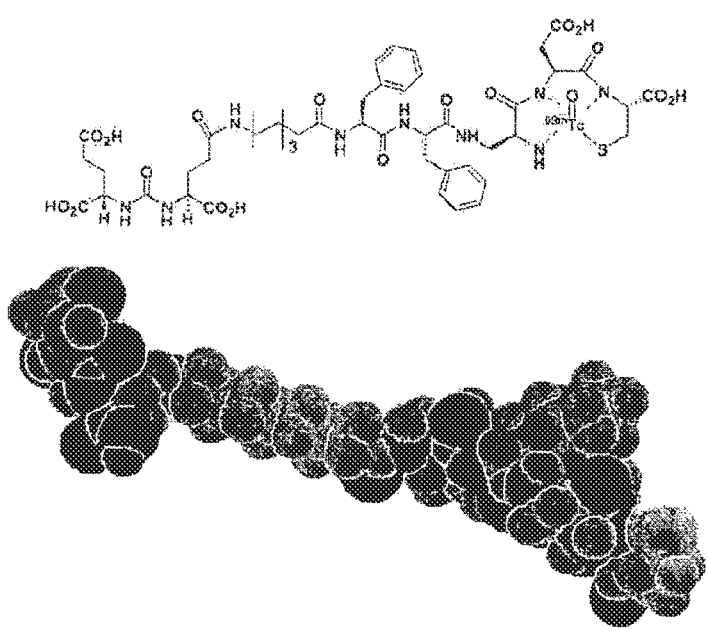
FIG. 15B. MUPA 99 mTc imaging agent conjugate (syn-SK33, 14-atom linker) with energy minimized computer model.

In another illustrative embodiment, the following molecular models were created for a conjugate of MUPA and a tripeptide $^{99m}$Tc imaging agent connected by a 9-atom linker, as shown in FIG. 15A, and syn-SK33 including a branched 14-atom linker, as shown in FIG. 15B. The models were created using PC Model 7 (MMX) with energy minimization, and using the following bond length parameters: C—C ($sp^3$-$sp^3$)=1.53 Å, C—C ($sp^3$-$sp^2$)=1.51 Å, C—N ($sp^3$-N)=1.47 Å, C—N ($sp^2$-N)=1.38 Å. Such models may be used to calculate the length of the linker connecting the binding ligand (B) and the drug (D). In addition, such models may be modified to create extended conformations, and subsequently used to calculate the length of the linker connecting the binding ligand (B) and the drug (D).

The first human PSMA gene was cloned from LNCaP cells and is reported to be located in chromosome 11p11-12. In addition, there is a PSMA-like gene located at the loci 11q14.3. The crystal structure of PSMA has been reported by two different groups at different resolutions, and each shows that the active site contains two zinc atoms, confirming that PSMA is also considered a zinc metalloprotease. Davis et al, PNAS, 102:5981-86, (2005) reported the crystal structure at low resolution (3.5 Å), while Mesters et al, The EMBO Journal, 1-10 (2006) reported the crystal structure at higher resolution (2-2.2 Å), the disclosures of which are incorporated herein by reference. The crystal structures show that PSMA is a homodimer that contains a protease domain, an apical domain, a helical domain and a CPG2 dimerization domain. The protease domain of PSMA contains a binuclear zinc site, catalytic residues and a substrate binding region including three arginine residues (also referred to as a substrate binding arginine patch). In the crystal structure, the two zinc ions in the active site are each ligated to an oxygen of phosphate, or to the phosphinate moiety of the inhibitor GPI 18431 for the co-crystal structure. In the high resolution crystal structures of the extracelluar domain, PSMA was co-crystallized with both potent inhibitors, weak inhibitors, and glutamate at 2.0, 2.4, and 2.2 Å, respectively. The high resolution crystal structure shows a 20 Å deep funnel shaped tunnel leads to the catalytic site or active site of PSMA. The funnel is lined with the side chains of a number of Arg and Lys residues, Asp and Glu residues, and Tyr and Phe residues.

In another embodiment, the linker (L) is a chain of atoms selected from C, N, O, S, Si, and P. The linker may have a wide variety of lengths, such as in the range from about 7 to about 100. The atoms used in forming the linker may be combined in all chemically relevant ways, such as chains of carbon atoms forming alkylene groups, chains of carbon and oxygen atoms forming polyoxyalkylene groups, chains of carbon and nitrogen atoms forming polyamines, and others. In addition, it is to be understood that the bonds connecting atoms in the chain may be either saturated or unsaturated, such that for example, alkanes, alkenes, alkynes, cycloalkanes, arylenes, imides, and the like may be divalent radicals that are included in the linker. In addition, it is to be understood that the atoms forming the linker may also be cyclized upon each other to form divalent cyclic radicals in the linker. In each of the foregoing and other linkers described herein the chain forming the linker may be substituted with a wide variety of groups.

In another embodiment, linkers (L) are described that include at least one releasable linker. In one variation, linkers (L) are described that include at least two releasable linkers. In another variation, linkers (L) are described that include at least one self-immolative linker. In another variation, linkers (L) are described that include at least one releasable linker that is not a disulfide. In another embodiment, linkers (L) are described that do not include a releasable linker.

It is appreciated that releasable linkers may be used when the drug to be delivered is advantageously liberated from the binding ligand-linker conjugate so that the free drug will have the same or nearly the same effect at the target as it would when administered without the targeting provided by the conjugates described herein. In another embodiment, the linker L is a non-releasable linker. It is appreciated that non-releasable linkers may be used when the drug is advantageously retained by the binding ligand-linker conjugate, such as in imaging, diagnosing, uses of the conjugates described herein. It is to be understood that the choice of a releasable linker or a non-releasable linker may be made independently for each application or configuration of the conjugates, without limiting the invention described herein. It is to be further understood that the linkers L described herein comprise various atoms, chains of atoms, functional groups, and combinations of functional groups. Where appropriate in the present disclosure, the linker L may be referred to by the presence of spacer linkers, releasable linkers, and heteroatoms. However, such references are not to be construed as limiting the definition of the linkers L described herein.

The linker (L) comprising spacer and/or releasable linkers (i.e., cleavable linkers) can be any biocompatible linker. The releasable or cleavable linker can be, for example, a linker susceptible to cleavage under the reducing or oxidizing conditions present in or on cells, a pH-sensitive linker that may be an acid-labile or base-labile linker, or a linker that is cleavable by biochemical or metabolic processes, such as an enzyme-labile linker. In one embodiment, the spacer and/or releasable linker comprises about 1 to about 30 atoms, or about 2 to about 20 atoms. Lower molecular weight linkers (i.e., those having an approximate molecular weight of about 30 to about 300) are also described. Precursors to such linkers may be selected to have either nucleophilic or electrophilic functional groups, or both, optionally in a protected form with a readily cleavable protecting group to facilitate their use in synthesis of the intermediate species.

The term "releasable linker" as used herein refers to a linker that includes at least one bond that can be broken under physiological conditions (e.g., a pH-labile, acid-labile, oxidatively-labile, or enzyme-labile bond). The cleavable bond or bonds may be present in the interior of a cleavable linker and/or at one or both ends of a cleavable linker. It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH. Illustratively, the bivalent linkers described herein may undergo cleavage under other physiological or metabolic conditions, such as by the action of a glutathione mediated mechanism. It is appreciated that the lability of the cleavable bond may be adjusted by including functional groups or fragments within the bivalent linker L that are able to assist or facilitate such bond breakage, also termed anchimeric assistance. The lability of the cleavable bond can also be adjusted by, for example, substitutional changes at or near the cleavable bond, such as including alpha branching adjacent to a cleavable disulfide bond, increasing the hydrophobicity of substituents on silicon in a moiety having a silicon-oxygen bond that may be hydrolyzed, homologating alkoxy groups that form part of a ketal or acetal that may be hydrolyzed, and the like. In addition, it is appreciated that additional functional groups or fragments may be included within the bivalent linker L that are able to assist or facilitate additional fragmentation of the PSMA binding drug linker conjugates after bond breaking of the releasable linker.

In another embodiment, the linker includes radicals that form one or more spacer linkers and/or releasable linkers that are taken together to form the linkers described herein having certain length, diameter, and/or functional group requirements.

Another illustrative embodiment of the linkers described herein, include releasable linkers that cleave under the conditions described herein by a chemical mechanism involving beta elimination. In one aspect, such releasable linkers include beta-thio, beta-hydroxy, and beta-amino substituted carboxylic acids and derivatives thereof, such as esters, amides, carbonates, carbamates, and ureas. In another aspect, such releasable linkers include 2-and 4-thioarylesters, carbamates, and carbonates.

It is to be understood that releasable linkers may also be referred to by the functional groups they contain, illustratively such as disulfide groups, ketal groups, and the like, as described herein. Accordingly, it is understood that a cleavable bond can connect two adjacent atoms within the releasable linker and/or connect other linkers, or the binding ligand B, or the therapeutic, diagnostic, or imaging agent D, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, a spacer linker, another releasable linker, the drug D, or analog or derivative thereof, or the binding ligand B, or analog or derivative thereof, following breakage of the bond, the releasable linker is separated from the other moiety.

In another embodiment, the releasable and spacer linkers may be arranged in such a way that subsequent to the cleavage of a bond in the bivalent linker, released functional groups anchimerically assist the breakage or cleavage of additional bonds, as described above. An illustrative embodiment of such a bivalent linker or portion thereof includes compounds having the formula:

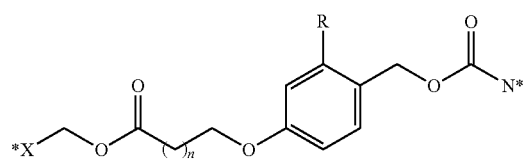

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment for additional spacer or releasable linkers, or heteroatoms, forming the bivalent linker, or alternatively for attachment of the drug, or analog or derivative thereof, or the vitamin, or analog or derivative thereof. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

In this embodiment, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge may begin a cascade of fragmentation of this illustrative bivalent linker, or fragment thereof. Alternatively, acid-catalyzed hydrolysis of the carbamate may facilitate the beta elimination of the hydroxyalkanoic acid, which may cyclize, and facilitate cleavage of methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein may initiate such a cascade of fragmentation.

Illustrative mechanisms for cleavage of the bivalent linkers described herein include the following 1,4 and 1,6 fragmentation mechanisms

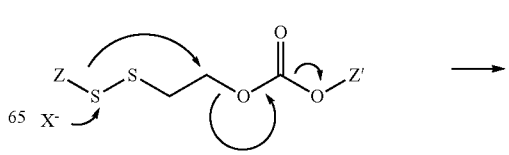

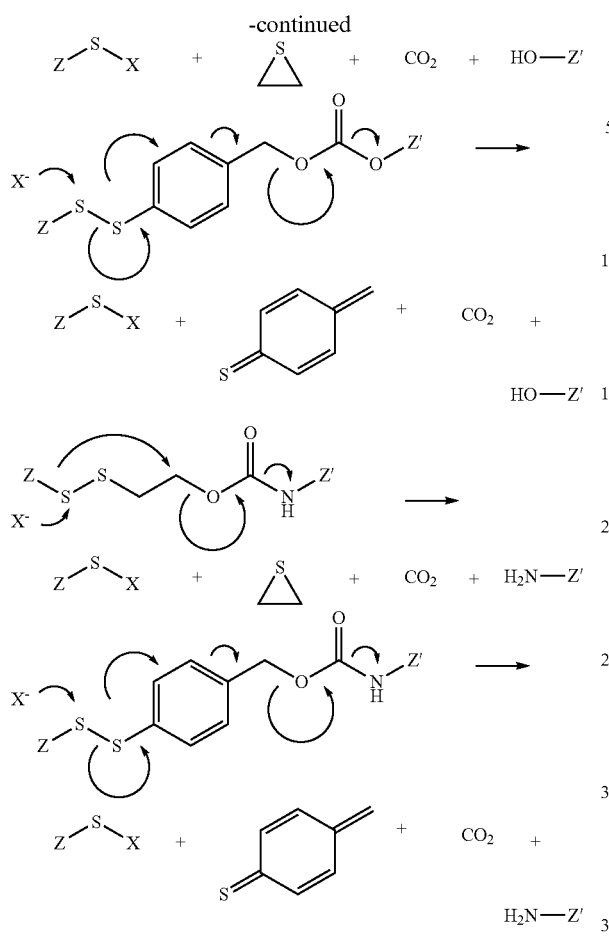

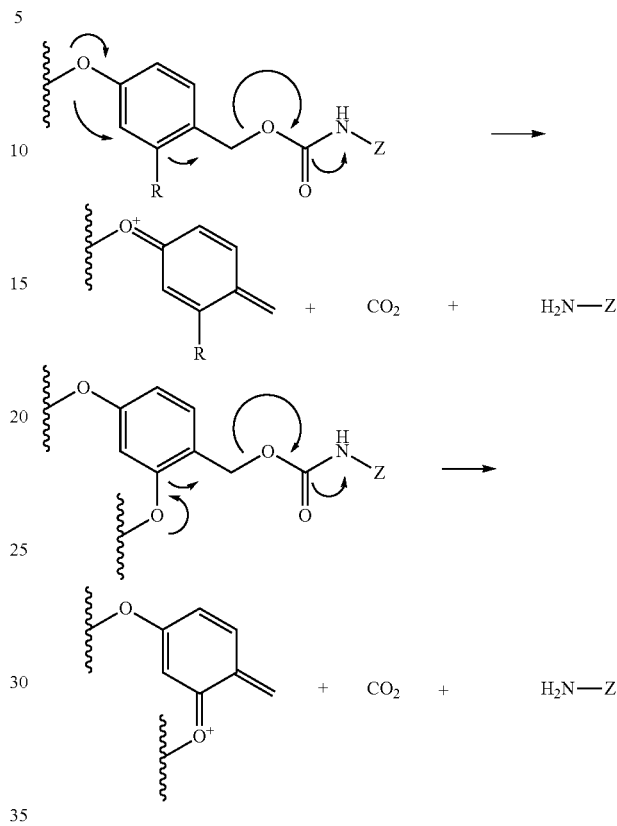

Other illustrative mechanisms for bond cleavage of the releasable linker include oxonium-assisted cleavage as follows:

where X is an exogenous or endogenous nucleophile, glutathione, or bioreducing agent, and the like, and either of Z or Z' is a PSMA binding ligand, or a drug, therapeutic agent, diagnostic agent, or imaging agent, or either of Z or Z' is a PSMA binding ligand, or a drug, therapeutic agent, diagnostic agent, or imaging agent connected through other portions of the bivalent linker. It is to be understood that although the above fragmentation mechanisms are depicted as concerted mechanisms, any number of discrete steps may take place to effect the ultimate fragmentation of the bivalent linker to the final products shown. For example, it is appreciated that the bond cleavage may also occur by acid catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing bivalent linkers, following an illustrative breaking of the disulfide bond, the resulting phenyl thiolate may further fragment to release a carbonic acid or carbamic acid moiety by forming a resonance stabilized intermediate. In any of these cases, the releaseable nature of the illustrative bivalent linkers described herein may be realized by whatever mechanism may be relevant to the chemical, metabolic, physiological, or biological conditions present.

where Z is the vitamin, or analog or derivative thereof, or the drug, or analog or derivative thereof, or each is a vitamin or drug moiety in conjunction with other portions of the polyvalent linker, such as a drug or vitamin moiety including one or more spacer linkers and/or other releasable linkers. In this embodiment, acid-catalyzed elimination of the carbamate leads to the release of $CO_2$ and the nitrogen-containing moiety attached to Z, and the formation of a benzyl cation, which may be trapped by water, or any other Lewis base.

In one embodiment, the releasable linker includes a disulfide.

In another embodiment, the releasable linker may be a divalent radical comprising alkyleneaziridin-1-yl, alkylenecarbonylaziridin-1-yl, alkylenesulfoxylaziridin-1-yl, sulfoxylalkylaziridin-1-yl, sulfonylalkylaziridin-1-yl, or alkylenesulfonylaziridin-1-yl, wherein each of the releasable linkers is optionally substituted with a substituent $X^2$, as defined below.

Additional illustrative releasable linkers include methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio, wherein each of the releasable linkers is optionally substituted with a substituent $X^2$, as defined below.

In the preceding embodiment, the releasable linker may include oxygen, and the releasable linkers can be methylene, 1-alkoxyalkylene, 1-alkoxycycloalkylene, 1-alkoxyalkylenecarbonyl, and 1-alkoxycycloalkylenecarbonyl, wherein each of the releasable linkers is optionally substituted with a substituent $X^2$, as defined below, and the releasable linker is bonded to the oxygen to form an acetal or ketal. Alternatively, the releasable linker may include oxygen, and the releasable linker can be methylene, wherein the methylene is substituted with an optionally-substituted aryl, and the releasable linker is bonded to the oxygen to form an acetal or ketal. Further, the releasable linker may include oxygen, and the releasable linker can be sulfonylalkyl, and the releasable linker is bonded to the oxygen to form an alkylsulfonate.

In another embodiment of the above releasable linker embodiment, the releasable linker may include nitrogen, and the releasable linkers can be iminoalkylidenyl, carbonylalkylideniminyl, iminocycloalkylidenyl, and carbonylcycloalkylideniminyl, wherein each of the releasable linkers is optionally substituted with a substituent $X^2$, as defined below, and the releasable linker is bonded to the nitrogen to form an hydrazone. In an alternate configuration, the hydrazone may be acylated with a carboxylic acid derivative, an orthoformate derivative, or a carbamoyl derivative to form various acylhydrazone releasable linkers.

Alternatively, the releasable linker may include oxygen, and the releasable linkers can be alkylene(dialkylsilyl), alkylene(alkylarylsilyl), alkylene(diarylsilyl), (dialkylsilyl)aryl, (alkylarylsilyl)aryl, and (diarylsilyl)aryl, wherein each of the releasable linkers is optionally substituted with a substituent $X^2$, as defined below, and the releasable linker is bonded to the oxygen to form a silanol.

In the above releasable linker embodiment, the drug can include a nitrogen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom nitrogen to form an amide, and also bonded to the drug nitrogen to form an amide.

In the above releasable linker embodiment, the drug can include an oxygen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can form an amide, and also bonded to the drug oxygen to form an ester.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the releasable linker can include nitrogen, and the substituent $X^2$ and the releasable linker can form an heterocycle.

The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

In one embodiment, the polyvalent linkers described herein are or include compounds of the following formulae:

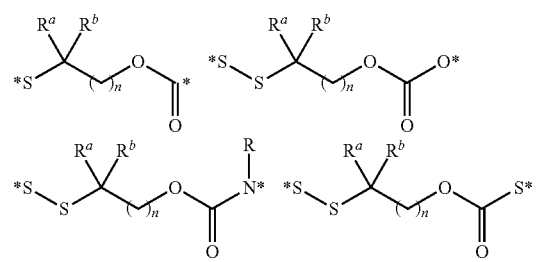

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein are or include compounds of the following formulae

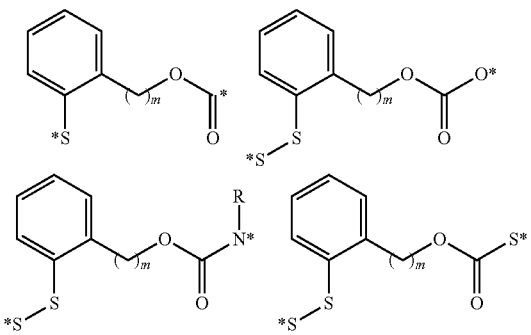

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein are or include compounds of the following formulae

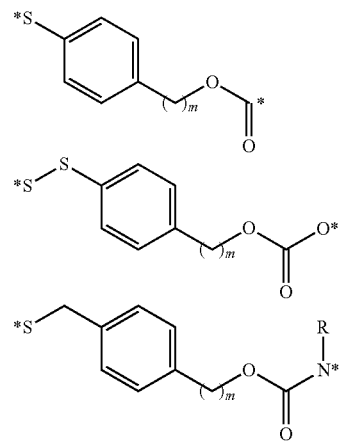

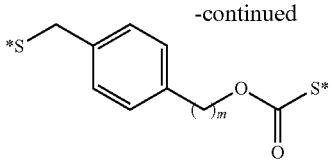

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the linker L includes one or more spacer linkers. Such spacer linkers can be 1-alkylenesuccinimid-3-yl, optionally substituted with a substituent $X^1$, as defined below, and the releasable linkers can be methylene, 1-alkoxyalkylene, 1-alkoxycycloalkylene, 1-alkoxyalkylenecarbonyl, 1-alkoxycycloalkylenecarbonyl, wherein each of the releasable linkers is optionally substituted with a substituent $X^2$, as defined below, and wherein the spacer linker and the releasable linker are each bonded to the spacer linker to form a succinimid-1-ylalkyl acetal or ketal.

The spacer linkers can be carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of the spacer linkers is optionally substituted with a substituent $X^1$ as defined below. In this embodiment, the spacer linker may include an additional nitrogen, and the spacer linkers can be alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and the spacer linker is bonded to the nitrogen to form an amide. Alternatively, the spacer linker may include an additional sulfur, and the spacer linkers can be alkylene and cycloalkylene, wherein each of the spacer linkers is optionally substituted with carboxy, and the spacer linker is bonded to the sulfur to form a thiol. In another embodiment, the spacer linker can include sulfur, and the spacer linkers can be 1-alkylenesuccinimid-3-yl and 1-(carbonylalkyl)succinimid-3-yl, and the spacer linker is bonded to the sulfur to form a succinimid-3-ylthiol.

In an alternative to the above-described embodiments, the spacer linker can include nitrogen, and the releasable linker can be a divalent radical comprising alkyleneaziridin-1-yl, carbonylalkylaziridin-1-yl, sulfoxylalkylaziridin-1-yl, or sulfonylalkylaziridin-1-yl, wherein each of the releasable linkers is optionally substituted with a substituent $X^2$, as defined below. In this alternative embodiment, the spacer linkers can be carbonyl, thionocarbonyl, alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and wherein the spacer linker is bonded to the releasable linker to form an aziridine amide.

The substituents $X^1$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides.

In this embodiment the spacer linker can include nitrogen, and the substituent $X^1$ and the spacer linker to which they are bound to form an heterocycle.

Additional illustrative spacer linkers include alkyleneamino-alkylenecarbonyl, alkylene-thio-(carbonylalkylsuccinimid-3-yl), and the like, as further illustrated by the following formulae:

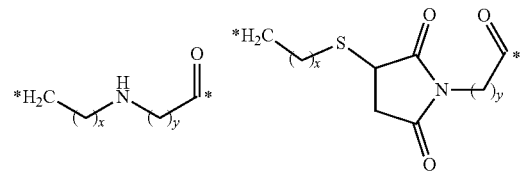

where the integers x and y are 1, 2, 3, 4, or 5:

In another embodiment, linkers that include hydrophilic regions are also described. In one aspect, the hydrophilic region of the linker forms part or all of a spacer linker included in the conjugates described herein. Illustrative hydrophilic spacer linkers are described in PCT international application serial No. PCT/US2008/068093, filed Jun. 25, 2008, the disclosure of which is incorporated herein by reference.

The term "cycloalkyl" as used herein includes molecular fragments or radicals comprising a bivalent chain of carbon atoms, a portion of which forms a ring. It is to be understood that the term cycloalkyl as used herein includes fragments and radicals attached at either ring atoms or non-ring atoms, such as, such as cyclopropyl, cyclohexyl, 3-ethylcyclopent-1-yl, cyclopropylethyl, cyclohexylmethyl, and the like.

The term "cycloalkylene" as used herein includes molecular fragments or radicals comprising a bivalent chain of carbon atoms, a portion of which forms a ring. It is to be understood that the term cycloalkyl as used herein includes fragments and radicals attached at either ring atoms or non-ring atoms, such as cycloprop-1,1-diyl, cycloprop-1,2-diyl, cyclohex-1,4-diyl, 3-ethylcyclopent-1,2-diyl, 1-methylenecyclohex-4-yl, and the like.

The terms "heteroalkyl" and "heteroalkylene" as used herein includes molecular fragments or radicals comprising monovalent and divalent, respectively, groups that are formed from a linear or branched chain of carbon atoms and heteroatoms, wherein the heteroatoms are selected from nitrogen, oxygen, and sulfur, such as alkoxyalkyl, alkyleneoxyalkyl, aminoalkyl, alkylaminoalkyl, alkyleneaminoalkyl, alkylthioalkyl, alkylenethioalkyl, alkoxyalkylaminoalkyl, alkyl aminoalkoxyalkyl, alkyleneoxyalkylaminoalkyl, and the like.

The term "heterocyclyl" as used herein includes molecular fragments or radicals comprising a monovalent chain of carbon atoms and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like. Accordingly, as used herein, heterocyclyl includes alkylheterocyclyl, heteroalkylheterocyclyl, heterocyclylalkyl, heterocyclylheteroalkyl, and the like. It is to be understood that the term heterocyclyl as used herein includes fragments and radicals attached at either ring atoms or non-ring atoms, such as tetrahydrofuran-2-yl, piperidin-1-yl, piperidin-4-yl, piperazin-1-yl, morpholin-1-yl, tetrahydrofuran-2-ylmethyl, piperidin-1-ylethyl, piperidin-4-ylmethyl, piperazin-1-ylpropyl, morpholin-1-ylethyl, and the like.

The term "aryl" as used herein includes molecular fragments or radicals comprising an aromatic mono or polycyclic ring of carbon atoms, such as phenyl, naphthyl, and the like.

The term "heteroaryl" as used herein includes molecular fragments or radicals comprising an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term "substituted aryl" or "substituted heteroaryl" as used herein includes molecular fragments or radicals comprising aryl or heteroaryl substituted with one or more substituents, such as alkyl, heteroalkyl, halo, hydroxy, amino, alkyl or dialkylamino, alkoxy, alkylsulfonyl, aminosulfonyl, carboxylate, alkoxycarbonyl, aminocarbonyl, cyano, nitro, and the like. It is to be understood that the alkyl groups in such substituents may be optionally substituted with halo.

The term "iminoalkylidenyl" as used herein includes molecular fragments or radicals comprising a divalent radical containing alkylene as defined herein and a nitrogen atom, where the terminal carbon of the alkylene is double-bonded to the nitrogen atom, such as the formulae —(CH)═N—, —(CH$_2$)$_2$(CH)═N—, —CH$_2$C(Me)═N—, and the like.

The term "amino acid" as used herein includes molecular fragments or radicals comprising an aminoalkylcarboxylate, where the alkyl radical is optionally substituted with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like.

For example, in one embodiment, amino acid is a divalent radical having the general formula:

—N(R)—(CR'R")$_q$—C(O)— where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornitine, threonine, and the like. In one variation, the amino acid may be selected from phenylalanine, tyrosine, and the like, derivatives thereof, and substituted variants thereof.

The terms "arylalkyl" and "heteroarylalkyl" as used herein includes molecular fragments or radicals comprising aryl and heteroaryl, respectively, as defined herein substituted with a linear or branched alkylene group, such as benzyl, phenethyl, α-methylbenzyl, picolinyl, pyrimidinylethyl, and the like.

It is to be understood that the above-described terms can be combined to generate chemically-relevant groups, such as "haloalkoxyalkyl" referring to for example trifluoromethyloxyethyl, 1,2-difluoro-2-chloroeth-1-yloxypropyl, and the like.

The term "amino acid derivative" as used herein refers generally to aminoalkylcarboxylate, where the amino radical or the carboxylate radical are each optionally substituted with alkyl, carboxylalkyl, alkylamino, and the like, or optionally protected; and the intervening divalent alkyl fragment is optionally substituted with alkyl, hydroxy alkyl, sulfhydrylalkyl, aminoalkyl, carboxyalkyl, and the like, including groups corresponding to the side chains found in naturally occurring amino acids, such as are found in serine, cysteine, methionine, aspartic acid, glutamic acid, and the like.

The term "peptide" as used herein includes molecular fragments or radicals comprising a series of amino acids and amino acid analogs and derivatives covalently linked one to the other by amide bonds.

In another embodiment, the bivalent linker comprises a spacer linker and a releasable linker taken together to form 3-thiosuccinimid-1-ylalkyloxymethyloxy, where the methyl is optionally substituted with alkyl or substituted aryl.

In another embodiment, the bivalent linker comprises a spacer linker and a releasable linker taken together to form 3-thiosuccinimid-1-ylalkylcarbonyl, where the carbonyl forms an acylaziridine with the drug, or analog or derivative thereof.

In another embodiment, the bivalent linker comprises an a spacer linker and a releasable linker taken together to form 1-alkoxycycloalkylenoxy.

In another embodiment, the bivalent linker comprises a spacer linker and a releasable linker taken together to form alkyleneaminocarbonyl(dicarboxylarylene)carboxylate.

In another embodiment, the bivalent linker comprises a releasable linker, a spacer linker, and a releasable linker taken together to form dithioalkylcarbonylhydrazide, where the hydrazide forms an hydrazone with the drug, or analog or derivative thereof.

In another embodiment, the bivalent linker comprises a spacer linker and a releasable linker taken together to form 3-thiosuccinimid-1-ylalkylcarbonylhydrazide, where the hydrazide forms an hydrazone with the drug, or analog or derivative thereof.

In another embodiment, the bivalent linker comprises a spacer linker and a releasable linker taken together to form 3-thioalkylsulfonylalkyl(disubstituted silyl)oxy, where the disubstituted silyl is substituted with alkyl or optionally substituted aryl.

In another embodiment, the bivalent linker comprises a plurality of spacer linkers selected from the group consisting of the naturally occurring amino acids and stereoisomers thereof.

In another embodiment, the bivalent linker comprises a releasable linker, a spacer linker, and a releasable linker taken together to form 3-dithioalkyloxycarbonyl, where the carbonyl forms a carbonate with the drug, or analog or derivative thereof.

In another embodiment, the bivalent linker comprises a releasable linker, a spacer linker, and a releasable linker taken together to form 3-dithioarylalkyloxycarbonyl, where the carbonyl forms a carbonate with the drug, or analog or derivative thereof, and the aryl is optionally substituted.

In another embodiment, the bivalent linker comprises a spacer linker and a releasable linker taken together to form 3-thiosuccinimid-1-ylalkyloxyalkyloxyalkylidene, where the alkylidene forms an hydrazone with the drug, or analog or derivative thereof, each alkyl is independently selected, and the oxyakloxy is optionally substituted with alkyl or optionally substituted aryl.

In another embodiment, the bivalent linker comprises a releasable linker, a spacer linker, and a releasable linker taken together to form 3-dithioalkyloxycarbonylhydrazide.

In another embodiment, the bivalent linker comprises a releasable linker, a spacer linker, and a releasable linker taken together to form 3-dithioalkylamino, where the amino forms a vinylogous amide with the drug, or analog or derivative thereof.

In another embodiment, the bivalent linker comprises a releasable linker, a spacer linker, and a releasable linker taken together to form 3-dithioalkylamino, where the amino forms a vinylogous amide with the drug, or analog or derivative thereof, and the alkyl is ethyl.

In another embodiment, the bivalent linker comprises a releasable linker, a spacer linker, and a releasable linker taken together to form 3-dithioalkylaminocarbonyl, where the carbonyl forms a carbamate with the drug, or analog or derivative thereof.

In another embodiment, the bivalent linker comprises a releasable linker, a spacer linker, and a releasable linker taken together to form 3-dithioalkylaminocarbonyl, where the carbonyl forms a carbamate with the drug, or analog or derivative thereof, and the alkyl is ethyl.

In another embodiment, the bivalent linker comprises a releasable linker, a spacer linker, and a releasable linker taken together to form 3-dithioarylalkyloxycarbonyl, where the carbonyl forms a carbamate or a carbamoylaziridine with the drug, or analog or derivative thereof.

In another embodiment, the polyvalent linker includes spacer linkers and releasable linkers connected to form a polyvalent 3-thiosuccinimid-1-ylalkyloxymethyloxy group, illustrated by the following formula

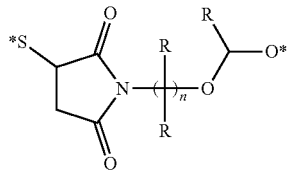

where n is an integer from 1 to 6, the alkyl group is optionally substituted, and the methyl is optionally substituted with an additional alkyl or optionally substituted aryl group, each of which is represented by an independently selected group R. The (*) symbols indicate points of attachment of the polyvalent linker fragment to other parts of the conjugates described herein.

In another embodiment, the polyvalent linker includes spacer linkers and releasable linkers connected to form a polyvalent 3-thiosuccinimid-1-ylalkylcarbonyl group, illustrated by the following formula

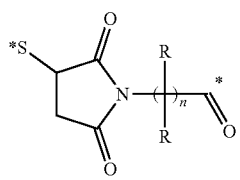

where n is an integer from 1 to 6, and the alkyl group is optionally substituted. The (*) symbols indicate points of attachment of the polyvalent linker fragment to other parts of the conjugates described herein. In another embodiment, the polyvalent linker includes spacer linkers and releasable linkers connected to form a polyvalent 3-thioalkylsulfonyl-alkyl(disubstituted silyl)oxy group, where the disubstituted silyl is substituted with alkyl and/or optionally substituted aryl groups.

In another embodiment, the polyvalent linker includes spacer linkers and releasable linkers connected to form a polyvalent dithioalkylcarbonylhydrazide group, or a polyvalent 3-thiosuccinimid-1-ylalkylcarbonylhydrazide, illustrated by the following formulae

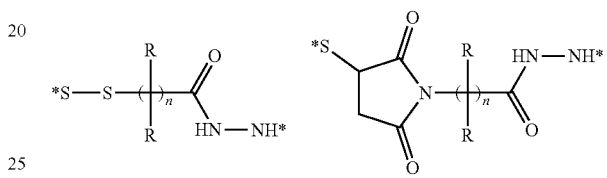

where n is an integer from 1 to 6, the alkyl group is optionally substituted, and the hydrazide forms an hydrazone with (B), (D), or another part of the polyvalent linker (L). The (*) symbols indicate points of attachment of the polyvalent linker fragment to other parts of the conjugates described herein.

In another embodiment, the polyvalent linker includes spacer linkers and releasable linkers connected to form a polyvalent 3-thiosuccinimid-1-ylalkyloxyalkyloxyalkylidene group, illustrated by the following formula

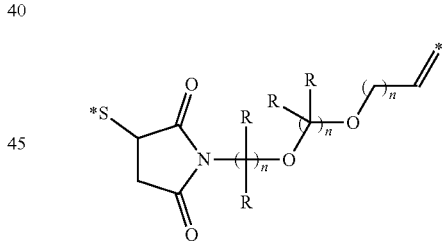

where each n is an independently selected integer from 1 to 6, each alkyl group independently selected and is optionally substituted, such as with alkyl or optionally substituted aryl, and where the alkylidene forms an hydrazone with (B), (D), or another part of the polyvalent linker (L). The (*) symbols indicate points of attachment of the polyvalent linker fragment to other parts of the conjugates described herein.

Additional illustrative linkers are described in WO 2006/012527, the disclosure of which is incorporated herein by reference. Additional linkers are described in the following Table, where the (*) atom is the point of attachment of additional spacer or releasable linkers, the drug, and/or the binding ligand.

Illustrative releasable linkers.
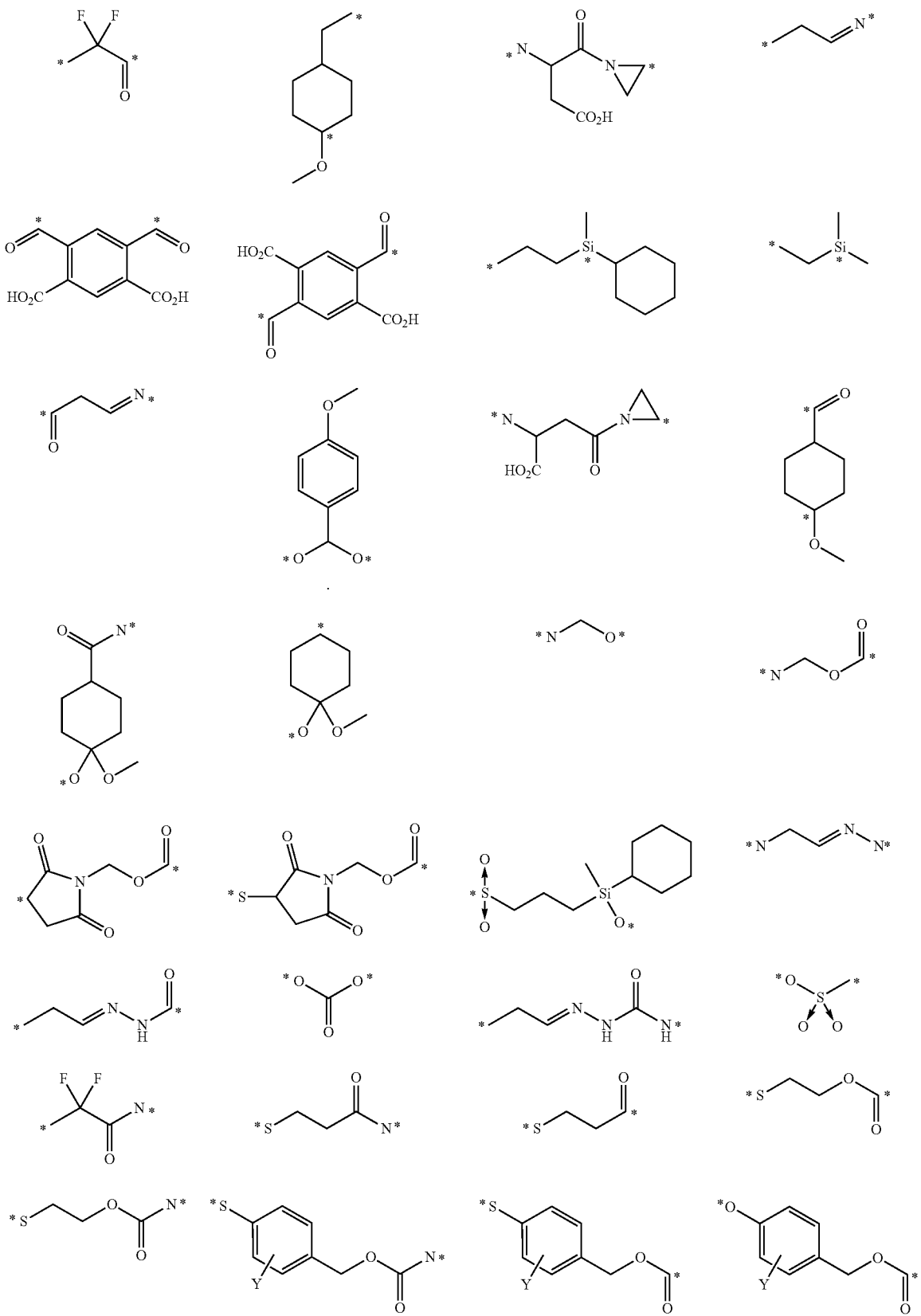

Illustrative releasable linkers.

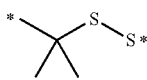 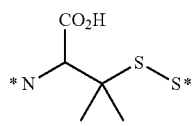 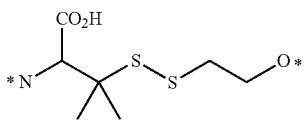

Each of the spacer and releasable linkers described herein is bivalent. In addition, the connections between spacer linkers, releasable linkers, drugs D and ligands B may occur at any atom found in the various spacer linkers, releasable linkers, drugs D, and ligands B.

The drug can include a nitrogen atom, and the releasable linker can be haloalkylenecarbonyl, optionally substituted with a substituent $X^2$, and the releasable linker is bonded to the drug nitrogen to form an amide.

The drug can include an oxygen atom, and the releasable linker can be haloalkylenecarbonyl, optionally substituted with a substituent $X^2$, and the releasable linker is bonded to the drug oxygen to form an ester.

The drug can include a double-bonded nitrogen atom, and in this embodiment, the releasable linkers can be alkylenecarbonylamino and 1-(alkylenecarbonylamino)succinimid-3-yl, and the releasable linker can be bonded to the drug nitrogen to form an hydrazone.

The drug can include a sulfur atom, and in this embodiment, the releasable linkers can be alkylenethio and carbonylalkylthio, and the releasable linker can be bonded to the drug sulfur to form a disulfide.

In another embodiment, the binding or targeting ligand capable of binding or targeting PSMA is a phosphoric, phosphonic, or phosphinic acid or derivative thereof. In one aspect, the phosphoric, phosphonic, or phosphinic acid or derivative thereof includes one or more carboxylic acid groups. In another aspect, the phosphoric, phosphonic, or phosphinic acid or derivative thereof includes one or more thiol groups or derivatives thereof. In another aspect, the phosphoric, phosphonic, or phosphinic acid or derivative thereof includes one or more carboxylic acid bioisosteres, such as an optionally substituted tetrazole, and the like.

In another embodiment, the PSMA ligand is a derivative of pentanedioic acid. Illustratively, the pentanedioic acid derivative is a compound of the formula:

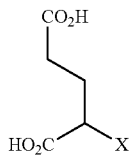

wherein X is $RP(O)(OH)CH_2$— (see, e.g., U.S. Pat. No. 5,968,915 incorporated herein by reference); $RP(O)(OH)N(R^1)$— (see, e.g., U.S. Pat. No. 5,863,536 incorporated herein by reference); $RP(O)(OH)O$— (see, e.g., U.S. Pat. No. 5,795,877 incorporated herein by reference); $RN(OH)C(O)Y$— or $RC(O)NH(OH)Y$, wherein Y is —$CR_1R_2$—, —$NR_3$— or —O— (see, e.g., U.S. Pat. No. 5,962,521 incorporated herein by reference); $RS(O)Y$, $RSO_2Y$, or $RS(O)(NH)Y$, wherein Y is —$CR_1R_2$—, —$NR_3$— or —O— (see, e.g., U.S. Pat. No. 5,902,817 incorporated herein by reference); and RS-alkyl, wherein R is for example hydrogen, alkyl, aryl, or arylalkyl, each of which may be optionally substituted (see, e.g., J. Med. Chem. 46:1989-1996 (2003) incorporated herein by reference).

In each of the foregoing formulae, R, $R_1$, $R_2$, and $R_3$ are each independently selected from hydrogen, $C_1$-$C_9$ straight or branched chain alkyl, $C_2$-$C_9$ straight or branched chain alkenyl, $C_3$-$C_8$ cycloalkyl, $C_5$-$C_7$ cycloalkenyl, and aryl. In addition, in each case, each of R, $R_1$, $R_2$, and $R_3$ may be optionally substituted, such as with one or more groups selected from $C_3$-$C_8$ cycloalkyl, $C_5$-$C_7$ cycloalkenyl, halo, hydroxy, nitro, trifluoromethyl, $C_1$-$C_6$ straight or branched chain alkyl, $C_2$-$C_6$ straight or branched chain alkenyl, $C_1$-$C_4$ alkoxy, $C_2$-$C_4$ alkenyloxy, phenoxy, benzyloxy, amino, aryl. In one aspect, aryl is selected from 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl, and phenyl, and in each case aryl may be optionally substituted with one or more, illustratively with one to three, groups selected from halo, hydroxy, nitro, trifluoromethyl, $C_1$-$C_6$ straight or branched chain alkyl, $C_2$-$C_6$ straight or branched chain alkenyl, $C_1$-$C_4$ alkoxy, $C_2$-$C_4$ alkenyloxy, phenoxy, benzyloxy, and amino. In one variation of each of the above formulae, R is not hydrogen.

Illustrative PSMA ligands described in U.S. Pat. No. 5,968,915 include 2-[[methylhydroxyphosphinyl]methyl]pentanedioic acid; 2-[[ethylhydroxyphosphinyl]methyl]pentanedioic acid; 2-[[propylhydroxyphosphinyl]methyl]pentanedioic acid; 2-[[butylhydroxyphosphinyl]methyl]pentanedioic acid; 2-[[cyclohexylhydroxyphosphinyl]methyl]pentanedioic acid; 2-[[phenylhydroxyphosphinyl]methyl]pentanedioic acid; 2-[[2-(tetrahydrofuranyl)hydroxyphosphinyl]methyl]pentanedioic acid; 2-[[(2-tetrahydropyranyl)hydroxyphosphinyl]methyl]pentanedioic acid; 2-[[((4-pyridyl)methyl)hydroxyphosphinyl]methyl] pentanedioic acid; 2-[[((2-pyridyl)methyl)hydroxyphosphinyl]methyl] pentanedioic acid; 2-[[(phenylmethyl)hydroxyphosphinyl]methyl]pentanedioic acid; 2-[[((2-phenylethyl)methyl)hydroxyphosphinyl]methyl]pentanedioic acid; 2[[((3-phenylpropyl) methyl)phydroxyphosphinyl]methyl] pentanedioic acid; 2-[[((3-phenylbutyl)methyl)hydroxyphosphinyl]methyl]pentanedioic acid; 2-[[((2-phenylbutyl)methyl)hydroxyphosphinyl]methyl]pentanedioic acid; 2-[[(4-phenylbutyl)hydroxyphosphinyl]methyl]pentanedioic acid; and 2-[[(aminomethy)hydroxyphosphinyl]methyl]pentanedioic acid.

Illustrative PSMA ligands described in U.S. Pat. No. 5,863,536 include N-[methylhydroxyphosphinyl]glutamic acid; N[ethylhydroxyphosphinyl]glutamic acid; N-[propylhydroxyphosphinyl]glutamic acid; N[butylhydroxyphosphinyl]glutamic acid; N-[phenylhydroxyphosphinyl]glutamic acid; N-[(phenylmethyl)hydroxyphosphinyl]glutamic acid; N-[((2-phenylethyl)methyl)hydroxyphosphinyl]glutamic acid; and N-methyl-N-[phenylhydroxyphosphinyl]glutamic acid.

Illustrative PSMA ligands described in U.S. Pat. No. 5,795,877 include 2-[[methylhydroxyphosphinyl]oxy]pentanedioic acid; 2-[[ethylhydroxyphosphinyl]oxy]pentanedioic acid; 2-[[propylhydroxyphosphinyl]oxy]pentanedioic acid; 2-[[butylhydroxyphosphinyl]oxy] pentanedioic acid; 2-[[phenylhydroxyphosphinyl]oxy] pentanedioic acid; 2-[[((4-pyridyl)methyl) hydroxyphosphinyl]oxy]pentanedioic acid; 2-[[((2-pyridyl) methyphydroxyphosphinyl]oxy]pentanedioic acid; 2-[[(phenylmethyl)hydroxyphosphinyl]oxy]pentanedioic acid; and 2[[((2-phenylethyl)methyl)hydroxyphosphinyl] oxy] pentanedioic acid.

Illustrative PSMA ligands described in U.S. Pat. No. 5,962,521 include 2-[[(N-hydroxy)carbamoyl]methyl]pentanedioic acid; 2-[[(N-hydroxy-N-methy)carbamoyl] methyl]pentanedioic acid; 2-[[(N-butyl-N-hydroxy) carbamoyl]methyl]pentanedioic acid; 2-[[(N-benzyl-N-hydroxy)carbamoyl]methyl]pentanedioic acid; 2-[[(N-hydroxy-N-phenyl)carbamoyl]methyl]pentanedioic acid; 2-[[(N-hydroxy-N-2-phenylethyl)carbamoyl]methyl]pentanedioic acid; 2-[[(N-ethyl-N-hydroxy) carbamoyl]methyl] pentanedioic acid; 2-[[(N-hydroxy-N-propyl)carbamoyl] methyl]pentanedioic acid; 2-[[(N-hydroxy-N-3-phenylpropyl)carbamoyl]methyl]pentanedioic acid; 2-[[(N-hydroxy-N-4-pyridyl) carbamoyl]methyl]pentanedioic acid; 2-[[(N-hydroxy)carboxamido]methyl]pentanedioic acid; 2-[[N-hydroxy (methyl) carboxamido]methyl]pentanedioic acid; 2-[[N-hydroxy (benzyl) carboxamido]methyl]pentanedioic acid; 2-[[N-hydroxy(phenyl)carboxamido]methyl] pentanedioic acid; 2-[[N-hydroxy(2-phenylethyl)carboxamido]methyl]pentanedioic acid; 2-[[N-hydroxy(ethyl) carboxamido]methyl]pentanedioic acid; 2-[[N-hydroxy (propyl) carboxamido]methyl]pentanedioic acid; 2-[[N-hydroxy (3-phenylpropyl) carboxamido]methyl] pentanedioic acid; and 2-[[N-hydroxy(4-pyridyl) carboxamido]methyl]pentanedioic acid.

Illustrative PSMA ligands described in U.S. Pat. No. 5,902,817 include 2-[(sulfinyl)methyl]pentanedioic acid; 2-[(methylsulfinyl)methyl]pentanedioic acid; 2-[(ethylsulfinyl)methyl]pentanedioic acid; 2-[(propylsulfinyl)methyl] pentanedioic acid; 2-[(butylsulfinyl)methyl]pentanedioic acid; 2-[(phenylsulfinyl)methyl]pentanedioic acid; 2-[[(2-phenylethyl)sulfinyl]methyl]pentanedioic acid; 2-[[(3-phenylpropyl)sulfinyl]methyl]pentanedioic acid; 2-[[(4-pyridyl) sulfinyl]methyl]pentanedioic acid; 2-[(benzylsulfinyl) methyl]pentanedioic acid; 2-[[(sulfonyl)methyl] pentanedioic acid; 2-[(methylsulfonyl)methyl]pentanedioic acid; 2-[(ethylsulfonyl)methyl]pentanedioic acid; 2-[(propylsulfonyl)methyl]pentanedioic acid; 2-[(butylsulfonyl) methyl]pentanedioic acid; 2-[(phenylsulfonyl) methyl]pentanedioic acid; 2-[[(2-phenylethyl)sulfonyl]methyl] pentanedioic acid; 2-[[(3-phenylpropyl)sulfonyl]methyl] pentanedioic acid; 2-[[(4-pyridyl) sulfonyl]methyl] pentanedioic acid; 2-(benzylsulfonyl)methyl]pentanedioic acid; 2-[(sulfoximinyl)methyl]pentanedioic acid; 2-[(methylsulfoximinyl)methyl]pentanedioic acid; 2-[(ethylsulfoximinyl)methyl]pentanedioic acid; 2-[(propylsulfoximinyl) methyl]pentanedioic acid; 2-[(butylsulfoximinyl)methyl] pentanedioic acid; 2-[(phenylsulfoximinyl)methyl] pentanedioic acid; 2-[[(2-phenylethyl)sulfoximinyl]methyl] pentanedioic acid; 2-[[(3-phenylpropyl) sulfoximinyl] methyl]pentanedioic acid; 2-[[(4-pyridyl)sulfoximinyl] methyl]pentanedioic acid; and 2-[(benzylsulfoximinyl) methyl]pentanedioic acid.

Pentanedioic acid derivatives described herein have been reported to have high binding affinity at PSMA, including but not limited to the following phosphonic and phosphinic acid derivatives

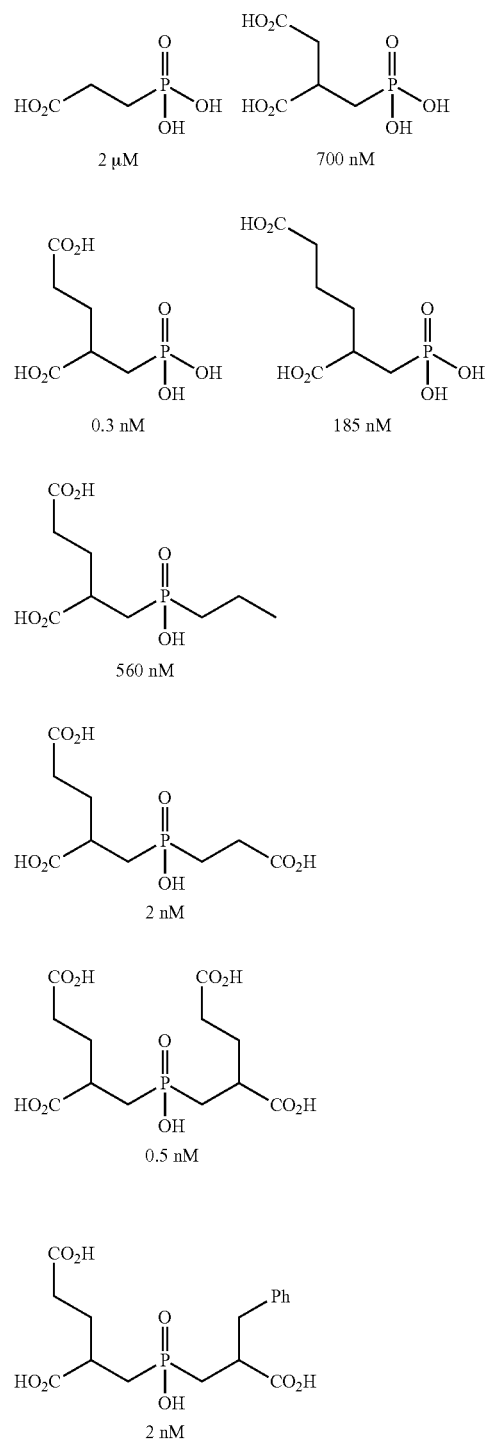

with the dissociation constants ($K_i$; values) shown for the E-I complex (see, Current Medicinal Chem. 8:949-.957 (2001); Silverman, "The Organic Chemistry of Drug Design and Drug Action," Elsevier Academic Press ($2^{nd}$ Ed. 2003), the disclosures of which are incorporated herein by reference);

In another illustrative embodiment, the pentanedioic acid derivative includes a thiol group, such as compounds of the following formulae:

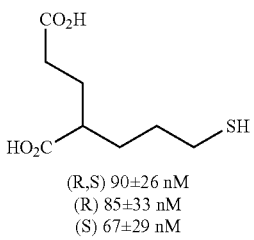 [SMILES: O=C(O)CCC(CCCS)C(=O)O]

(R,S) 90±26 nM
(R) 85±33 nM
(S) 67±29 nM with the inhibition constants ($IC_{50}$ values) shown for the E-I complex.

In another embodiment, the PSMA ligand is a urea of two amino acids. In one aspect, the amino acids include one or more additional carboxylic acids. In another aspect, the amino acids include one or more additional phosphoric, phosphonic, phosphinic, sulfinic, sulfonic, or boronic acids. In another aspect, the amino acids include one or more thiol groups or derivatives thereof. In another aspect, the amino acids includes one or more carboxylic acid bioisosteres, such as tetrazoles and the like.

In another embodiment, the PSMA ligand is a aminocarbonyl derivative of pentanedioic acid. Illustratively, the aminocarbonylpentanedioic acid derivative is a compound of the formula:

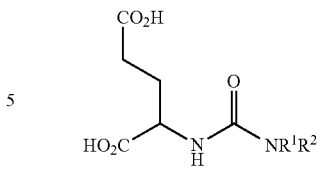

wherein $R^1$ and $R^2$ are each selected from hydrogen, optionally substituted carboxylic acids, such as thiolacetic acids, thiolpropionic acids, and the like; malonic acids, succinic acids, glutamic acids, adipic acids, and the like; and others. Illustrative aminocarbonylpentanedioic acid derivatives are described in J. Med. Chem. 44:298-301 (2001) and J. Med. Chem. 47:1729-38 (2004), the disclosures of which are incorporated herein by reference.

In another embodiment, the PSMA ligand is a compound of the formula:

It is appreciated that the urea compounds described herein may also be advantageous in the preparation of the ligands also described herein due to the sub-nanomolar potency, water solubility, and/or long term stability of these compounds. The urea compounds described herein may generally be prepared from commercially available starting materials as described herein.

It is appreciated that in each of the above illustrative pentanedioic acid compounds and urea compounds, there is at least one asymmetric carbon atom. Accordingly, the above illustrative formulae are intended to refer both individually and collectively to all stereoisomers as pure enantiomers, or mixtures of enantiomers and/or diastereomers, including but not limited to racemic mixtures, mixtures that include one epimer at a first asymmetric carbon but allow mixtures at other asymmetric carbons, including racemic mixtures, and the like.

In another illustrative embodiment, the binding agent is a urea of an amino dicarboxylic acid, such as aspartic acid, glutamic acid, and the like, and another amino dicarboxylic acid, or an analog thereof, such as a binding agent of the formulae

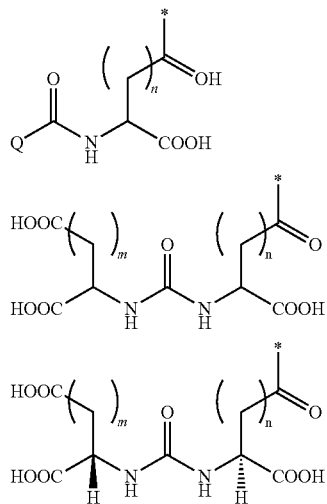

wherein Q is a an amino dicarboxylic acid, such as aspartic acid, glutamic acid, or an analog thereof, n and m are each selected from an integer between 1 and about 6, and (*) represents the point of attachment for the linker L.

In another embodiment, the PSMA ligand includes at least four carboxylic acid groups, or at least three free carboxylic acid groups after the PSMA ligand is conjugated to the agent or linker. It is understood that as described herein, carboxylic acid groups on the PSMA ligand include bioisosteres of carboxylic acids.

Illustratively, the PSMA ligand is a compound of the formulae:

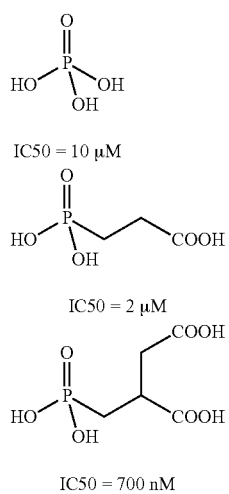

-continued

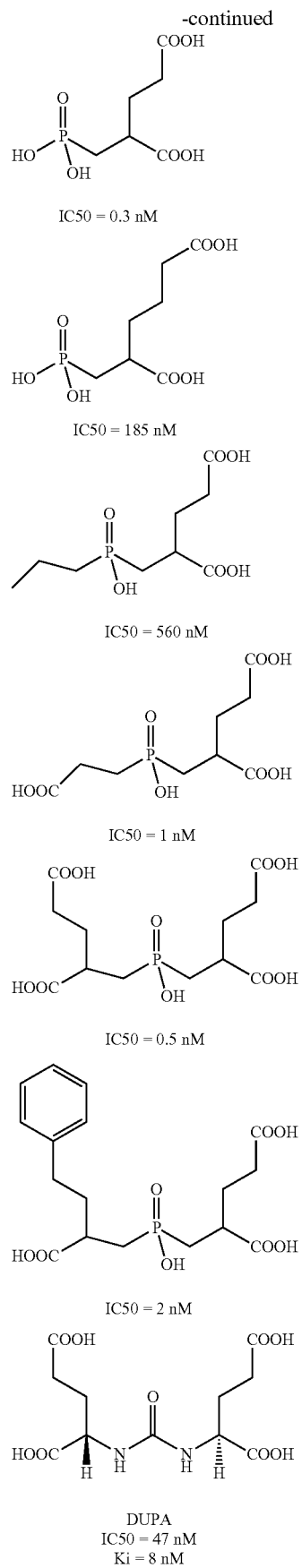

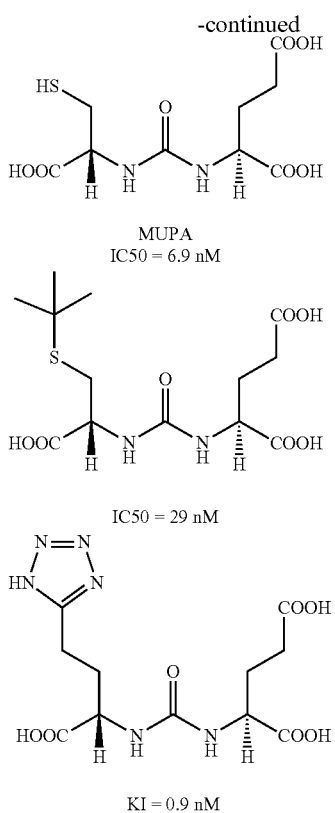

MUPA
IC50 = 6.9 nM

IC50 = 29 nM

KI = 0.9 nM

In another embodiment, the PSMA ligand is 2-[3-(1-Carboxy-2-mercapto-ethyl)-ureido]-pentanedioic acid (MUPA) or 2-[3-(1,3-Dicarboxy-propyl)-ureido]-pentanedioic acid (DUPA)

Other illustrative examples of PSMA ligands include peptide analogs such as quisqualic acid, aspartate glutamate (Asp-Glu), Glu-Glu, Gly-Glu, γ-Glu-Glu, beta-N-acetyl-L-aspartate-L-glutamate (β-NAAG), and the like.

In another illustrative embodiment, the binding agent is a urea of an amino dicarboxylic acid, such as aspartic acid, glutamic acid, and the like, and another amino dicarboxylic acid, or an analog thereof, and the linker is peptide of amino acids, including naturally occurring and non-naturally occurring amino acids. In one embodiment, the linker is a peptide comprising amino acids selected from Glu, Asp, Phe, Cys, beta-amino Ala, and aminoalkylcarboxylic acids, such as Gly, beta Ala, amino valeric acid, amino caproic acid, and the like. In another embodiment, the linker is a peptide consisting of amino acids selected from Glu, Asp, Phe, Cys, beta-amino Ala, and aminoalkylcarboxylic acids, such as Gly, beta Ala, amino valeric acid, amino caproic acid, and the like. In another embodiment, the linker is a peptide comprising at least one Phe. In variations, the linker is a peptide comprising at least two Phe residues, or at least three Phe residues. In another embodiment, the linker is a peptide comprising Glu-Phe or a dipeptide of an aminoalkylcarboxylic acid and Phe. In another embodiment, the linker is a peptide comprising Glu-Phe-Phe or a tripeptide of an aminoalkylcarboxylic acid and two Phe residues. In another embodiment, the linker is a peptide comprising one or more Phe residues, where at least one Phe is about 7 to about 11, or about 7 to about 14 atoms from the binding ligand B. In another embodiment, the linker is a peptide comprising Phe-Phe about 7 to about 11, or about 7 to about 14 atoms from the binding ligand B. It is to be understood that in each of the foregoing embodiments and variations, one or more Phe residues may be replaced with Tyr, or another substituted variation thereof.

In another illustrative embodiment, the binding agent is a urea of an amino dicarboxylic acid, such as aspartic acid, glutamic acid, and the like, and another amino dicarboxylic acid, or an analog thereof, and the linker includes one or more aryl or arylalkyl groups, each of which is optionally substituted, attached to the backbone of the linker. In another embodiment, the linker is a peptide comprising one or more aryl or arylalkyl groups, each of which is optionally substituted, attached to the backbone of the linker about 7 to about 11 atoms from the binding ligand B. In another embodiment, the linker is a peptide comprising two aryl or arylalkyl groups, each of which is optionally substituted, attached to the backbone of the linker, where one aryl or arylalkyl group is about 7 to about 11, or about 7 to about 14 atoms from the binding ligand B, and the other aryl or arylalkyl group is about 10 to about 14, or about 10 to about 17 atoms from the binding ligand B.

As described herein, the conjugates are targeted to cells that express or over-express PSMA, using a PSMA binding ligand. Once delivered, the conjugates bind to PSMA. It is understood that in certain embodiments the conjugates remain on the surface of the cell for a period of time sufficient for imaging and/or diagnosis. In other embodiments, the conjugates are internalized in the cell expressing or over-expressing PSMA by endogenous cellular mechanisms, such as endocytosis, for subsequent imaging and/or diagnosis, or treatment. Once internalized, the conjugates may remain intact or be decomposed, degraded, or otherwise altered to allow the release of the agent forming the conjugate. It is appreciated that in imaging and/or diagnostic configurations, the agent may remain intact as the conjugate or be released once it has been internalized into the targeted cell. It is further appreciated that in therapeutic configurations, the agent is advantageously released from the conjugate once it has been internalized into the targeted cell.

In one illustrative embodiment, the drug is an imaging agent. In another illustrative variation, the drug is a diagnostic agent. In another illustrative variation, the drug is an chemotherapeutic agent.

In one aspect, the imaging agent is a radioisotope covalently attached to the linker. In another aspect, the imaging agent is a radioactive isotope, such as a radioactive isotope of a metal, coordinated to a chelating group. Illustrative radioactive metal isotopes include technetium, rhenium, gallium, gadolinium, indium, copper, and the like, including isotopes $^{111}$In, $^{99m}$Tc, $^{64}$Cu, $^{67}$Cu, $^{67}$Ga, $^{68}$Ga, and the like. Additional illustrative examples of radionuclide imaging agents are described in U.S. Pat. No. 7,128,893, the disclosure of which is incorporated herein by reference. Additional illustrative chelating groups are tripeptide or tetrapeptides, including but not limited to tripeptides having the formula:

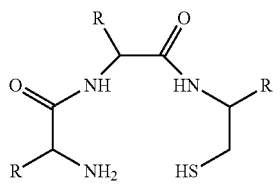

wherein R is independently selected in each instance H, alkyl, heteroalkyl, cycloalkyl, heterocyclyl, alkenyl, alkynyl, aryl, heteroaryl, arylalkyl, heteroarylalkyl, and the like, each of which is optionally substituted. It is to be understood that one R includes a heteroatom, such as nitro, oxygen, or sulfur, and is the point of attachment of linker L. Illustratively, the following chelating groups are described:

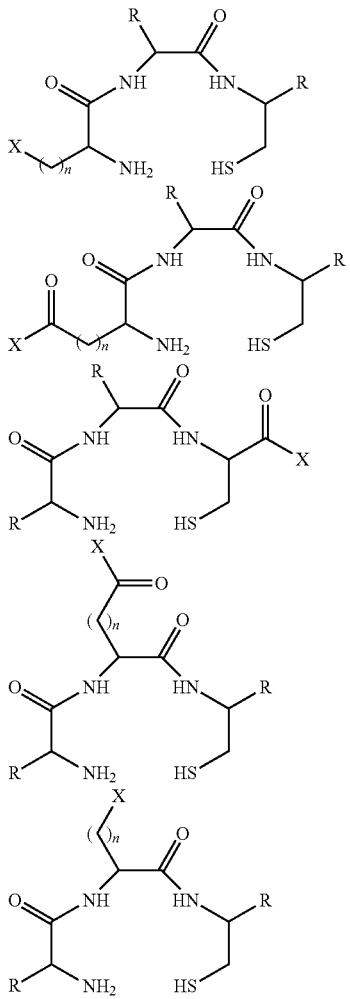

where X is oxygen, nitrogen, or sulfur, and where X is attached to linker L, and n is an integer from 1 to about 5.

In another aspect, the imaging agent is a fluorescent agent. Fluorescent agents include OREGON GREEN™ fluorescent agents (Thermo Fischer Scientific), a series of bright, green-fluorescent dyes with an excitation and emission spectra series that covers the visible spectrum, including but not limited to OREGON GREEN™ 488 (2',7'-Difluoro-3',6' dihydroxy-3H-spiro[isbenzofuran- 1, 9'-xanthen]-3-one), OREGON GREEN™ 514 (4-[(carboxymethyl)sulfanyl]-2-(2,7-difluoro-6-hydroxy-3-oxo-3H-xanthen-9-yl)-3,5,6-trifluorobenzoic acid), and the like, ALEXA FLUOR™ fluorescent agents (Invitrogen), a series of fluorescent dyes with an excitation and emission spectra series that covers the visible spectrum and extend into the infrared, including but not limited to ALEXA FLUOR™ 488 (dilithium2-(6-amino-3-iminio-4,5-disulfonato-3H-xanthen-9-yl)-4-((2,3,5,6-tetrafluorophenoxy)carbonyl)benzoate), ALEXA FLUOR™ 647 (2-[5-[3,3-dimethyl-5-sulfo-1-(3-sulfopropyl) indol-1-ium-2-yl]penta-2,4-dienylidene]-3-methyl-3-[5-oxo-5-(6-phosphonooxyhexylamino) pentyl]-1-(3-sulfopropyl)indole-5-sulfonic acid), and the like, fluorescein, and related analogs, BODIPY fluorescent agents, including but not limited to BODIPY F1, BODIPY 505, and the like, rhodamine fluorescent agents, including but not limited to tetramethylrhodamine, and the like, DYLIGHT™ fluorescent agents (Thermo Fischer Scientific), a series of dyes with an excitation and emission spectra series that covers the visible spectrum and extend into the infrared, including but not limited to DYLIGHT™ 680, DYLIGHT™ 800, and the like, CW 800, Texas Red, phycoerythrin, and others. Illustrative fluorescent agent are shown in the following illustrative general structures:

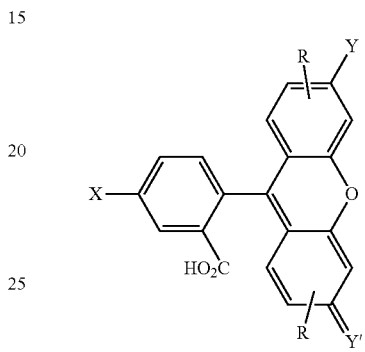

where X is oxygen, nitrogen, or sulfur, and where X is attached to linker L; Y is $OR^a$, $NR^a_2$, or $NR^a_3{}^+$; and Y' is O, $NR^a$, or $NR^a_2{}^+$; where each R is independently selected in each instance from H, fluoro, sulfonic acid, sulfonate, and salts thereof, and the like; and $R^a$ is hydrogen or alkyl.

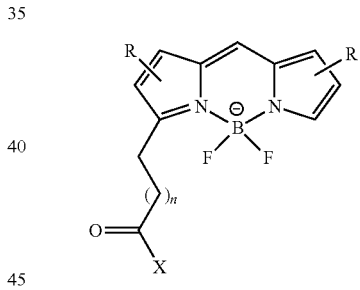

where X is oxygen, nitrogen, or sulfur, and where X is attached to linker L; and each R is independently selected in each instance from H, alkyl, heteroalkyl, and the like; and n is an integer from 0 to about 4.

In another aspect, the imaging agent is a PET imaging agent, or a FRET imaging agent. PET imaging agents 18F, $^{11}C$, $^{64}CU$, $^{65}Cu$, and the like. FRET imaging agents include $^{64}Cu$, $^{65}Cu$, and the like. It appreciated that in the case of $^{18}F$, $^{11}C$, the imaging isotope may be present on any part of the linker, or alternatively may be present on a structure attached to the linker. For example in the case of $^{18}F$, fluoroaryl groups, such as fluorophenyl, difluorophenyl, fluoronitrophenyl, and the like are described. For example in the case of $^{11}C$, alkyl and alkyl aryl are described.

In another aspect, the chemotherapeutic agent is a cytotoxic compound. The cytotoxic compounds described herein operate by any of a large number of mechanisms of action. Generally, cytotoxic compounds disrupt cellular mechanisms that are important for cell survival and/or cell proliferation and/or cause apoptosis.

The drug can be any molecule capable of modulating or otherwise modifying cell function, including pharmaceutically active compounds. Suitable molecules can include, but are not limited to: peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

Further, the drug can be any drug known in the art which is cytotoxic, enhances tumor permeability, inhibits tumor cell proliferation, promotes apoptosis, decreases anti-apoptotic activity in target cells, is used to treat diseases caused by infectious agents, enhances an endogenous immune response directed to the pathogenic cells, or is useful for treating a disease state caused by any type of pathogenic cell. Drugs suitable for use in accordance with this invention include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, taxanes, such as tamoxiphen, taxol, paclitaxel, paclitaxel derivatives, Taxotere®, and the like, maytansines and analogs and derivatives thereof, cyclophosphamide, daunomycin, doxorubicin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, vincristine, vinblastine. and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other art-recognized antimicrobial compound.

Illustrative drugs and other therapeutic agents are described in U.S. Patent Application Publication Nos. US-2005-0002942-A1, US-2001-0031252-A1, and US-2003-0086900-A1. Illustrative imaging agents and diagnostic agents are described in U.S. Patent Application Publication No. US-2004-0033195-A1 and International Patent Application Publication No. WO 03/097647. The disclosures of each of the foregoing patent application publications are incorporated herein by reference.

The invention described herein also includes pharmaceutical compositions comprising an amount of a binding ligand (B) drug delivery conjugate effective to eliminate a population of pathogenic cells in a host animal when administered in one or more doses. The binding ligand drug delivery conjugate is preferably administered to the host animal parenterally, e.g., intradermally, subcutaneously, intramuscularly, intraperitoneally. intravenously, or intrathecally. Alternatively, the binding ligand drug delivery conjugate can be administered to the host animal by other medically useful processes, such as orally, and any effective dose and suitable therapeutic dosage form, including prolonged release dosage forms, can be used.

Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form in accordance with this invention can be in the form of a reconstitutable lyophilizate comprising the dose of the drug delivery conjugate. In one aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

In one illustrative aspect, at least one additional composition comprising a therapeutic factor can be administered to the host in combination or as an adjuvant to the above-detailed methodology, to enhance the binding ligand drug delivery conjugate-mediated elimination of the population of pathogenic cells, or more than one additional therapeutic factor can be administered. The therapeutic factor can be selected from a chemotherapeutic agent, or another therapeutic factor capable of complementing the efficacy of the administered binding ligand drug delivery conjugate.

In one illustrative aspect, therapeutically effective combinations of these factors can be used. In one embodiment, for example, therapeutically effective amounts of the therapeutic factor, for example, in amounts ranging from about 0.1 $MIU/m^2$/dose/day to about 15 $MIU/m^2$/dose/day in a multiple dose daily regimen, or for example, in amounts ranging from about 0.1 $MIU/m^2$/dose/day to about 7.5 $MIU/m^2$/dose/day in a multiple dose daily regimen, can be used along with the binding ligand drug delivery conjugates to eliminate, reduce, or neutralize pathogenic cells in a host animal harboring the pathogenic cells (MIU=million international units; $m^2$=approximate body surface area of an average human).

In another embodiment, chemotherapeutic agents, which are, for example, cytotoxic themselves or can work to enhance tumor permeability, are also suitable for use in the method of the invention in combination with the binding ligand drug delivery conjugates. Such chemotherapeutic agents include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, doxorubicin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O-Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, maytansines and analogs and derivatives thereof, gemcitabine. and any other art-recognized antimicrobial compound.

The therapeutic factor can be administered to the host animal prior to, after, or at the same time as the binding ligand drug delivery conjugates and the therapeutic factor can be administered as part of the same composition containing the binding ligand drug delivery conjugate or as part of a different composition than the binding ligand drug delivery conjugate. Any such therapeutic composition containing the therapeutic factor at a therapeutically effective dose can be used in the present invention.

Additionally, more than one type of binding ligand drug delivery conjugate can be used. Illustratively, for example, the host animal can be treated with conjugates with different vitamins, but the same drug in a co-dosing protocol. In other embodiments, the host animal can be treated with conjugates comprising the same binding ligand linked to different drugs, or various binding ligands linked to various drugs. In another illustrative embodiment, binding ligand drug delivery conjugates with the same or different vitamins, and the same or different drugs comprising multiple vitamins and multiple drugs as part of the same drug delivery conjugate could be used.

In another illustrative aspect, any effective regimen for administering the binding ligand drug delivery conjugates can be used. For example, the binding ligand drug delivery conjugates can be administered as single doses, or can be divided and administered as a multiple-dose daily regimen. In other embodiments, a staggered regimen, for example, one to three days per week can be used as an alternative to daily treatment, and for the purpose of defining this invention such intermittent or staggered daily regimen is considered to be equivalent to every day treatment and within the scope of this invention. In one embodiment, the host is treated with multiple injections of the binding ligand drug delivery conjugate to eliminate the population of pathogenic cells. In another embodiment, the host is injected multiple times (preferably about 2 up to about 50 times) with the binding ligand drug delivery conjugate, for example, at 12-72 hour intervals or at 48-72 hour intervals. In other embodiments, additional injections of the binding ligand drug delivery conjugate can be administered to the patient at an interval of days or months after the initial injections(s) and the additional injections prevent recurrence of the disease state caused by the pathogenic cells.

Illustratively, the binding ligand drug delivery conjugates can be administered parenterally to the animal or patient suffering from the disease state, for example, intradermally, subcutaneously, intramuscularly, intraperitoneally, or intravenously in combination with a pharmaceutically acceptable carrier. In another embodiment, the binding ligand drug delivery conjugates can be administered to the animal or patient by other medically useful procedures and effective doses can be administered in standard or prolonged release dosage forms. In another aspect, the therapeutic method can be used alone or in combination with other therapeutic methods recognized for treatment of disease states mediated by activated macrophages.

Described herein is a method for imaging pathogenic cell populations that express or over-express PSMA.

Described herein is a method for diagnosing diseases and disease states that are related to pathogenic cell populations that express or over-express PSMA. The compounds described herein bind selectively and/or specifically to cells that express or over-express PSMA. In addition, they not only show selectivity between pathogenic cells and normal tissues, they show selectivity among pathogenic cell populations (see FIGS. 8 where PSMA expressing LnCAP cells are preferentially visualized compared to A549 tumors or KB tumos, which are not). In addition, the response is specific to PSMA binding as indicated by competition studies conducted with the conjugates described herein where binding is determined with the conjugate alone or in the presence of excess PMPA, a known binding ligand of PSMA. Binding at both the kidney and tumor is blocked in the presence of excess PMPA (see, for example, Method Examples described herein).

In another embodiment, the conjugate has a binding constant $K_d$ of about 100 nM or less. In another aspect, the conjugate has a binding constant $K_d$ of about 75 nM or less. In another aspect, the conjugate has a binding constant $K_d$ of about 50 nM or less. In another aspect, the conjugate has a binding constant $K_d$ of about 25 nM or less.

In another embodiment, the conjugates described herein exhibit selectivity for PSMA expressing or PSMA over-expressing cells or tissues relative to normal tissues such as blood, hear, lung, liver, spleen, duodenum, skin, muscle, bladder, and prostate, with at least 3-fold selectivity, or at least 5-fold selectivity. In one variation, the conjugates described herein exhibit selectivity for PSMA expressing or PSMA over-expressing cells or tissues relative to normal tissues with at least 10-fold selectivity. It is appreciated that the selectivity observed for imaging is indicative of the selectivity that may be observed in treating disease states responsive to the selective or specific elimination of cells or cell populations that express or over-express PSMA.

The unitary daily dosage of the drug delivery conjugate can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. Effective doses can range, for example, from about 1 ng/kg to about 1 mg/kg, from about 1 μg/kg to about 500 μg/kg, from about 1 μg/kg to about 100 μg/kg, and from about 1 μg/kg to about 10 μg/kg.

Generally, any manner of forming a conjugate between the bivalent linker (L) and the binding ligand (B), or analog or derivative thereof, between the bivalent linker (L) and the drug, or analog or derivative thereof, including any intervening heteroatoms, can be utilized in accordance with the present invention. Also, any art-recognized method of forming a conjugate between the spacer linker, the releasable linker, and one or more heteroatoms to form the bivalent linker (L) can be used. The conjugate can be formed by direct conjugation of any of these molecules, for example, through hydrogen, ionic, or covalent bonds. Covalent bonding can occur, for example, through the formation of amide, ester, disulfide, or imino bonds between acid, aldehyde, hydroxy, amino, sulfhydryl, or hydrazo groups.

The synthetic methods are chosen depending upon the selection of the optionally included heteroatoms or the heteroatoms that are already present on the spacer linkers, releasable linkers. the drug, and/or the binding ligand. In general, the relevant bond forming reactions are described in Richard C. Larock, "Comprehensive Organic Transformations, a guide to functional group preparations," VCH Publishers, Inc. New York (1989), and in Theodora E. Greene & Peter G.M. Wuts, "Protective Groups ion Organic Synthesis," 2d edition, John Wiley & Sons, Inc. New York (1991), the disclosures of which are incorporated herein by reference.

More specifically, disulfide groups can be generally formed by reacting an alkyl or aryl sulfonylthioalkyl derivative, or the corresponding heteroaryldithioalkyl derivative such as a pyridin-2-yldithioalkyl derivative, and the like, with an alkylenethiol derivative. For example, the required alkyl or aryl sulfonylthioalkyl derivative may be prepared according to the method of Ranasinghe and Fuchs, Synth. Commun. 18(3), 227-32 (1988), the disclosure of which is incorporated herein by reference. Other methods of preparing unsymmetrical dialkyl disulfides are based on a transthiolation of unsymmetrical heteroaryl-alkyl disulfides, such as 2-thiopyridinyl, 3-nitro-2-thiopyridinyl, and like disulfides, with alkyl thiol, as described in WO 88/01622, European Patent Application No. 0116208A1, and U.S. Pat. No. 4,691,024, the disclosures of which are incorporated herein by reference. Further, carbonates, thiocarbonates, and carbamates can generally be formed by reacting an hydroxy-substituted compound, a thio-substituted compound, or an amine-substituted compound, respectively, with an activated alkoxycarbonyl derivative having a suitable leaving group.

EXAMPLES

The compounds described herein may be prepared by conventional organic synthetic methods. In addition, the compounds described herein may be prepared as indicated below. Unless otherwise indicated, all starting materials and reagents are available from commercial supplies. All amino acid starting materials were purchased from Chem-Impex Int (Chicago, Ill.). $^1$H NMR spectra were obtained using a Bruker 500 MHz cryoprobe, unless otherwise indicated.

Example 1A. General synthesis of PSMA inhibitor intermediates for conjugation. Illustrated for specific synthesis of DUPA derivative 2-[3-(1,3-Bis-tert-butoxycarbonyl-propyl)-ureido]-pentanedioic acid 1-tert-butyl ester (I).

Scheme 2.1

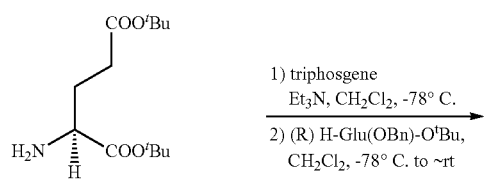

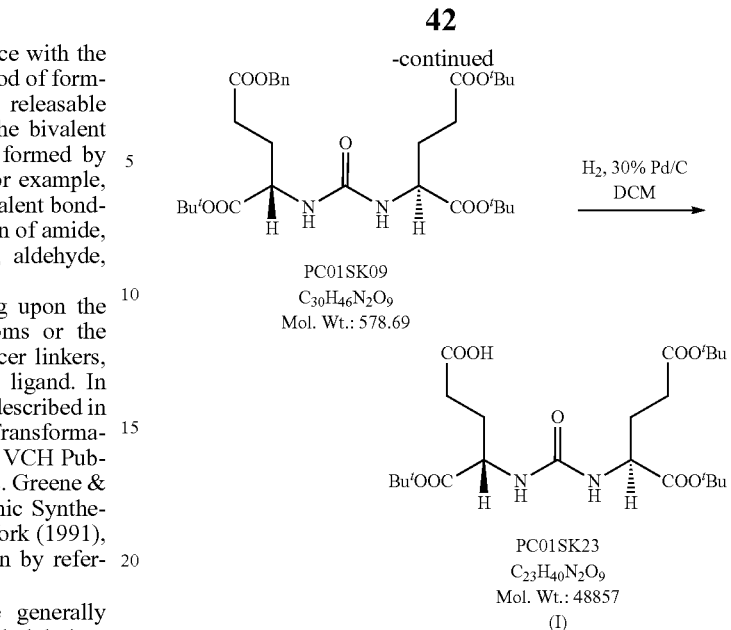

SK09. To a mixture of L-glutamate di-tert-butylester HCl (1.0 g, 3.39 mmol) and triphosgene (329.8 mg, 1.12 mmol) in $CH_2Cl_2$ (25.0 mL) cooled to $-78°$ C., triethylamine (1.0 mL, 8.19 mmol) was added. After stirring for 2 h at $-78°$ C. under nitrogen, mixture of L-Glu(OBn)-O-tert-Bu (1.2 g, 3.72 mmol) and triethylamine (600 µL, 4.91 mmol) in $CH_2Cl_2$ (5.0 mL) was added. The reaction mixture was allowed to come to room temperature over a period of 1 h and continued to stir at room temperature overnight. The reaction mixture was washed with 1N HCl, brine and dried over $Na_2SO_4$. The crude product was purified using a flash chromatography (hexane: EtOAc=1:1, $R_f$=0.67) to give SK09 (1.76 g, 90.2%). $C_{30}H_{46}N_2O_9$; MW=578.69 g/mol; colorless oil; $^1$H NMR ($CDCl_3$) δ 1.43 (s, 9H, $CH_3$-$^t$Bu); 1.44 (s, 9H, $CH_3$-$^t$Bu); 1.46 (s, 9H, $CH_3$-$^t$Bu); 1.85 (m, 1H, Glu-H); 1.87 (m, 1H, Glu-H); 2.06 (m, 1H, Glu-H); 2.07 (m, 1H, Glu-H); 2.30 (m, 2H, Glu-H); 2.44 (m, 2H, Glu-H); 4.34 [s (broad), 1H, αH]; 4.38 [s (broad), 1H, α-H]; 5.10 (s, 2H, $CH_2$-Ar); 5.22 [s (broad), 2H, Urea-H]; 7.34 (m, 5H, Ar-H). $^{13}$C NMR ($CDCl_3$) δ 28.16; 28.25; 28.54; 28.60; 30.52; 31.73; 53.13; 53.22; 66.58; 80.71; 82.25; 82.35; 128.39; 128.71; 136.03; 156.96; 172.01; 172.16; 172.65; 173.13: CI-MS=579 (M+H)$^+$, ESI-MS=579 (M+H)+, 601 (M+Na adduct).

SK23. To a solution of compound SK09 (250 mg, 432 mmol) in $CH_2Cl_2$, 30% Pd/C (50 mg) was added. The reaction mixture was hydrogenated at 1 atm, room temperature for 24 h. Pd/C was filtered through celite pad and washed with $CH_2Cl_2$. The crude product was purified using a flash chromatography (hexane: EtOAc=40:60, $R_f$=0.58) to give SK23 (169 mg, 80.2%). $C_{23}H_{40}N_2O_9$; MW=488.57 g/mol; colorless oil; $^1$H NMR ($CDCl_3$) δ 1.46 (m, 27H, $CH_3$-$^t$Bu); 1.91 (m, 2H, Glu-H); 2.07 (m, 1H, Glu-H); 2.18 (m, 1H, Glu-H); 2.33 (m, 2H, Glu-H); 2.46 (m, 2H, Glu-H); 4.31 (s (broad), 1H, αH); 4.35 (s (broad), 1H, α-H); 5.05 (t, 2H, Urea-H); CI-MS=489 (M+H)$^+$, ESI-MS=489 (M+H)$^+$, 511 (M+Na adduct), 487 (M–H)$^-$.

Example 1B. General synthesis of PSMA inhibitor intermediates for conjugation. Illustrated for specific synthesis of tertiary butyl protected MUPA derivative 2-[3-(1-tert-Butoxycarbonyl-2-mercapto-ethyl)-ureido]-pentanedioic acid di-tert-butyl ester (II).

Scheme 2.2

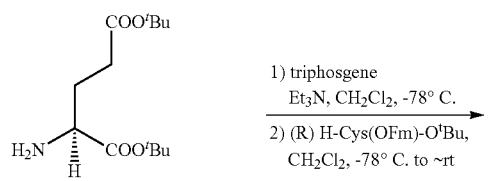
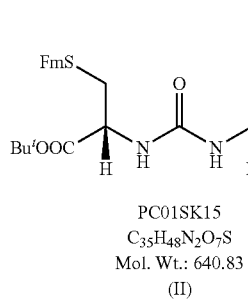

PC01SK15
C₃₅H₄₈N₂O₇S
Mol. Wt.: 640.83
(II)

SK15. To a mixture of L-glutamate di-tert-butylester HCl (200 mg, 0.676 mmol) and triphosgene (67 mg, 0.228 mmol) in CH$_2$Cl$_2$ (5.0 mL), cooled to −78° C., triethylamine (50 L, 0.410 mmol) was added. After stirring for 2 h at −78° C. under nitrogen, mixture of D-Cys(Fm)-O$^t$Bu (291.4 mg, 0.774 mmol) and triethylamine (30 μL, 240 mmol) in CH$_2$Cl$_2$ (1.0 mL) was added. The reaction mixture was allowed to come to room temperature over a period of 1 h and continued to stir at room temperature overnight. The reaction mixture was washed with 1N HCl, brine and dried over Na$_2$SO$_4$. The crude product was purified using a flash chromatography (hexane: EtOAc=50:50, R$_f$=0.6) to give SK15 (374 mg, 86.4%). C$_{35}$H$_{48}$N$_2$O$_7$S; MW=640.83 g/mol; pale yallow oil; $^1$H NMR (CDCl$_3$) δ 1.45 (s, 27H, CH$_3$-$^t$Bu); 1.88 (m, 1H, Glu-H); 2.10 (m, 1H, Glu-H); 2/32)(m, 2H, Glu-H); 2.97 (m, 2H, Fm-CH2); 3.13 (m, 2H, Cys-H); 4.09 (t, 1H, Fm-H); 4.38 (m, 1H, αH); 4.66 (m, 1H, α-H); 5.55 (d, 1H, Urea-H); 5.67 (d, 1H, Urea-H); 7.30 (q, 2H, Ar-H); 7.36 (q, 2H, Ar-H); 7.73 (m, 4H, Ar-H). $^{13}$C NMR (CDCl$_3$) δ 28.05; 28.14; 28.42; 31.64; 36.27; 37.25; 53.07; 53.73; 80.51; 81.98; 82.42; 119.85; 124.95; 125.09; 127.09; 127.51; 141.09; 145.99; 156.76; 170.80; 172.15; 172.43; CI-MS=641 (M+H)$^+$, ESI-MS=641 (M+H)$^+$.

Example 2A. General synthesis of PSMA imaging agent conjugates. Illustrated by synthesis of 14-atom linker compound SK28.

Scheme 2.3

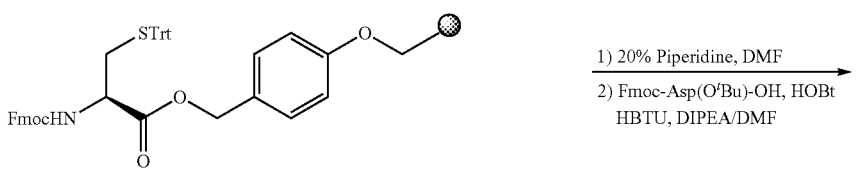

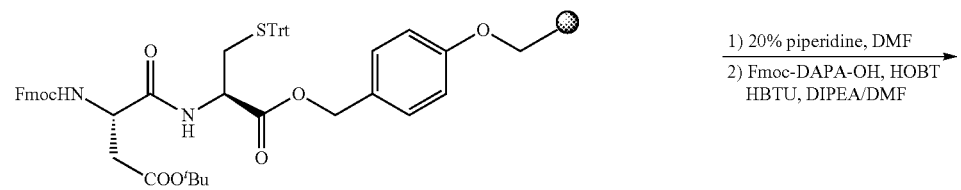

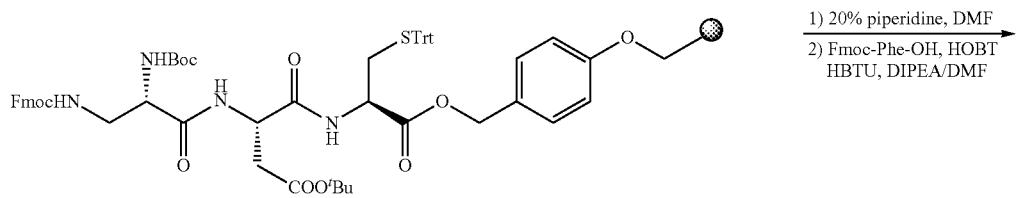

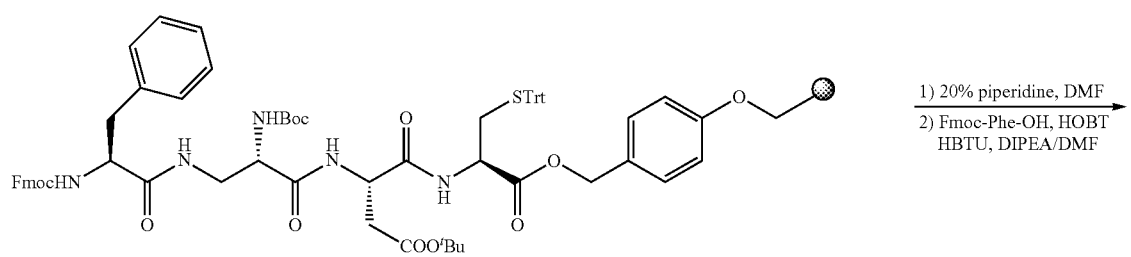

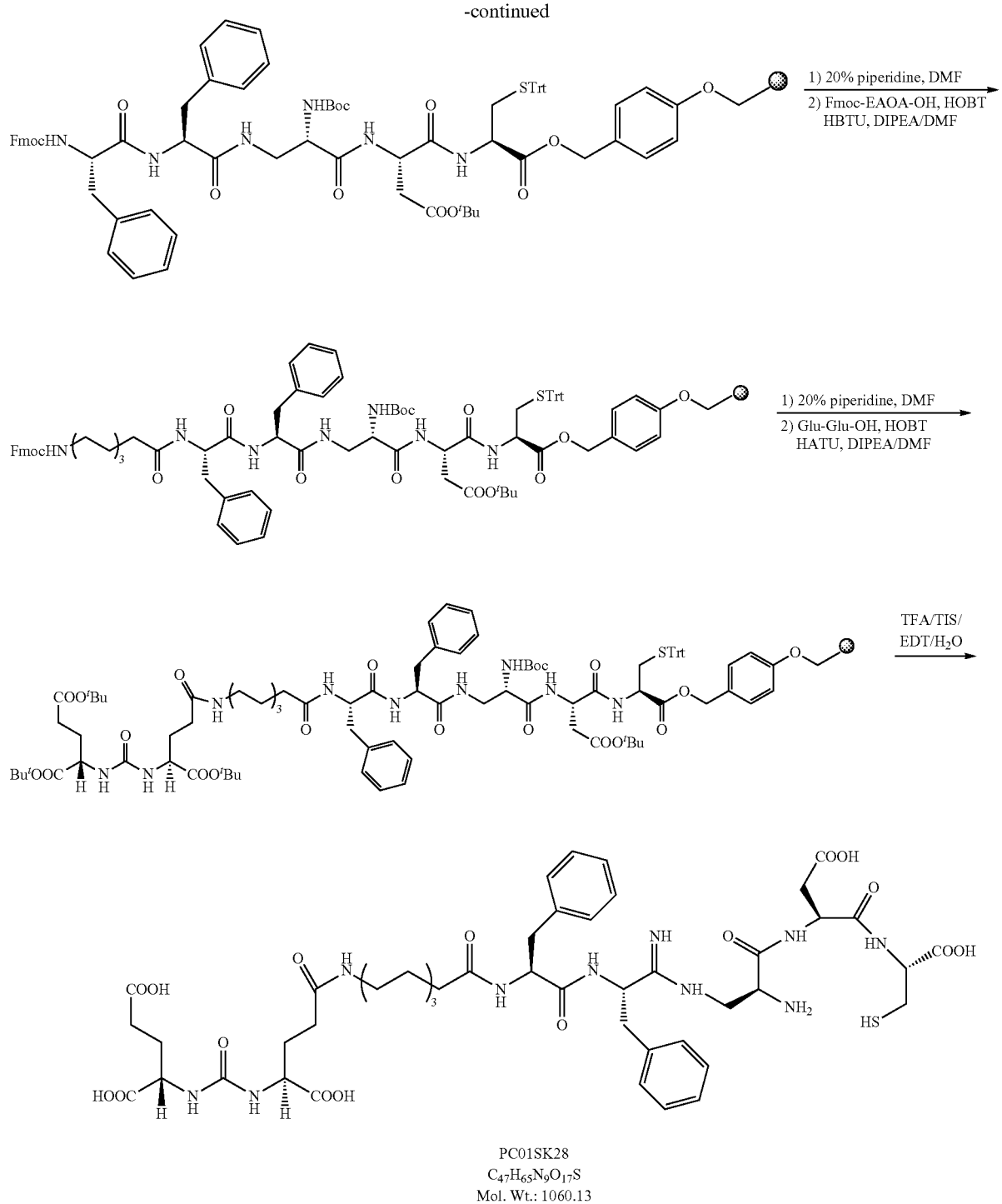

PC01SK28
C<sub>47</sub>H<sub>65</sub>N<sub>9</sub>O<sub>17</sub>S
Mol. Wt.: 1060.13

SK28 was synthesized using standard Fluorenylmethyloxycarbonyl (Fmoc) solid phase peptide synthesis (SPPS) starting from Fmoc-Cys(Trt)-Wang resin (Novabiochem; Catalog #04-12-2050). SK28 was purified using reverse phase preparative HPLC (Waters, xTerra $C_{18}$ 10 µm; 19×250 mm) A=0.1 TFA, B=Acetonitrile (ACN); λ=257 nm; Solvent gradient: 5% B to 80% B in 25 min. 80% B wash 30 min run, (61%). Purified compounds were analyzed using reverse phase analytical HPLC (Waters, X-Bridge $C_{18}$ 5 µm; 3.0×15 mm); A=0.1 TFA, B=ACN; λ=257 nm, 5% B to 80% B in 10 min, 80% B wash 15 min run. $C_{47}H_{65}N_2O_{17}S$; MW=1060.13 g/mol; white solid; $R_t$=7.7 min; $^1$H NMR (DMSO-$d_6$D$_2$O) δ 0.93 (m, 2H); 1.08 (m, 5H); 1.27 (m, 5H); 1.69 (m, 2H); 1.90 (m, 2H); 1.94 (m, 2H); 2.10 (m, 2H); 2.24 (q, 2H); 2.62 (m, 2H); 2.78 (m, 4H); 2.88 (dd, 1H); 2.96 (t, 2H); 3.01 (dd, 1H); 3.31 (dd, 1H); 3.62 (dd, 1H); 3.80 (q, 1H, αH); 4.07 (m, 1H, αH); 4.37 (m, 1H, αH); 4.42 (m, 2H, αH); 4.66 (m, 1H, αH); 7.18 (m, 10H, Ar-H): LC-MS=1061 (M+H)$_+$; ESI-MS=1061 (M+H)$^+$.

Example 2AA. The following example compound was synthesized by an analogous process.

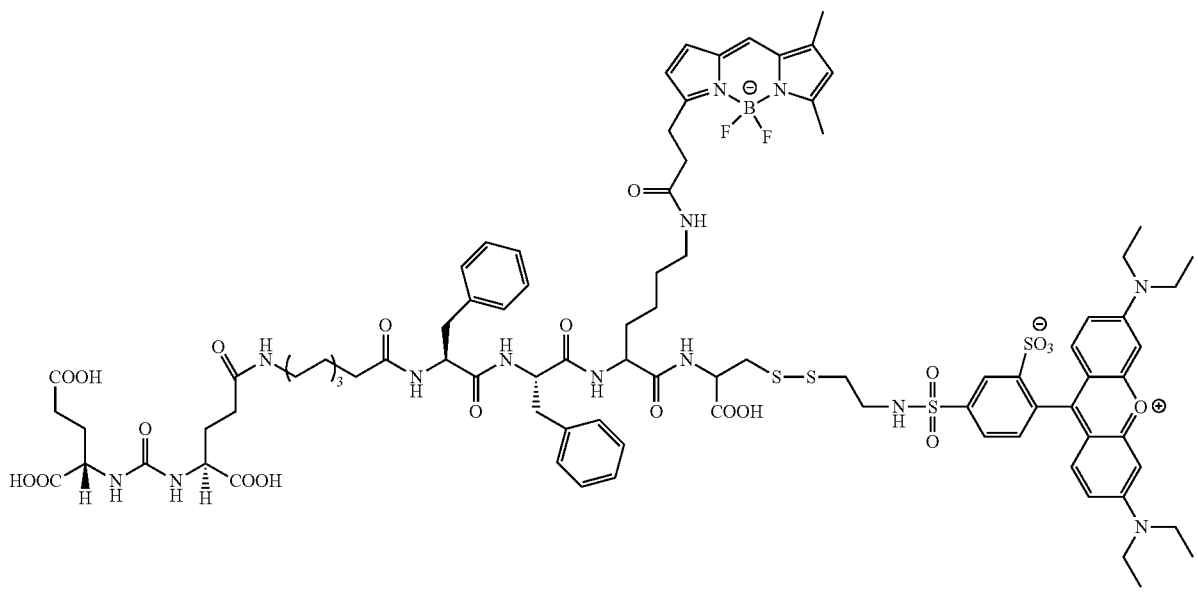

Examples 2B-2E. The following compounds were synthesized according to the processes described herein using Ftnoc SPPS starting from Fmoc-Cys(Trt)-Wang resin (Novabiochem; Catalog #04-12-2050), and purified using reverse phase preparative HPLC (Waters, xTerra $C_{18}$ 10 μm ; 19×250 mm) and analyzed using reverse phase analytical HPLC (Waters, X-Bridge $C_{18}$ 5 μm; 3.0×15 mm):

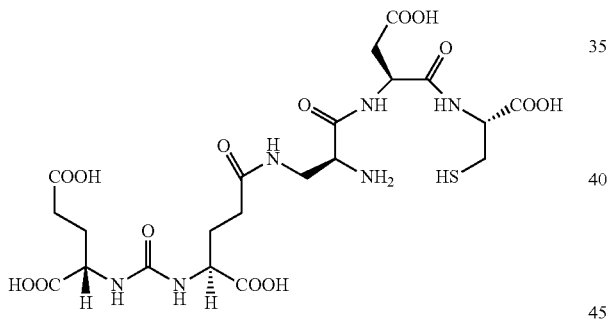

SK60 (0-atom linker): solvent gradient A=0.1 TFA, B=ACN; λ=220 nm; Solvent gradient: 1% B to 50% B in 25 min, 80% B wash 30 min run, (75.3%). $C_{21}H_{32}N_6O_{14}S$; MW=624.58 g/mol; white solid; $R_t$=6.3 min; $^1$H NMR (DMSO-$d_6$/$D_2O$) δ1.70 (m, 2H); 1.92 (m, 2H); 2.17 (m, 2H); 2.23 (m, 2H); 2.57 (m, 1H); 2.77 (m, 4H); 3.45 (dd, 1H); 3.54 (dd, 1H); 3.83 (t, 1H, αH); 4.06 (m, 1H, αH); 4.38 (m, 1H, α-H); 4.63 (m, 1H, α-H); ESI-MS=625 (M+H)$^+$

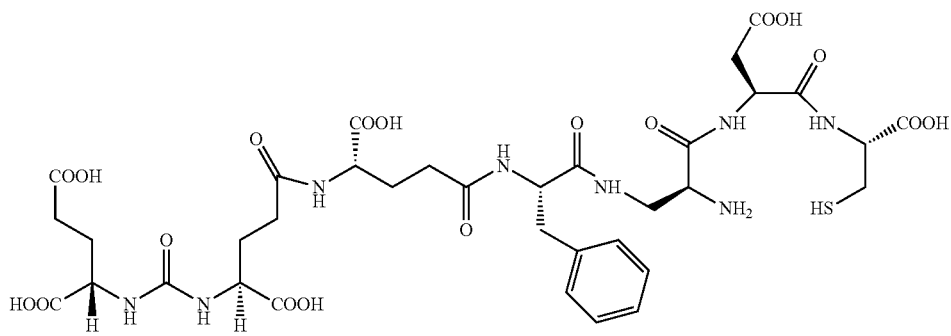 [SMILES: N[C@@H](CNC(=O)[C@H](Cc1ccccc1)NC(=O)CC[C@H](NC(=O)CC[C@H](NC(=O)N[C@@H](CCC(=O)O)C(=O)O)C(=O)O)C(=O)O)C(=O)N[C@@H](CC(=O)O)C(=O)N[C@@H](CS)C(=O)O]

SK62 (7 atom linker): solvent gradient A=0.1 TFA, TFA, B=ACN; X=220, 257 nm; Solvent gradient: 1% B to 50% B in 25 min, 80% B wash 30 min run, (72%). $C_{35}H_{48}N_8O_{18}S$; MW=900.86 g/mol; white solid; $R_t$=8.2 min; $^1$H NMR (DMOS-$d_6$/$D_2O$) δ 1.62 (m, 1H); 1.70 (m, 2H); 1.79 (m, 1H); 1.90 (m, 2H); 2.09 (t, 2H); 2.16 (in, 2H); 2.24 (m, 2H); 2.60 (m, 1H); 2.75 (m, 4H);2.81 (m, 1H); 2.97 (m, 1H); 3.33 (dd, 1H); 3.60 (dd, 11-1); 3.81 (t, 1H, αH); 4.07 (m, 2H, αH); 4.33 [m, 1H, αH]; 4.39 (t, α-H); 4.65 (m, 1H, α-H); 7.20 (m, 5H, Ar-H); ESI-MS=901 (M+H)$^+$.

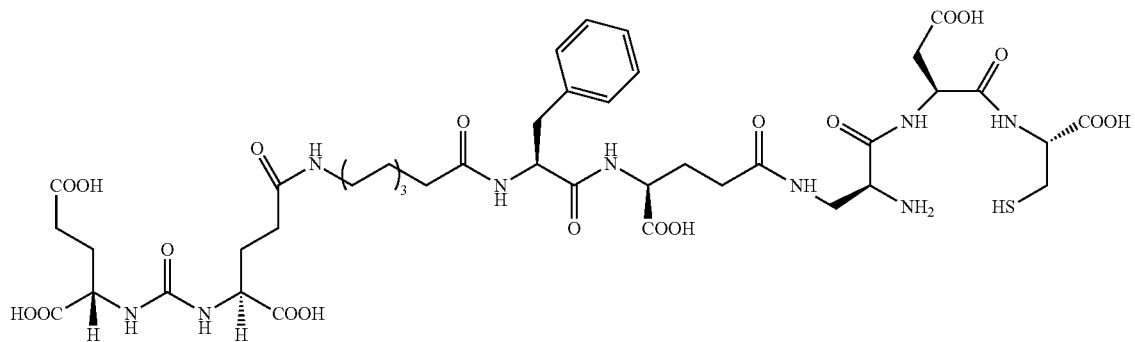

SK38 (16 atom linker): solvent gradient A=10 mM NH$_4$OAc, B=ACN; λ=257 nm; Solvent gradient: 1% B to 80% B in 25 min, 80% B wash 30 min run, (63%). $C_{43}H_{63}N_9O_{19}S$, MW=1042.07 g/mol; white solid; $R_t$=min; $^1$H NMR (DMSO-$d_6$/$D_2O$) δ 0.94 (m, 2H); 1.08 (m, 5H); 1.27 (m, 5H); 1.66 (m, 2H);1.70 (m, 2H); 1.79 (m, 1H); 1.90 (m, 2H); 2.09 (t, 2H); 2.74 (m, 2H); 2.84 (m, 1H); 2.95 (t, 3H); 3.07 (d, 2H); 3.23 (m, 1H); 3.43 (dd, 1H); 3.52 (dt, 1H); 3.78 (m, 1H, αH); 3.81 (m, 1H, αH); 3.88 (m, 1H, αH); 4.11 (m, 1H, αH); 4.39 [m, 2H, α-H]; 4.65 (m, 1H, α-H); 7.14 (m, 1H, Ar-H); 7.21 (m, 4H, Ar-H): ESI-MS=1043 (M+H)$^+$.

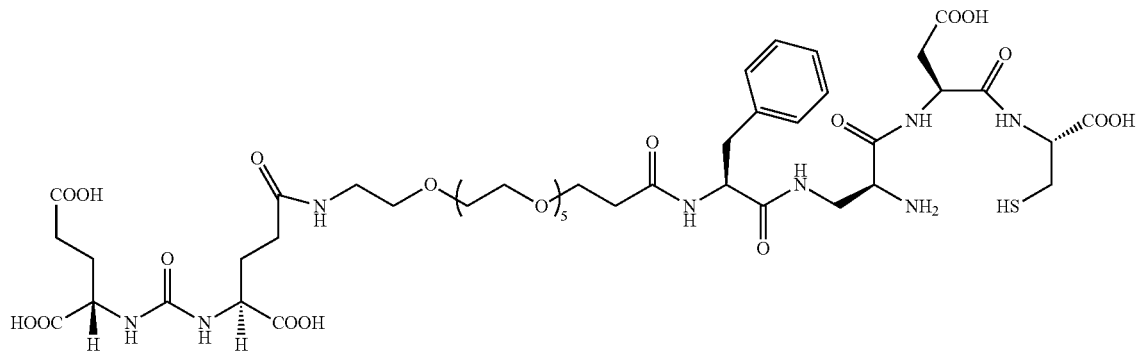

SK57 (24 atom linker): solvent gradient A=0.1 TFA, B=ACN; λ=257 nm; Solvent gradient: 1% B to 50% B in 25 min, 80% B wash 30 min run, (56%). $C_{45}H_{70}N_8O_{22}S$, MW=1107.14 g/mol; colorless solid; $^1$H NMR (DMSO-$d_6$/$D_2O$) δ 1.66 (m, 2H); 2.07 (m, 4H); 2.31 (t, 1H); 2.43 (m, 1H); 2.77 (m, 2H); 2.98 (dd, 1H); 3.14 (t, 2H); 3.24 (d, 1H); 3.40 (m, 4H, PEG-H); 3.46 (s, 24H, PEG-H); 3.78 (t, 1H); 3.81 (t, 1H); 4.03 (m, 1H, αH); 4.40 (m, 2H, α-H); 7.16 (m, 1H, Ar-H); 7.22 (m, 4H, Ar-H): ESI-MS=1108 (M+H)$^+$.

Example 2F. The following compound may be synthesized according to the processes described herein.
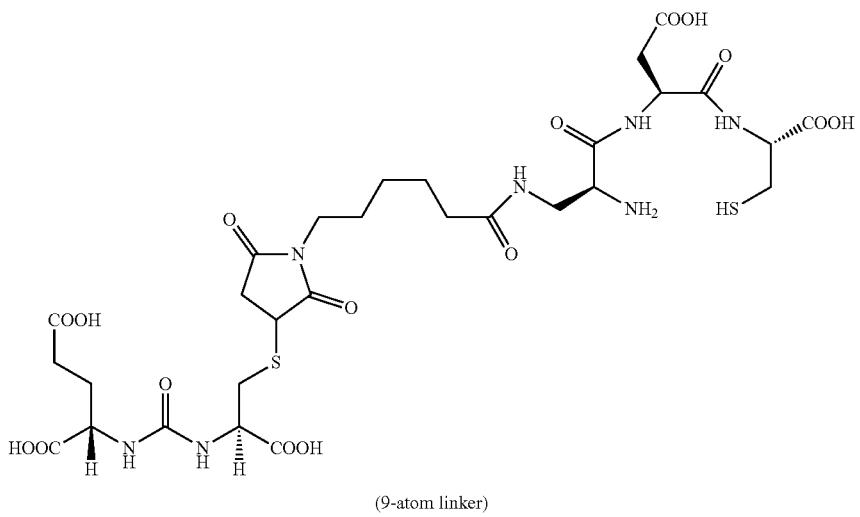 [SMILES: N[C@@H](CNC(=O)CCCCCN1C(=O)CC(SC[C@H](NC(=O)N[C@@H](CCC(=O)O)C(=O)O)C(=O)O)C1=O)C(=O)N[C@@H](CC(=O)O)C(=O)N[C@@H](CS)C(=O)O]
(9-atom linker)
Example 3A. General process for adding radionuclide to chelating group. Illustrated for radio labeling of SK28 with $^{99m}$Tc to prepare SK33.
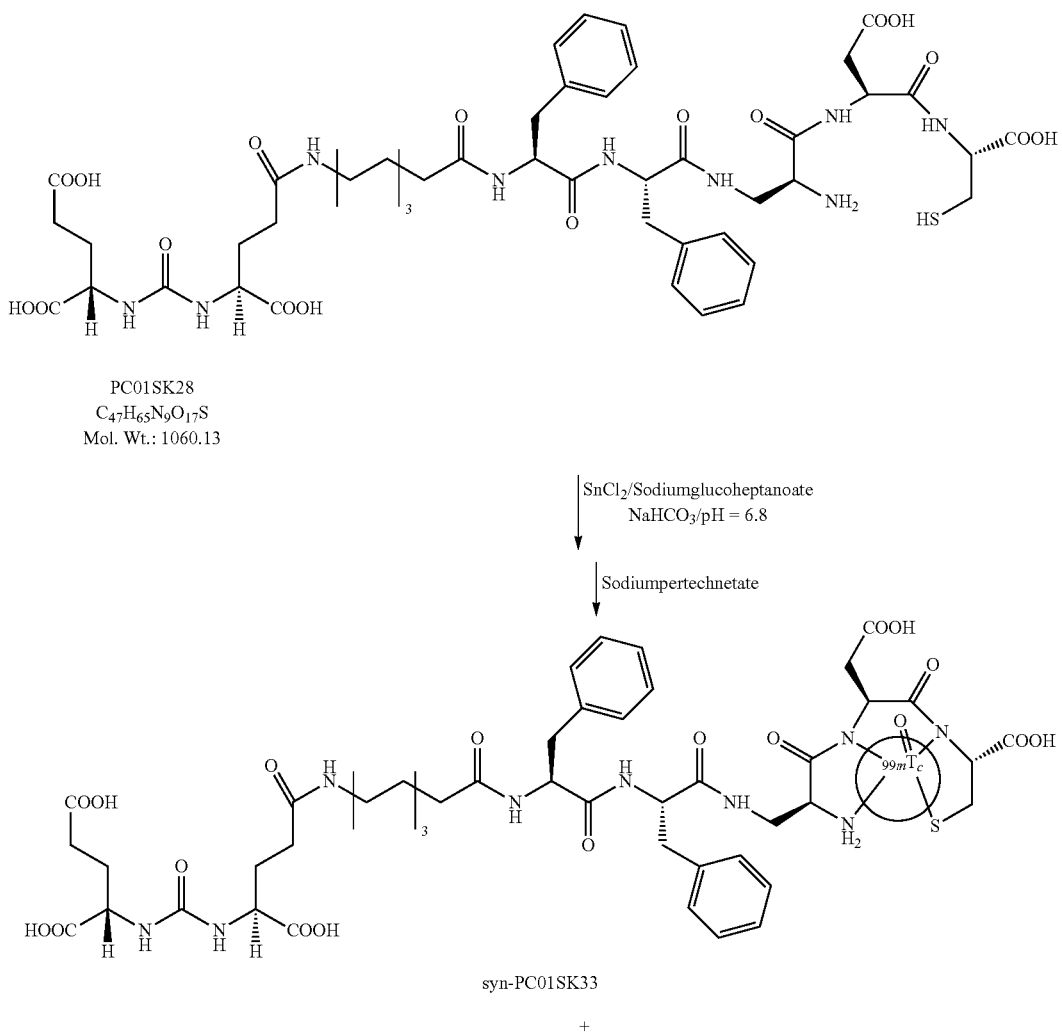

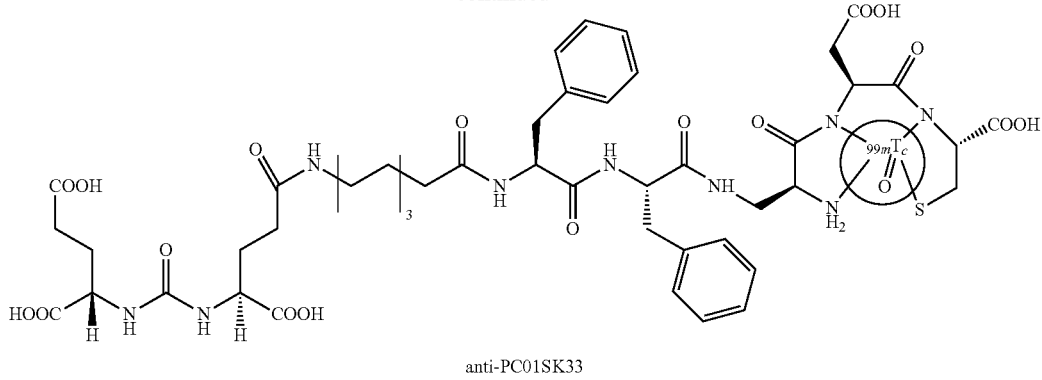

anti-PC01SK33

Preparation of SK28 formulation kits. HPLC grade Millipore filtered water (50 mL) was added to a 100 mL bottle and argon was purged for at least 10 min. Sodium α-D-glucoheptonate dihydrate (800 mg) was dissolved in argon purged water (5 mL). Stannous chloride dihydrate (10 mg) was dissolved in 0.02 M HCl (10 mL) while bubbling argon. Stannous chloride (0.8 mL) was added to the sodium glucoheptonate solution under argon. SK28 (1.4 mg) was added to the sodium glucoheptonate/stannous chloride solution under argon. The pH of the reaction mixture was adjusted to 6.8±0.2 using 0.1 N NaOH. Argon purged water (5.2 mL) was added to the reaction mixture to make total volume as 10 mL. 1.0 mL of reaction mixture was dispensed to each vial (10 vials) under argon atmosphere and lyophilized for 36-48 h. The vials were sealed with rubber stoppers and aluminum seals under argon atmosphere to make SK28 formulation kits. The formulation kit vials were stored at −20° C. until they used.

Labeling SK28 with $^{99m}$Tc. Radio labeling of SK28 with $^{99m}$Tc may be performed according to published procedures. A formulation vial was warmed to room temperature for 10 min and heated in a boiling water bath for 3 min. Then 15 mCi of sodium pertechnetate $^{99m}$Tc (1.0 mL) was injected and an equal volume of gas was withdrawn from the vial to normalize the pressure. The vial was heated in the boiling water bath for 15-20 min and then cooled to room temperature before using in the experiment. Radiochemical purity was analyzed by radioactive TLC (>98%), that showed syn and anti isomers of the radio labeled compound (SK33/SK28-$^{99m}$Tc).

Examples 3B-3E. The following Examples were prepared according to the processes described herein (both syn and anti isomers were obtained; only the syn isomer is shown):

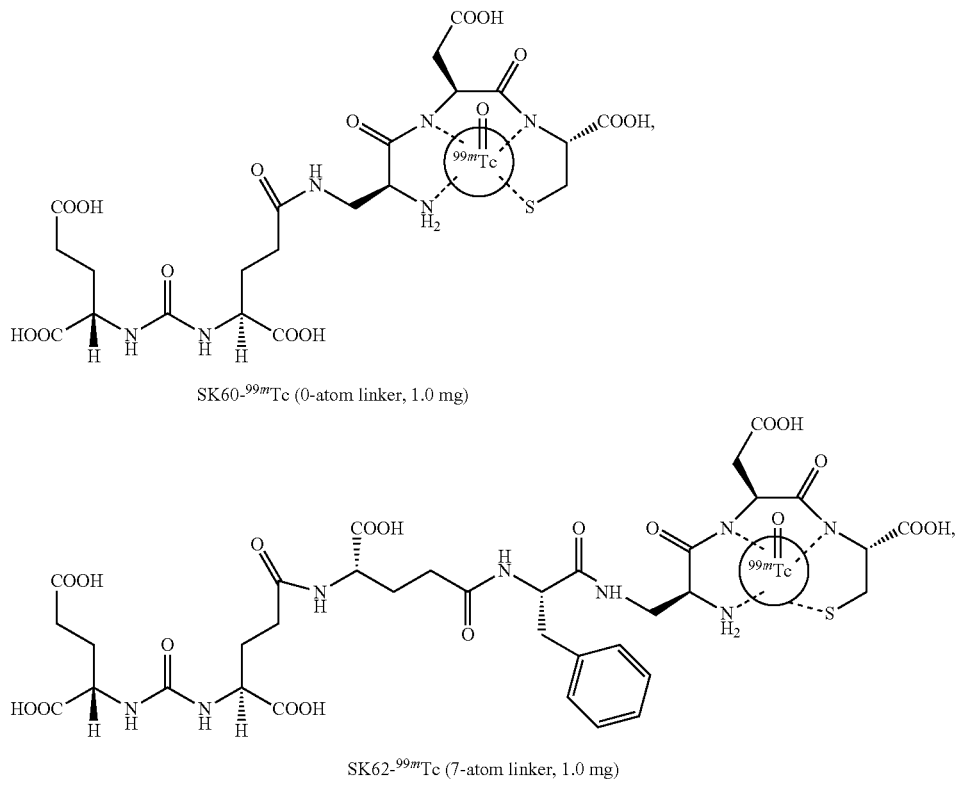

SK60-$^{99m}$Tc (0-atom linker, 1.0 mg)

SK62-$^{99m}$Tc (7-atom linker, 1.0 mg)

-continued
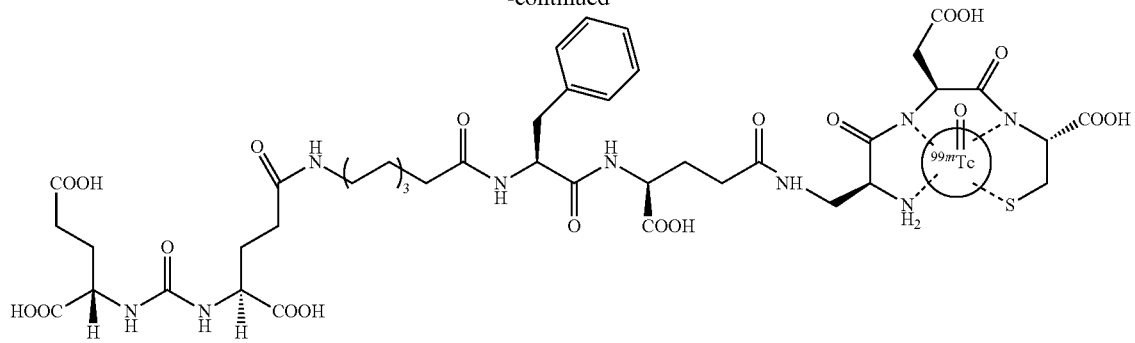
SK38-$^{99m}$Tc (16-atom linker, 1.4 mg)
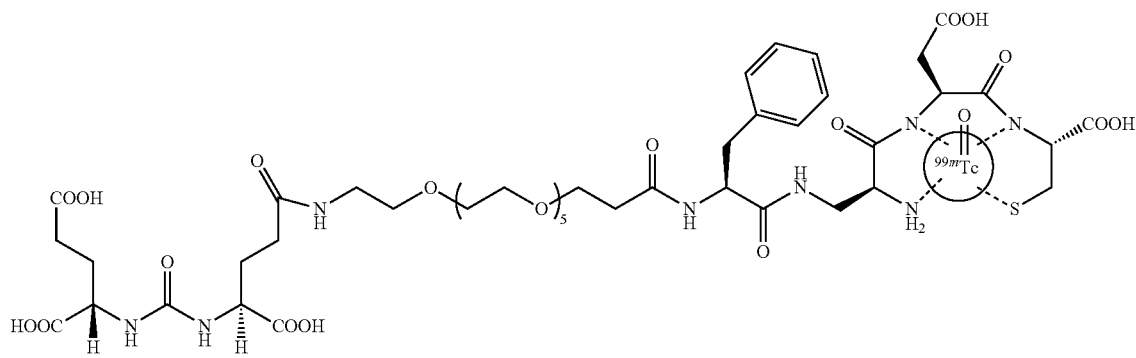
SK57-$^{99m}$Tc (24-atom linker, 1.8 mg)
Example 3F. The following compound may be synthesized according to the processes described herein.
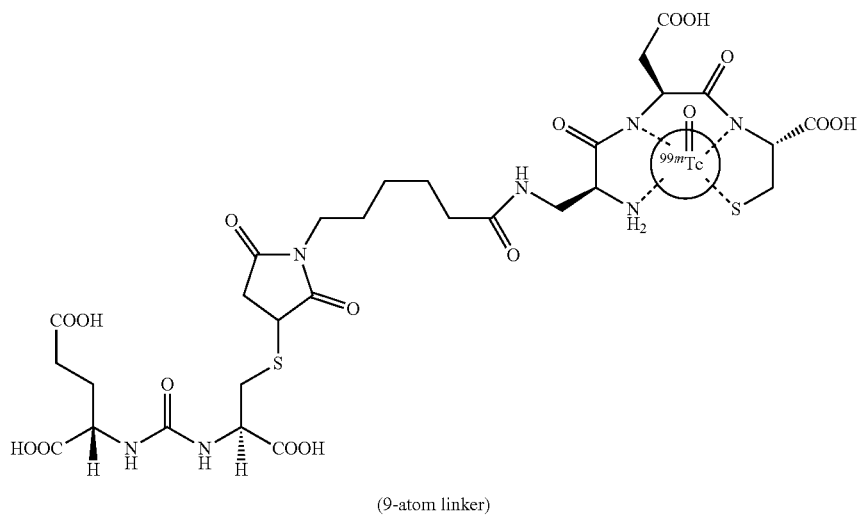
(9-atom linker)

Example 4. General synthesis of PSMA imaging agent conjugates illustrated for SK59 using Universal PSMA (DUPA) resin, a 2-atom linker, and FITC. This conjugate may also be used for detecting circulating tumor cells in prostate cancer patients.
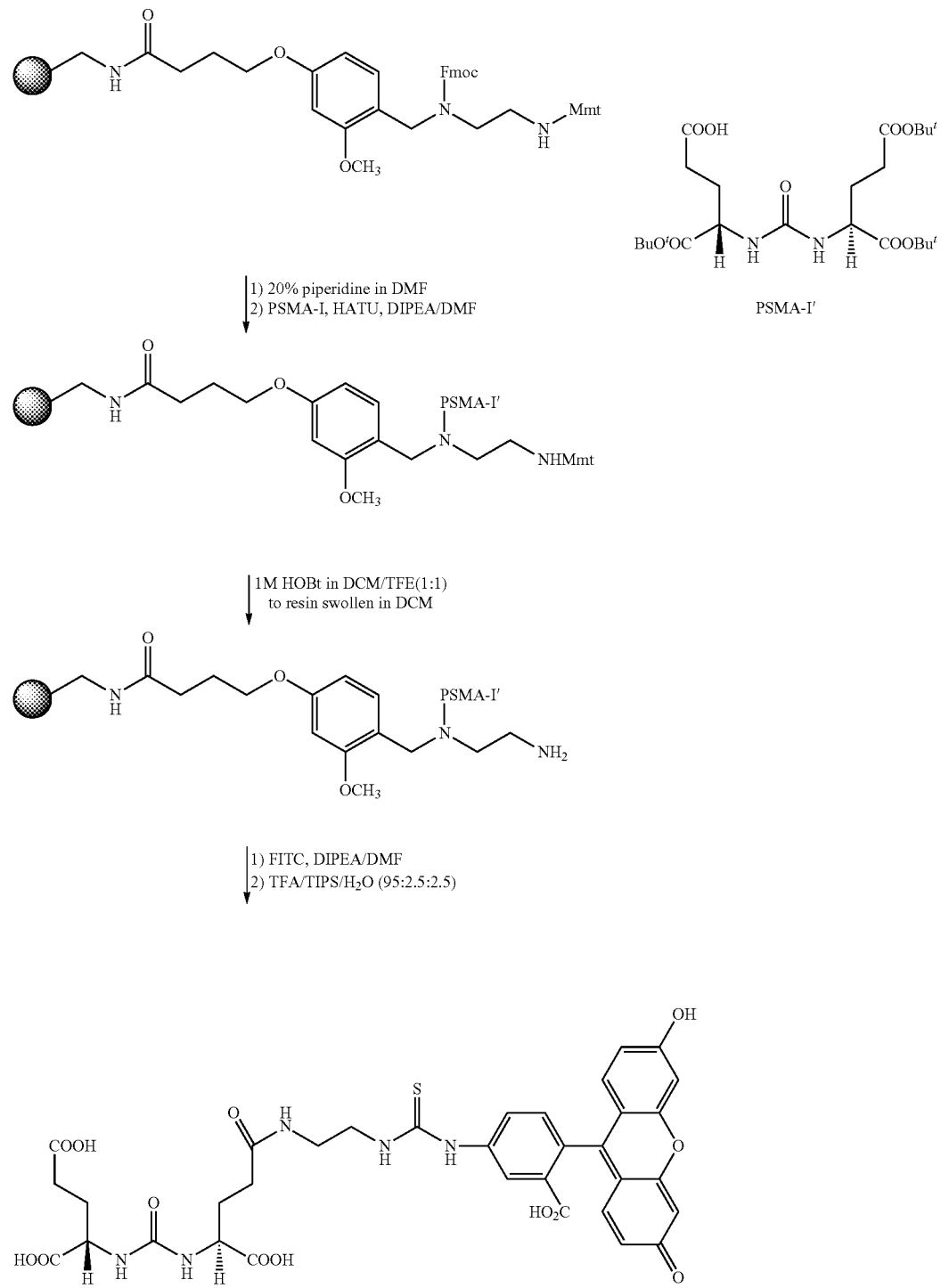
PC01SK59
$C_{34}H_{33}N_5O_{14}$
Mol. Wt.: 735.65

Synthesis of PSMA universal resin and SK59. Universal PSMA ligand (DUPA) resin was synthesized using Universal NovaTag™ resin (Novabiochem; Catalog #04-12-3910). Fmoc group was deprotected using 20% piperidine/DMF (N,N-dimethylformamide), after swelling the resin with DCM (CH$_2$Cl$_2$) and DMF. tert-Butyl protected DUPA was coupled using HATU [2-(1H-7-azabenzotriazol-1-yl)-,1,3,3-tetramethyl uronium hexafluorophosphate] and DIPEA (N,N-diisopropylethylamine) in DMF. The pendant Mmt (4-Methoxytrityl) was removed with 1M HOBT (1-Hyroxybenzotriazole) in DCM/TFE (trifluoroethanol). The resin intermediate can be washed with DMF and used immediately in subsequent synthetic steps or washed with DCM/DMF and then with MeOH, and dried for later use.

Universal PSMA resin was reacted with commercially available FITC (1.25 equiv) in the presence of DIPEA (4 equiv) in DMF to yield SK59 (2 atom linker) construct. The final compound was cleaved from the resin using a mixture of TFA (trifluoro acetic acid), TIPS (triisopropylsilane), and water. Purification was by reverse phase preparative HPLC (Waters, xTerra C$_{18}$ 5 μm; 19×150 mm) A=10 mM NH$_4$OAc, B=ACN; λ=488 nm; Solvent gradient: 1% B to 50% B in 25 min. 80% B wash 40 min run, (63%). SK59 was analyzed using reverse phase analytical HPLC (Waters, X-Bridge C$_{18}$ 5 μm; 3.0×15 mm); A=10 mM NH$_4$OAc, B=ACN; λ=488 nm, 1% B to 50% B in 10 min, 80% B wash 15 min run; C$_{34}$H$_{33}$N$_6$O$_{13}$ S; MW=751.72 g/mol; orange color solid, R$_f$=7.2 min; ESI-MS=752 (M+H)$^+$; 774 (M+Na)$^+$; 750 (M−H)$^−$.

Example 5A. General synthesis of PSMA imaging agent conjugates illustrated for SK64 using Universal PSMA (DUPA) resin, a 16-atom linker, and FITC.

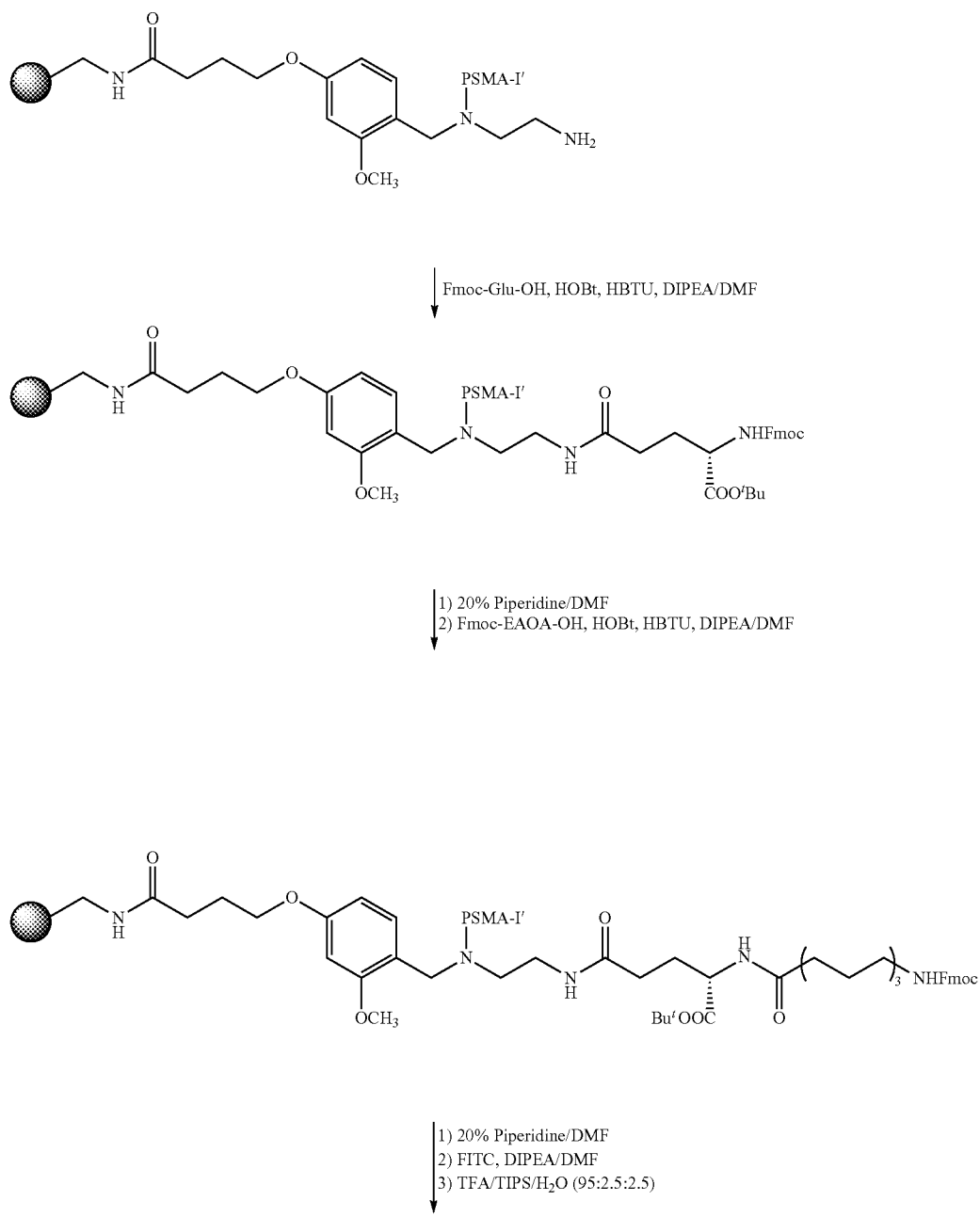

-continued

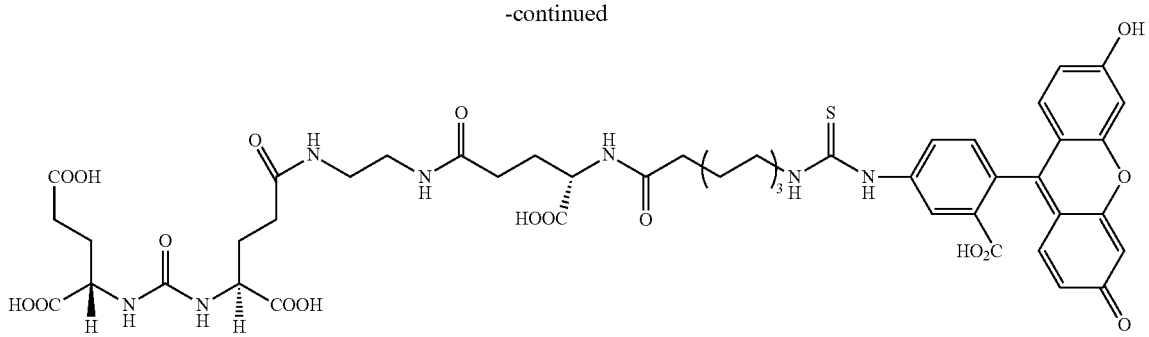

PC01SK64
$C_{47}H_{55}N_7O_{17}S$
Mol. Wt.: 1022.04

Universal PSMA resin was coupled with Fmoc-Glu-(O'Bu)-OH and Fmoc-EAOA (8-aminooctonoic acid) using standard Fmoc SPPS. After conjugating with fluorescein-isothiocyanate (1.25 equiv) in the presence of DIPEA (4 equiv) in DMF, SK64 (16 atom linker) compound was cleaved from the resin using TFA/TIPS/H$_2$O. Purification was performed using reverse phase preparative HPLC (Waters, xTerra C$_{18}$ 5 μm; 19×150 mm) A=10 mM NH$_4$OAc, B=ACN; λ=488 nm; Solvent gradient: 1% B to 50% B in 25 min, 80% B wash 40 min run, (57%). SK64 was analyzed using reverse phase analytical HPLC (Waters, X-Bridge C$_{18}$ 5 μm; 3.0×150 mm); A=10 mM NH$_4$OAc, B=ACN; λ=488 nm, 1% B to 50% B in 10 min, 80% B wash 15 min run; $C_{47}H_{55}N_7O_{17}$ S; MW=1022.04 g/mol; orange color solid, R$_t$=7.8 min; ESI-MS=1022 (M+H)$^+$; 1020 (M−H)$^−$.

Examples 5B-5C. The following compounds were prepared using the synthetic processes described herein:

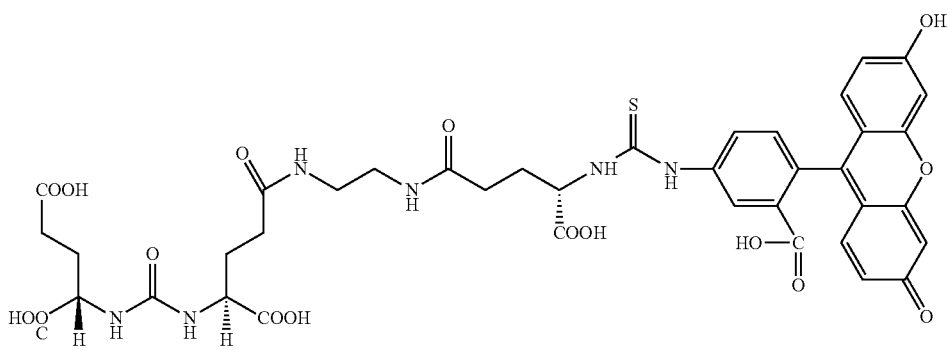 [SMILES: O=C(O)CC[C@H](NC(=O)N[C@@H](CCC(=O)NCCNC(=O)CC[C@H](NC(=S)Nc1ccc(-c2c3ccc(=O)cc-3oc3cc(O)ccc23)c(C(=O)O)c1)C(=O)O)C(=O)O)C(=O)O]

SK63(7-atom linker, C39H40N6O17, Mol. Wt.: 864.76). was prepared using universal PSMA resin and standard Fmoc SPPS conjugated with Fmoc-Glu-(O'Bu)-OH. After coupling with FITC, compounds were cleaved from the resin using TFA/TIPS/H$_2$O cocktail and purified with reverse phase preparative HPLC (Waters, xTerra C$_{18}$ 5 μm; 19×150 mm) A=10 mM NH$_4$OAc, B=ACN; λ=488 nm; Solvent gradient: 1% B to 50% B in 25 min, 80% B wash 40 min run, (65%); analyzed using reverse phase analytical HPLC (Waters, X-Bridge C$_{18}$ 5 μm; 3.0×150 mm); A=10 mM NH$_4$OAc, B=ACN; λ=488 nm, 1% B to 50% B in 10 min, 80% B wash 15 min run; SK63: $C_{39}H_{40}N_6O_{16}S$; MW=880.83 g/mol; orange color solid, R$_t$=6.8 min; ESI-MS=881 (M+H)$^+$; 903 (M+Na)+; 863(M−H)−.

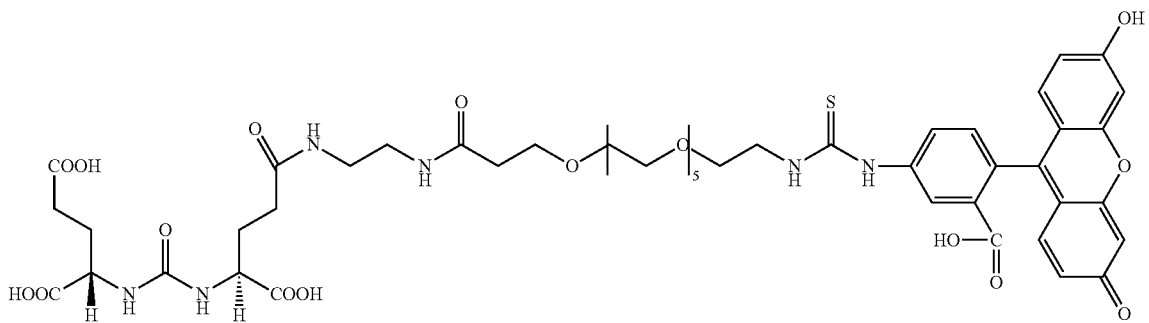 [SMILES: O=C(O)CC[C@H](NC(=O)N[C@@H](CCC(=O)NCCNC(=O)CCOCCOCCNC(=S)Nc1ccc(-c2c3ccc(=O)cc-3oc3cc(O)ccc23)c(C(=O)O)c1)C(=O)O)C(=O)O]

SK58 (24-atom linker, C49H62N6O20S, Mol. Wt.: 1087.11) was prepared using universal PSMA resin and standard Fmoc SPPS conjugated with Fmoc-(PEG)$_6$-OH and purified by HPLC 1% B to 60% B in 25 min, 80% B wash 40 min run, (65%); analyzed using reverse phase analytical HPLC (Waters, X-Bridge C$_{18}$ 5 µm; 3.0×150 mm); A=10 mM NH$_4$OAc, B=ACN; λ=488 nm, 1% B to 60% B in 10 min, 80% B wash 15 min run; C$_{49}$H$_{60}$N$_6$O$_{20}$S; MW=1087.11 g/mol; orange color solid, Rt=7.3 min; ESI-MS=1087 (M+H)$^+$; 1109 (M+Na)+; 1085(M−H)−.

Example 6A. General synthesis of Cys-maleimide PSMA imaging agent conjugates illustrated for SK56 using Wang PSMA (DUPA) resin, a 28-atom linker, and OREGON GREEN™ 488. where n=3.

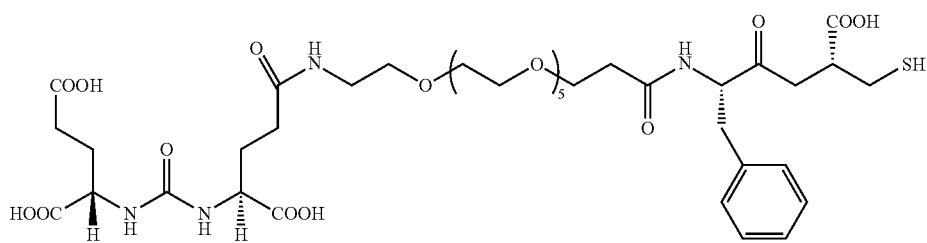

PC01SK54
C$_{38}$H$_{59}$N$_5$O$_{18}$S
Mol. Wt.: 905.96

Oregon Green 488 maieimide/THF
Water/pH~7/Ar

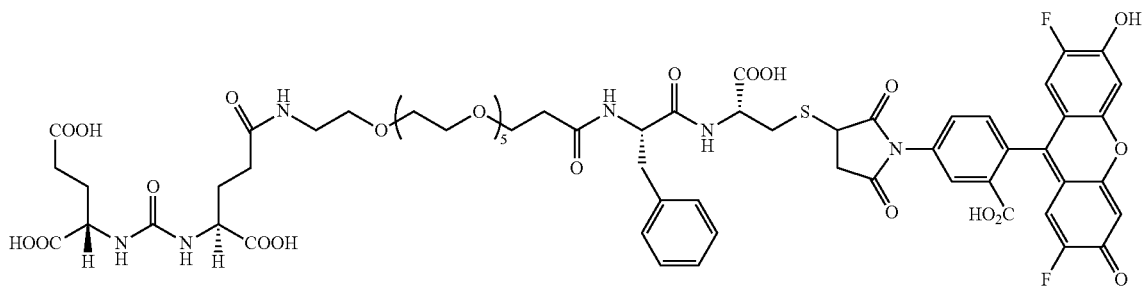

PC01SK56
C$_{52}$H$_{70}$F$_2$N$_6$O$_{25}$S
Mol. Wt.: 1369.31

Related analogs where n is an integer from 4 to about 30 may also be prepared according to the processes described herein.

SK54 was prepared using standard Fmoc SPPS starting from Fmoc-Cys(Trt)-Wang resin (Novabiochem; Catalog #04-12-2050), purified using reverse phase preparative HPLC (Waters, xTerra $C_{18}$ 10 µm; 19×250 mm) A=0.1 TFA; B=ACN; λ=257 nm; Solvent gradient: 1% B to 60% B in 25 min, 80% B wash 40 min run, (63%), and analyzed using reverse phase analytical HPLC (Waters, X-Bridge $C_{18}$ 5 gm; 3.0×50 mm); A=10 mM $NH_4OAc$, B=ACN; λ=257 nm, 1% B to 50% B in 10 min, 80% B wash 15 min run; $C_{38}H_{59}N_5O_{18}S$, MW=905.96 g/mol; colorless solid; $R_f$=9.2 min, LC-MS=906.3 g/mol; ESI-MS=906 (M+H)$^+$; 904 (M−H)$^−$.

SK56 (24 atom linker). HPLC grade Milli-Q water and satd $NaHCO_3$ were purged with argon for 10 min. SK54 was dissolved in 1.0 mL of argon purged water while bubbling argon. The pH of the solution was increased up to 6.8 and Oregon Green™ 488 maleimide dissolved in 1.0 mL of THF was added to the reaction mixture. The reaction was monitored by analytical HPLC (10 mM $NH_4OAc$, pH=7.0; 1% B to 50% B in 10 min 80% B wash 15 min run) and reaction was completed within 10 min. THF was evaporated and reaction mixture was diluted with 5.0 mL of 7 mM phosphate buffer. Purification was performed using reverse phase preparative HPLC (Waters, xTerra $C_{18}$ 10 µm; 19×250 mm) A=7 mM Phosphate buffer pH=7.2, B=ACN; λ=488 nm; Solvent gradient: 1% B to 50% B in 25 min, 80% B wash 40 min run, (89%); and analyzed using reverse phase analytical HPLC (Waters, X-Bridge $C_{18}$ 5 µm; 3.0×150 mm); A=10 mM $NH_4OAc$, B=ACN; λ=488 nm, 1% B to 50% B in 10 min, 80% B wash 15 min run; $C_{62}H_{70}F_2N_6O_{25}S$; MW=1369.31 g/mol; orange color solid, $R_f$=7.0 min; LC-MS=1370.2; ESI−MS=1391 (M+Na)$^+$. The following 24-atom linker compounds were prepared in an analogous manner to those described herein using the General syntheses described herein.

Example 6B. The following ALEXAFLUOR™ 488 conjugate compound was prepared according to the processes described herein starting with SK55, where n=3.

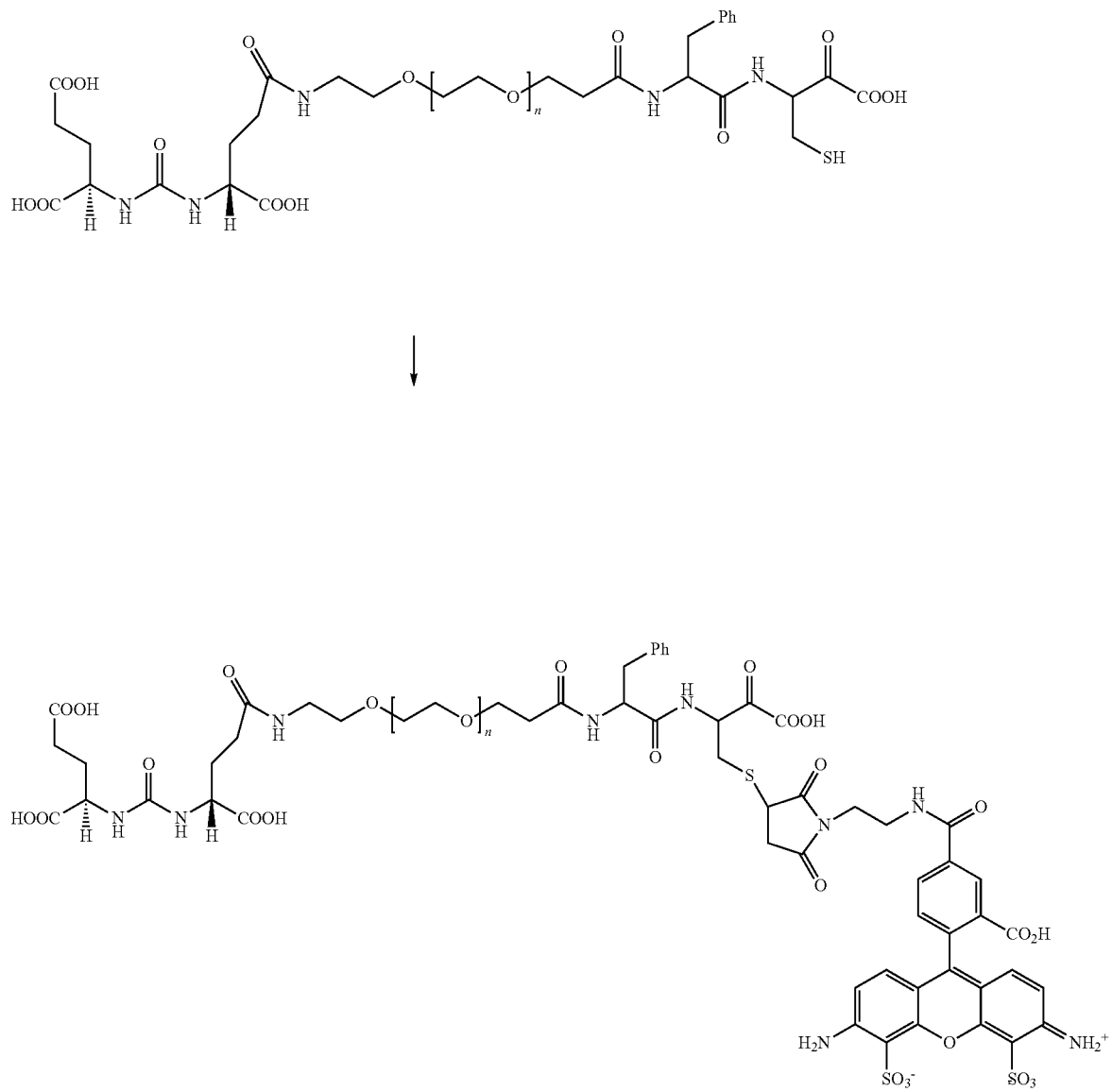

Related analogs where n is an integer from 4 to about 30 may also be prepared according to the processes described herein.

Examples 7A-7C. The following DUPA imaging agent conjugate compounds, SK51, SK45, and SK49 were prepared according to the processes described herein, where n is 5:

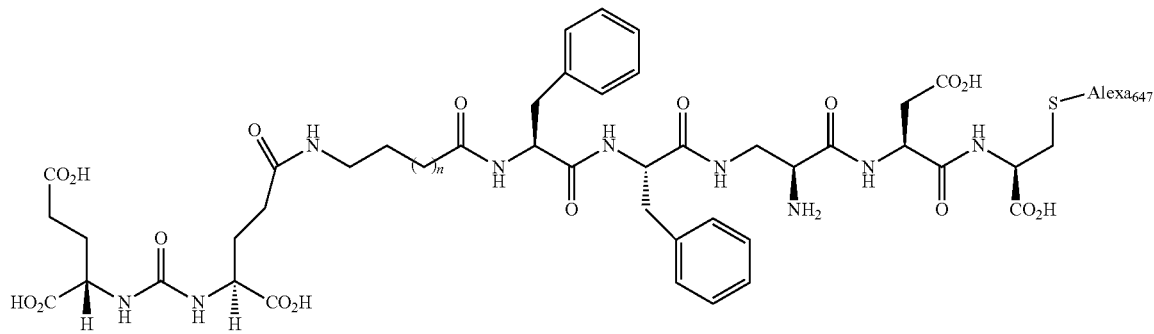

SK51 (25-atom linker, and ALEXAFLUOR™ 647, MW ~2300 (commercially available from Invitrogen))

Related analogs where n is an integer from 0 to about 12 may also be prepared according to the processes described herein.

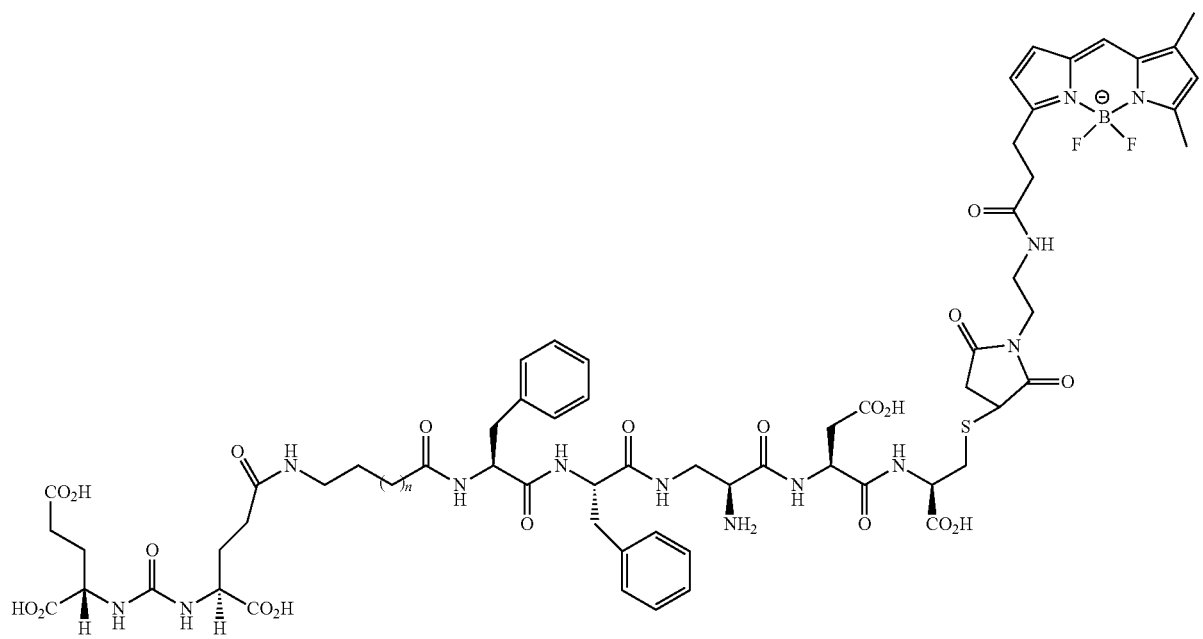

SK45 (25 Atom linker BODIPY 505, C67H87BF2-N13O20S, Mol. Wt.: 1475.35)

Related analogs where n is an integer from 0 to about 12 may also be prepared according to the processes described herein.

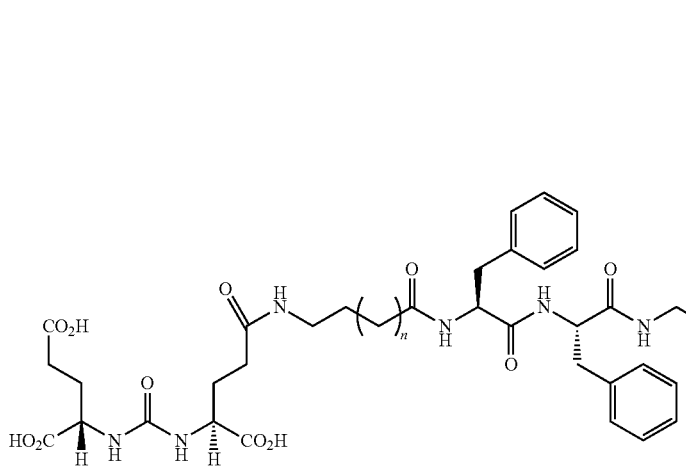
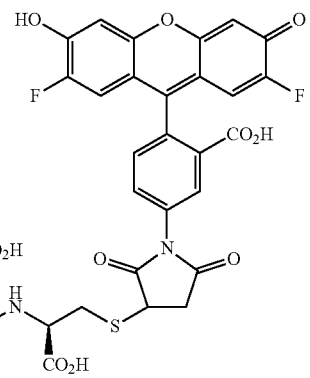

SK49 (25 Atom linker-OREGON GREEN™ 488, C71H76F2N10O24, Mol. Wt.: 1523.48) Related analogs where n is an integer from 0 to about 12 may also be prepared according to the processes described herein.

Synthesis of the Linker. In each of the foregoing Examples, the linker was synthesized using standard Fmoc SPPS starting from Fmoc-Cys(Trt)-Wang resin (Novabiochem; Catalog #04-12-2050); $C_{47}H_{65}N_2O_{17}S$; MW=1060.13 g/mol; white solid; $R_t$=7.7 min; $^1$H NMR (DMSO-d$_6$/D$_2$O) δ0.93 (m, 2H); 1.08 (m, 5H); 1.27 (m, 5H); 1.69 (m, 2H); 1.90 (m, 2H); 1.94 (m, 2H); 2.10 (m, 2H); 2.24 (q, 2H); 2.62 (m, 2H); 2.78 (m, 4H); 2.88 (dd, 1H); 2.96 (t, 2H); 3.01 (dd, 1H); 3.31 (dd, 1H); 3.62 (dd, 1H); 3.80 (q, 1H, aα); 4.07 (m, 1H, αH); 4.37 (m, 1H, αH); 4.42 (m, 2H, αH); 4.66 (m, 1H, αH); 7.18 (m, 10H, Ar-H): LC–MS=1061 (M+H)$_+$; ESI–MS=1061 (M+H)$^+$.

Synthesis of SK51 (ALEXA FLUOR™ 647 conjugate), SK45 (BODIPY conjugate) and SK49 (OREGON GREEN™ 488 conjugate). HPLC grade Milli-Q water and satd NaHCO$_3$ were purged with argon for 10 min. Linker was dissolved in 1.0 mL of argon purged while bubbling argon. The pH of the solution was increased to 6.8 and ALEXA FLUOR™ maleimide, BODIPY maleimide, or OREGON GREEN™ 488 maleimide, respectively, was dissolved in 1.0 mL of tetrahydrofuran (THF) was added to the reaction mixture. Progress of the reaction was monitored by analytical HPLC (10 mM NH$_4$OAc, pH=7.0; 1% B to 50% B in 10 min 80% B wash 15 min run) and reaction was completed within 10 min. THF was evaporated and reaction mixture was diluted with 5.0 mL of 1 mM phosphate buffer (pH=7.2).

Compounds were purified using reverse phase preparative HPLC (Waters, xTerra C$_{18}$5 μm, 18×150 mm) A=1 mM Phosphate buffer pH=7.2, B=ACN; λ=647 or 488 nm; Solvent gradient: 1% B to 50% B in 25 min, 80% B wash 40 min run; and analyzed using reverse phase analytical HPLC (Waters, X-Bridge C$_{18}$ 5 μm; 3.0×50 mm); A=10 mM NH$_4$OAc, B=ACN; λ=588 or 488 nm, 1% B to 50% B in 10 min, 80% B wash 15 min run.

SK51: MW~2360.13 g/mol; blue color solid, $R_t$=6.7 min; (structure of the ALEXA FLUOR™ 647 is not known);

SK45: $C_{67}H_{87}BF_2N_{13}O_{20}S$; MW=1475.35 g/mol; orange color solid, $R_t$=7.6 min; LC–MS=1475.3 (M+H)$^+$;

SK49: $C_{71}H_{76}F^2N_{10}O_{24}$ S; MW=1523.48 g/mol; orange color solid, $R_t$=6.7 min; LC–MS=1524 (M+H)$^+$.

Example 8A. General synthesis of PSMA disulfide linker intermediate for releasable agent conjugate, illustrated for SK68.

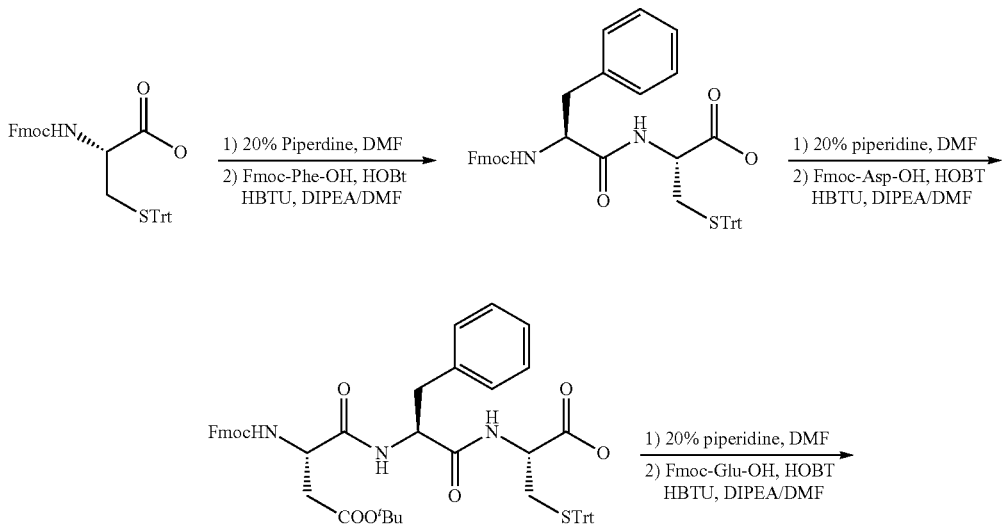

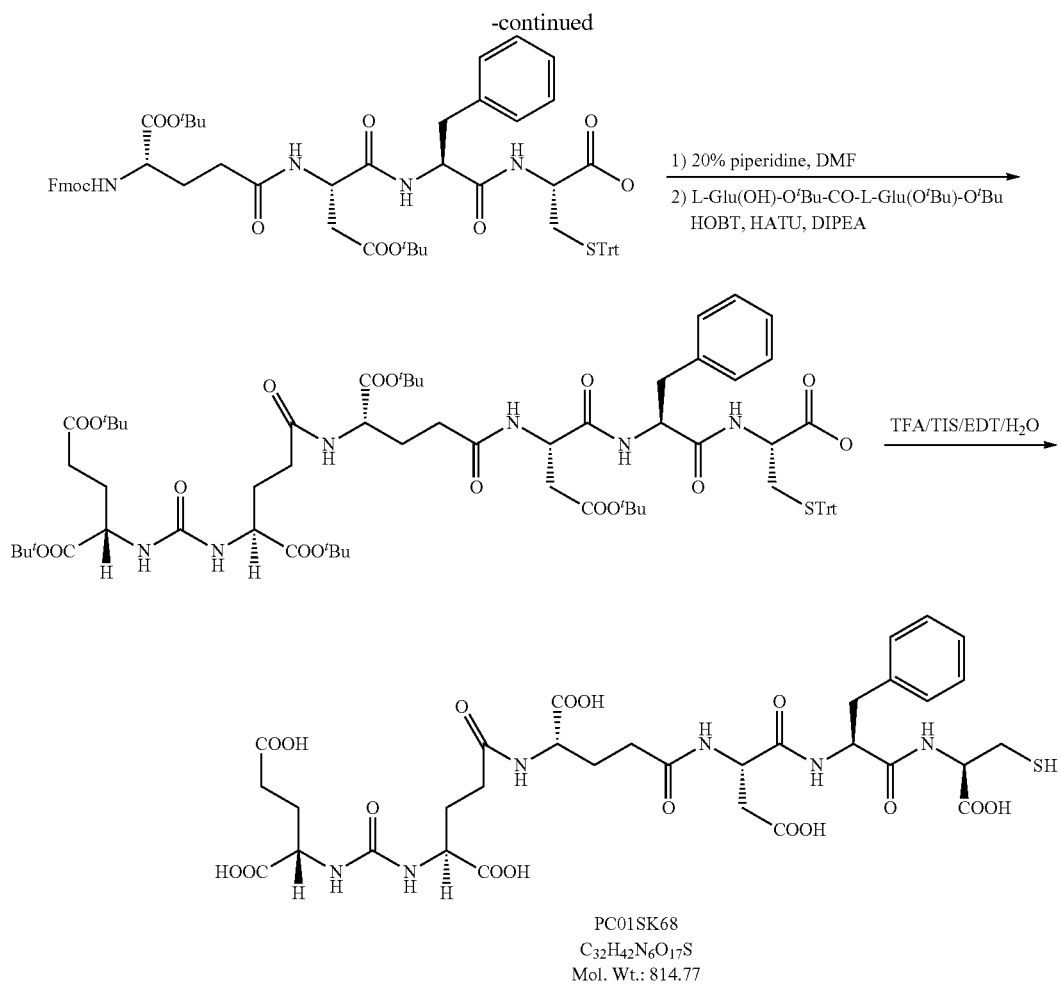

SK68 was synthesized using standard Fmoc SPPS starting from Fmoc-Cys(Trt)-Wang resin (Novabiochem; Catalog #04-12-2050), purified using reverse phase preparative HPLC (Waters, xTerra $C_{18}$ 10 μm, 19×250 mm) A=0.1 TFA, B=ACN; λ=257 nm; Solvent gradient: 1% B to 50% B in 30 min, 80% B wash 40 min run, (68%); and analyzed using reverse phase analytical HPLC (Waters, X-Bridge $C_{18}$ 5 μm; 3.0×15 mm); A=0.1 TFA, B=ACN; λ=257 nm, 1% B to 50% B in 10 min, 80% B wash 15 min run. $C_{32}H_{42}N_6O_{17}S$; MW=814.77 g/mol; white solid; $R_t$=8.2 min; $^1$H NMR (DMOS-$d_6$/$D_2O$) δ 1.70 (m, 3H);1.90 (m, 3H); 2.10 (m, 2H); 2.17 (m, 2H); 2.23 (m, 2H); 2.36 (m, 1H); 2.59 (dd, 1H); 2.79 (m,3H); 3.04 (dd, 1H); 4.07 (in, 2H, αH); 4.13 (in, 1H, αH); 4.37 [in, 1H, α-H]; 4.47 (m, 2H, α-H); 7.19 (m, 5H, Ar-H); 7.87 (d , Ures-NH); 8.20 (d, 1H, Urea-NH); LC-MS=815.3 (M+H)$^+$.

Example 8B. General synthesis of PSMA disulfide linker intermediate for releasable agent conjugate, illustrated for SK28L.

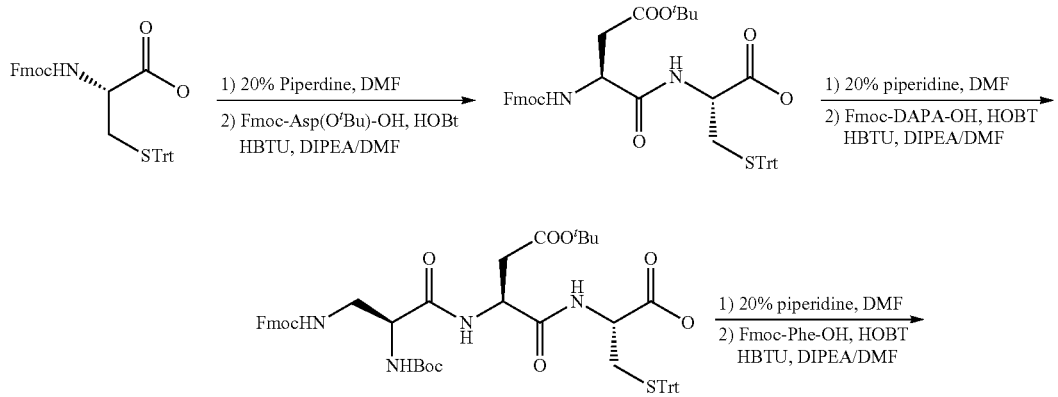

-continued
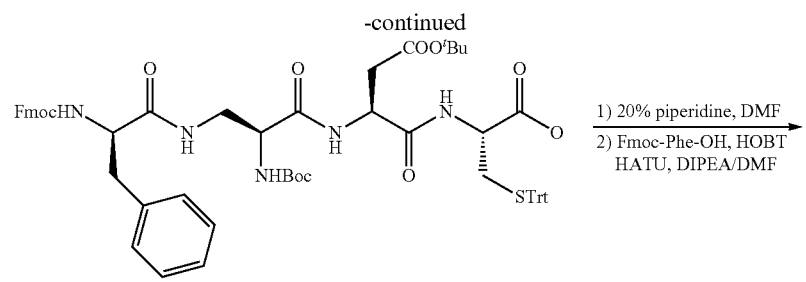
1) 20% piperidine, DMF
2) Fmoc-Phe-OH, HOBT HATU, DIPEA/DMF
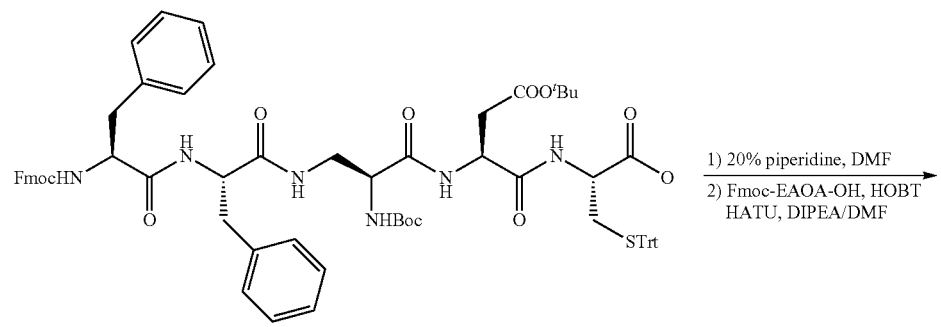
1) 20% piperidine, DMF
2) Fmoc-EAOA-OH, HOBT HATU, DIPEA/DMF
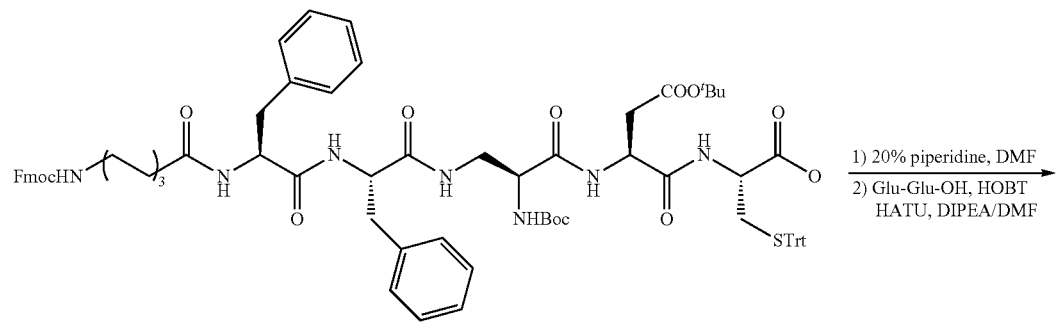
1) 20% piperidine, DMF
2) Glu-Glu-OH, HOBT HATU, DIPEA/DMF
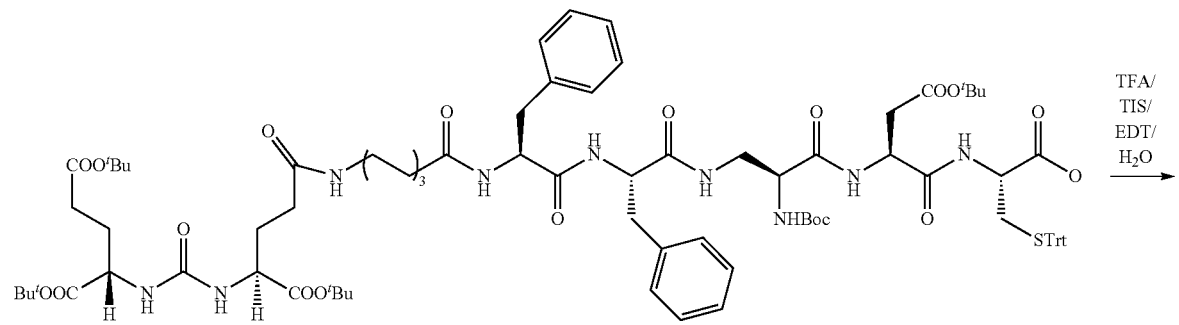
TFA/ TIS/ EDT/ H₂O

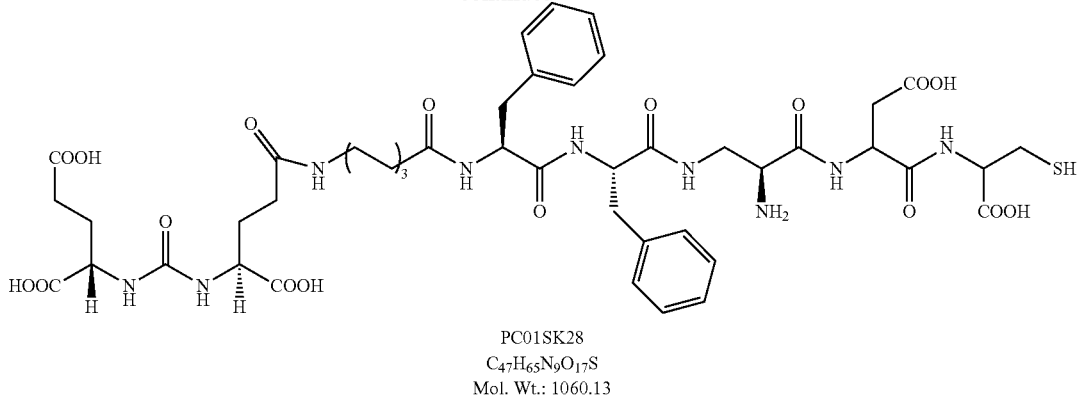

PC01SK28
C$_{47}$H$_{65}$N$_9$O$_{17}$S
Mol. Wt.: 1060.13

SK28 was synthesized using standard Fmoc-SPPS starting from Fmoc-Cys(Trt)-Wang resin (Novabiochem; Catalog #04-12-2050); purified using reverse phase preparative HPLC (Waters, xTerra C$_{18}$ 10 μm; 19×250 mm) A=0.1 TFA, B=ACN; λ=257 nm; Solvent gradient: 5% B to 80% B in 25 min, 80% B wash 30 min run, (61%); and analyzed using reverse phase analytical HPLC (Waters, X-Bridge C$_{18}$ 5 μm; 3.0×15 mm); A=0.1 TFA, B=ACN; λ=257 nm, 5% B to 80% B in 10 min, 80% B wash 15 min run. SK28L: C$_{47}$H$_{65}$N$_2$O$_{17}$S; MW=1060.13 g/mol; white solid; R$_t$=7.7 min; $^1$H NMR (DMSO-d$_6$/D$_2$O) δ 0.93 (m, 2H); 1.08 (m, 5H); 1.27 (m, 5H); 1.69 (m, 2H); 1.90 (m, 2H); 1.94 (m, 2H); 2.10 (m, 2H); 2.24 (q, 2H); 2.62 (m, 2H); 2.78 (m, 4H); 2.88 (dd, 1H); 2.96 (t, 2H); 3.01 (dd, 1H); 3.31 (dd, 1H); 3.62 (dd, 1H); 3.80 (q, 1H, αH); 4.07 (m, 1H, αH); 4.37 (m, 1H, αH); 4.42 (m, 2H, αH); 4.66 (m, 1H, αH); 7.18 (m, 10H, Ar-H): LC-MS=1061 (M+H)$_+$; ESI-MS=1061 (M+H)+.

Example 9A. General synthesis for preparing disulfide-linked conjugates, illustrated for tubulysin B conjugate SK71 (20-atom linker).

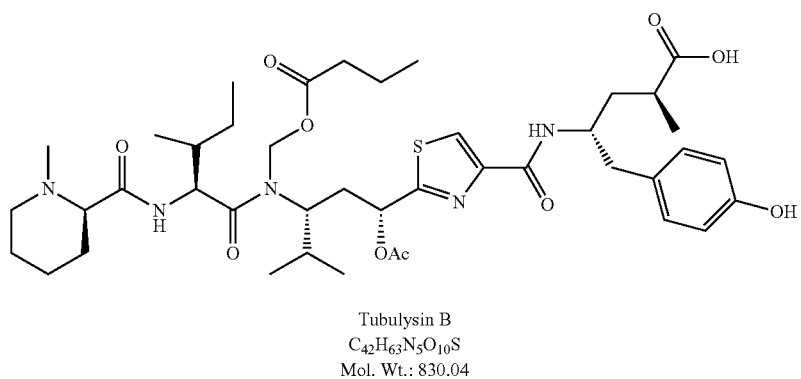

Tubulysin B
C$_{42}$H$_{63}$N$_5$O$_{10}$S
Mol. Wt.: 830.04

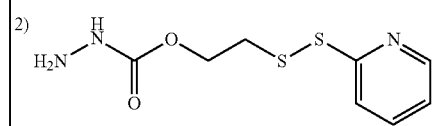

EC0311
C$_8$H$_{11}$N$_3$O$_2$S$_2$
Mol. Wt.: 245.32

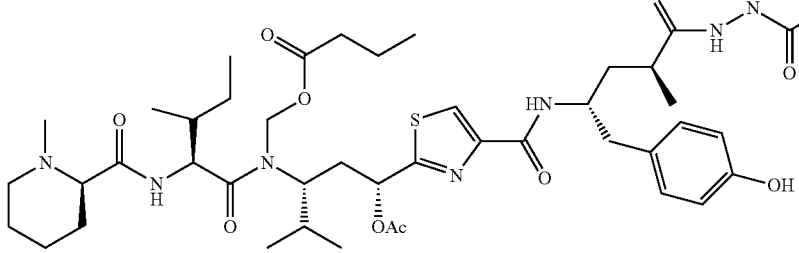
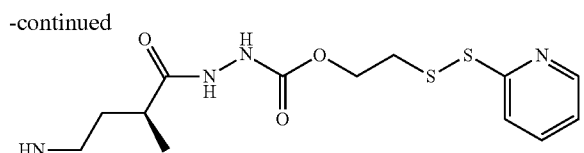

EC0312
C₅₀H₇₂N₈O₁₁S₃
Mol. Wt.: 1057.35

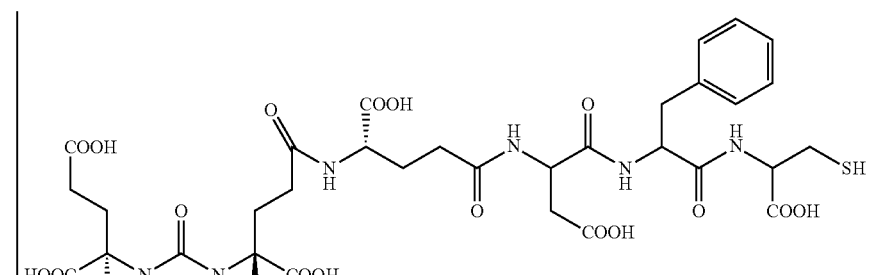

PC01SK68
C₃₂H₄₂N₆O₁₇S
Mol. Wt.: 814.77

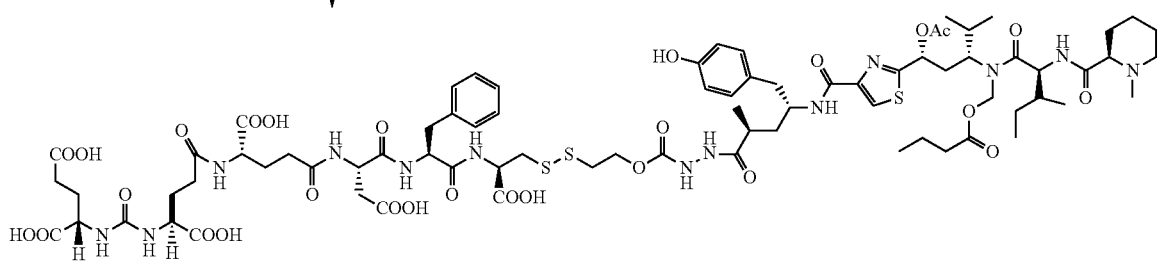

PC01SK71
C₇₇H₁₀₉N₁₃O₂₉S₃
Mol. Wt.: 1760.95

Synthesis of EC0312. Tubulysin B (30 mg, 0.036 mmol) was dissolved in ethylacetate (600 µL) under argon at −15° C. Isobutyl chlorofomate (4.7 µL, 0.054 mmol) and diisopropylethylamine (13.2 µL, 0.076 mmol) were added to the reaction mixture; reaction was stirred at −15° C. for 45 min under argon. EC0311 (13.4 mg, 0.054 mmol) dissolved in ethylacetate (500 µL) was added. Reaction mixture was stirred at −15° C. for another 15 min and then at room temperature for 45 min. Solvent was evaporated and residue was purified using short column (2%-8% methanol in CH₂Cl₂) to get EC0312 (34.4 mg, 90.5%). EC0312 was characterized using NMR (Varian 300 MHz, in CDCl₃), and LC-MS=1058.3 (M+H)⁺.

Synthesis of SK71. HPLC grade Milli-Q water and satd NaHCO₃ were purged with argon for 10 min. SK68 was dissolved in 1.0 mL of argon purged water while bubbling argon through the solution. The pH of the solution was increased to 6.8 using argon purged NaHCO₃ and EC0312 dissolved in THF (2.0 mL) was added to the reaction mixture. Progress of the reaction was monitored by analytical HPLC (10 mM NH₄OAc, pH=7.0; λ=254; 1% B to 50% B in 10 min 80% B wash 15 min run) and reaction was completed within 10 min. THF was evaporated and reaction mixture was diluted with 5.0 mL of 2 mM phosphate buffer. SK71 (61.3%) was purified using reverse phase preparative HPLC (Waters, xTerra C₁₈ 10 µm; 19×250 mm) A=2 mM Phosphate buffer, B=ACN; λ=254 nm; 5% B to 80% B in 25 min 80% B wash 40 min run; and analyzed using reverse phase analytical HPLC (Waters, X-Bridge C₁₈ 5 µm; 3.0×15 mm); A=10 mM NH₄OAc, B=ACN; λ=254 nm, 1% B to 50% B in 10 min, 80% B wash 15 min run. C₇₇H₁₀₉N₁₃O₂₈S₃: MW=1760.95 g/mol; white color solid, R$_t$7.6 min; ¹H NMR (DMSO-d₆/D₂O) was consistent with the SK71 structure; HRMS (MALDI) (m/z): (M−H)— calcd. for, C₇₇H₁₁₀N₁₃O₂₈S₃, 1758.6594; found, 1758.7033; LRMS (LCMS) (m/z) (M+H)+ calcd. for 1761.9; found, 1761.8; UVNis: λmax=254 nm.

Example 9B. Similarly, the D-Cys analog of SK71 was prepared as described herein.
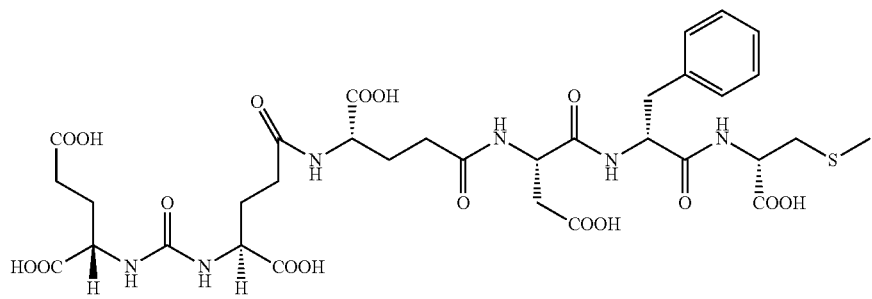
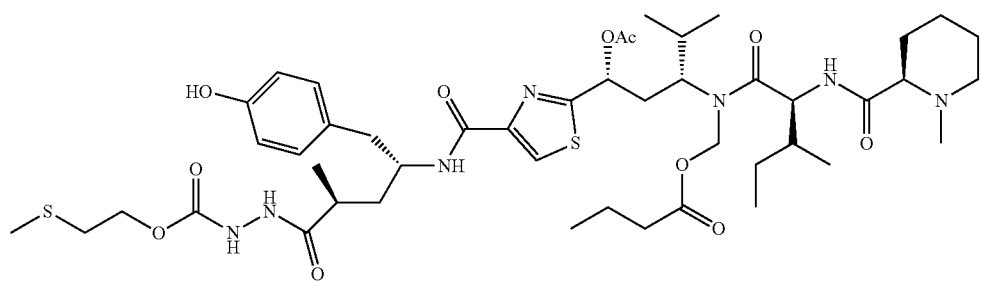
Example 9C. General synthesis for preparing disulfide-linked conjugates, illustrated for tubulysin B conjugate SK77 (31-atom linker).
Scheme 6.4
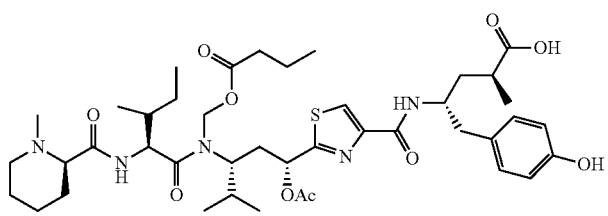
Tubulysin B
$C_{42}H_{63}N_5O_{10}S$
Mol. Wt.: 830.04
1) DIPEA/Isobutylchloroformate
   EtOAc/-15 oC
2) 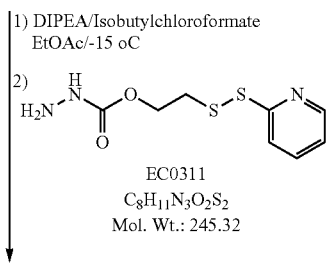
EC0311
$C_8H_{11}N_3O_2S_2$
Mol. Wt.: 245.32

-continued

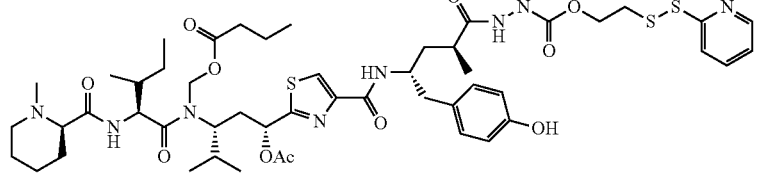

EC0312
C₅₀H₇₂N₈O₁₁S₃
Mol. Wt.: 1057.35

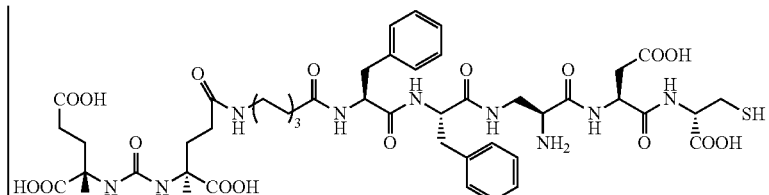

PC01SK28
C₄₃H₀₅N₉O₁₁S
Mol. Wt.: 1060.13

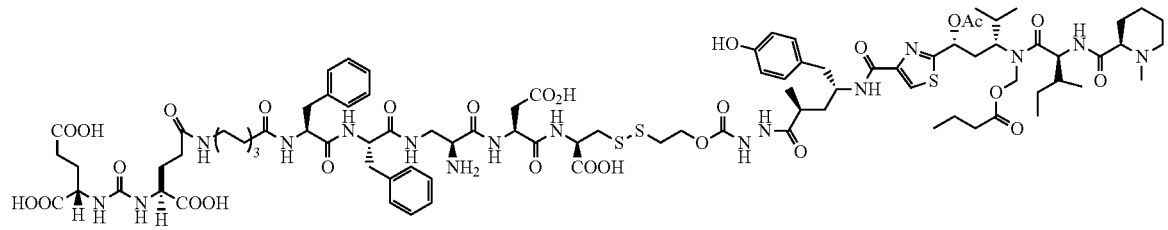

PC01SK77
C₉₃H₁₃₃N₁₆O₂₆S₃
Mol. Wt.: 2006.32

HPLC grade Milli-Q water and satd NaHCO₃ were purged with argon for 10 min. SK68 was dissolved in 1.0 mL of argon purged water while bubbling argon. The pH of the solution was increased to 6.8 using argon purged NaHCO₃ and EC0312 dissolved in THF (2.0 mL) was added to the reaction mixture. Progress of the reaction was monitored by analytical HPLC (10 mM NH₄OAc, pH=7.0; λ=254; 1% B to 50% B in 10 min 80% B wash 15 min run) and reaction was completed within 10 min. THF was evaporated and reaction mixture was diluted with 5.0 mL of 2 mM phsphate buffer. SK77 (61%) was purified using reverse phase preparative HPLC (Waters, xTerra C₁₈ 10 μm; 19×250 mm) A=2 mM phosphate buffer, B=ACN; λ=254 nm; 5% B to 80% B in 25 min 80 % B wash 40 min run; and analyzed using reverse phase analytical HPLC (Waters, X-Bridge C₁₈ 5 μm; 3.0×15 mm); A=10 mM NH₄OAc, B=ACN; λ=254 nm, 1% B to 50% B in 10 min, 80% B wash 15 min run. C₉₃H₁₃₃N₁₆O₂₈S₃: MW=2006.32 g/mol; white color solid, $R_t$=7.7 min; ¹H NMR (DMSO-d₆/D₂O); LC–MS=2007.0 (M+H)⁺.

Example 9D. Similarly, the D-Cys analog of SK77 was prepared as described herein.

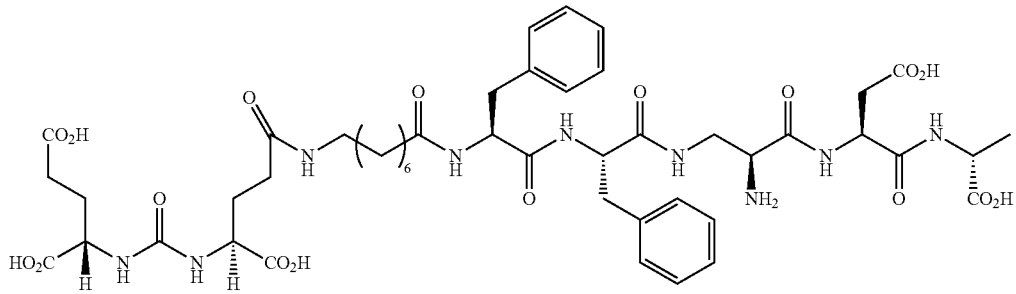

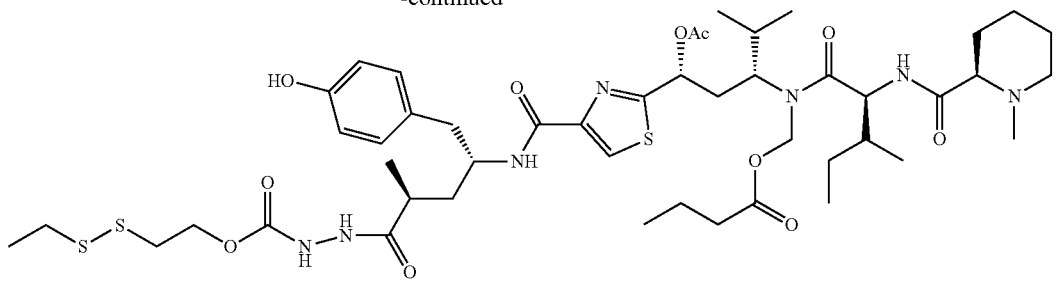
Example 9E. Similarly, the D-Cys, propanoic acid analog of SK77 was prepared as described herein.
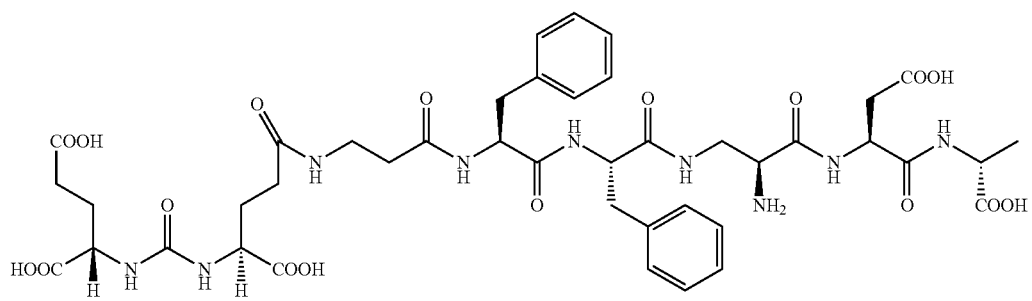
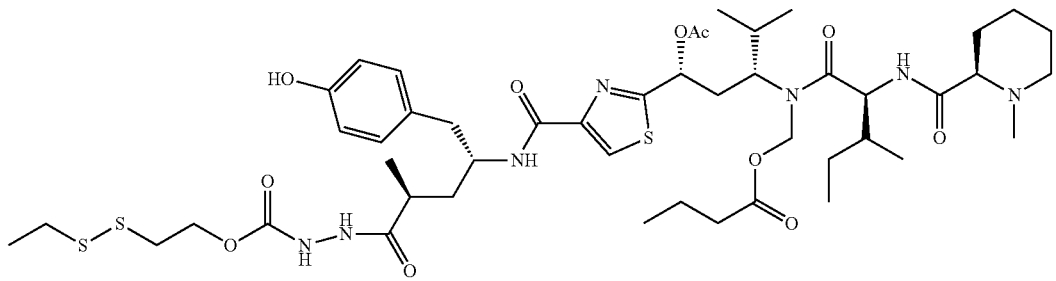
Example 9F-9G. The following DUPA vinblastine and DUPA camptothecin compounds, SK37 and SK45, respectively, were prepared according to the processes described herein.
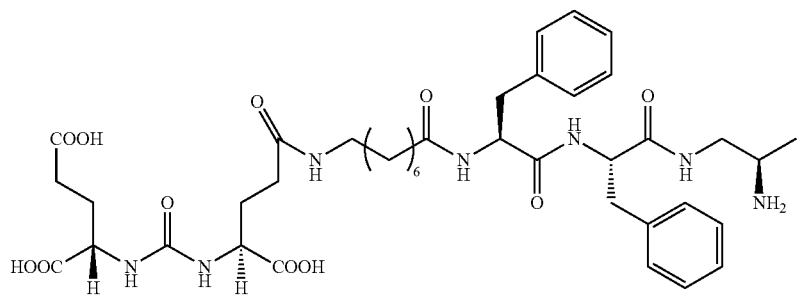

-continued

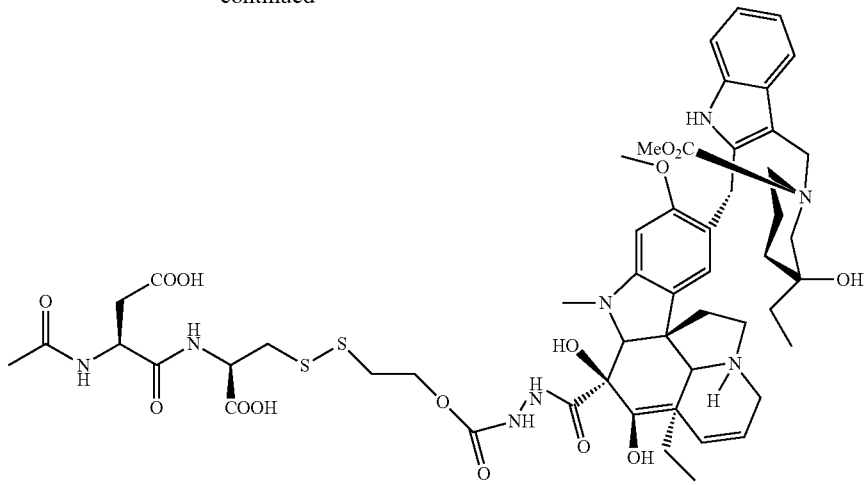

SK37 (vinblastine conjugate, $C_{93}H_{123}N_{15}O_{26}S_2$, Mol. Wt.: 1931.19) prepared in 63.1% yield. $C_{93}H_{123}N_{15}O_{26}S_2$: MW=1931.19 g/mol; white color solid, $R_t$=7.7 min; $^1$H NMR (DMSO-$d_6$/$D_2$O); LC-MS=1932.6 (M+H)$^+$.

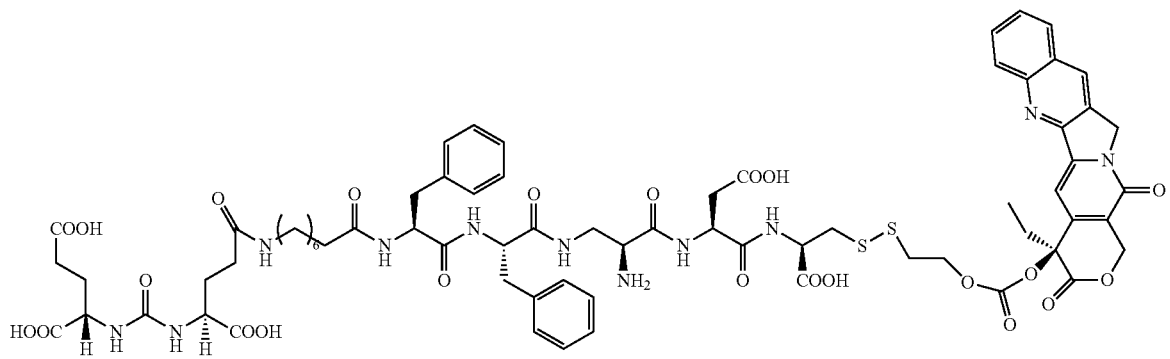

SK45 (camptothecin conjugate, $C_{70}H_{83}N_{11}O_{23}S_2$, Mol. Wt.: 1510.60) prepared in 66% yield. $C_{70}H_{83}N_{11}O_{23}S_2$: MW=1510.60 g/mol; white color solid, $R_t$=7.5 min; $^1$H NMR (DMSO-$d_6$/$D_2$O); LC-MS=1511.1 (M+H)$^+$.

Example 9H. Similarly, the Glu-Asp-Phe analog of SK37 was prepared as described herein.

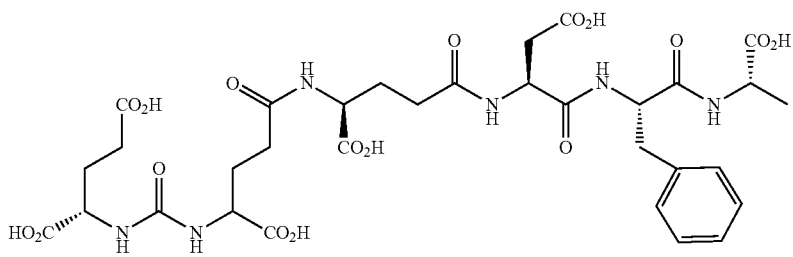

-continued
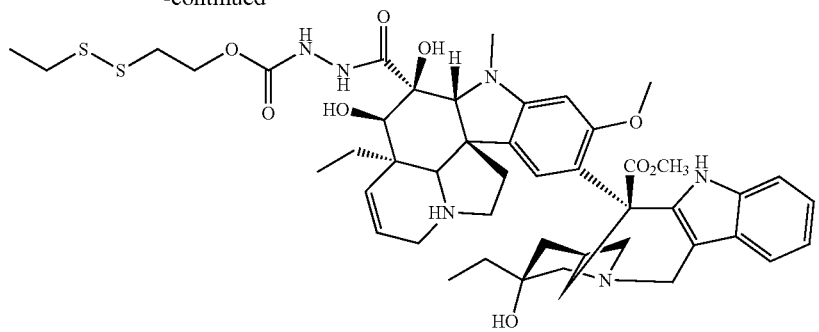
Example 10. The following compounds were prepared using the synthetic processes described herein:
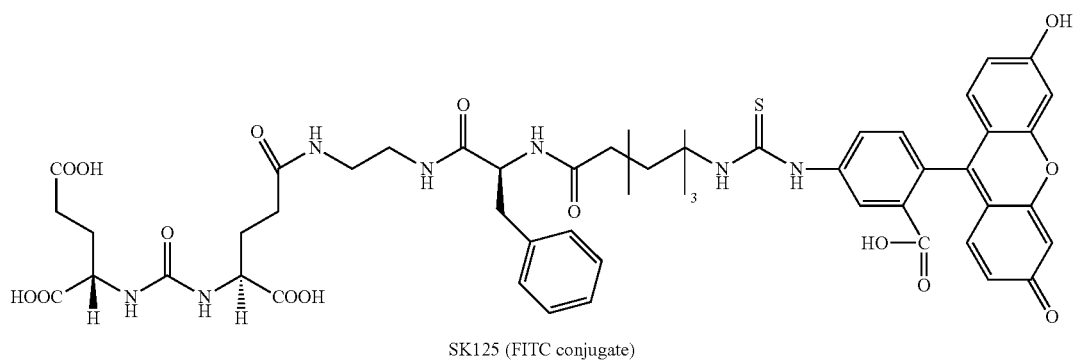
SK125 (FITC conjugate)
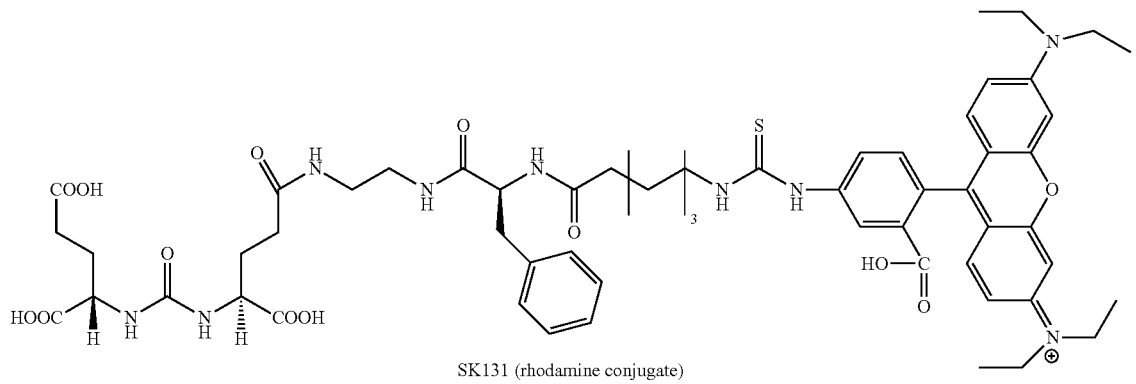
SK131 (rhodamine conjugate)
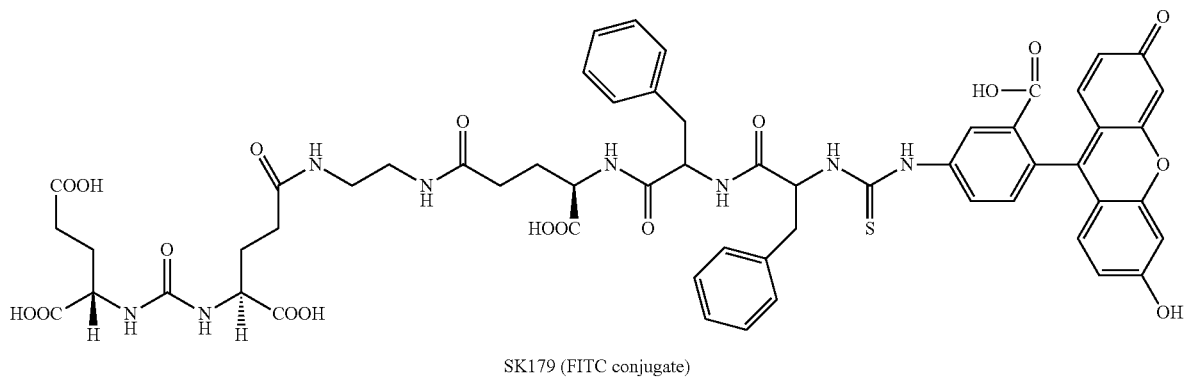
SK179 (FITC conjugate)

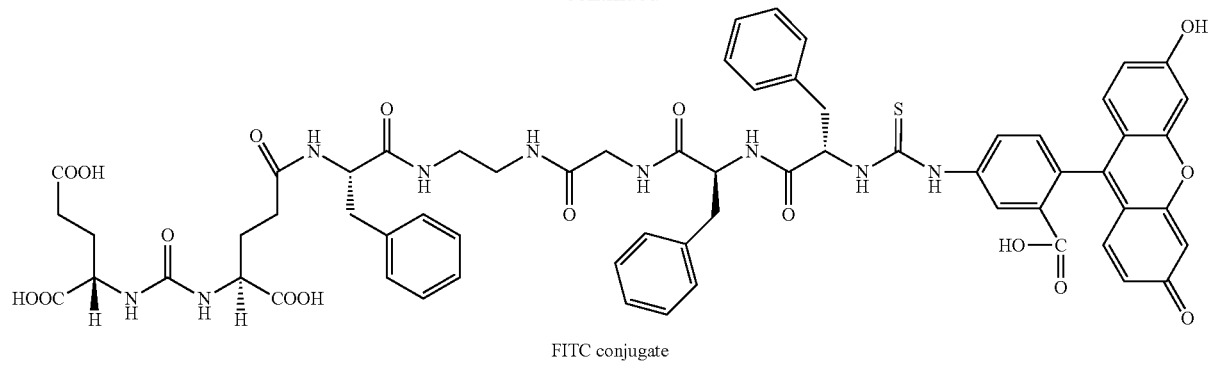
FITC conjugate
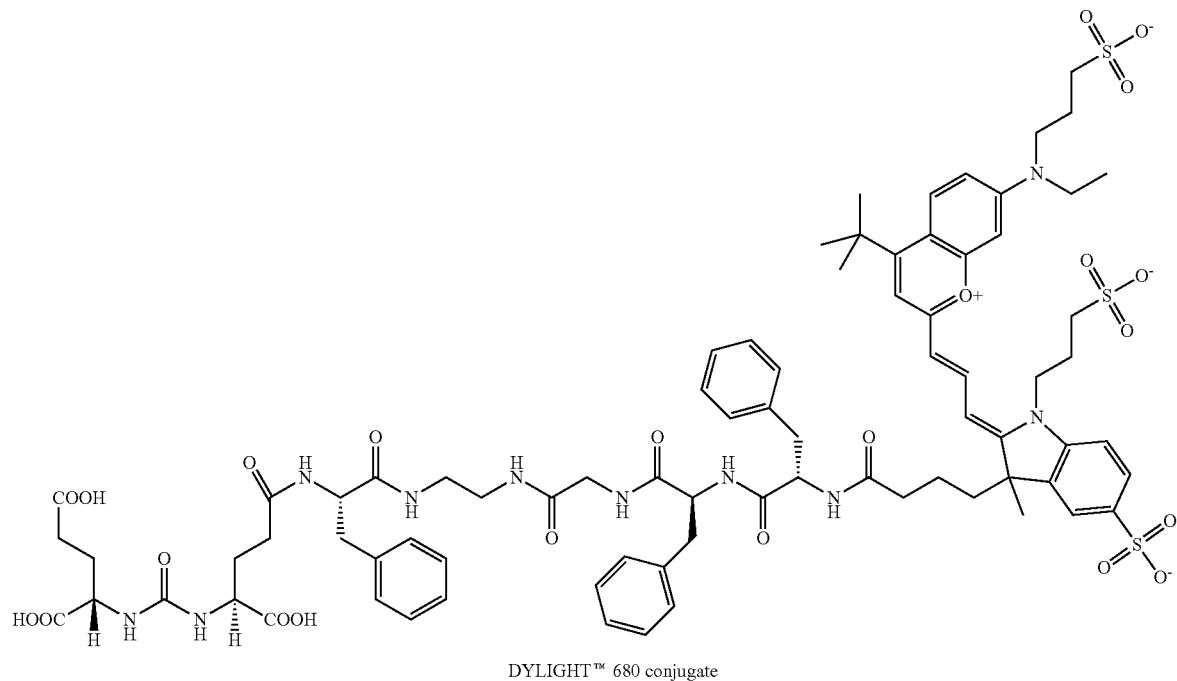
DYLIGHT™ 680 conjugate
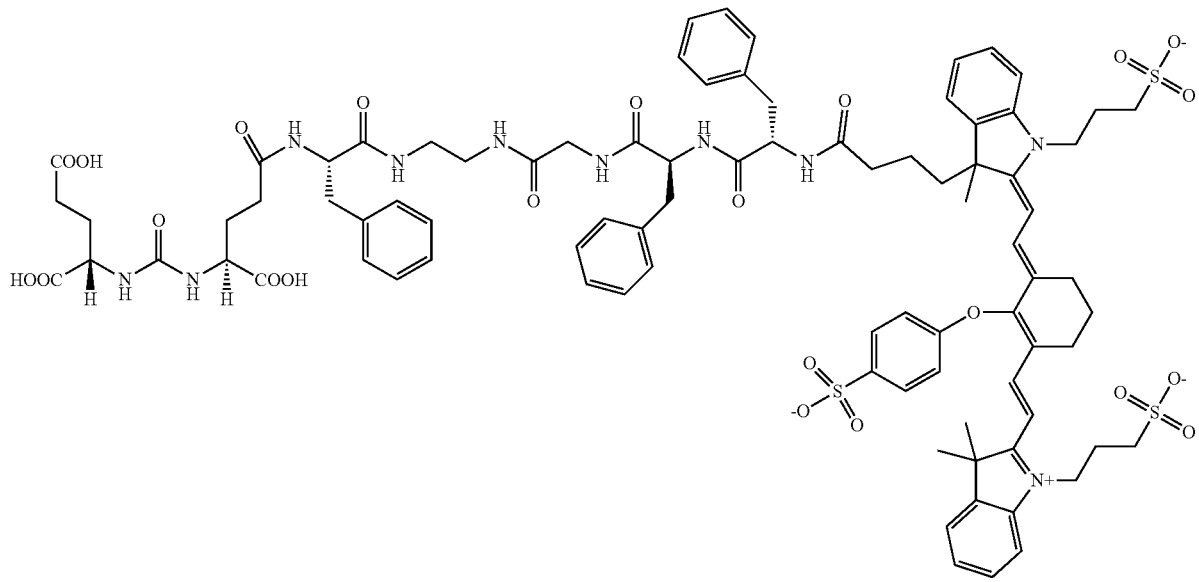
DYLIGHT™ 800 conjugate

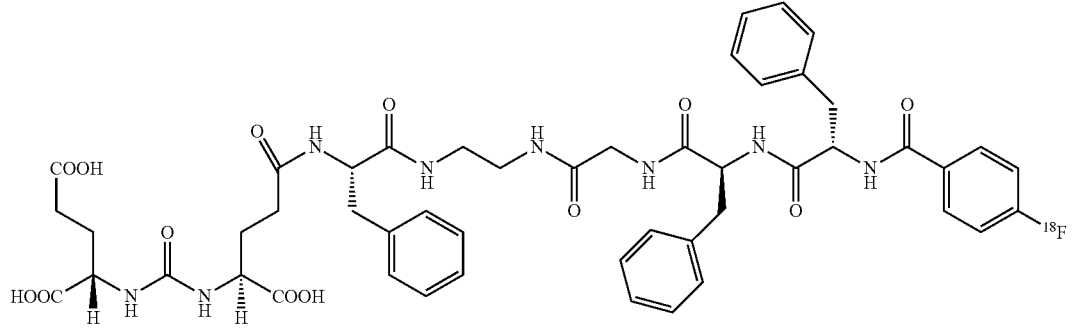
PET agent conjugate
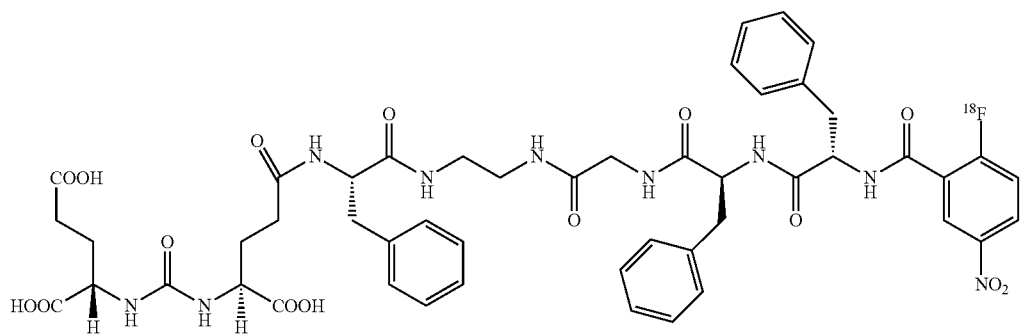
PET agent conjugate
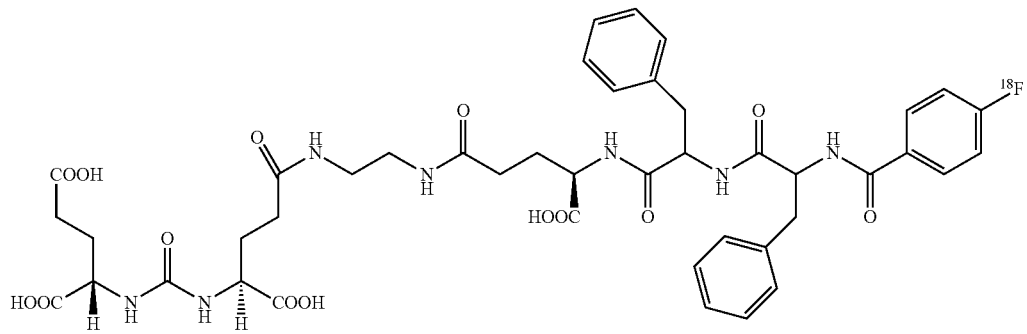
PET agent conjugate
DOTA conjugate capable of chelating for example $^{64}$Cu, $^{65}$Cu, and the like
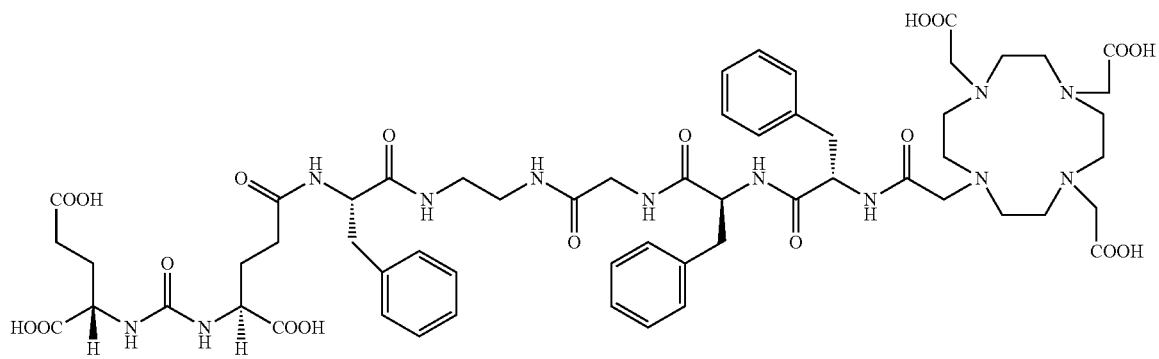 [SMILES: O=C(O)CC[C@H](NC(=O)N[C@@H](CCC(=O)N[C@@H](Cc1ccccc1)C(=O)NCCNC(=O)CNC(=O)[C@H](Cc1ccccc1)NC(=O)[C@H](Cc1ccccc1)NC(=O)CN1CCN(CC(=O)O)CCN(CC(=O)O)CCN(CC(=O)O)CC1)C(=O)O)C(=O)O]

DOTA conjugate capable of chelating for example $^{64}$Cu, $^{65}$Cu, and the like

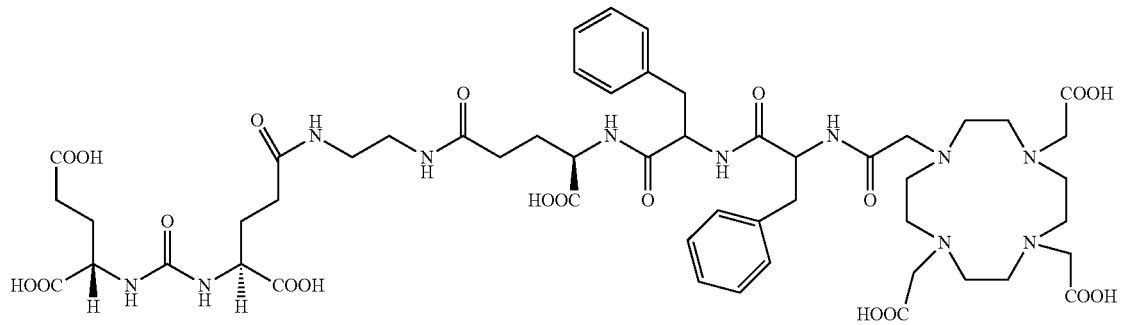 [SMILES: O=C(O)CC[C@H](NC(=O)N[C@@H](CCC(=O)NCCNC(=O)CC[C@@H](NC(=O)C(Cc1ccccc1)NC(=O)C(Cc1ccccc1)NC(=O)CN1CCN(CC(=O)O)CCN(CC(=O)O)CCN(CC(=O)O)CC1)C(=O)O)C(=O)O)C(=O)O]

DTPA conjugate capable of chelating for example In, Ga, Ir, Yr, and the like

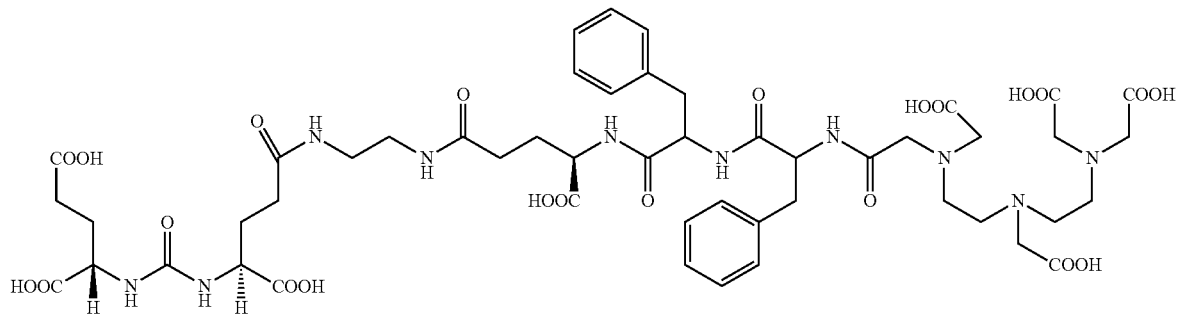 [SMILES: O=C(O)CC[C@H](NC(=O)N[C@@H](CCC(=O)NCCNC(=O)CC[C@@H](NC(=O)C(Cc1ccccc1)NC(=O)C(Cc1ccccc1)NC(=O)CN(CCN(CCN(CC(=O)O)CC(=O)O)CC(=O)O)CC(=O)O)C(=O)O)C(=O)O)C(=O)O]

Tripeptide conjugate capable of chelating for example Tc, Tc oxides, and the like

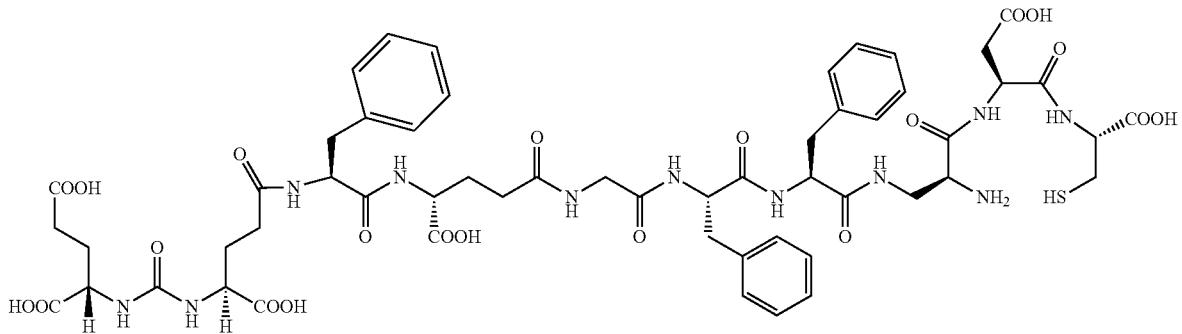 [SMILES: N[C@@H](CNC(=O)[C@H](Cc1ccccc1)NC(=O)[C@H](Cc1ccccc1)NC(=O)CNC(=O)CC[C@@H](NC(=O)[C@H](Cc1ccccc1)NC(=O)CC[C@H](NC(=O)N[C@@H](CCC(=O)O)C(=O)O)C(=O)O)C(=O)O)C(=O)N[C@@H](CC(=O)O)C(=O)N[C@@H](CS)C(=O)O]

The foregoing exemplary embodiments are intended to be illustrative of the invention, and should not be interpreted or construed as limiting in any way the invention as described herein.

METHOD EXAMPLES

Example 1A

In Vitro Binding Studies Using Lncap Cells and SK28 (14 Atom Spacer). LNCaP cells (a human prostate cancer cell line over-expressing PSMA, purchased from American Type Culture Collection (ATCC)) were seeded in two 24-well (120,000 cells/well) falcon plates and allowed to grow to adherent monolayers for 48 hours in RPMI with glutamine (2 mM)(Gibco RPMI medium 1640, catalog #22400) plus 10% FBS (Fetal Bovine Serum), 1% sodium pyruvate (100 mM) and 1% PS (penicillin streptomycin) in a 5%-CO2 atmosphere at 37° C. Cells of one 24-well plate were incubated with increasing concentrations of SK28-99 mTc from 0 nM-450 nM (triplicates for each concentration) in a 5%-CO2 atmosphere at 37° C. for 1 hour. Cells of the second 24-well plate were incubated with 50 uM PMPA in a 5%-CO2 atmosphere at 37° C. for 30 minutes, then incubated with increasing concentrations of SK28-99 mTc from 0 nM-450 nM (triplicates for each concentration) in a 5%-CO2 atmosphere at 37° C. for 1 hour (competition study). Cells were rinsed three times with 1.0 mL of RPMI. Cells were lysed with tris-buffer, transferred to individual gamma scintigraphy vials, and radioactivity was counted. The plot of cell bound radioactivity verses concentration of radiolabeled compound was used to calculate the Kd value.

The competition study was used to determine the binding specificity of the ligand (DUPA) to the PSMA (Figure 1A).

Example 1B

Figure 1B:
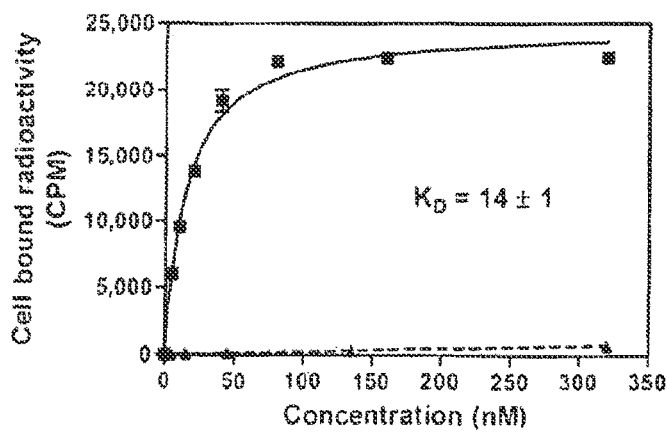
FIG. 1B. In Vitro Binding Studies Using LNCaP Cells and SK33 (14 atom linker). LNCaP cells containing increasing concentrations of DUPA-$^{99m}$Tc in the presence (▲) or absence (■) of excess PMPA FIG. 2. Cell bound radioactivity verses concentration of SIC28-$^{99m}$Tc; at 4° C. (■) and at 37° C. (▲).

In Vitro Binding Studies Using LNCaP Cells and SK33 (14 atom spacer). LNCaP cells (150,000 cells/well) were seeded onto 24-well Falcon plates and allowed to form confluent monolayers over 48 h. Spent medium in each well was replaced with fresh medium (0.5 mL) containing increasing concentrations of DUPA-99 mTc in the presence (▲) or absence (■) of excess PMPA. After incubating for 1 h at 37° C., cells were rinsed with culture medium (2×1.0 mL) and tris buffer (1×1.0 mL) to remove any unbound radioactivity. After suspending cells in tris buffer (0.5 mL). cell bound radioactivity was counted using a y-counter (Packard, Packard Instrument Company). The dissociation constant (KD) was calculated using a plot of cell bound radioactivity versus the concentration of the radiotracer using nonlinear regression in GraphPad Prism 4. Error bars represent 1 standard deviation (n=3). Experiment was performed three times with similar results. (FIG. 1B).

Example 2

Quantification of PSMA Molecules on LNCaP Cells. LNCaP cells were seeded in a 24-well falcon plate and allowed to grow to adherent monolayers for 48 hours in RPMI (Gibco RPMI medium 1640, catalog #22400) plus 10% FBS (Fetal Bovine Serum), 1% glutaric and 1% PS (penicillin streptomycin) in a 5%-CO2 atmosphere at 37° C. Cells were then incubated with increasing concentrations of SK28-99 mTc from 0 nM-450 nM (triplicates for each concentration) in a 5%-CO2 atmosphere at 4° C. or at 37° C. for 1 hour. Cells were rinsed three times with 1.0 mL of RPMI. Cells were lysed with tris-buffer, transferred to individual gamma scintigraphy vials, and radioactivity was counted. The plot of cell bound radioactivity verses concentration of radiolabeled compound was used to calculate number of PSMA/LNCaP cell. The radioactivity of a 30 nM sample of SK28-99 mTc (20 uL) was counted. At 4° C. (to prevent endocytosis of PSMA), the number of moles in the 30 nM sample=30 nM×20 uL=(30×10-9 mol/L)×(20×10-6 L)=6×10-13 mol. The number of atoms in the 30 nM sample=(6×10-13 mol)×(6.023×1023 atom/mol)=3.6×1011 atom. The radio count of 20 uL of the 30 nM sample=20477 cpm (cpm/atom=3.6×1011/20477 =1.76×107). The cell bound radioactivity at the saturation point at 4° C.=12 000 cpm. The number of atoms at the saturation point=(1.76× 107 atom)×(12000 cpm). The number of cells/well=245, 000. The number of PSMA/cell at 4° C. =(2.12×1011)/2.45× 105=864 396.4~0.9×106 PSMA/LNCaP cell.

Figure 2:
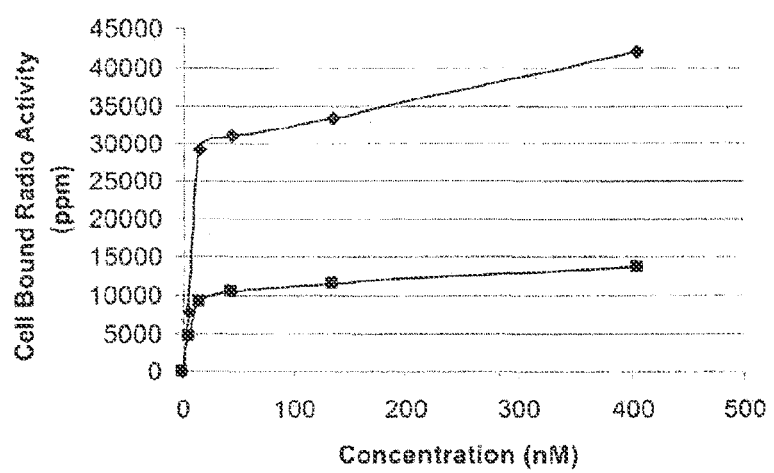

The cell bound radioactivity at the saturation point at 37° C.=33,000 cpm (approximately three fold higher than at 4° C.). This shows that PSMA undergoes endocytosis, unloading the drug and recycling, similar to cell surface receptors. See FIG. 2.

Example 3

Figure 3A:
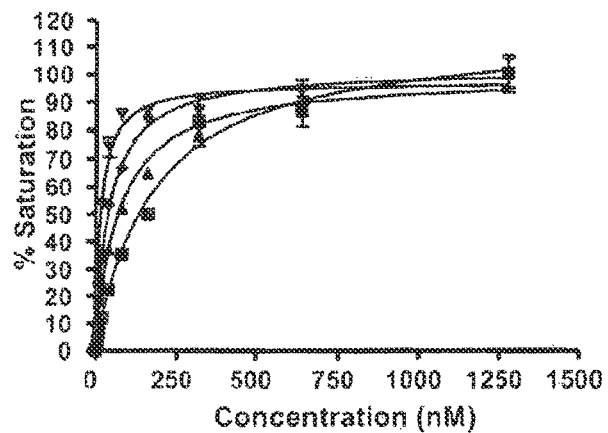
FIG. 3A. Plot of cell bound radioactivity versus concentration of DUPA-Linker-$^{99m}$Tc imaging agents: (■) 0-atom linker ($K_d$=171 nM); (▲) 7-atom linker ($K_d$=68 nM); (▼) 14-atom linker ($K_d$=15 nM); (♦)16-atom linker($K_d$=40 nM).
Figure 3B:
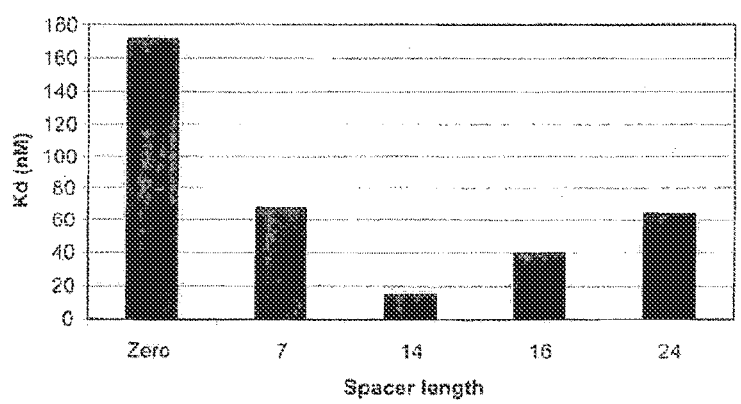
FIG. 3B. $K_D$ values for DUPA-Linker-$^{99m}$Tc compounds binding to LNCaP cells.

Spacer-Dependent Binding Studies. LNCaP cells were seeded in 24-well (120,000 cells/plate) falcon plates (10 plates) and allowed to grow to adherent monolayers for 48 hours in RPMI (Gibco RPMI medium 1640, catalog #22400) plus 10% FBS (Fetal Bovine Serum), 1% sodium pyruvate and 1% PS (penicillin streptomycin) in a 5%-CO2 atmosphere at 37° C. Cells were then incubated with increasing concentrations of SK60- 99 mTc (zero atom spacer), SK62-99 mTc (7 atom spacer), SK28-99 mTc (14 atom spacer), SK38-99 mTc (16 atom spacer) and SK57-99 mTc (24 atom spacer) from 0nM-1280 nM (triplicates for each concentration) in a 5%-CO2 atmosphere at 37° C. for 1 hour. Also, in separate plates, cells was incubated with 50 uM PMPA in a 5%-CO2 atmosphere at 37° C. for 30 minutes and then incubated with increasing concentration of SK60-99 mTc (zero atom spacer), SK62-99 mTc (7 atom spacer), SK28-99 mTc (14 atom spacer), SK38-99 mTc (16 atom spacer) and SK57-99 mTc (24 atom spacer) from 0 nM-1280 nM (triplicates for each concentration) in a 5%-CO2 atmosphere at 37° C. for 1 hour (competition studies; data not shown). Cells were rinsed three times with 1.0 mL of RPMI. Cells were lysed with tris-buffer, transferred to individual gamma scintigraphy vials, and radioactivity was counted. The plot of cell bound radioactivity verses concentration of the radiolabeled compound was used to calculate the Kd value. The plot of % saturation verses concentration of the radiolabeled compound as well as the plot for Kd verses spacer length are shown (FIG. 3A and B).

Example 4

In Vivo Growth of Human LNCaP Tumor Cells in Nude Mice. LNCaP cells were maintained in RPMI 1640 (Gibco RPMI medium 1640, catalog #22400) with glutamine (2 mM), 10% FBS (Fetal Bovine Serum), 1% sodium pyruvate (100 mM) and 1% PS (penicillin streptomycin) in a 5%-CO2 atmosphere at 37° C. . Four to five week-old athymic male nude mice (nu/nu) were obtained from the NCI Charles River and maintained in a sterile environment. Mice were housed in polycarbonate shoebox cages with wire top lids and maintained on a normal diet. Mice were allowed to acclimate for one week prior to inoculation of LNCaP cells. Matrigel and high concentrated (HC) matrigel were purchased from BD Biosciences. Nude mice were inoculated with either 2.5×106 or 5.0×10 6 in vitro propagated LNCaP cells in 50% matrigel (100 uL RPMI medium+100 uL of matrigel) or 50% high concentrated matrigel (100 uL RPMI medium +100 uL of IIC matrigel) to determine optimal conditions. including number of cells, vehicle, etc. Cells were subcutaneously injected into each axial and each flank of the nude mice to determine the optimal site. The volume of each tumor was measured in perpendicular directions twice a week using a caliper and body weight was measured once a week (data not shown).

Figure 4:
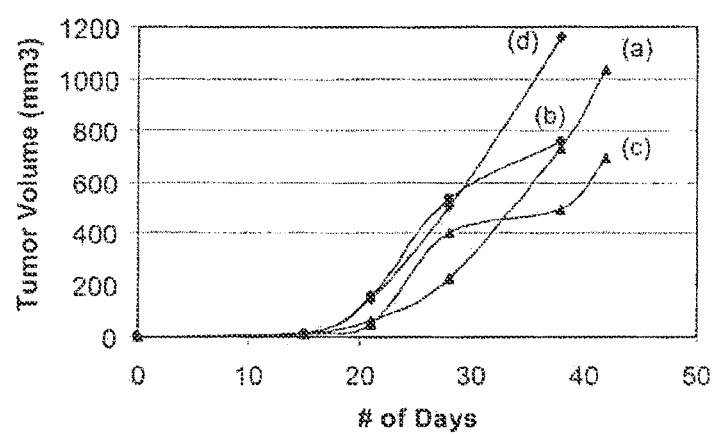
FIG. 4. Plot of days post injection verses tumor volume for LNCaP tumors: (a) 2.5 million+Matrigel; (b) 2.5 million+HC Matrigel; (c) 5 million+Matrigel; (d) 5 million+HC Matrigel.

The volume of each tumor was calculated as 0.5×L×W2, where L=measurement of longest axis in millimeters and W=measurement of axis perpendicular to L in millimeters. Approximately 5.0×106 LNCaP cells in 50% HC matrigel on the axial gave 600 mm3 tumors within 30 days. See FIG. 4.

Example 5

Comparison of lncap, kb and a549 Cell Tumor Growth in Mice. LNCaP, KB, and A549 cells were maintained in RPMI 1640 (Gibco RPMI medium 1640, catalog #22400) with glutamine (2 mM), 10% FBS (Fetal Bovine Serum), 1% sodium pyruvate (100 mM) and 1% PS (penicillin streptomycin) in a 5%-CO2 atmosphere at 37° C. Four-five weeks old male nude mice (nu/nu) were obtained from the NCI Charles River and maintained in a sterile environment. Mice were housed in polycarbonate shoebox cages with wire top lids and maintained on a normal diet. Mice were allowed to acclimate for one week prior to inoculation of cells.

Figure 5A:
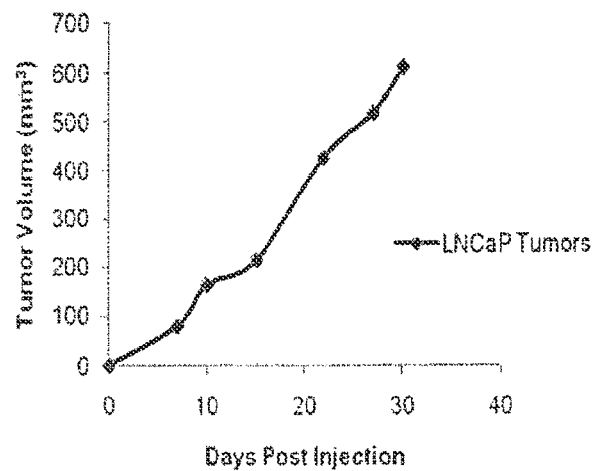
FIG. 5A. Plot of days post injection verses tumor volume for LNCaP tumors (27 mice) and (b) KB cells (5 mice) and A549 cells (5 mice).
Figure 5B:
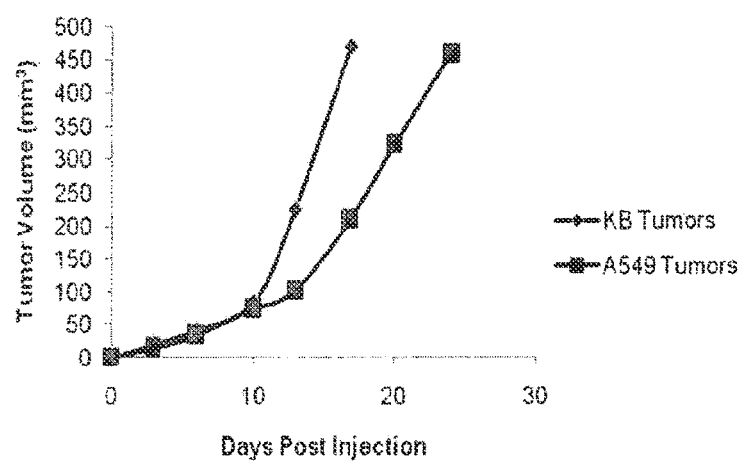
FIG. 5B. Plot of days post injection versus rumor volume for KB cells (5 mice) and A549 cells (5 mice).

For tumor cell inoculation, 5.0×106 LNCaP cells in 50% high concentrated matrigel, 1.0×106 KB cells in RPMI medium, or 1.0×10 6 A549 cells in RPMI medium were subcutaneously injected into the right axial (some animals were injected in both) of the nude mice. The volume of each tumor was measured in two perpendicular directions twice a week using a caliper (See FIGS. 5A and 5B) and body weight was measured once a week (data not shown). The volume of the tumors were calculated as 0.5×L×W2, where L=measurement of longest axis in millimeters and W=measurement of axis perpendicular to L in millimeters.

Example 6A

Figure 6A:
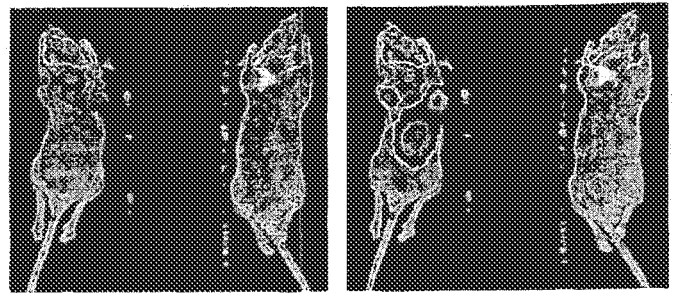
FIG. 6A. Mice (Set 1) previously injected with LNCaP tumors, treated with 1 ng/kg SK28-$^{99m}$Tc (14-atom linker), the left hand image shows white light images and image shows an overlay of the radioimage with the white light image. In each panel, the right mouse was treated with 50 mg/kg PMPA (to block PSMA binding) and the left mouse was treated without added PMPA.
Figure 6B:
FIG. 6B. Mice (Set 2) previously injected with LNCaP tumors, treated with 1 ng/kg SK28-$^{99m}$Tc (14-atom linker), the left hand image shows white light images and image shows an overlay of the radioimage with the white light image. In each panel, the right mouse was treated with 50 mg/kg PMPA (to block PSMA binding) and the left mouse was treated without added PMPA.
Figure 6C:
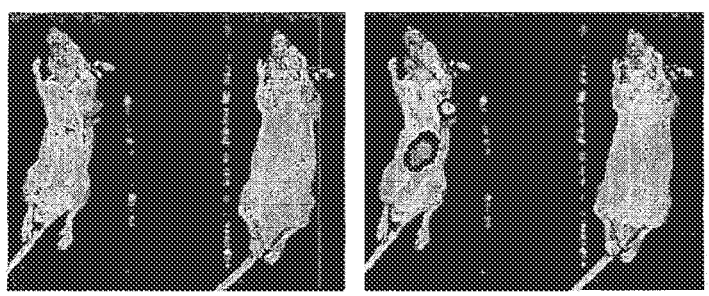
FIG. 6C. Mice (Set 3) previously injected with LNCaP tumors, treated with 1 ng/kg SK28-$^{99m}$Tc (14-atom linker), the left hand image shows white light images and image shows an overlay of the radioimage with the white light image. In each panel, the right mouse was treated with 50 mg/kg PMPA (to block PSMA binding) and the left mouse was treated without added PMPA.
Figure 7A:
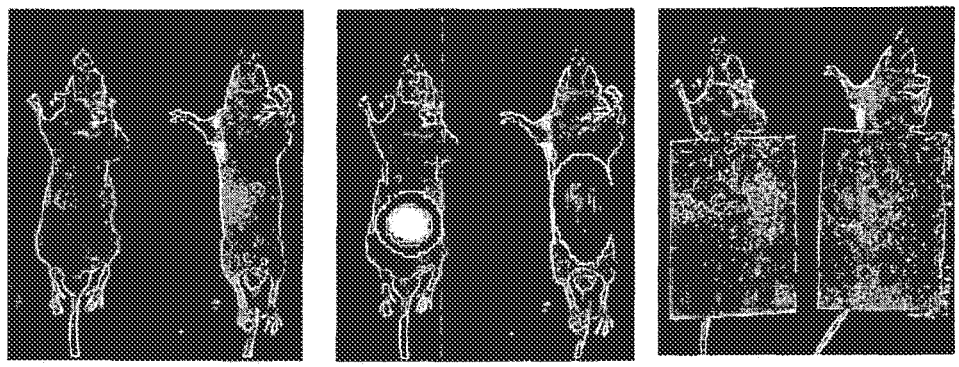
FIG. 7A. Mice previously injected with LNCaP tumors treated using SK60-$^{99m}$Tc (zero atom linker). The left image shows white light images, the center image shows overlay of radioimage with white light image, and the right image shows overlay of radioimage with white light image by shielding the kidney of mice.
Figure 7B:
FIG. 7B. Mice previously injected with KB cells treated using SK28-$^{99m}$Tc (14 atom linker). The left image shows white light images, the center image shows overlay of radioimage with white light image, and the right image shows overlay of radioimage with white light image by shielding the kidney of mice.
Figure 7C:
FIG. 7C. Mice previously injected with A549 cells treated using SK28-$^{99m}$Tc (14 atom linker). The left image shows white light images, the center image shows overlay of radioimage with white light image, and the right image shows overlay of radioimage with white light image by shielding the kidney of mice.

In Vivo Imaging of Tumors in Mouse Using PSMA-99 mTc. When tumors reached a volume of between 500-600 mm3, 99 mTc-labeled compounds (e.g. SK28-99 mTc, SK60-99 mTc, etc) prepared as described, were administered through intraperitoneal injection (subcutaneously). Four hours later, animals were euthanized and blood was taken by cardio punch and transferred to individual gamma scintigraphy vials per each animal. The imaging experiments were carried out using either a Kodak or gamma scintigraphic camera imager (FIGS. 6A, 6B, 6C, 7A, 7B and 7C). [Note: PMPA was injected 30 minutes before injecting SK28 -99 mTc. Other than uptake in the cancerous masses, SK28-99 mTc distribution was limited to kidneys (FIGS. 6A, 6B and 6C). Both mice (FIGS. 7A, 7B and 7C) were injected with SK60-99 mTc and distribution was limited mostly to the kidneys (no tumor uptake even after shielding both kidneys.)]

Figure 6D:
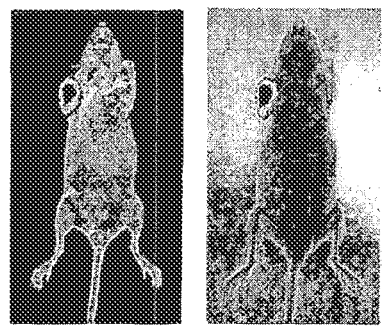
FIG. 6D. Shows a single mouse study for LNCaP tumors imaged using Kodak imager 4 hours after subcutaneous (administered through intraperitoneal) injection of 1 ng/kg SK28-$^{99m}$Tc showing in the left hand image an overlay of radioimage with kidney shield and white light image with no shield and in the right hand image an overlay of radioimage with kidney shield and X-ray image with no shield.

FIGS. 6A, 6B, and 6C show images of mice with human LNCaP tumors using SK28-99 mTc (radiolabeled 14 Atom spacer). FIGS. 6A-6C represent 3 separate sets of mice: the left hand image shows white light images and the right hand image shows an overlay of the radioimage with the white light image of mice with LNCaP tumors imaged using a Kodak camera imager 4 hours after subcutaneous (administered through intraperitoneal) injection of 1 ng/kg SK28-99 mTc without [left mouse in each set of images] and with 50 mg/kg PMPA [right mouse in both sets of images] to block PSMA (as a competitor). FIG. 6D shows a single mouse study for LNCaP tumors imaged using Kodak imager 4 hours after subcutaneous (administered through intraperitoneal) injection of 1 ng/kg SK28-99 mTc showing in the left hand image an overlay of radioimage with kidney shield and white light image with no shield and in the right hand image an overlay of radioimage with kidney shield and X-ray image with no shield.

Example 6B

Figure 7D:
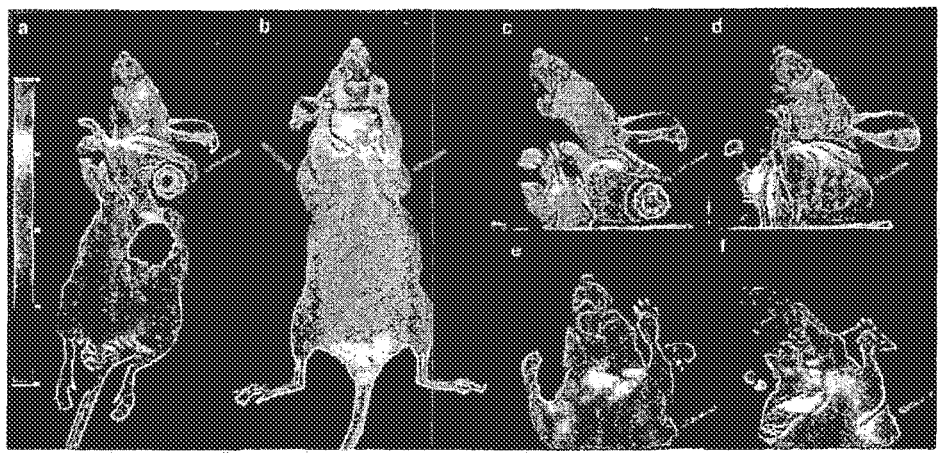
FIG. 7D. Whole body images of solid tumor xenografts in nu/nu mice taken 4 h after injection of 150 µCi DUPA-$^{99m}$Tc. Overlay of whole-body radioimages on white light images of mice bearing LNCaP tumors that were treated with DUPA-$^{99m}$Tc in the absence (a, c) or presence (b, d) of 100-fold molar excess PMPA. Overlay of radioimages on white light images of mice bearing an A549 tumor (e) or a KB tumor (f) that were similarly treated with DUPA-$^{99m}$Tc.

In Vivo Imaging of Tumors in Mouse Using dupa-99 mTc. To further establish the specificity of our DUPA conjugates for prostate cancer cells, DUPA-99 mTc was injected intraperitoneally (i.p.) into athymic nude mice bearing LNCaP tumors on their shoulders. After 4 h to allow for clearance of unbound conjugate, the distribution of the retained DUPA-99 mTc was imaged by gamma scintigraphy. As seen in FIG. 7D(a) and 7D(c), the targeted 99 mTc radiotracer accumulated mainly in the PSMA positive LNCaP tumor, with little or no radioactivity in other tissues except the kidneys. Importantly, kidney uptake may be peculiar to the mouse, since immunohistochemical and RT-PCR analyses suggest that PSMA expression is high in murine kidneys but minimal in human kidneys. In vivo specificity of the PSMA-targeted imaging agent was further tested by prior administration of excess PMPA to block all PSMA sites before DUPA-99 mTc administration. As shown in FIG. 7D(b) and 7D(d), blocked LNCaP tumors display no DUPA-99 mTc uptake, confirming the specificity of the DUPA conjugate for PSMA in vivo. To further document this specificity, the radiotracer was also administered to two PSMA negative mouse xenograft models [A549 (a human lung cancer cell line) and KB (a human nasopharyngeal cancer cell line)], and again whole body images were taken. As anticipated, no radioactivity was observed in either KB or A549 tumors (FIGS. 7D(e) and 7D(f)), even after shielding of the kidneys was performed to allow detection of low levels of DUPA-99 mTc in other tissues. These studies thus confirm that very little DUPA-99 mTc binding occurs to sites unrelated to PSMA in vivo.

FIG. 7D shows the whole body images of solid tumor xenografts in nu/nu mice taken 4 h after injection of 150 μCi DUPA-99 mTc. Overlay of whole-body radioimages on white light images of mice bearing LNCaP tumors that were treated with DUPA-99 mTc in the absence 7D(a, c) or presence 7D(b, d) of 100-fold molar excess PMPA. Overlay of radioimages on white light images were also obtained of mice bearing an A549 tumor 7D(e) or a KB tumor 7D(f) that were similarly treated with DUPA-99 mTc. Except in images 7D(a) and 7D(b), kidneys were shielded with lead pads. All images were taken using a Kodak Imaging Station 4 h after an intraperitoneal injection of DUPA-99 mTc. Arrows indicate solid tumor xenografts. Similar images were obtained on all 5 mice in each treatment group.

Example 7A

Figure 8A:
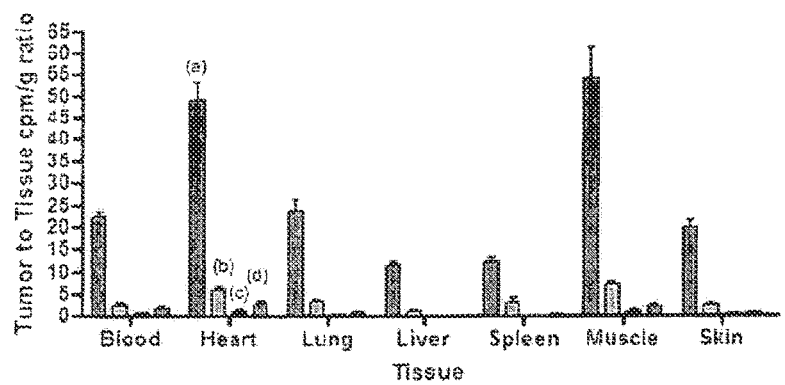
FIG. 8A. Bio-distribution data as measured for direct cpm count verses tissue for SK28-$^{99m}$Tc with or without PMPA (as a competitor) on LNCaP, (a) without, (b) with; (c) A549; and (d) KB tumors implanted on axial of male nude mice.
Figure 8B:
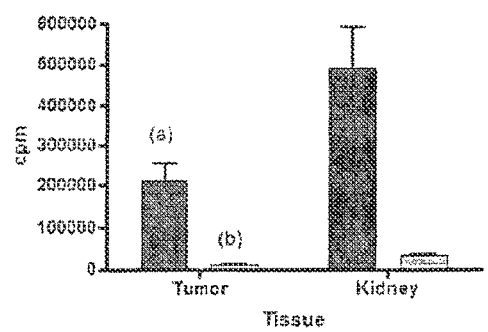
FIG. 8B. Bio-distribution data just for tumor and kidney for SK28-$^{99m}$Tc with (b) or without (a) PMPA (as a competitor) on LNCaP tumors implant on axial of male nude mice.

Biodistribution Studies. After imaging, all animals were dissected approximately 6-7 h after administering SK28-99 mTc or SK60-99 mTc [or other radiolabeled compounds (data not shown)] and organs (blood, tumor, heart, liver, kidney, spleen, skin, muscle, etc) were transferred to individual gamma scintigraphy vials for each animal and radioactivity was counted. Note: blood samples were collected (using cardio punch) immediately after sacrificing the animal and before imaging the animal. The plot of tumor to tissue cpm/g ratio verses tissue was used to determine bio-distribution of the imaging agent (FIGS. 8A and 8B).

Example 7B

Figure 8C:
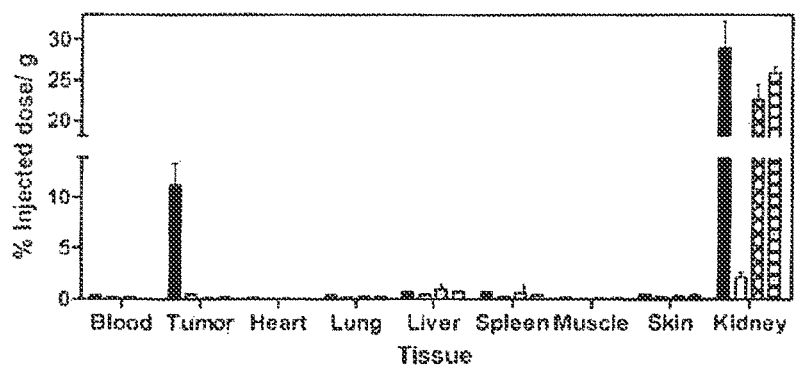
FIG. 8C. Biodistribution studies of DUPA-$^{99m}$Tc in nu/nu mice bearing LNCaP, A549, or KB tumors.

Biodistribution studies of DUPA-99 mTc in nu/nu mice bearing LNCaP, A549, or KB tumors. Tumor-bearing mice were euthanized 4 h after intraperitoneal injection of DUPA-99 mTc (50 μmol/kg, 150 μCi) and tissue-accumulated radioactivity was counted using a γ-counter. The percent injected dose per gram wet tissue was calculated as described in the Methods. The data were obtained in a single experiment and error bars represent s.d. (n=5). LNCaP tumors (solid bars), LNCaP tumors in mice pre-injected with 100-fold molar excess of PMPA (open bars), A549 tumors (cross-hatched bars), KB tumors (horizontally-hatched bars) (FIG. 8C).

Example 8

Figure 9A:
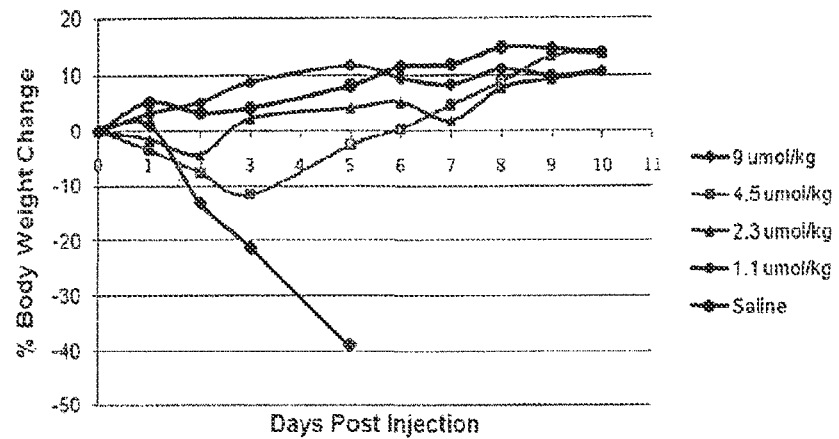
FIG. 9A. Acute MTD (single dose) showing percentage weight change after a single dose of SK71; saline alone, 1.1 µmol/kg, 2.3 µmol/kg, 4.5 µmol/kg, and 9 µmol/kg.

Single dose toxicity in live mice. Administration of SK71 was in a single dose as indicated. The data show that the MTh for the conjugate is about 4.5 μmol/kg for single dosing. (See FIG. 9A)

Example 9

Figure 9B:
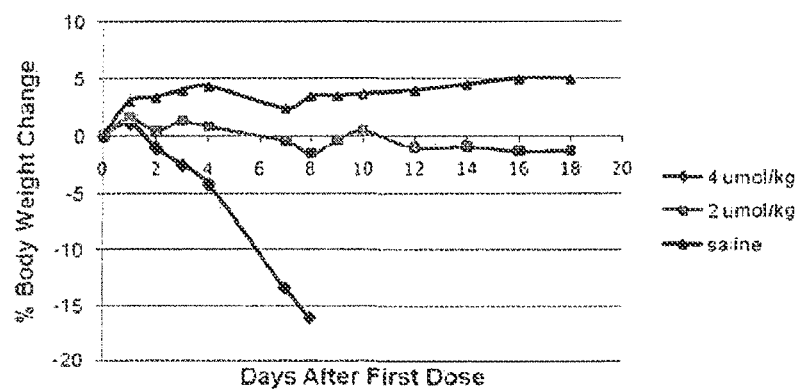
FIG. 9B. Chronic MTD showing percentage weight change after 5 doses given on alternate days (M, W, F, M, W); saline alone, 2 µmol/kg and 4µmol/kg.

Multiple dose toxicity in live mice. SK71 was administered in 5 doses on alternate days (M, W, F, M, W). The data show that the MTD for SK71 is 2 µmol/kg for multiple dosing, and that the conjugate is effective on LNCaP tumors (mice used for MTD 2 weeks after implantation of LNCaP cells before treatment was initiated). All 4 mice in the saline control group had large tumors, whereas no mice in the two treated groups had visible tumors after 18 days of treatment. (See FIG. 9B)

Example 10

Figure 10A:
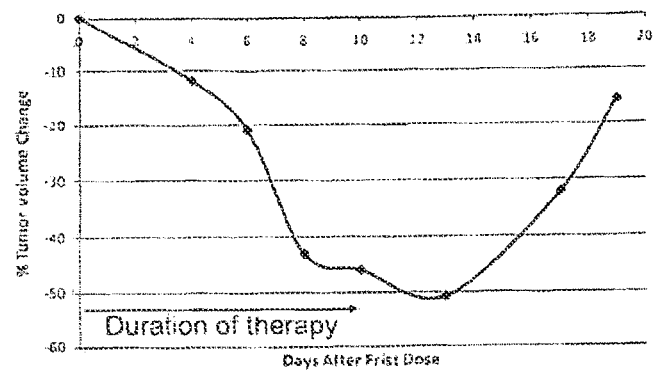
FIG. 10A. Efficacy study showing tumor volume in animals treated with the conjugate SK71 administered in 5 doses on alternate days (M, W, F, M, W) at 1 µmol/kg.
Figure 10B:
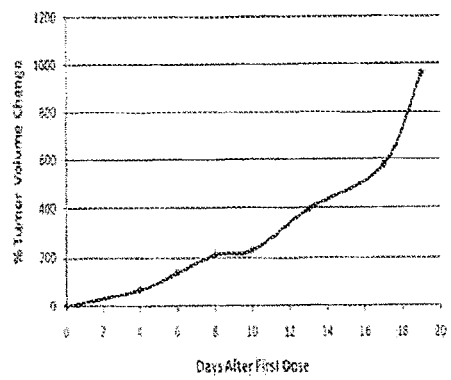
FIG. 10B. Efficacy study (control group) showing tumor volume in animals treated with saline alone administered in 5 doses on alternate days (M, W, F, M, W).
Figure 10C:
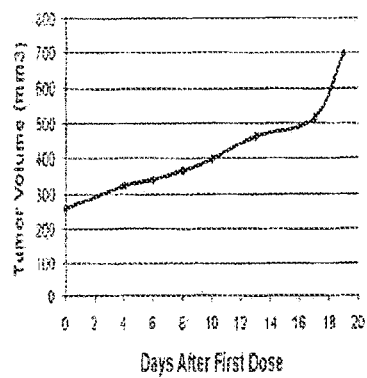
FIG. 10C. Efficacy study (competition) showing tumor volume in animals treated with excess PSMA and the conjugate SK71 administered in 5 doses on alternate days (M, W, F, M, W) at 1 µmol/kg.

Efficacy study compared to control group and competition group. Animals were treated with (a) the conjugate SK71 administered in 5 doses on alternate days (M, W, F, M, W) at 1 mol.kg, and compared to (b) vehicle treated animals (FIG. 10B), and to (c) animals treated with the conjugate in conjunction with PMPA. Treatment at 1 µmol/kg shows a successive decrease in tumor size (starting tumor size approximately 250 mm3) during the course of treatment. At the lower dose of 1 µmol/kg shown in FIG. 10A, tumor volumes rebounded at the cessation of dosing. At the higher dose of at least 2 µmol/kg, complete disappearance of the tumor was observed during the testing period. The competition experiments (See FIG. 10C) indicate that the successful treatment of the implanted tumor is related to selective or specific targeting of PSMA mediated delivery.

Example 11

Figure 11:
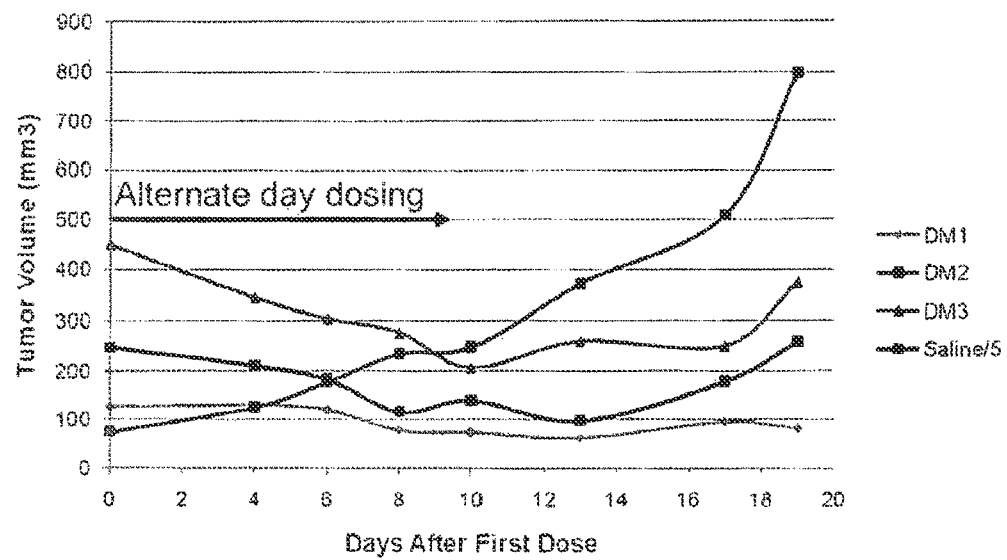
FIG. 11. Efficacy Study (1 micromole/kg every other day for 10 days; i.e. 5 doses).

Efficacy Study (1 micromole/kg every other day for 10 days; i.e. 5 doses). The data (See FIG. 11) indicate that tumors in treated animals decreased in size during the duration of treatment.

Example 12

Figure 12A:
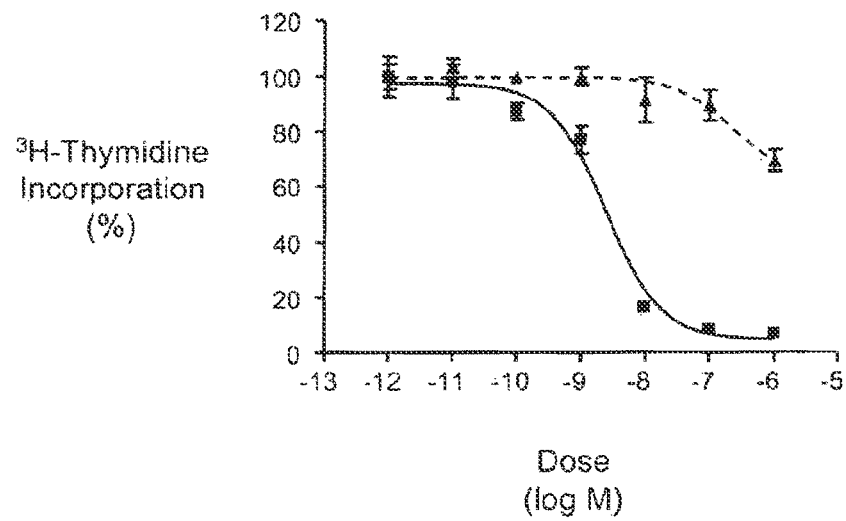
FIG. 12A. [$^3$H]-Thymidine incorporation of LNCaP cells after treatment with SK71 (IC$_{50}$~2 nM).
Figure 12:
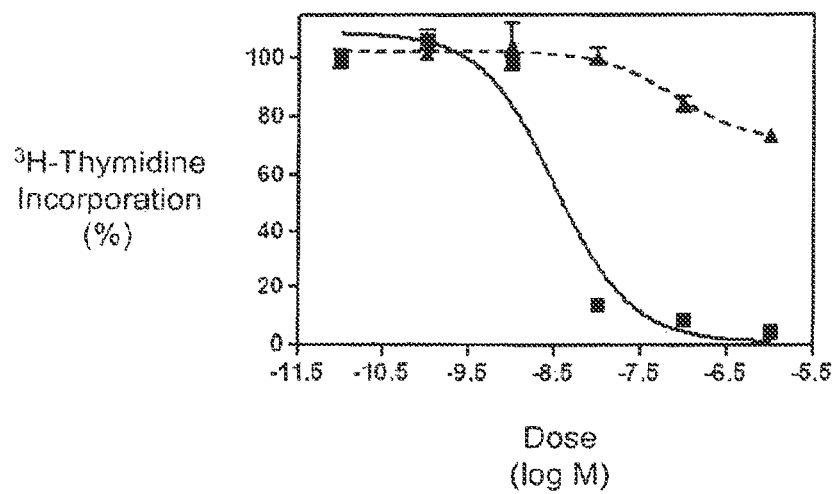
FIG. 12B. [$^3$H]-Thymidine incorporation of LNCaP cells after treatment with SK77 (IC$_{50}$~3 nM).
FIG. 12C. [$^3$H]-Thymidine incorporation of LNCaP cells after treatment with SK37 (IC$_{50}$~33 nM).
FIG. 12D. [$^3$H]-Thymidine incorporation of LNCaP cells after treatment with SK45 (IC$_{50}$~29 nM).
Figure 12C:
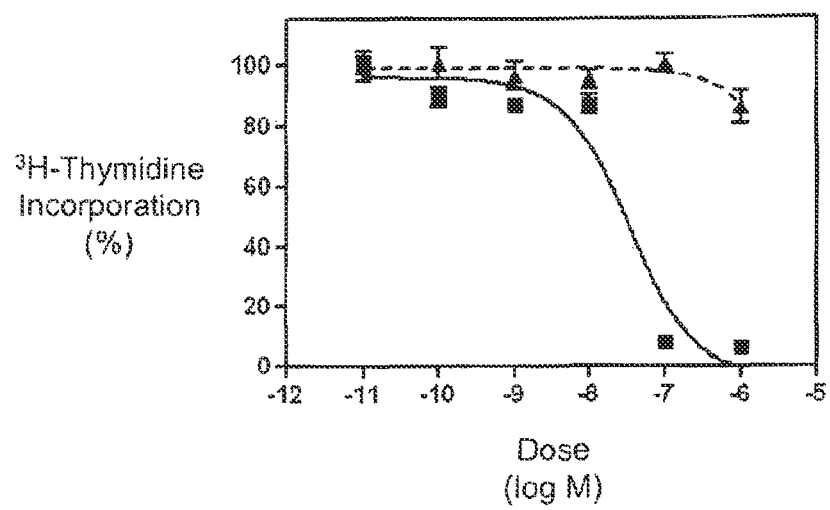
Figure 12D:
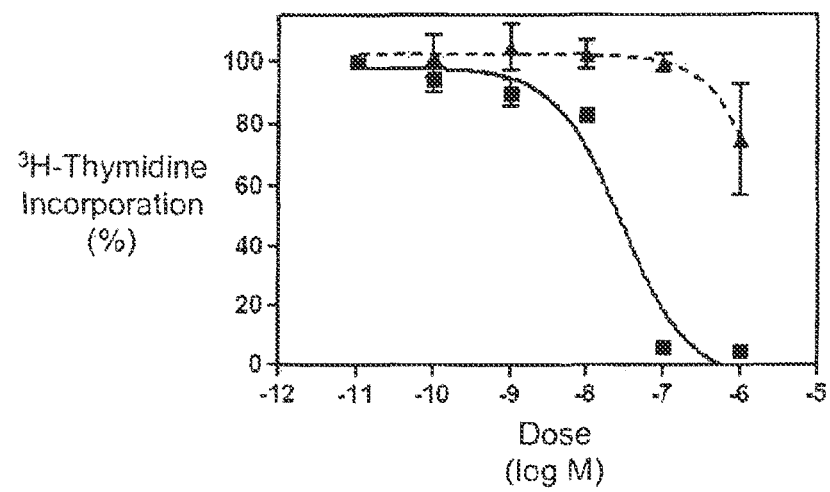

Evaluation of a PSMA-Targeted Therapeutic Agent in Vitro. Analysis of SK71 (FIG. 12A), SK77 (FIG. 12B), SK37 (FIG. 12C), and SK45 (FIG. 12D), toxicity to LNCaP cells in culture. LNCaP cells were pulsed for 2 h with increasing concentrations of SK71 or SK77 in the presence (▲) or absence (■) of 100-fold molar excess PMPA. After 2× washes, cells were incubated an additional 66 h in fresh medium at 37° C. Cell viability was then analyzed using the [3H]-thymidine incorporation assay, as described herein. Data were obtained in a single experiment and error bars represent s.d. (n=3 wells per concentration).

Example 13

Figure 13A:
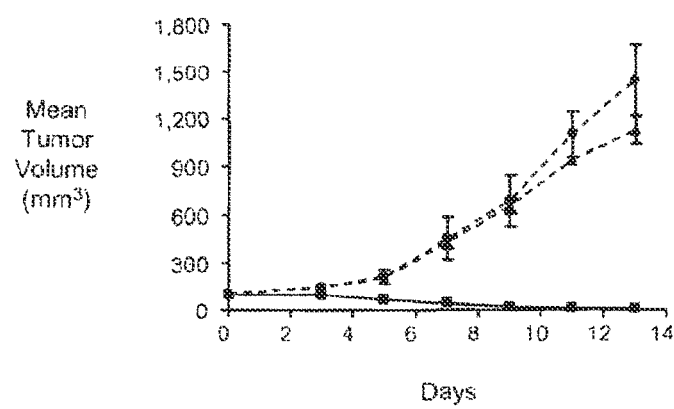
FIG. 13A. The effect of treatment with SK71 (1.5 µmol/kg) on tumor volume in nu/nu mice previously treated with LNCaP cells in HC Matrigel. Treated mice (■), untreated mice (●), treated mice pre-injected with 100-fold molar excess of PMPA (▲).
Figure 13B:
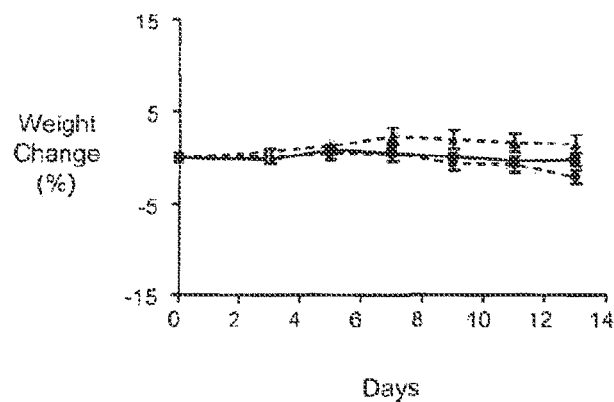
FIG. 13B. The effect of treatment with SK71 (1.5 µµmol/kg) on percentage weight change in nu/nu mice previously treated with LNCaP cells in HC Matrigel. Treated mice (■), untreated mice (●), treated mice pre-injected with 100-fold molar excess of PMPA (▲).
Figure 13C:
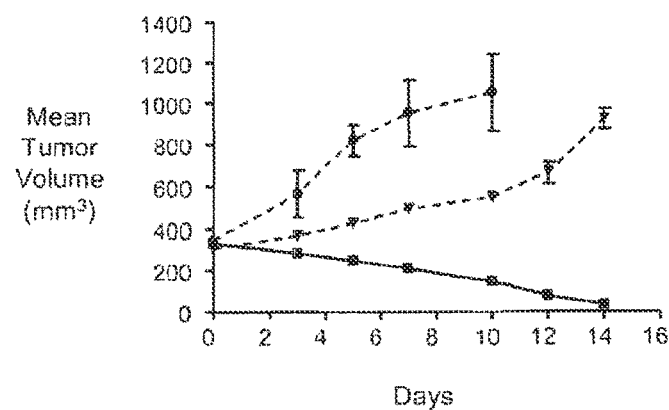
FIG. 13C. The effect of treatment with SK71 (2.0 µmol/kg) on tumor volume in nu/nu mice previously treated with LNCaP cells in HC Matrigel. Treated mice (■), untreated mice (●), treated mice pre-injected with 30-fold molar excess of PMPA (▼).
Figure 13D:
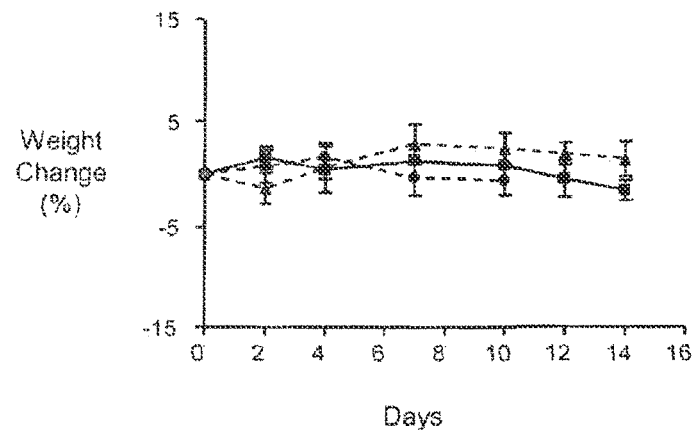
FIG. 13D. The effect of treatment with SK71 (2.0 µl/kg) on percentage weight change in nu/nu mice previously treated with LNCaP cells in HC Matrigel. Treated mice (■), untreated mice (●), treated mice pre-injected with 30-fold molar excess of PMPA (▼).

Potency In Vivo. Effect of SK71 on the growth of subcutaneous tumors (FIG. 13A and 13C, and on the weights of the treated mice (FIG. 13B and 13D). LNCaP cells in HC Matrigel were implanted subcutaneously into shoulders of nu/nu male mice. Once tumors reached either 100 mm3 (13A, 13B) or 330 mm3 (13C, 13D) in volume, animals were treated with SK71 [1.5 µmol/kg (a, b) or 2.0 µmol/kg (c, d)]. Treated mice (■), untreated mice (●), treated mice pre-injected with 100-fold (13A, 13B) or 30-fold (13C, 13D) molar excess of PMPA (▲ and ▼, respectively). Data were obtained in a single experiment and error bars represent s.d. [n=4 (13A, 13B) or 3 (13C, 13D)]. FIGS. 10. SK71 potency in vivo.

Figure 14A:
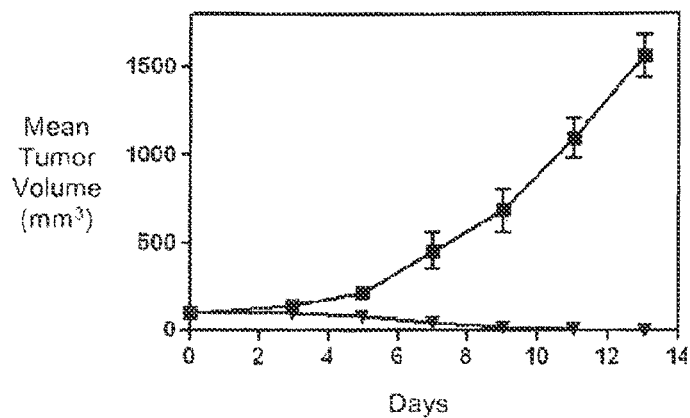
FIG. 14A. The effect of treatment with SK77 (2.0 µmol/kg) on tumor volume in nu/nu mice previously treated with LNCaP cells in HC Matrigel. Untreated mice (■), treated mice (▼).
Figure 14B:
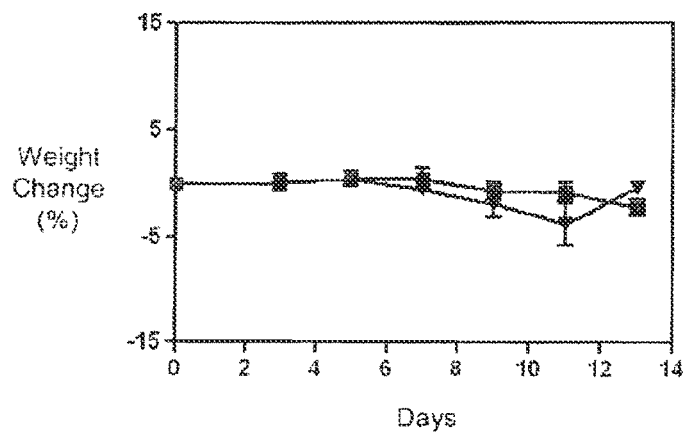
FIG. 14B. The effect of treatment with SK77 (2.0 µmol/kg) on percentage weight change in nu/nu mice previously treated with LNCaP cells in HC Matrigel. Untreated mice (■), treated mice (▼).

Potency In Vivo. Effect of SK77 on the growth of subcutaneous tumors (FIG. 14A), and on the weights of the treated mice (FIG. 14B). LNCaP cells in HC Matrigel were implanted subcutaneously into shoulders of nu/nu male mice. Once tumors reached 100 mm3 in volume, animals were treated with SK77 (2 µmol/kg). Untreated mice (■), treated mice (▼). Data were obtained in a single experiment and error bars represent s.d. (n=4 mice/group).

What is claimed is:

1. A compound of the formula.

B-L-D or a salt thereof, wherein
B is a urea of two amino acids;
L comprises (i) a divalent alkylenecarbonyl and (ii) at least one nitrogen atom, wherein the divalent alkylenecarbonyl is optionally substituted with one or more substituents $X^1$ selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, arylalkyl, heteroaryl, carboxy, carboxyalkyl, and alkyl carboxylate, and wherein L is about 7 to about 9 atoms in length; and
D comprises a radioactive isotope of a metal coordinated to a chelating group.

2. The compound of claim 1, or a salt thereof, wherein B is of the formula

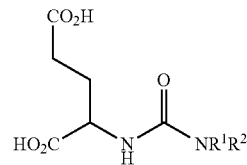

wherein $R^1$ is hydrogen and $R^2$ is a substituted carboxylic acid, and the substituted carboxylic acid is covalently bound to L.

3. The compound of claim 1, or a salt thereof, wherein L is covalently bound to B through an amide bond.

4. The compound of claim 1, or a salt thereof, wherein L is covalently bound to D through an amide bond.

5. The compound of claim 1, or a salt thereof, wherein the radioactive isotope of a metal is $^{68}$Ga.

6. The compound of claim 3, or a salt thereof, wherein the radioactive isotope of a metal is $^{68}$Ga.

7. The compound of claim 4, or a salt thereof, wherein the radioactive isotope of a metal is $^{68}$Ga.

8. The compound of claim 2, or a salt thereof, wherein L is covalent boundd to B through an amide bond.

9. The compound of claim 2, or a salt thereof, wherein L is covalently bound to D through an amide bond.

10. The compound of claim 2, or a salt thereof, wherein the radioactive isotope of a metal is $^{68}$Ga.

11. The compound of claim 8, or a salt thereof, wherein the radioactive isotope of a metal is $^{68}$Ga.

12. The compound of claim 9, or a salt thereof, wherein the radioactive isotope of a metal is $^{68}$Ga.

13. A pharmaceutical composition comprising a compound of the formula

B-L-D or a salt thereof, wherein
B is a urea of two amino acids;
L comprises (i) a divalent alkylenecarbonyl and (ii) at least one nitrogen atom, wherein. the divalent alkylenecarbonyl is optionally substituted with one or more substituents $X^1$ selected from the group consisting of alkyl, alkoxy, alkoxyalkyl, hydroxy, h.ydroxyalkyl, amino, aminoalkyl, alkylaminoalkyl, dialkylaminoalkyl, halo, haloalkyl, sulfhydrylalkyl, alkylthioalkyl, aryl, arylalkyl, heteroaryl, carboxy, carboxyalkyl, and alkyl carboxylate, and wherein L is about 7 to about 9 atoms in length; and D comprises a radioactive isotope of a metal coordinated to a chelating group; and one or more carriers, diluents or excipients.

14. The pharmaceutical composition of claim 13, wherein the carrier is an aqueous solution.

15. The pharmaceutical composition of claim 13, wherein B is of the formula

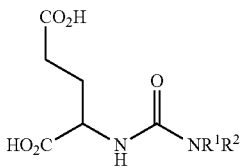

wherein $R^1$ is hydrogen and $R^2$ is a substituted carboxylic acid, and the substituted carboxylic acid is covalently bound to L.

16. The pharmaceutical composition of claim 15, wherein the carrier is an aqueous solution.

17. The pharmaceutical composition of claim 13, wherein the radioactive isotope of a metal is $^{68}$Ga.

18. The pharmaceutical composition of claim 14, wherein the radioactive isotope of a metal is $^{68}$Ga.

19. The pharmaceutical composition of claim 15, wherein the radioactive isotope of a metal is $^{68}$Ga.

20. The pharmaceutical composition of claim 16, wherein the radioactive isotope of a metal is $^{68}$Ga.

21. The pharmaceutical composition of claim 13, wherein L is covalently bound to B through an amide bond and the radioactive isotope of a metal is $^{68}$Ga.

22. The pharmaceutical composition of claim 13, wherein L is covalently bound to D through an amide bond and the radioactive isotope of a metal is $^{68}$Ga.

23. The pharmaceutical composition of claim 14, wherein L is covalently bound to B through an amide bond and the radioactive isotope of a metal is $^{68}$Ga.

24. The pharmaceutical composition of claim 14, wherein L is covalently bound to D through an amide bond and the radioactive isotope of a metal is $^{68}$Ga.

25. A method of imaging comprising administering to a subject a compound of claim 1, or a salt thereof, in an amount effective to image tissue or cells associated with pathogenic populations of cells expressing or over-expressing prostate-specific membrane antigen.

26. The method of claim 25, wherein the radioactive isotope of a metal is $^{68}$Ga.

27. A method of imaging comprising administering to a subject a pharmaceutical composition of claim 13, or a salt thereof, in an amount effective to image tissue or cells associated with pathogenic populations of cells expressing or over-expressing prostate-specific membrane antigen.

28. The method of claim 27, wherein the radioactive isotope of a metal is $^{68}$Ga.

29. The method of claim 27, wherein B is of the formula

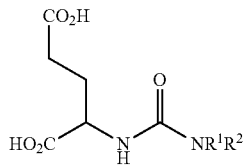

wherein $R^1$ is hydrogen and $R^2$ is a substituted carboxylic acid, and the substituted carboxylic acid is covalently bound to L.

30. The method of claim 29, wherein the radioactive isotope of a metal is $^{68}$Ga.

* * * * *